(12) United States Patent
Dancu

(10) Patent No.: US 8,409,847 B2
(45) Date of Patent: *Apr. 2, 2013

(54) SYSTEM AND METHOD FOR CONTROLLING THE DIAMETER OF A MAMMILIAN HYBRID CORONARY BYPASS GRAFT

(75) Inventor: Michael Dancu, Pompton Lakes, NJ (US)

(73) Assignee: ICE Development Technologies, LLC, Ridgewood, NJ (US)

( * ) Notice: Subject to any disclaimer, the term of this patent is extended or adjusted under 35 U.S.C. 154(b) by 574 days.

This patent is subject to a terminal disclaimer.

(21) Appl. No.: 11/966,799

(22) Filed: Dec. 28, 2007

(65) Prior Publication Data

US 2009/0007923 A1 Jan. 8, 2009

Related U.S. Application Data

(63) Continuation of application No. PCT/US2006/045715, filed on Nov. 30, 2006, and a continuation-in-part of application No. 11/440,152, filed on May 25, 2006, now Pat. No. 8,318,414, and a continuation-in-part of application No. 11/440,156, filed on May 25, 2006, now abandoned, and a continuation-in-part of application No. 11/440,155, filed on May 25, 2006, now abandoned, and a continuation-in-part of application No. 11/440,091, filed on May 25, 2006, now abandoned, and a continuation-in-part of application No. 11/440,148, filed on May 25, 2006, now abandoned, which is a continuation of application No. 09/973,433, filed on Oct. 9, 2001, now Pat. No. 7,063,942, and a continuation of application No. PCT/US01/42576, filed on Oct. 9, 2001.

(60) Provisional application No. 60/239,015, filed on Oct. 6, 2000.

(51) Int. Cl.
*A01N 1/00* (2006.01)
*A01N 1/02* (2006.01)
*A61F 2/04* (2006.01)

(52) U.S. Cl. ............... 435/284.1; 435/289.1; 435/293.1; 435/304.1; 435/305.1; 435/1.1; 435/1.2; 435/285.1; 435/299.1; 435/297.2; 600/36; 623/915; 623/916; 623/921

(58) Field of Classification Search ............... 435/284.1, 435/289.1, 293.1, 304.1, 305.1, 1.1, 1.2, 435/285.1, 299.1, 297.2; 600/36; 623/915, 623/916, 921

See application file for complete search history.

(56) References Cited

U.S. PATENT DOCUMENTS 5,338,662 A * 8/1994 Sadri ...................... 435/284.1
5,510,254 A * 4/1996 Naughton et al. ............ 435/370

(Continued)

*Primary Examiner* — Nathan Bowers
(74) *Attorney, Agent, or Firm* — Rene A. Vazquez, Esq.

(57) ABSTRACT

Systems and methods are provided for controlling the diameter of a mammalian hybrid coronary bypass graft. The system includes a controller having at least one input for receiving information and feedback information and an output for outputting control signals, including at least one steady flow system control signal; and a pressure/flow loop subsystem coupled to the controller. The pressure/flow loop subsystem includes a specimen holder, an external flow loop system coupled to the specimen holder, a steady flow system, and an output for outputting the feedback information. The pressure/flow loop subsystem receives the control signals and is capable of adjusting a diameter of a specimen in accordance with the control signals, when the specimen holder contains the specimen.

41 Claims, 79 Drawing Sheets

U.S. PATENT DOCUMENTS 5,531,791 A * 7/1996 Wolfinbarger, Jr. ........ 623/23.63
5,792,603 A * 8/1998 Dunkelman et al. ........... 435/1.2
6,174,719 B1 * 1/2001 Elizondo et al. ........... 435/284.1
6,416,995 B1 * 7/2002 Wolfinbarger ............. 435/289.1
7,348,175 B2 * 3/2008 Vilendrer et al. .......... 435/284.1

* cited by examiner

Types of Dynamic Conditions $g_i(t)$ (Including, electromechanical, electrical, mechanical, chemical, biological, physiological, pathophysiological dynamic conditions)

| | |
|---|---|
| Pressure | tubular structure: longitudinal radial or combinations thereof |
| Flow | tubular structure: longitudinal radial or combinations thereof |
| Diameter or shape of tubular structure | tubular structure: inner/outer wall diameter along 1, 2, 3 or more directions<br>cross-sectional shape of tubular structure<br>wall thickness along 1, 2, 3 or more directions<br>*interstitial*<br>multiple diameters/wall thickness along 1 direction<br>multiple diameters/wall thickness along multiple directions/dimensions |
| Length or stretch | tubular structure |
| Twist or torque | tubular structure |
| Stress | tubular structure: wall shear stress (WSS), longitudinal, other |
| Strain | tubular structure: longitudinal, circumferential (CS), torsional or combination thereof |
| Inertia | |
| Unsteadiness parameters | |
| Viscous forces | |
| Distal resistance | |
| Compliance | |
| Phase angle between two dynamic conditions | $g_1(t), g_2(t)$<br>e.g., pressure and flow |
| Impedance | |
| Impedance phase angle | |
| Kinetic viscosity | |
| Temperature | fluid and/or tubular structure |
| pH | fluid and/or tubular structure |
| Conductivity/resistance | fluid and/or tubular structure |
| NMR | fluid and/or tubular structure |
| PET MRI | fluid and/or tubular structure |
| Adsorption, reflection, emission of electromagnetic radiation, fluorescence and/or ultrasound | fluid and/or tubular structure |
| Second order dynamic conditions | fluid and/or tubular structure: vortices, pressure, varying flow diameter; microgrooves, bumps, density, permeability, elasticity, etc. |
| Directional dynamic conditions | velocity, curl, flow, pressure,... |

Figure 17A

Types of Dynamic Conditions $g_i(t)$ (cont)

| Presence, expression, flow, velocity, curl, amounts, volumes and/or concentrations of: | Fluid Materials (Exemplary) liquids, solids, gases, cells, bacteria, minimum essential Eagles medium, growth factor, cell differentiating small molecule, cell differentiating biologics, cell culture medium, plasma, saline, blood, water, immune cells, cell culture medium, fetal bovine serum (FBS), bovine serum albumin (BSA), cerebral spinal fluid, inorganic molecules, fluid sensor, fluid nanosensor, fluid transmitter, fluid receiver, fluid transceiver, MEMS device, MEMS sensor, biological substances or biologics hormones, proteins, genes, virus, lipids, peptides, nucleotide, a glycol, an antibiotic, metabolites, a pharmacological agents, nanoparticles, free electrons, minerals, iron, zinc, copper, magnesium, calcium, gases, oxygen, nitric oxide, carbon dioxide, carbon monoxide, or exemplary items above in various combinations, concentrations or mixtures, exemplary items above individually or in various combinations grown or emerging from a specimen |
|---|---|

Figure 17B

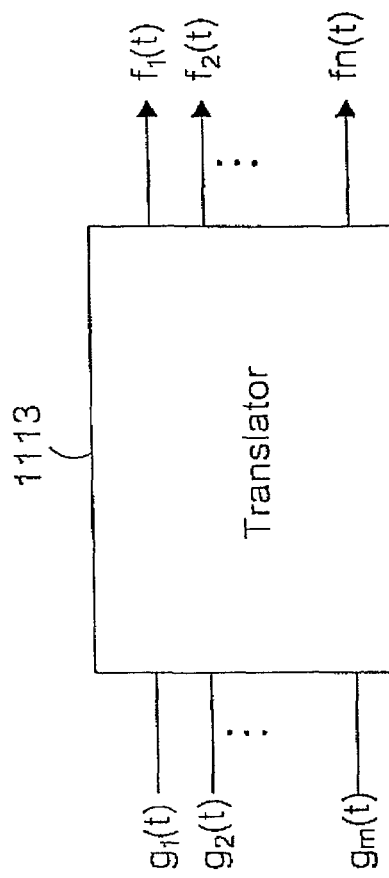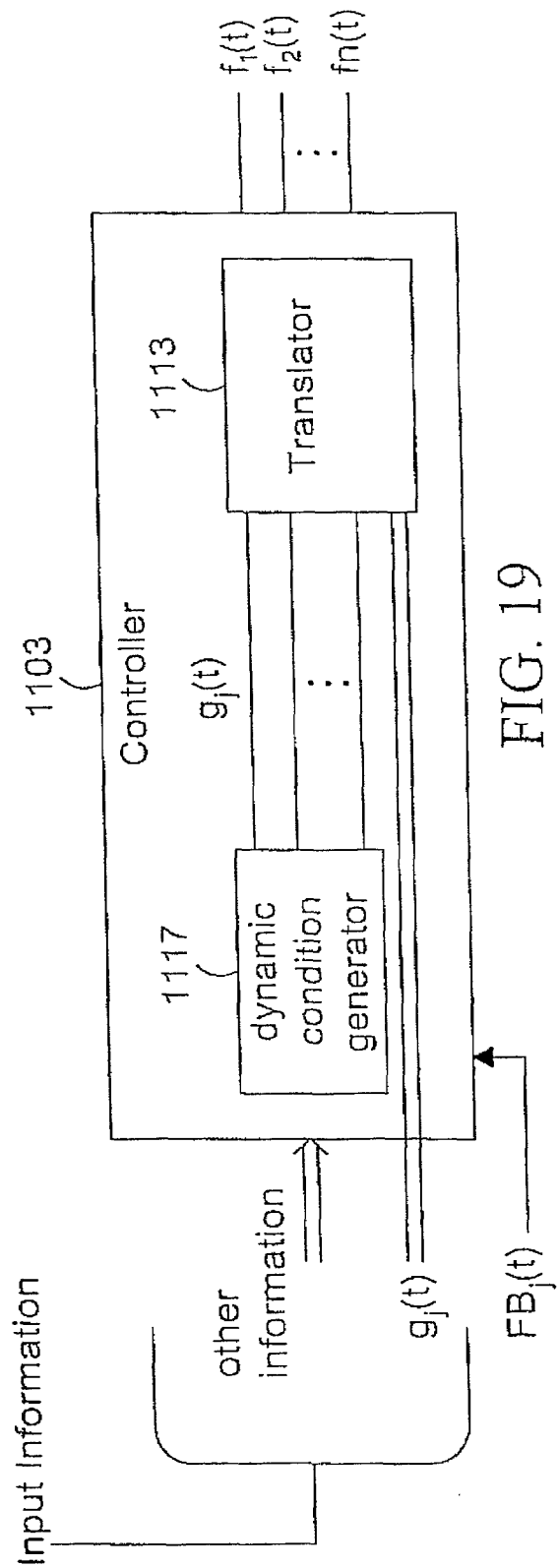

Phase $\theta_j$ of the first three harmonics of dynamic condition g(t)

Amplitude of the first three harmonics $G_1$, $G_2$ and $G_3$ of dynamic condition g(t)

ically alter endothelial cell function and phenotype (i.e., higher shear stress [low SPA] is associated with an atherogenic gene expression profile, and a low shear stress [large SPA] is associated with an atherogenic gene expression profile).

SYSTEM AND METHOD FOR CONTROLLING THE DIAMETER OF A MAMMILIAN HYBRID CORONARY BYPASS GRAFT

CROSS-REFERENCE TO RELATED APPLICATIONS

This application is a Continuation of PCT/US2006/045715, filed Nov. 30, 2006 and a Continuation-in-Part of U.S. application Ser. Nos. 11/440,152, now U.S. Pat. No. 8,318,414 filed May 25, 2006; 11/440,156, now abandoned filed May 25, 2006; 11/440,148, now abandoned filed May 25, 2006; 11/440,155, now abandoned filed May 25, 2006; 11/440,091, now abandoned filed May 25, 2006, which in turn are Continuations of U.S. application Ser. No. 09/973,433, filed Oct. 9, 2001, now U.S. Pat. No. 7,063,942 and International Application No. PCT/US2001/042576, filed Oct. 9, 2001, now Publication No. WO 2002/032224 A1, which claim the benefit of U.S. Provisional Application No. 60/239,015, filed Oct. 6, 2000. The entire disclosure of the prior applications are considered as being part of the disclosure of the accompanying application and are hereby incorporated by reference therein.

BACKGROUND OF THE INVENTION

1. Field of the Invention

The invention relates to systems and methods for controlling the diameter of a mammalian hybrid coronary bypass graft

2. Background of the Related Art

Hemodynamics plays an obligate role on the function and phenotype of vascular cells (i.e. endothelial cells, smooth muscle cells, fibroblast s, etc.) and tissues in the cardiovascular system during disease and healthy states. Cardiovascular disease is the leading cause of death in North America, Europe and the developing world, with coronary heart disease and atherosclerosis being amongst the most prominent cardiovascular diseases. Atherosclerosis is a disorder in which the coronary arteries become clogged by the build up of plaque along the interior walls of the arteries, leading to decreased blood flow which can in turn cause hypertension, ischemias, strokes and, potentially, death. Associated systemic risk factors include hypertension, diabetes mellitus, and hyperlipidemia, among other factors.

Atherosclerosis and other cardiovascular diseases, such as peripheral arterial disease (PAD), occur regularly and predictably at sites of complex hemodynamic behavior and, consequently, motivates further investigation into the role of hemodynamics in cardiovascular diseases. For example, atherosclerosis has been shown to occur in sites of complex hemodynamic behavior. Surgical intervention is often employed to treat it, and may include insertion of a balloon catheter to clean out the plaque, and insertion of a stent within the vessel to enable it to remain open, or may include multiple bypasses of the clogged vessels. Bypass surgery involves the removal of a section of vein from the patient's lower leg, and its transplant into the appropriate cardiac blood vessels so that blood flows through the transplanted vein and thus bypasses the clogged vessels. A major problem associated with bypass surgery is the patency of the vessels to be used in the bypass. The bypass vessels are prone to failure, which may occur within a short period of time after bypass surgery, or after a period of several years. Hemodynamic forces have been implicated as a major factor contributing to the failure of the bypass vessels.

Hemodynamic forces, which are forces generated by irregular flow, and in particular, by the (sometimes irregular) flow of blood, are known to have numerous influences on blood vessels, including, but not limited to effects on blood vessel cell structure, pathology, function, and development. In the specific example of blood vessel structure and pathology, the vascular cells lining all blood vessels, endothelial cells (ECs), are important sensors and transducers of two of the major hemodynamic forces to which they are exposed. These forces include wall shear stress ("WSS"), which is the fluid frictional force per unit of surface area, and hoop stress, which is driven by the circumferential strain ("CS") of pressure changes. Wall shear stress acts along the blood vessel's longitudinal axis, while circumferential strain is associated with the deformation of the elastic artery wall (i.e., changes in the diameter of the vessel) in response to oscillation or variation in vascular pressure. Wave reflections in the circulation and the inertial effects of blood flow cause a phase difference, the stress phase angle ("SPA"), between CS and WSS. The SPA varies significantly throughout the circulation, and is most negative in disease prone locations, such as the outer walls of a blood vessel bifurcation such as the carotid sinus and the coronary arteries. Hemodynamic forces have been shown to dramat ECs can influence vasoactivity and cause vessels to contract or dilate depending on the blood flow (shear stress) and pressure (causing stretch or CS), and thus are one component which is critical to blood pressure regulation among the many important factors which influence and/or are dependent on the hemodynamics. ECs are just one type of cell which is directly influenced by hemodynamics. Numerous other cell types may also directly or indirectly influenced by hemodynamics and mechanical forces.

As discussed above, hemodynamic forces have been shown to dramatically alter endothelial function and phenotype. For example, the coronary arteries are the most disease prone arteries in the circulation and have the most extreme SPA in the circulatory system, typically having a large, negative value, yet do not have a particularly low shear stress magnitude, thus suggesting that complex hemodynamic factors that include the SPA are important in cardiovascular function and pathology. Accordingly, there is a great need to study vascular biology in a complete, integrated, and controlled hemodynamic environment, preferably in 3-dimensions. However, to date, detailed knowledge of the simultaneous, combined influence of the time varying patterns of WSS and CS on EC biological response has not been technologically feasible.

More specifically, existing systems have focused on the individual effects of either WSS or strain on ECs separately. The most common WSS systems use a 2-dimensional stiff surface, such as, for example, a glass slide, for the EC culture on the wall of a parallel plate flow chamber, or a cone-and-plate type chamber, to simulate wall shear stress alone, which is only one hemodynamic condition. In such a system, the WSS must usually remain steady due to difficulties in simulating pulsatile flow, and strain or stretch effects must be omitted. Further, cyclic straining devices can only generate strain by stretching cells on a compliant membrane, without flow, and typically only in 2 dimensions. Both types of systems are obviously limited in the fidelity with which they can simulate a true, complete hemodynamic environment.

To address the need for simultaneous pulsatile strain and shear stress, a silicone tube coated with ECs was introduced. However, simulators using these tubes could only achieve phase angles (SPA) of about −90 degrees, if any, which is inadequate for simulating coronary arteries (SPA>−180 or −250 degrees), the most disease prone vessels in the circulation, or other regions of the circulation such as peripheral circulation, carotid, renal, organ hemodynamics, or head and brain hemodynamics, to name a few. A more complete physiologic environment which provides time-varying uniform cyclic CS and pulsatile WSS in a 3-dimensional configuration over a complete range of SPA is still needed.

Substantially all past research and development has focused only on obvious, one-dimensional blood flow or shear stress hemodynamic force characteristics, even though, based on physics, mathematics, and experimentation, there are clearly a multitude of dimensions associated with the with many simultaneous hemodynamic forces present in vivo, such as pressure and strain. Physiologic environments are highly dynamic and nonlinear, the cardiovascular system is certainly no exception. There is a need to preserve 3-dimensional vascular geometry while simultaneously and independently controlling hemodynamic forces such as, for example, pressure, flow, and stretch, as well as many other parameters and forces) in a cell and tissue culture environment in order to more fully and more accurately recapitulate in vivo hemodynamic environments.

BRIEF DESCRIPTION OF THE DRAWINGS

The invention will be described in detail with reference to the following drawings in which like reference numerals refer to like elements, wherein:

FIGS. 9A-9C are flowcharts illustrating operation of the systems shown in FIGS. 2A-2E and 3A-3D.

FIGS. 17A and 17B show examples of various forms or types of dynamic conditions;

FIG. 19 shows a block diagram of a controller according to an embodiment of the invention;

FIG. 20 shows a block diagram of a translator according to an embodiment of the invention;

DETAILED DESCRIPTION OF PREFERRED EMBODIMENTS

Any reference in this specification to "one embodiment," "an embodiment," "example embodiment," "embodiments," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

A hemodynamic simulation system in accordance with embodiments of the invention as embodied and broadly described herein overcomes current technological limitations in biomedical research and, particularly, in vascular research are overcome by physically reproducing both normal and diseased physiologic states in a controlled environment. A precise and complete physiologic environment is achieved via control of salient dynamic conditions such as, for example, pressure, flow, and diameter, that consequently control the predominant dynamic forces, WSS and CS. This is achieved through independent control of these dynamic conditions, thus allowing for independent control over a variety of dynamic parameters and forces such as the magnitude and phase of the pulsatile WSS and CS at a wide range of SPA. The system provides for the recreation of real dynamic patterns, complex and simple, while also meeting the stringent requirements for sterility and minimal media volume critical in cell and tissue culture systems.

The system neatly integrates engineering and biological principles by imposing a realistic, time varying mechanical environment on a test specimen, such as, for example, living vascular cells, to provide a model of normal and diseased cardiovascular function to help guide many areas such as future therapeutic strategies, stem cell therapy, cell and tissue regeneration or engineering, genetic or pharmacologic. The independent control of pulsatile flow and pulsatile pressure to provide for independent control over WSS, CS and pressure is a significant breakthrough which, at first, seems paradoxical. That is, classically, pressure and flow are coupled. However, in a dynamic oscillatory or sinusoidal environment such as is present in this system, flow and pressure can be independently controlled in a variety of ways to achieve the desired result.

Figure 1A:
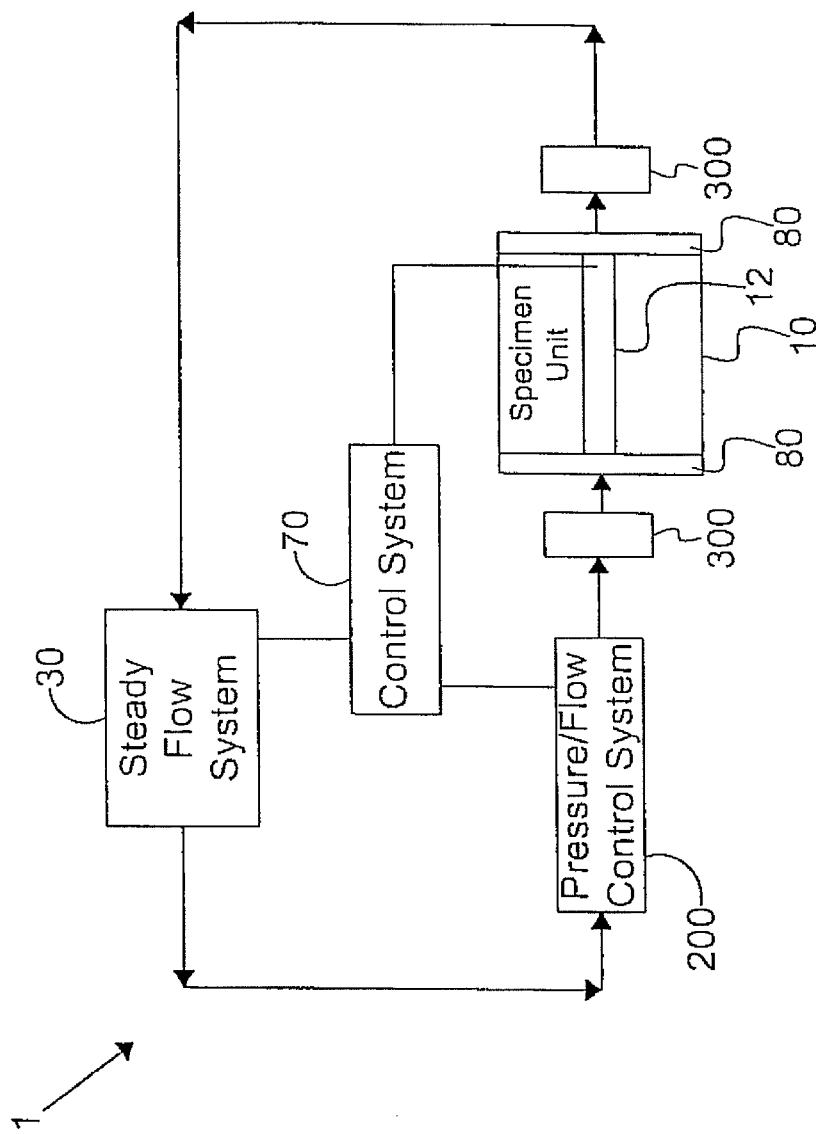
FIG. 1A is a schematic view of a system for recreating a hemodynamic environment in accordance with an embodiment of the invention.

FIG. 1A is a schematic view of a system for reproducing a hemodynamic environment and, more particularly, a schematic view of a flow loop of such a system, in accordance with one embodiment of the invention as broadly described herein. In this system 1, flow of fluid and/or media is initiated by a steady flow system 30 and introduced into a flow loop, where it passes into a specimen unit 10. An individual or multiple specimen 12 may be positioned in the specimen unit 10 by a mounting system 80. The single/multiple specimen 12 are exposed to fluid and/or media carried by the fluid, as well as to the dynamic environment produced by the system 1. The specimen unit 10 may be coupled, and preferably detachably coupled, to the flow loop by a coupling system 300.

Dynamic pressure and flow conditions within the specimen unit 10 may be generated and maintained by a pressure/flow control system 200, which acts on the fluid traversing through the flow. Fluid may be substantially continuously recirculated through the flow loop for a required amount of time/cycles, or based on another such controlling parameter which would govern the flow through the flow loop. In other embodiments, a predetermined amount of fluid/media may be introduced into the flow loop and held in the specimen unit 10 for a predetermined amount of time/cycles, or other such controlling parameter, as the pressure/flow control system 200 generates the required conditions in the specimen unit 10.

The action of the steady flow system 30 and the pressure/flow control system 200 may be controlled by a control system 70. The control system 70 may also receive data related to various parameters from various sensors positioned throughout various portions of the system 100, such as, for example, the specimen unit 10, the steady flow system 30, the pressure/flow control system 200, and other locations along the flow loop. In certain embodiments, the control system 70 provides for dynamic control of the system 1 based on feedback provided by a variety of sensing/detection systems (not shown in detail in FIG. 1A). In alternative embodiments, the control system 70 may simply operate the system 100 in accordance with a previously stored algorithm based on conditions desired in the specimen unit 10 and/or throughout the flow loop, without feedback.

Figure 1B:
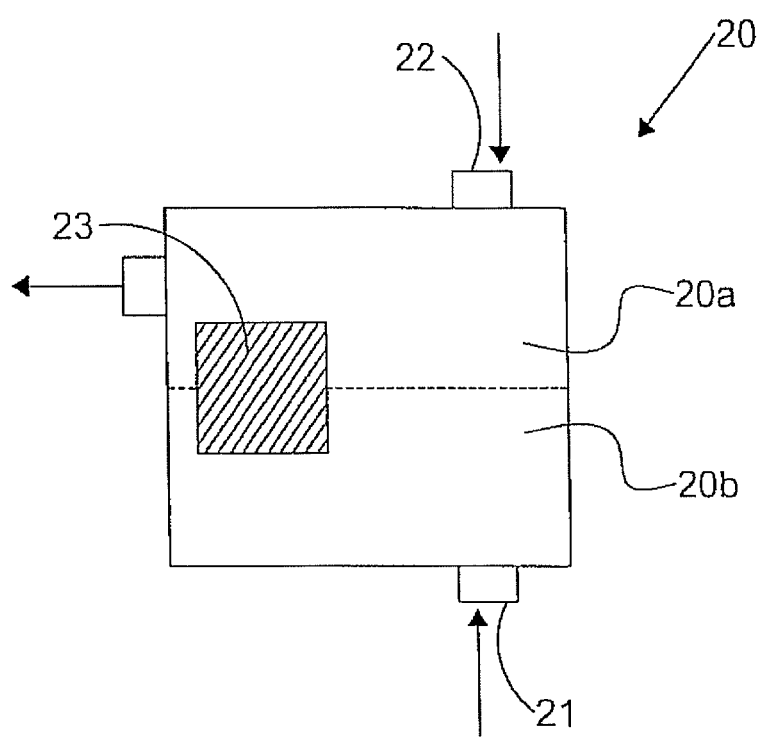
FIG. 1B is a schematic view of a reservoir for use with the system shown in FIG. 1A.

FIG. 1B is a schematic view of a reservoir 20 that may be optionally used in the steady flow system 30 shown in FIG. 1A. The reservoir 20 may hold fluid for initial and re-circulation, and may allow media to be introduced into or siphoned from the flow loop. That is, as fluid/media is returned to the reservoir 20, a portion, or all of the fluid/media may be redirected, or siphoned off and not recirculated. For this purpose, the reservoir 20 may be partitioned into inflow 20a and outflow 20b portions, or the siphoned fluid may be diverted to a holding tank or other such vessel or flow system (not shown).

The reservoir 20 may further include a sampling port 21 which samples incoming fluid before recirculation and/or diversion to the outflow portion 20b or a holding tank. The sampling port 21 may be adapted to divert incoming fluid based on, for example, its measurement of parameters such as, for example, concentration of media components, contamination levels, circulation time/cycles and the like. Likewise, the incoming portion 20a of the reservoir 20 may include an inflow port 22 to allow for the introduction of additional fluid and/or media as required, and may include sensors 23 linked to the control system 70 which continuously monitor levels/quantity of such fluid/media as it is introduced into the flow loop.

The reservoir 20 may also include a port to atmosphere (not shown), preferably with a sterile filter to preclude contamination from the atmosphere. Additionally, other cell or tissue types may be positioned throughout the system, such as, for example, near the reservoir 20 or a port thereof. For example, a chamber (not shown) containing hepatocytes may be positioned in the flow loop so as to be exposed to the fluid in the flow loop, as well as to at least some of the dynamic conditions in the flow loop, if desired. This type of exemplary setup can be used to provide other useful data such as, for example, drug metabolism data.

The positioning and interconnection of the components of the system 1 shown in FIG. 1A is merely exemplary in nature, and intended simply to illustrate the presence of these components and their respective functions within the system 1. Thus, for example, although the steady flow system 30 shown in FIG. 1 is positioned adjacent the reservoir 20 and the pressure/flow control system 200, followed in the flow loop by a portion of the coupling system 300, it is well understood that the steady flow system 30 may include various components positioned throughout the system 1 to provide the capabilities required of the steady flow system 30. Likewise, although the pressure/flow control system 200 is shown simply on an ingress side of the specimen unit 10, it is well understood that the pressure/flow control system 200 may include various components positioned throughout the system 1 to fulfill the requirements of the pressure/flow control system 200. Such reasoning applies to the remaining components of the system 1, including the coupling system 300, mounting system 80, control system 70, and specimen unit 10, as will be better understood from the following discussion.

Figure 2A:
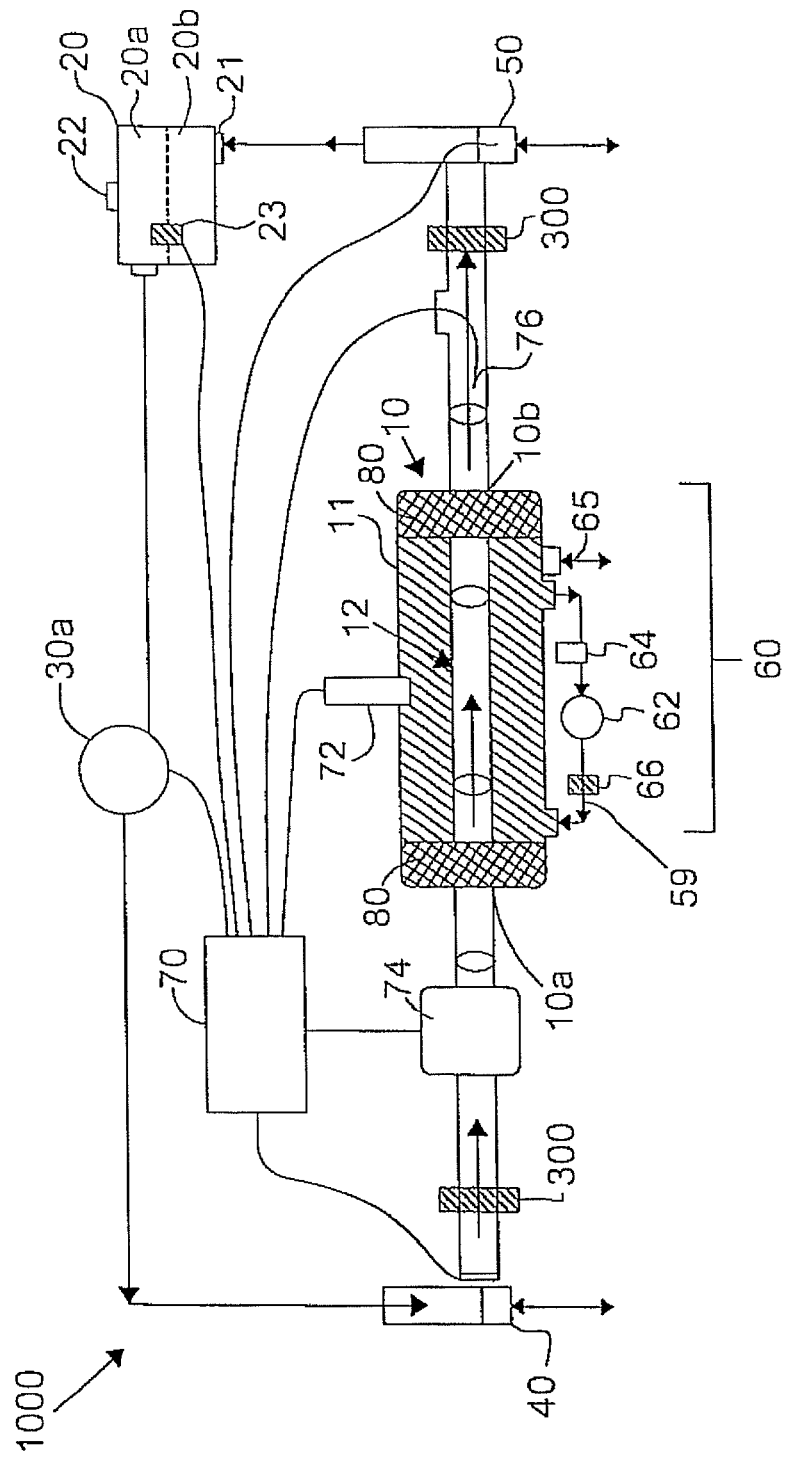
FIGS. 2A-2E are schematic views of systems for recreating a hemodynamic environment in accordance with embodiments of the invention.
Figure 6A:
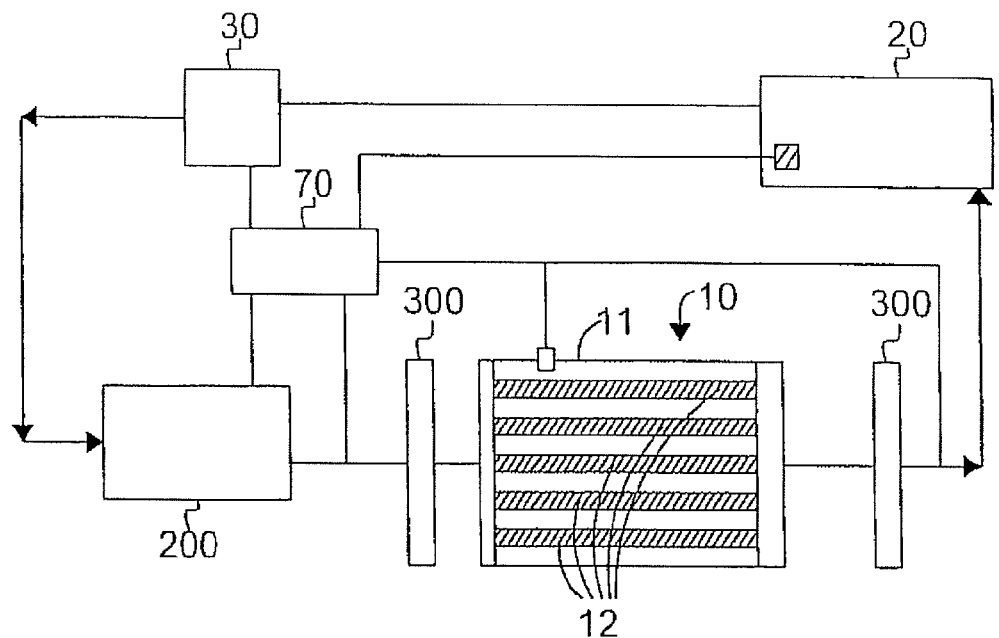
FIGS. 6A-6E illustrate exemplary chamber(s)s with specimen(s) mounted therein which may be applied with any of the systems shown in FIGS. 2A-2E and 3A-3D.
Figure 6B:
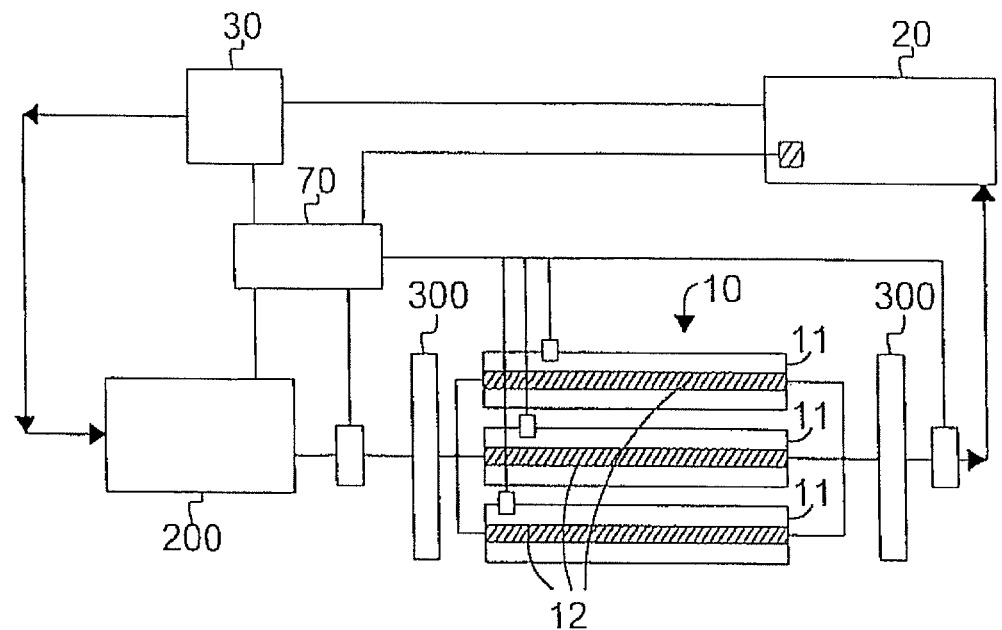
Figure 6C:
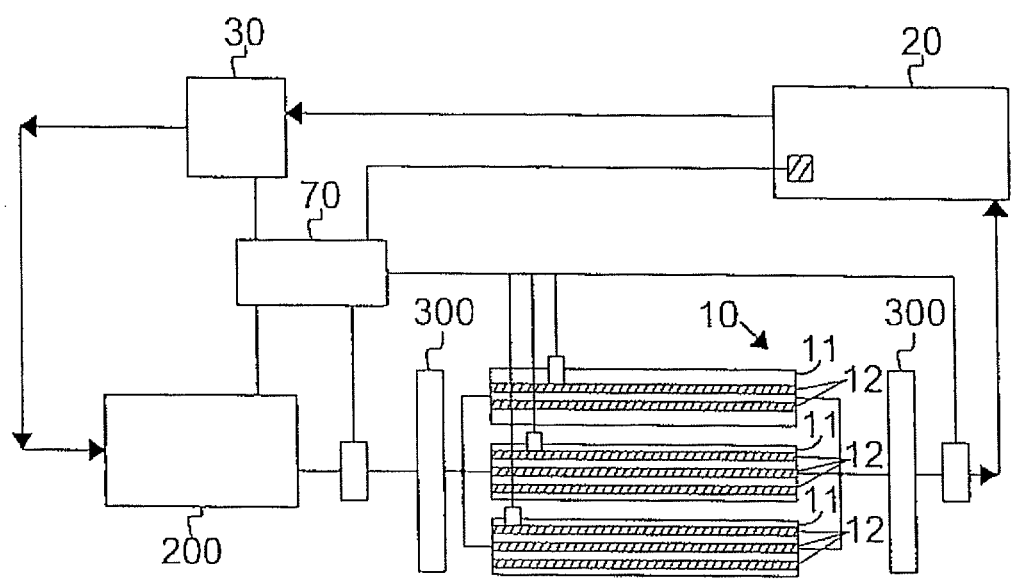
Figure 6D:
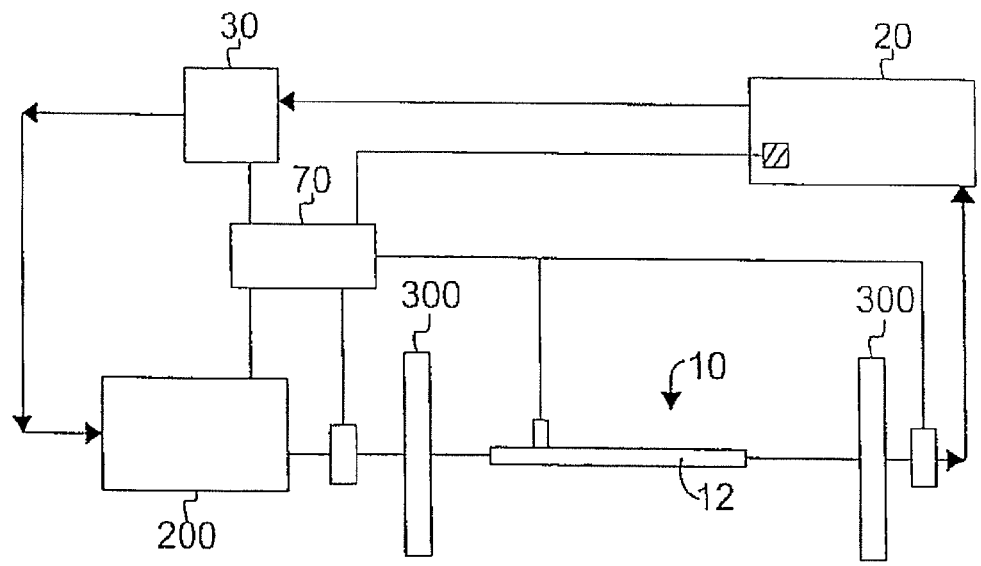
Figure 6E:
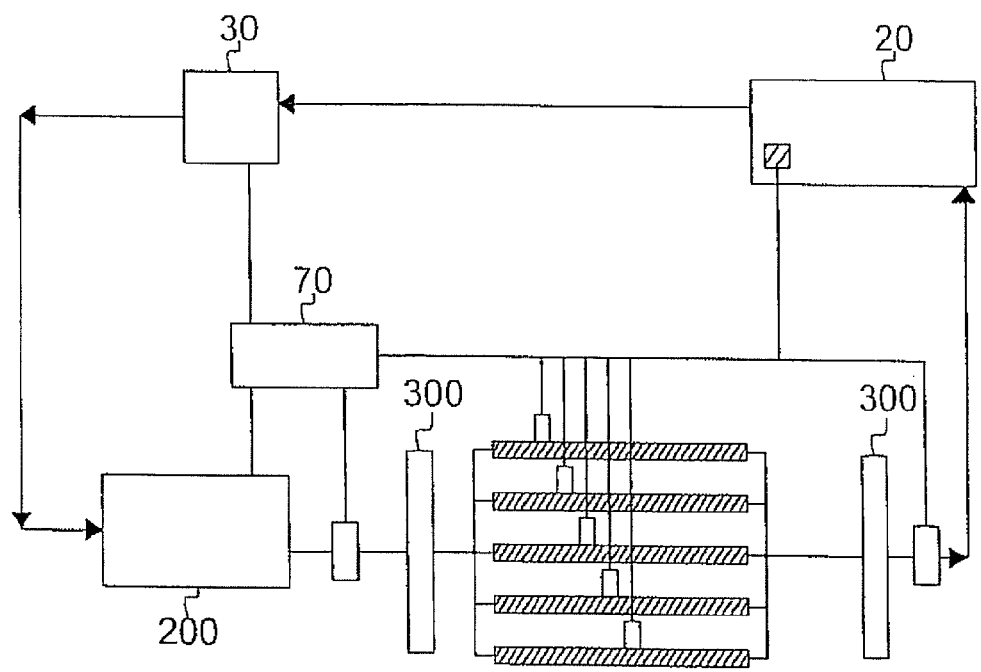

FIG. 2A is a schematic view of an exemplary system 1000 for reproducing a hemodynamic environment, in accordance with one embodiment of the invention as broadly described herein. Although the specimen unit 10 shown in FIG. 2A includes a chamber 11, which forms an enclosure for a single specimen 12, the system 1000 may also include a single chamber 11 housing a plurality of specimens 12, a plurality of chambers 11 each housing a single specimen 12, a plurality of chambers 11 each housing a plurality of specimens 12, and a plurality of chambers 11, some housing a single specimen 12, and some housing a plurality of specimens 12, as will be further described below in connection with FIGS. 6A-6C. Further, as shown in FIGS. 6D-6E, the system 1000 may also include an individual/multiple specimen 12 not surrounded by any type of enclosure or chamber 11. Instead, an individual/multiple specimen 12 may be aligned directly with the flow loop.

Figure 4A:
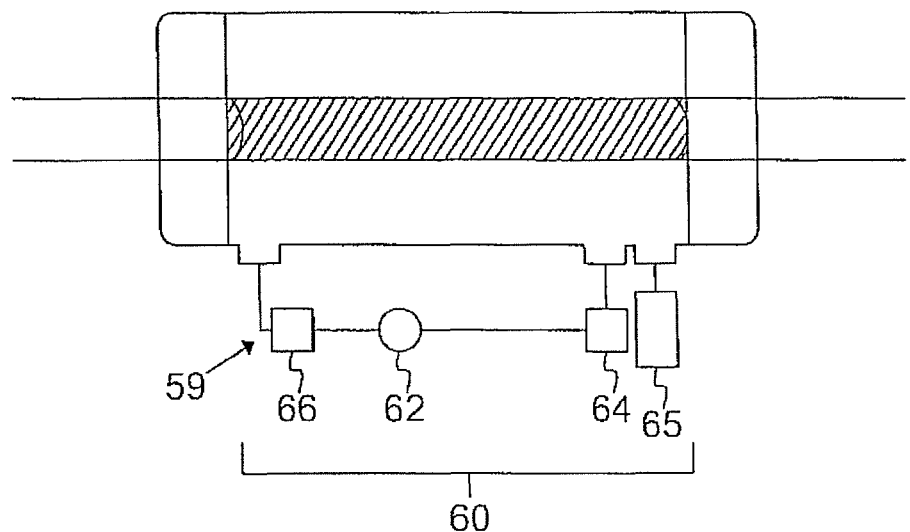
FIGS. 4A-4D are schematic views of a chamber which may be applied with any of the systems shown in FIGS. 2A-2E and 3A-3D.
Figure 4B:
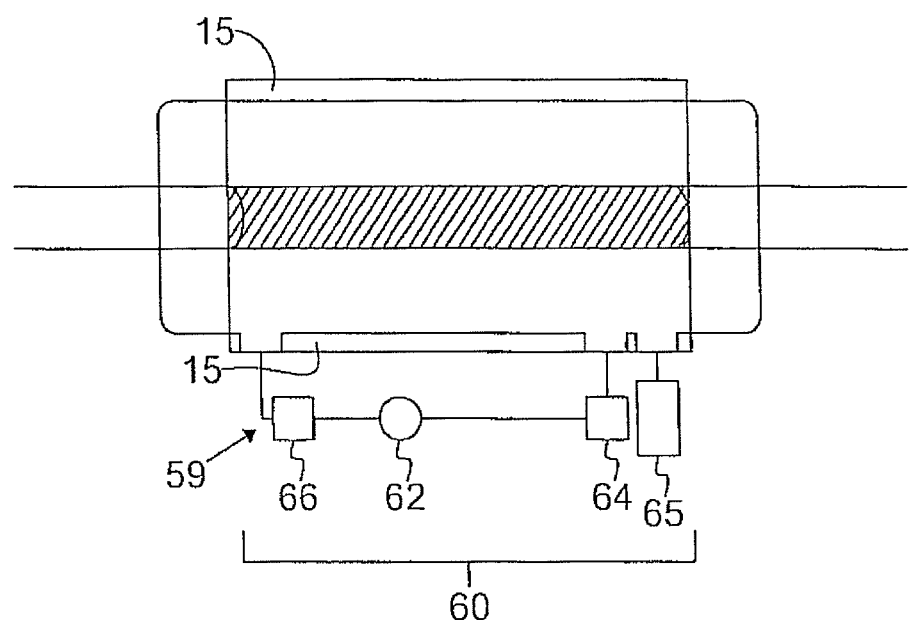
Figure 4C:
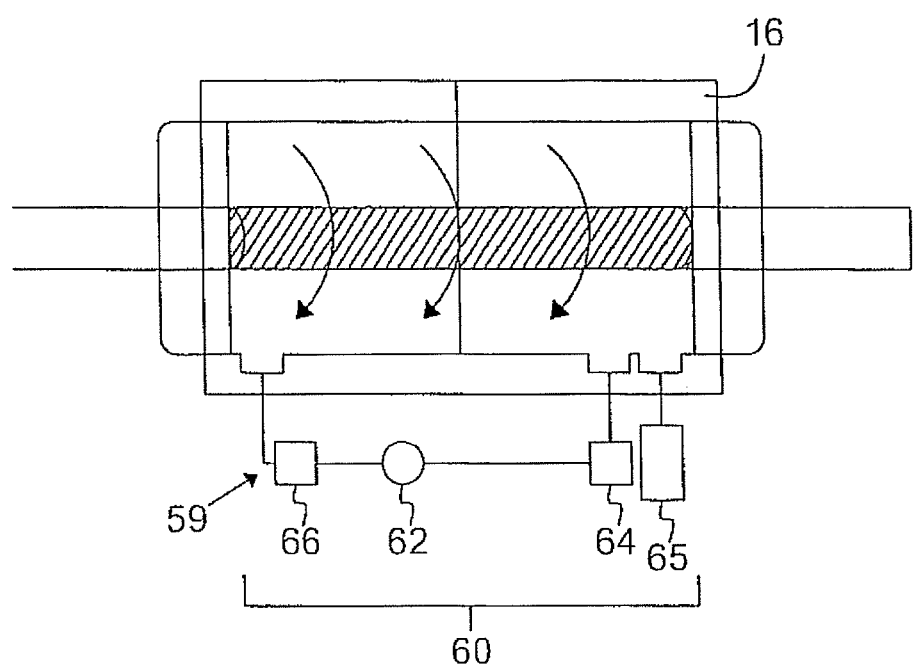
Figure 4D:
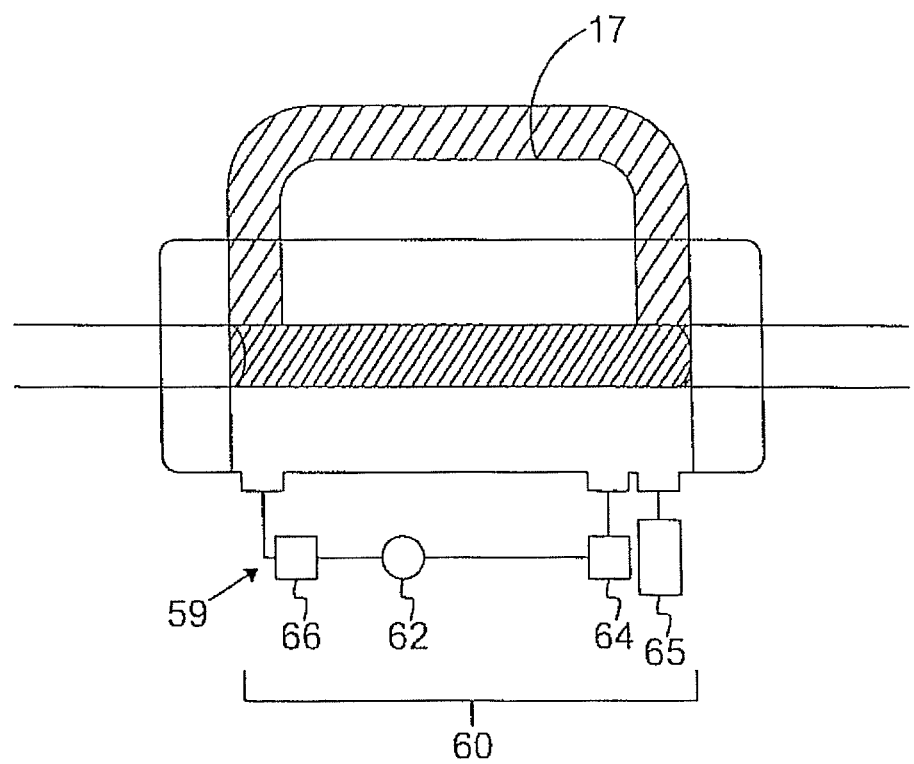

In alternative embodiments, the chamber 11 may be jacketed 15, as shown, for example, in FIG. 4B, thereby enabling circulation of a cooled or heated fluid through the chamber 11 and specimen 12, in order to maintain the temperature required by the specimen 12 and an associated trial. Alternatively, the chamber 11 may be immersed in a water bath 16 at an appropriate temperature, as shown, for example, in FIG. 4C, or may include a conditioned circulation path 17, as shown, for example, in FIG. 4D to achieve the desired temperature control effects.

The system 1000 may generally be run at a temperature of approximately 37 degrees Centigrade, but can be operated at temperatures ranging from approximately 20 degrees Centigrade to approximately 50 degrees Centigrade, or whatever temperature may be required for a particular trial.

Figure 5D:
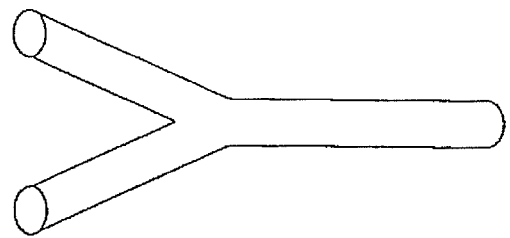
FIGS. 5A-5D illustrate specimen shapes which may be applied with any of the systems shown in FIGS. 2A-2E and 3A-3D.
Figure 5C:
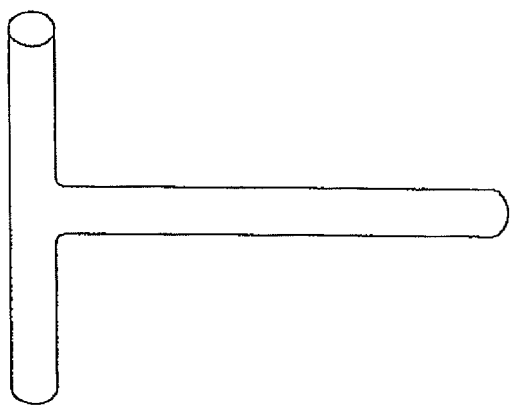
Figure 5B:
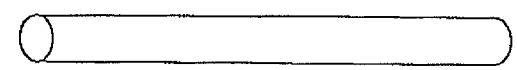
Figure 5A:
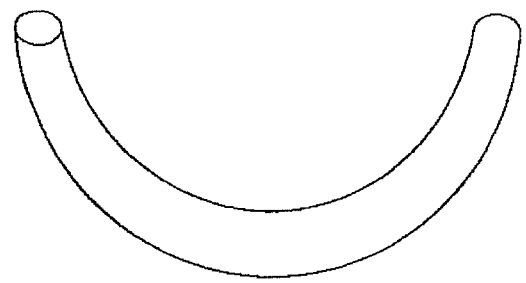

**The specimen 12 may take many forms. In certain embodiments, the specimen 12 may be a substantially tubular type, compliant structure made of materials such as, for example, silicone, collagen, PTFE, fibrin, and other such appropriate materials, which is lined with a variety of cellular compounds and/or cells, such as, for example, endothelial cells or stem cells on a fibronectin matrix used to simulate a vessel wall, a non-rigid tube that contains mammalian cells, a blood vessel excised from a mammal, or other biocompatible substrate containing cells or onto which cells can be grown or attached thereto. In other embodiments, the specimen 12 may be a portion of an actual vessel (ex vivo), such as, for example artery or vein, which is to be subjected to the hemodynamic environment produced by the system 1000. Likewise, while the specimen 12 discussed herein are, simply for ease of discussion, substantially tubular, the specimen 12 may also have an irregular form to more accurately represent an actual physiological condition or environment, such as, for example, a bifurcation, a curve, physiologic vascular segment, or changes in cross section to reproduce a constriction present in an actual vessel. Samples of some specimen 12 which have such irregular forms are shown in FIGS. 5A-5C.

The specimen 12 may include various entities, such as, for example, different cell types. These may be cells other than vascular cells which may be attached or integrated in the specimen 12, or which may be non-attached and circulating, such as, for example, immune cells, such as, for example, leukocytes, monocytes, and the like, stem cells, such as, for example, adult, embryonic, progenitor, and the like, cancer cells, red blood cells, platelets, and other such cell types. Other organ cells such as, for example, hepatocytes for liver toxicity assessment or adsorption distribution metabolism excretion (ADME) examination, may also be incorporated into the system for activities such as, for example, testing and screening purposes. Similarly, numerous different components may be added to the media to simulate different conditions, including, but not limited to, cholesterol for hypercholesterolimia, growth factors for growth and development, calcium for vulnerable plaque and lesion formation, and other such components.

In the system 1000 shown in FIG. 2A, the steady flow system 30 includes a reservoir 20 and a steady flow pump 30a. Fluid which is to be introduced into the specimen unit 10 may be drawn out of the reservoir 20 by the steady flow pump 30a which initiates and maintains a substantially constant, substantially uniform flow of fluid from the reservoir 20 into the flow loop. Other types of pumps or components which may be used to initiate and maintain such a steady flow may also be appropriate. The steady flow pump 30a shown in FIG. 2A is disposed between the reservoir 20 and the specimen unit 10, at a position upstream from an ingress 10a into the specimen unit 10. However, the steady flow pump 30a may also be disposed at other positions within the system 1000, based on the type of component(s) used to generate the steady flow from the reservoir 20, as well as the placement of other components of the system 1000.

Figure 2B:
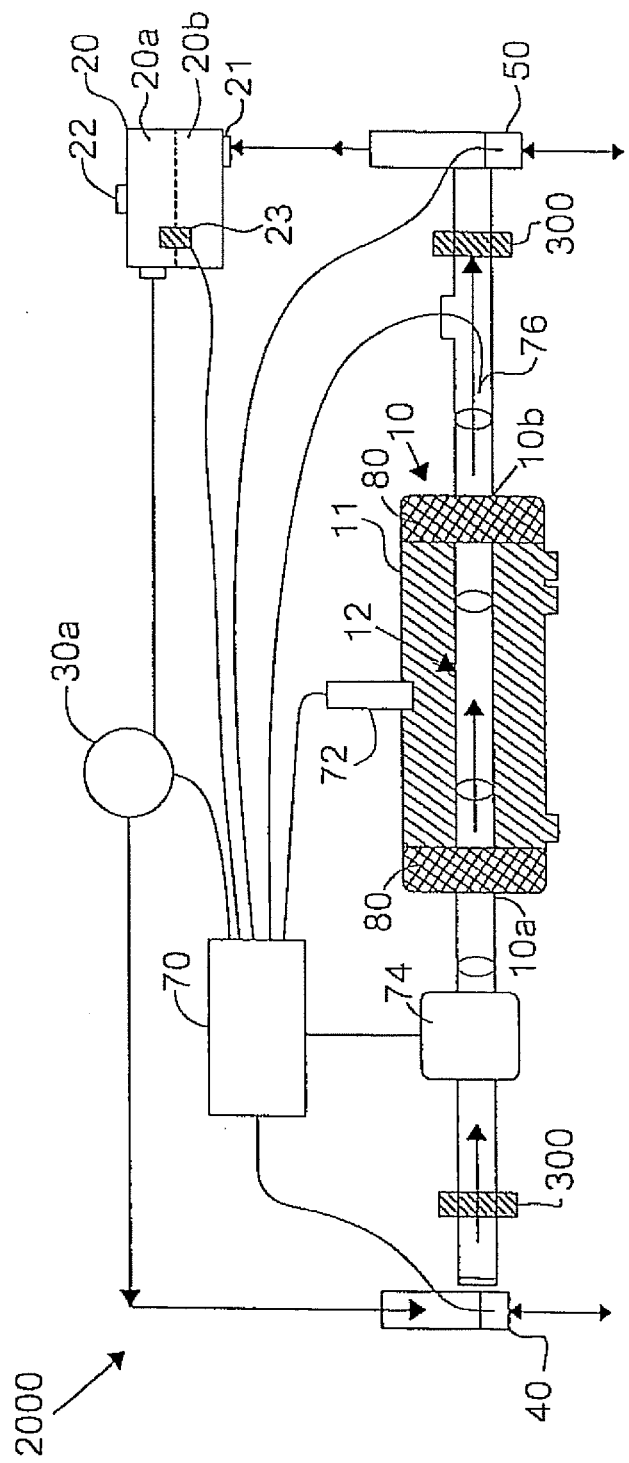

The desired test environment may be developed and maintained within the specimen unit 10 by the pressure/flow control system 200. In the system 1000 shown in FIG. 2A, the pressure/flow control system 200 may include a first pressure/flow control 40 positioned upstream of the ingress 10a into the specimen unit 10 and a second pressure/flow control 50 positioned downstream of an egress 10b from the specimen unit 10. In alternative embodiments, the system 1000 may also include a third pressure/flow control 60 which further controls an internal pressure and/or flow within the specimen unit 10, and/or an external pressure. The first, second and third pressure/flow controls 40, 50 and 60 may be combined as necessary during operation of the system 1000, depending on which conditions are to be reproduced in the specimen unit 10 and which properties are to be monitored/studied during a particular trial. For example, the third pressure/flow control 60 may not be required in some situations, such as, for example, when a specimen 12 is aligned directly with the flow loop, without a chamber 11 surrounding the specimen, as shown in FIGS. 6D-6E, or when there is a chamber 11 in use but all the required trial conditions can be reproduced with, for example, just the first and second pressure/flow controls 40, 50, as shown in the embodiment of the system 2000 shown in FIG. 2B. Preferably, the pressure/flow control system 200 includes at least a first pressure/flow control 40 and a second pressure/flow control 50.

Conditions throughout the flow loop, including within the specimen unit 10 and/or diose experienced by the specimen 12 itself, may be controlled and monitored by a control system 70. The control system 70 may include a processor (not shown in detail) which substantially continuously transmits parameters to be monitored and data to be gathered from at least one, and preferably a plurality of sensors provided at various positions within the flow loop. FIG. 2A shows an exemplary placement of sensors, in which a sensor 72 is provided proximate, and preferably within, the specimen unit 10, a sensor 74 is provided upstream of the specimen unit 10, between the ingress 10a to the specimen unit 10 and the first pressure/flow control 40, and a sensor 76 is provided downstream of the specimen unit 10, between the egress 10b of the specimen unit 10 and the second pressure/flow control 50.

The plurality of sensors may serve a variety of functions. For example, the sensor 72 may be a sensor which monitors a condition of the specimen 12, such as, for example, a size/diameter, growth rate or wall thickness of the specimen 12, or a condition of the fluid/media surrounding the specimen 12, such as, for example, concentration of components of fluid/media, or a diffusion of fluid/media (water flux) or of solutes (i.e. fluorescent labeled LDL or dextran, components of the fluid/media) through an outer wall of the specimen 12. Other functions for a so positioned sensor may also be appropriate. Likewise, the sensors 74, 76 may be, for example, sensors which measure a pressure and/or flow rate at a corresponding position in the flow loop. Other types of sensors and/or sensor placement may also be appropriate. Data collected by the plurality of sensors may be used by the control system 70 to adjust operation/control parameters for the steady flow system 30, the flow/pressure control system 200, and the like. Arrangement of any number and type of sensors may be varied as appropriate based on the control requirements and data gathering needs dictated by a particular trial.

Numerous types of sensors and actuators may be used to gather the data required by the control unit 70. For example, wireless nanotechnology, microelectromechanical systems (MEMS), or electrochemical based systems may be integrated at various points within the system 1000 to detect and transmit data such as, for example, real time metabolite and proteins present, % absorption and absorption rates, pressure, flow, and other such parameters. This type of technology may also be used as a vehicle to deliver a fluid, cells, or chemicals, such as a drug, to a specifically targeted area of the specimen 12, to transmit images from a specific area, or to take other types of readings from a specific area of the specimen 12 as required. Ultrasound technology may be used to monitor flow rates, dissipation/diffusion rates, growth rates, and the like. Strain gauges may be used to monitor pressure/pressure fluctuations throughout the flow loop. The numerous sensors and actuators can be placed in numerous locations throughout the system 1000, including both the overall system flow loop and the external flow loop (including the chamber 11).

Other appropriate sensing systems may include, but are not limited to, laser detection systems, and optical detection systems such as, for example, fluorometers, luminometers, or microscopes. These systems could also include probes to measure cell and/or layer integrity on the specimen 12, and/or to apply electrical stimuli to the specimen 12. For example, electrical stimuli may be applied directly to the specimen 12 at various locations such as, for example, at a mounting point to measure cell layer integrity or enhance growth, function or the like. Various other numbers, types and relative positioning of sensors may also be appropriate, depending on the particular conditions to be reproduced, and the amount and type of parameters to be monitored and the data to be gathered.

The first, second and third pressure/flow controls 40, 50, 60 may take many forms. For example, as shown in FIG. 2A, the first and second pressure/flow controls 40, 50 may be, for example, pumps connected to the flow loop upstream and downstream of the specimen unit 10, and the third pressure/flow control 60 may be an external pressure/flow control system connected to the specimen unit 10 to exert an external pressure on the specimen 12, or to control a flow of fluid in the chamber 11, such as, for example, the radial flow of fluid through the outer circumferential walls (transmural flow and transport) of the specimen 12. In this example, respective drive units (not shown) of the first, second and thirds pressure/flow controls 40, 50, 60 are preferably independently controlled. In certain embodiments, the pumps 40, 50 may be piston-type pumps, such as, for example, bellows pumps, which can be independently varied in oscillatory motion with typical waveform parameters such as magnitude and phase to produce a desired overall effect in the specimen unit 10.

Preferably, any oscillatory waveforms or signals can be programmed into such pumps which may be used in the first and second pressure/flow controls 40, 50. These oscillatory waveforms or signals may include, but are not limited to, for example, a blood pressure waveform, a blood flow waveform, a diameter waveform, a sinusoidal waveform, a saw-tooth waveform, a square waveform, a frequency control, a slew rate, a duty cycle, a period, a percent systolic or diastolic, harmonic frequencies, magnitude, phase, and the like. Other parameters may also be appropriate for programming into these exemplary pumps which may be used in the first and second pressure/flow controls 40, 50 depending on the effect desired in the specimen unit 10.

This control of magnitude and phase, amongst other features mentioned above, in the pertinent parameters provides simulation of a wide range of precise and controlled hemodynamic parameters such as WSS, CS, pressure, and the SPA, including in the range in which the most diseased prone coronary arteries fall (SPA>−250 deg). In other embodiments, the first and second pressure controls 40, 50 may include valves, and preferably occluder valves, which are controlled by the control unit 70 to control the flow there through in order to produce similar effects. Since the flow which runs through the flow loop, and, consequently, through the specimen 12, is related to wall shear stress (WSS), and the pressure exerted on the specimen 12 is related to the circumferential strain (CS), the pulsatile WSS and the pulsatile CS may be independently controlled and thus may be uncoupled within a certain range.

Figure 2C:
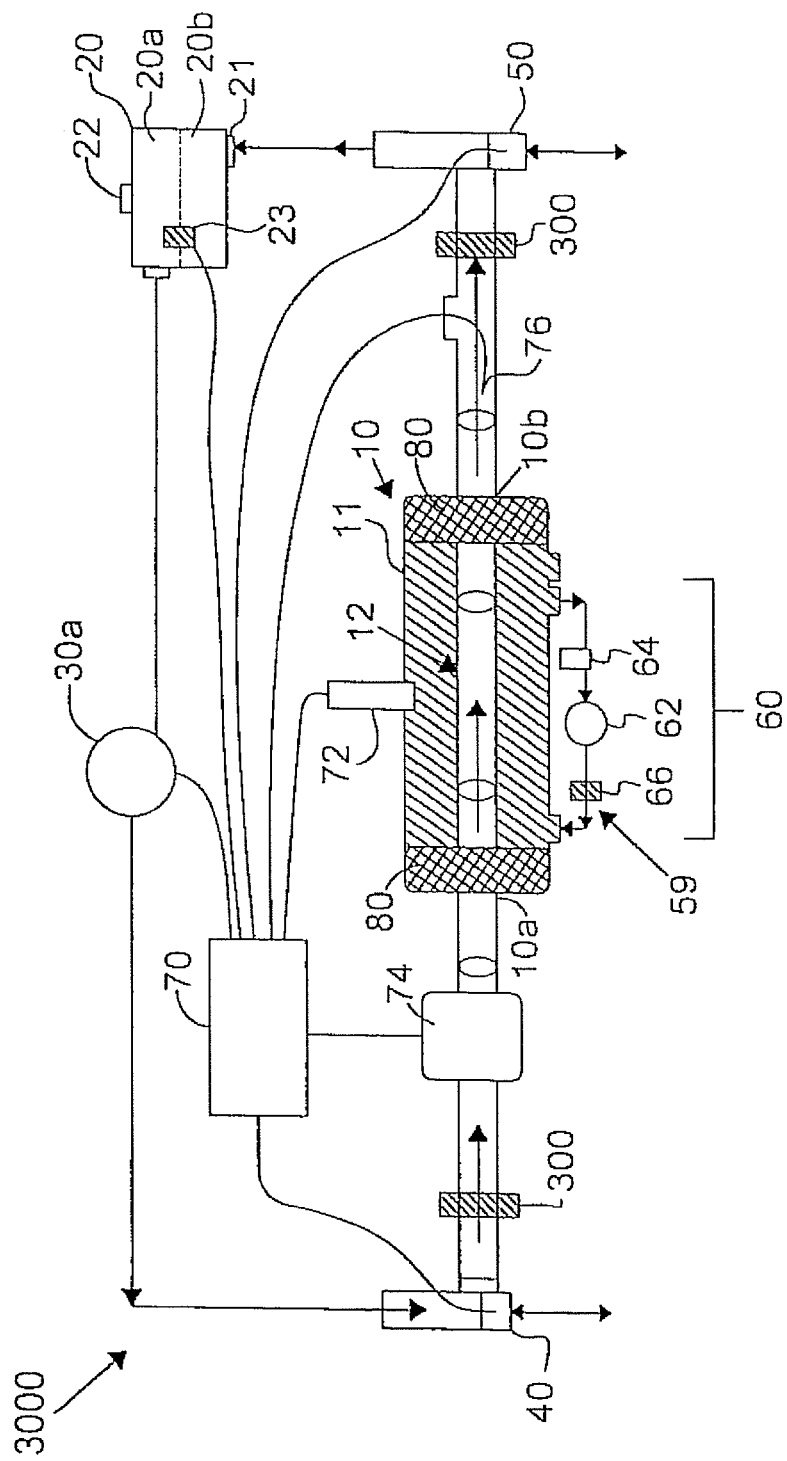
Figure 2D:
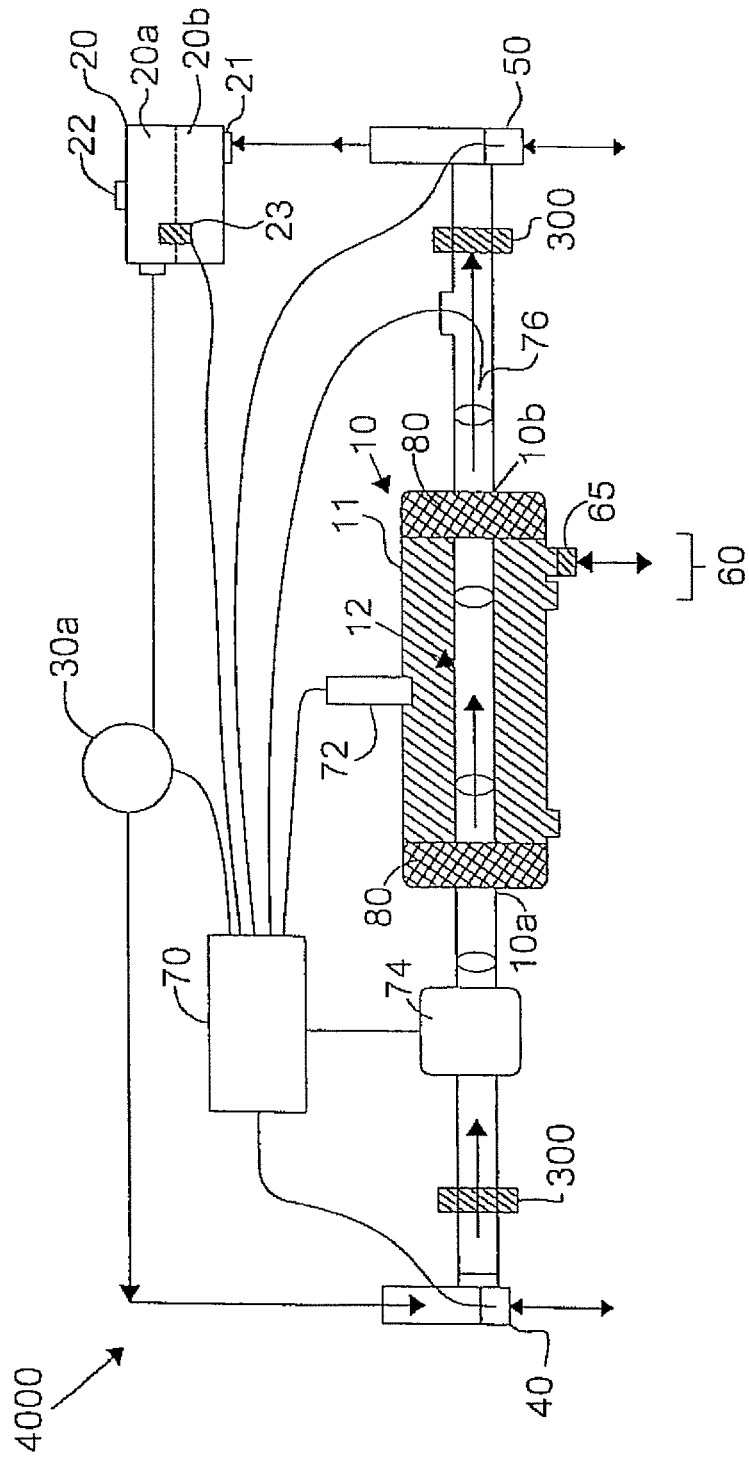
Figure 2E:
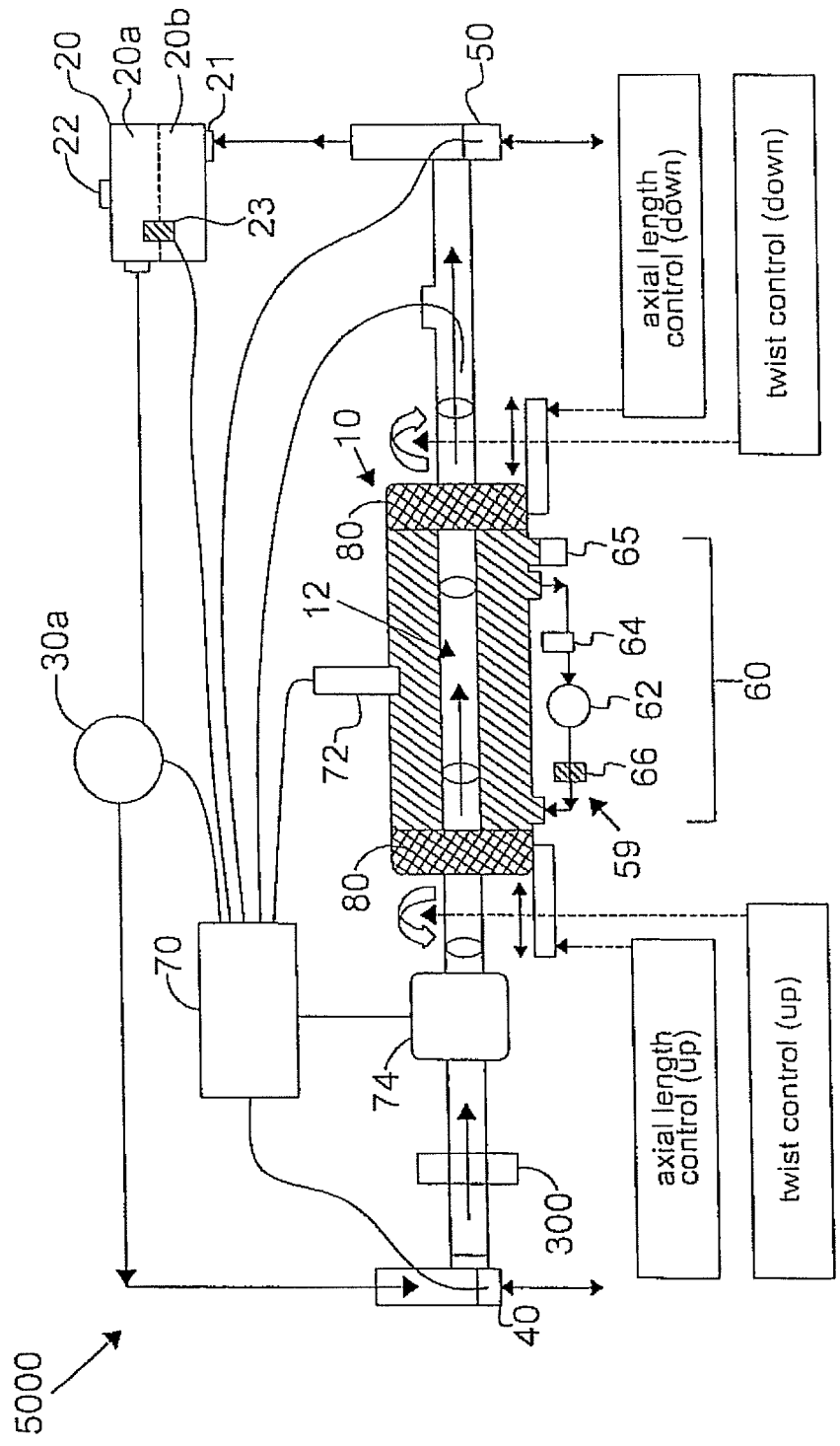

In alternative embodiments in which the pressure/flow control system 200 includes a third pressure/flow control 60, the third pressure/flow control 60 may provide for numerous different, additional conditions to be reproduced in the specimen unit 10, and thus may take numerous different forms. For example, in certain embodiments, the third pressure/flow control 60 may be an external pressure/flow control used in combination with a chamber 11 surrounding one or more specimen 12. This may include an external flow loop 59 which runs partially through the chamber 11, as shown in the embodiment of the system 3000 shown in FIG. 2C, or may include a pump 65, such as the piston or bellows type pumps discussed above with respect to the first and second pressure controls 40, 50, used to apply an external pressure to the specimen 12 within the chamber 11, as shown in the embodiment of the system 4000 shown in FIG. 2D. Alternatively, the third pressure/flow control 60 may be a combination of an external pump 65 and an external flow loop 59, as shown in the embodiment of the system 1000 shown in FIG. 2A.

This external flow loop 59 may facilitate the introduction and/or extraction of media from the chamber 11, or may be used to induce flow and/or circulation in a particular direction within the chamber 11, such as, for example, radially, such that the specimen 12 experiences conditions such as, for example, expansion in a radial direction, bending or other longitudinal deformation, or accelerated or decelerated diffusion of media through the specimen 12 wall or facilitate the generation of other conditions within the chamber 11 as appropriate. As shown in FIG. 2A and in more detail in FIG. 4A, the external flow loop 59 and external pump 65 may be combined to form the third pressure/flow control 60.

An exemplary external pressure/flow control is shown in more detail in FIG. 4A. In this embodiment, the third, or external pressure/flow control 60 includes an external flow loop 59 coupled to the chamber 11 to, for example, induce a circulatory, oscillatory, or pulsatile flow or pressure in the chamber 11, and/or to introduce additional media into or extract media from the chamber 11. This exemplary third, external pressure/flow control 60 may include an external steady flow unit 62 to initiate and maintain flow through the external flow loop 59. The flow through the external flow loop 59 may be a simple recirculation of fluid in the chamber 11. Alternatively, the external flow loop 59 may include its own reservoir 64 to hold, for example, media to be introduced into the chamber 11. The external flow loop 59 may also include a varying flow unit 66 to generate variations in the flow introduced into the chamber 11, such as, for example, a concentrated flow in a particular portion of the chamber 11, or a pulsatile flow to further simulate actual dynamic conditions. The varying flow unit may be a single piston or bellows type pump, or may be pairs of pumps which operate similar to the first and second pressure/flow controls 50, 60 described above. This type of external flow loop 59 may be combined with a separate external piston or bellows type pump 65 which may be separately coupled to the chamber 11, or, alternatively, which may be incorporated into the external flow loop 59, to introduce additional forces as discussed above with respect to the first and second pressure/flow controls 40, 50.

Numerous different algorithms and methodologies may be applied in controlling the first, second and/or third pressure/flow controls 40, 50, 60 to produce a desired condition in the specimen unit 10 and/or throughout the flow loop. For example, assuming, simply for purposes of discussion that the steady flow system 30 is a steady flow pump 30a, and the first and second pressure controls 40, 50 each include piston/bellows type pumps, as in the systems shown in FIGS. 2A-2E, and the third pressure/flow control 60 includes an external pump 65, control of the various pumps may be coordinated to produce a desired condition. If the pumps maintain a mechanical connection through, for example, an adjustable cam that was able to control the timing or phase between the external pump and the downstream pump, the external pump would operate at a certain magnitude, as would the downstream pump, but they may peak at different times. Likewise, the pumps may be coordinated electromechanically to control there respective timing and phase or synchrony. Thus, pressure/flow, whether it be upstream, downstream, or external, may be controlled by the coordinated action of the pumps at their respective location(s).

The specimen 12 is preferably positioned within the specimen unit 10 using a mounting system 80. The mounting system 80 may be used to appropriately position the specimen 12, whether a chamber 11 is used or not. Any number/type of mounting systems may be appropriate, depending on the parameters and characteristics to be reproduced in the specimen unit 10, the properties of the specimen 12 to be studied during operation of the flow loop, and the number of specimen 12 to be positioned in the specimen unit 10. It is also useful and important to be able to reproduce physical forces, such as, for example, axial strain, torsion and bending forces, which may be present in an actual physiological environment on the specimen 12 in the specimen unit 10, whether the specimen 12 is contained in a chamber 11 of the specimen unit 10, or is simply coupled to the flow loop through the mounting system 80.

As shown in FIGS. 7A-7D, in certain embodiments, fixed ends of the specimen 12, which may be, for example, a silicone tube, an expanded PTFE (ePFTE) tube, artery, vein, tissue engineered artery, and the like, may be attached to a rigid tube 14 that can rotate about its longitudinal axis. The tube 14 and/or specimen 12 are preferably sized so as to correspond to the actual vessel which it is intended to simulate. For example, in certain embodiments, the tube 14 and/or specimen 12 is preferably between approximately 0.5 mm and 30 mm in diameter and various lengths ranging from 1 cm and 80 cm (typically used in cardiovascular surgery). In other embodiments, the specimen 12 may be a 2D substrate such as a glass slide or other 2D silicone membrane structured appropriate to that which it is to simulate. Again, the chamber 11 may or not be present.

Figure 7A:
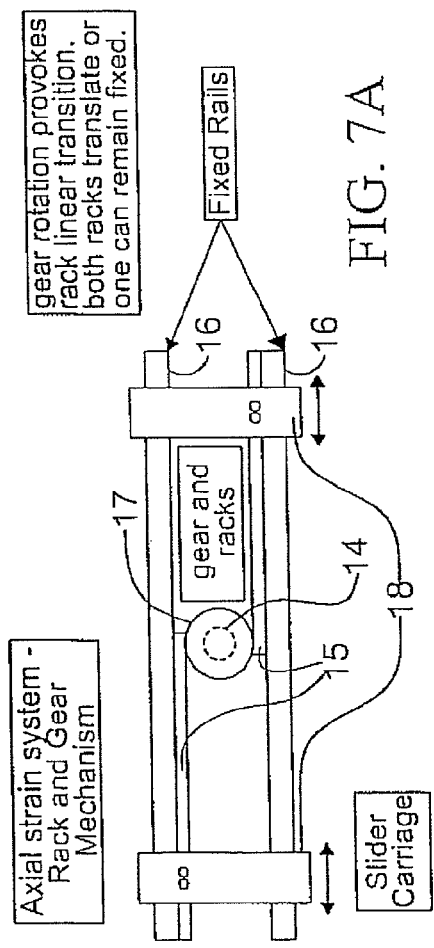
FIGS. 7A-7D illustrate an exemplary mounting system which may be applied with any of the systems shown in FIGS. 2A-2E and 3A-3D.

As shown, for example, in FIG. 7A, in certain embodiments the tube 14 may be attached to a mount 16 that is coupled to a carriage 18, allowing the mount 16 to translate in the longitudinal direction. The embodiment shown in FIG. 7A includes a carriage 18 at each end of the specimen unit 10, and either one or both carriages 18 may move at a particular time. However, only one carriage 18 may be necessary, depending on conditions required in the specimen unit 10.

A coupler 15 may be attached to both the tube 14 and the mount 16 to provide for independent movement within a predetermined range of motion. The coupler 15 may then be attached to a drive system 17 such as, for example, a linear actuator that imposes oscillatory or sinusoidal motion, a stepper motor, an electrodynamic transducer, and the like, to provide for motion in accordance with the prescribed conditions to be reproduced in/by the specimen unit 10. More particularly, as shown, for example, in FIG. 7B, gears 11 and racks 13 may be used to provide linear or torsional motion of the tube 14 and/or specimen 12, with the racks 13 directing motion to a corresponding gear 11 to turn the mount 16, to which the tube 14 and/or specimen 12 is attached, about its longitudinal axis. A gear 11 may also be used to move a rack 13 to translate the mount 16 in an axial direction.

Preferably, the tube 14 has two ends, an upstream and a downstream end, and either or both ends may experience controlled axial strain and/or torsion. Alternatively, one end may remain fixed and experience no motion, while the other end experiences some prescribed motion. More specifically, the carriage(s) 18 may translate so as to draw the two opposite ends of the tube 14 and/or specimen 12 apart to induce an axial force, such as, for example, a component of axial stretching or strain. The carriage(s) 18 may also translate so as to draw the two opposite ends of the tube 14 and/or specimen 12 towards each other so as to induce a force such as, for example, compressor or bending in the tube 14 and/or specimen 12. A mounting of the tube 14 and/or specimen 12 in the specimen unit 10 using the mounting system 80 is shown in FIG. 7C.

The oscillatory axial strain can be reproduced either with both fixed ends of the tube 14 and/or specimen 12 oscillating, or with one fixed end constant and the other end oscillating. The mean axial strain or fixed end(s) of the tube 14 and/or specimen 12 may also be adjusted. That is, variation in axial strain can remain constant, while the mean axial strain or fixed end position is slowly increased. Torsion may be achieved with both fixed ends of the tube 14 and/or specimen 12 rotating, or with one of the two fixed ends held constant. In one embodiment, the tube 14 to which specimen 12 may be attached may be connected to a gear 13, that provides torsion driven by a rack gear 11. Although the rotation angle can proceed to 360 degrees, the rotation angle is preferably limited to avoid buckling. Preferably, the rotation angle is limited to 0 degrees±45 degrees with both fixed ends rotating in opposition, or to 0 degrees±90 degrees with one fixed end held in a constant position. A relationship between axial strain and torsion can be simulated and varied independent of each other.

Figure 7B:
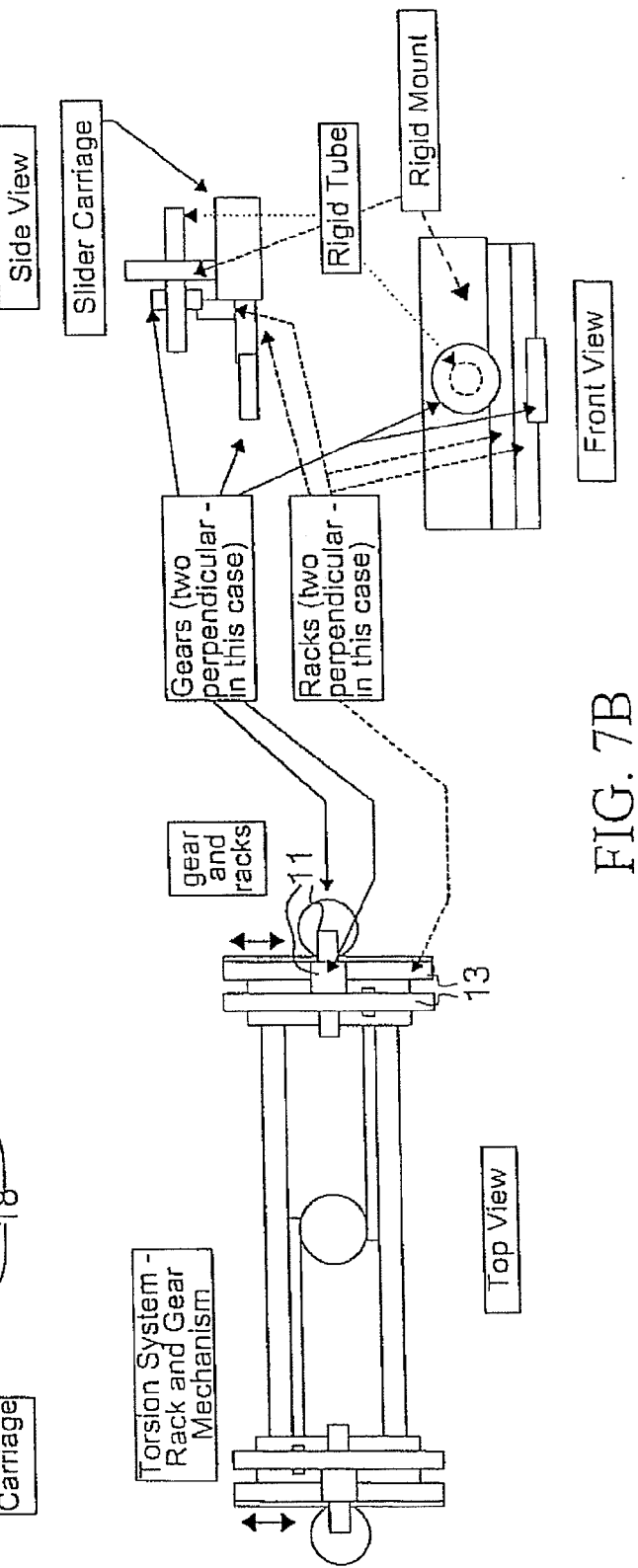
Figure 7C:
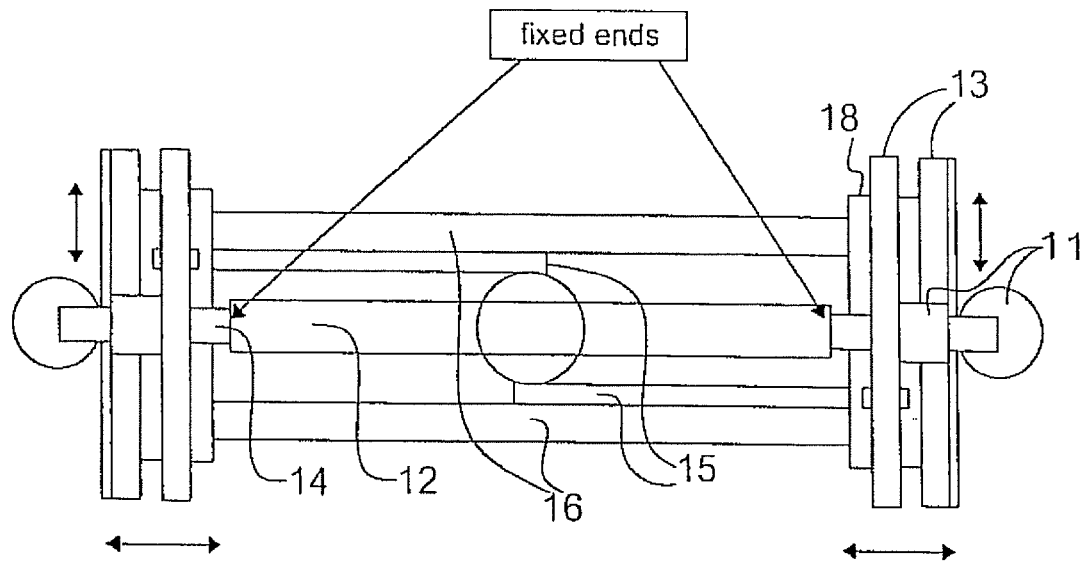
Figure 7D:
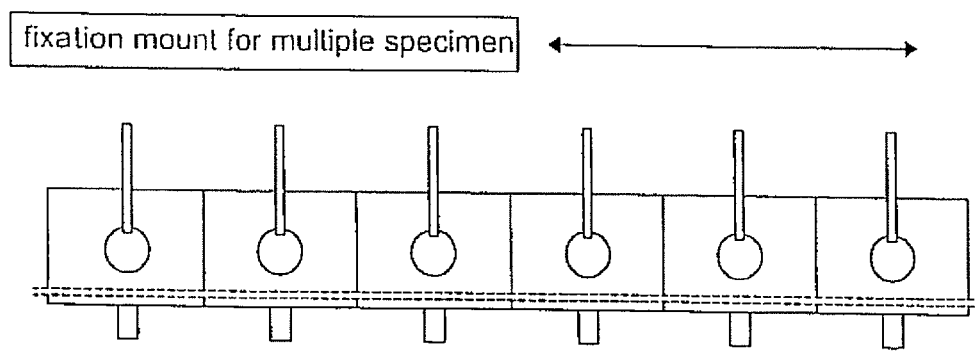
Figure 8A:
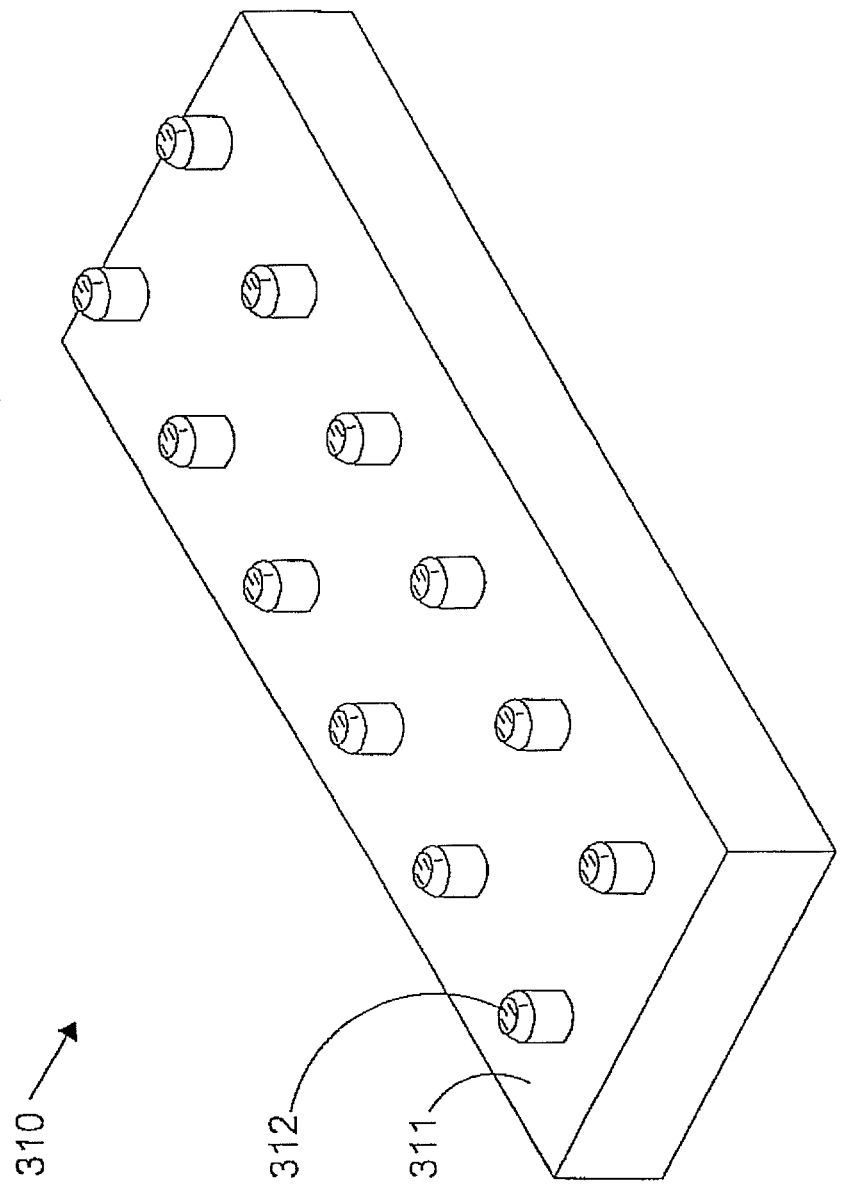
FIGS. 8A-8E illustrate a coupling system which may be applied with any of the systems shown in FIGS. 2A-2E and 3A-3D.
Figure 8B:
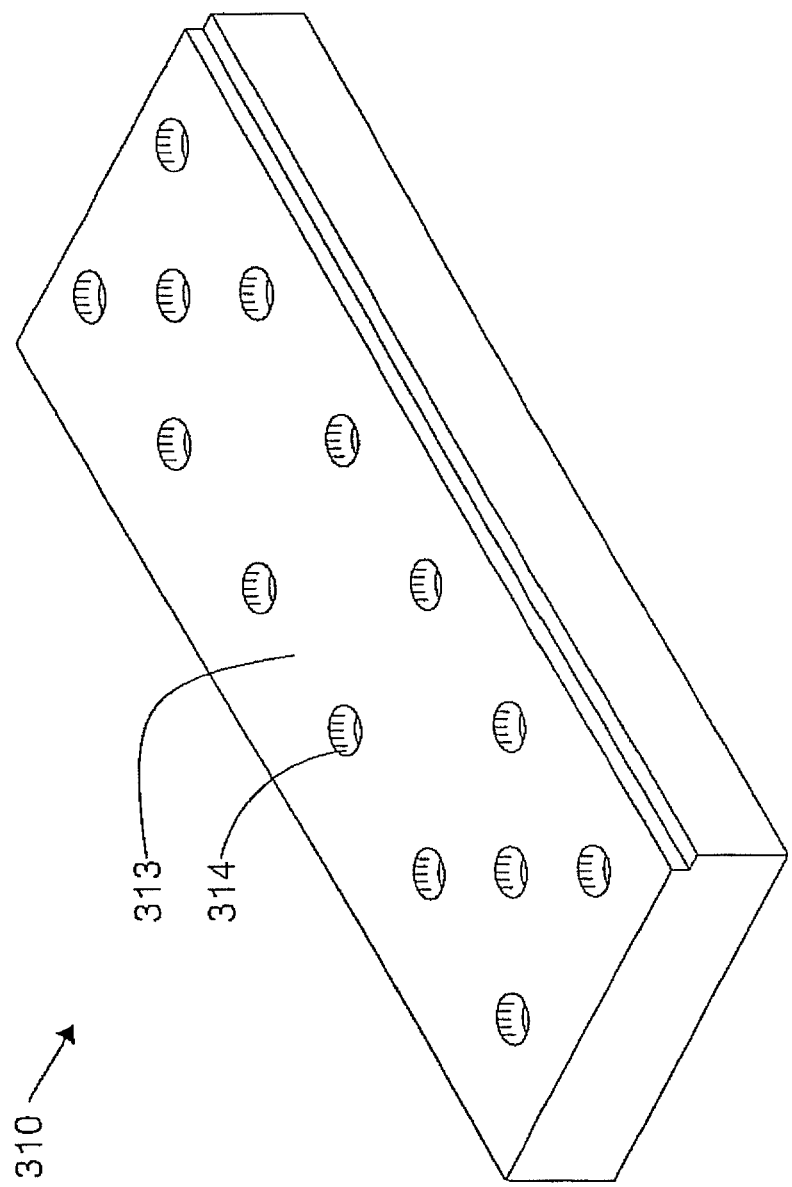
Figure 8C:
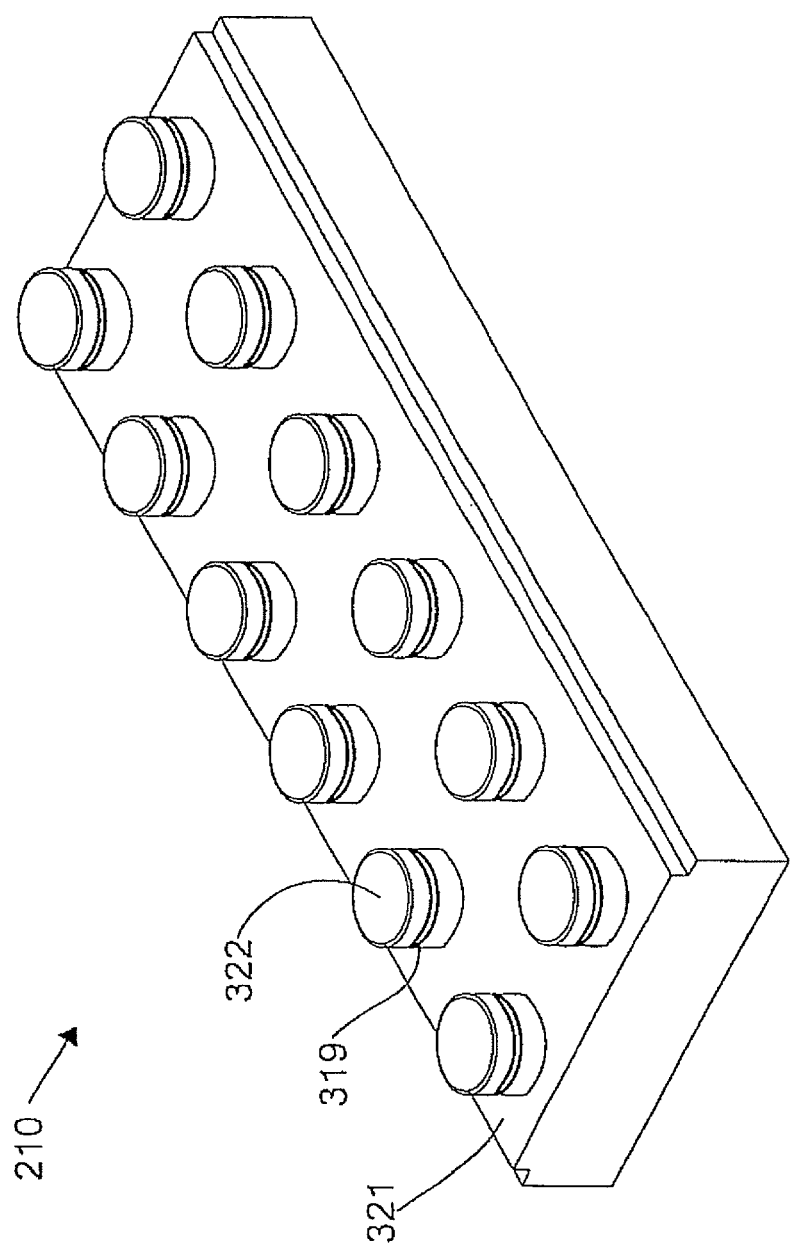
Figure 8D:
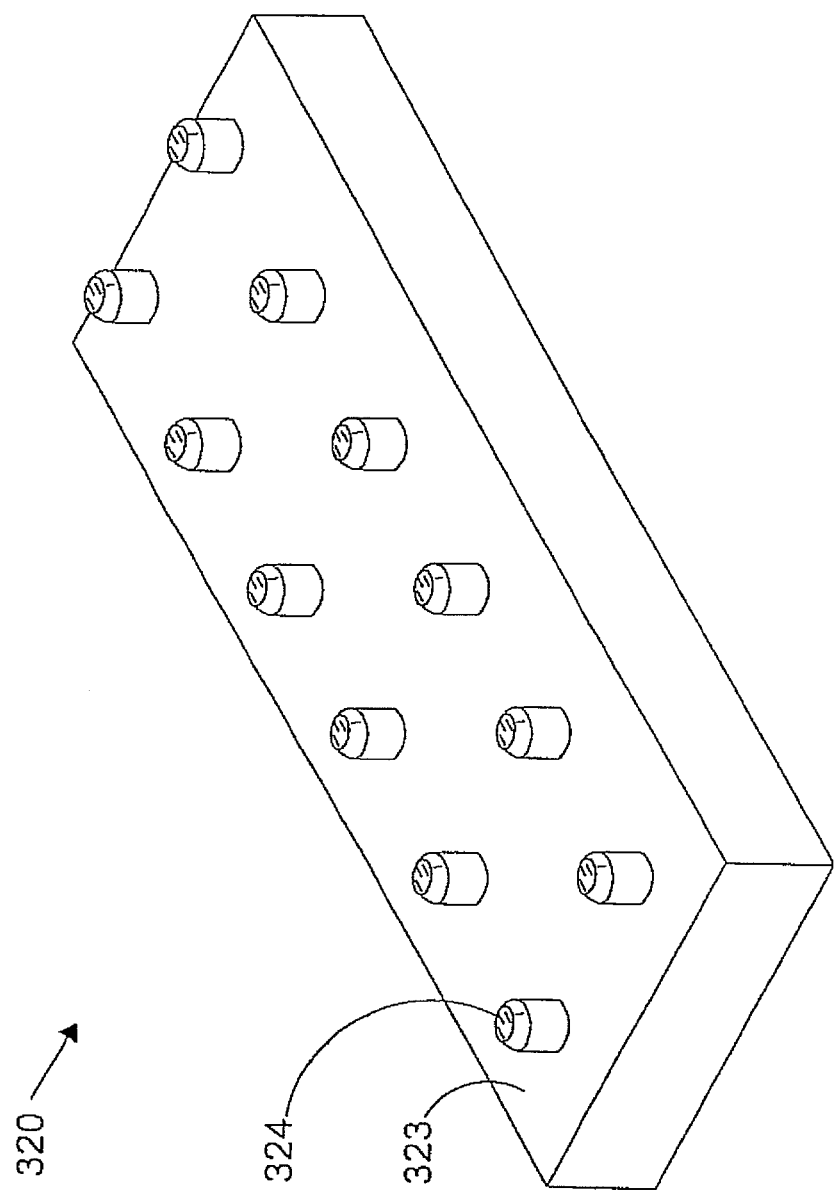
Figure 8E:
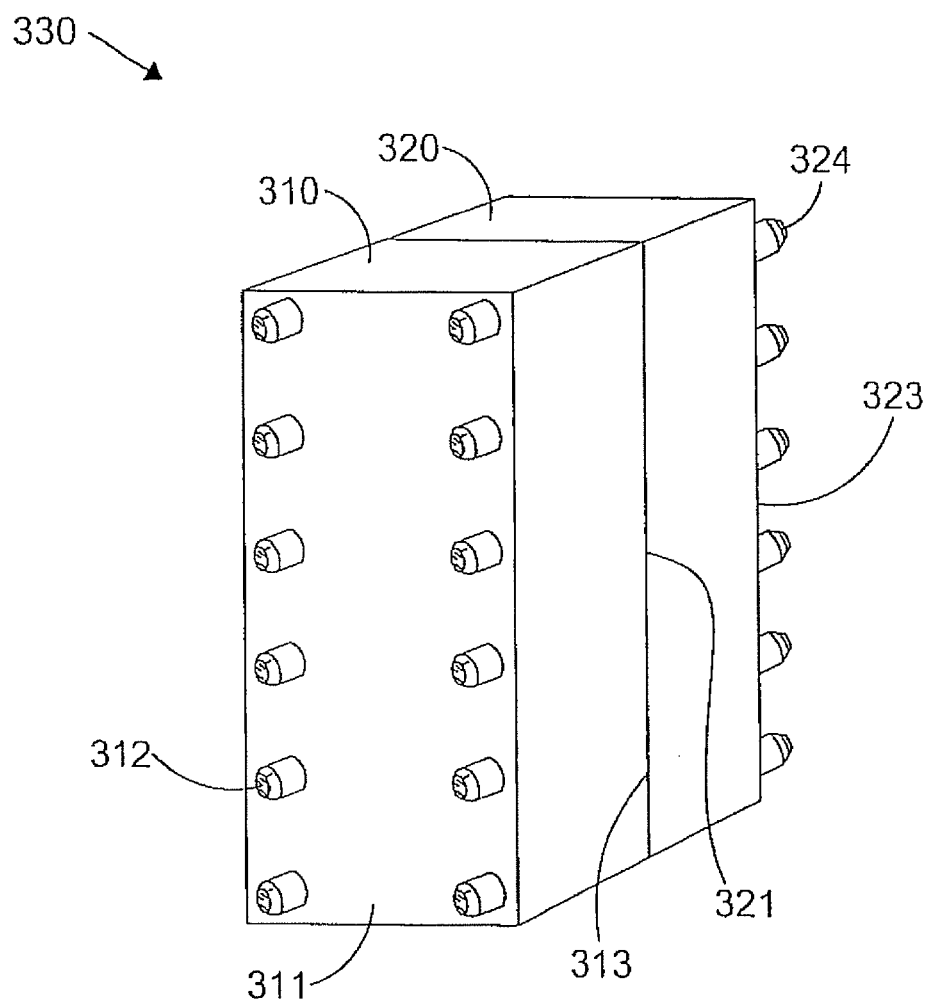

Although the exemplary mounting system 80 shown in FIGS. 7A-7C relies on the drive system 17 described above to provide the movement necessary to generate axial strain, bending, and/or torsion, other mechanisms which allow for control of the time varying position of the ends of the tube 14 and/or specimen 12 may also be appropriate. Likewise, although only one tube 14 and/or specimen 12 is shown mounted using the mounting system 80 shown in FIGS. 7A-7C, it would be well understood that the mounting system 80 could be readily adapted to receive multiple tubes 14 and/or specimen 12, as shown in FIG. 7D. In addition to the longitudinal strain and torsion in or about the X axis, as described above, in certain embodiments the mount positions may move in 3 dimensions, (X, Y and Z) so as to rotate about the respective axes, Y and Z.

This mounting system 80, which in some embodiments may be considered a hemodynamic axial strain and torsion simulator, may be incorporated into a flow loop as described herein to reproduce additional hemodynamic forces not reproduced by the various pumps and pressure/flow controls of the system so as to provide a more complete physiological hemodynamic environment. An embodiment of the system 5000 incorporating this hemodynamic axial strain and torsion simulator shown in FIG. 2E.

In certain embodiments, the mounting system 80 can include additional components such as additional drive systems 17 coupled to either or both ends of tube 14 to provide longitudinal strain (e.g., stretch) and torsion (e.g., twist) along the Y axis. Alternatively, such components may be directly or indirectly coupled to the specimen 12 or tubular structure 1112 to controllably provide Y axis longitudinal stretch and/or twist.

In additional embodiments, the mounting system 80 can include additional components such as additional drive systems 17 coupled to either or both ends of tube 14 to provide longitudinal strain and/or torsion along the Z axis. Alternatively, such components may be directly or indirectly coupled to the specimen 12 or tubular structure 1112 to controllably provide Z axis longitudinal stretch and/or twist.

Accordingly, embodiments of the specimen holder 10 or pressure flow loop subsystem 1105, for example using the mounting system 80 or components directly or indirectly coupled to specimen 12, can provide stretch and twist in single or opposite directions along individual or combinations of the X, Y and Z axis of specimen 12 or tubular structure 1112. Embodiments according to the invention can locate such strain and twist along the X, Y and Z axis at positions intermediate to ends of tubular structure 1112 (e.g., region A), at branches of specimen 12 (e.g., FIGS. 5C, 5D and XI) or for multiple specimens 12 coupled in series or parallel in specimen holder 10.

In certain embodiments, the specimen unit 10 may further include additional components to further modify the flow therein when the above-described components cannot achieve the desired result on their own. Such additional components may include, for example, jets or internal fins which could effect helical or secondary flow within the chamber 11 as necessary, or be positioned in the flow loop such that as the fluid enters the chamber 11, the fluid flow is substantially helical.

Alternative methods or components can be used to generate substantially helical flow, circular flow or wave reflections in specimen 12 or tubular structure 1112. In certain embodiments, systems 1, 5000, 1101 can be mounted on mechanical systems that rotate (e.g., horizontally) at a fixed distance around a center point combined with vertical movement relative to the center point. Such controlled circular and vertical motion (e.g., merry-go-round) of the systems 1, 5000, 1101 can controllably generate a helical flow of fluid in conduit 3701, specimen 12 or tubular structure 1112. Further, in certain embodiments, the rotation around and vertical movement relative to the center point can be at a steady or time varying speed (e.g., constant speed, increasing speed, pulsed speed, sinusoidal speed or the like). Additional movement of the systems 1, 5000, 1101 can be provided by varying the distance of the systems from the center point in a controlled fashion. Thus, additional embodiments can selectively provide one or more of these individual or reciprocal movements (e.g., tangential, vertical, radial or in combinations thereof) of the system 1, 5000, 1101 around a center point to generate controlled fluid dynamics (e.g., dynamic conditions) according to the viscosities of the fluids and tubular structures therein.

In certain embodiments, a coupling system 300 may be used to couple the specimen unit 10 to the flow loop. Although the coupling system 300 is not required in order for the system 1 to operate as described herein, the coupling system 300 may, for example, allow for quick disconnect of the specimen unit 10, and may be adapted to accommodate a specimen unit 10 which includes a chamber 11 with either single or multiple specimen 12, or may accommodate a specimen unit 10 including a single or multiple specimen 12 without a chamber 11. The coupling system 300 may also facilitate the removal and replacement of specimen unit(s) 10 while maintaining necessary sterility of the remainder of the flow loop. The coupling system 300 may also allow for quick removal for post-processing of the specimen(s) 12 for further analysis and the like.

An exemplary coupling system 300 is shown in FIGS. 8A-8E. The coupling system 300 includes a first coupler 310 which may be separably coupled to a second coupler 320 to form a coupling unit 330. Preferably, the coupling system 300 includes a coupling unit 330 (i.e., set of first and second couplers, 310, 320) positioned on opposite ends of the specimen unit 10 such that the specimen unit 10 may be removed from the flow loop by separating each second coupler 320 from its corresponding first coupler 310. In such an embodiment, the first coupler 310 remains connected to a portion of the flow loop, while the second coupler 320 remains coupled to a portion of the specimen unit 10.

In certain embodiments, the first and second couplers 310, 320 may include corresponding inter-engaging protrusions (male) and recesses (female) which couple the first and second couplers 310, 320 by, for example, snap fit, or other such means which would facilitate easy engagement and disengagement while maintaining seal and sterility integrity. When the corresponding inter-engaging protrusions and recesses are engaged, their respective through holes are aligned so as to allow fluid to pass therethrough. Upon disengagement of the first and second couplers 310, 320, flow inhibitors, such as, for example, simple disc valves (now shown) inhibit the flow of fluid therethrough, thereby maintaining seal and sterility integrity when separated as well.

It is well understood that any such position and number of corresponding protrusions and recesses would be appropriate, depending on a number of specimen 12 to be sampled and other such considerations. Likewise, although the exemplary first and second couplers shown in FIGS. 8A-8E are rectangular in shape, it is well understood that a shape of the first and second couplers 310 and 320 and the positioning and number of the associated protrusions and recesses may be adapted to suit the needs of a particular application. Thus, in this exemplary coupling system 300, the fluid/media in the flow loop may be supplied to the coupling system 300, and particularly, to the coupling unit 330 positioned upstream of the specimen unit 10, and split so as to supply fluid/media to twelve specimen 12. Likewise, if multiple specimen units 10 each with its own coupling unit 330 at its ingress 10a and egress 10b are aligned with the flow loop, one and/or all of the specimen unit(s) 10 may be removed and replaced without compromising critical features such as, for example, system integrity or sterility.

As discussed above, it is preferable that a coupling unit 330 be positioned on each end of the specimen unit 10. The first coupler 310 includes a number of protrusions 312 extending from a first side 311 towards its respective end of the flow loop. In the coupling unit 330 positioned upstream of the specimen unit 10, these protrusions 312 are coupled to flow loop supply lines which receive fluid/media from the reservoir 20. In the coupling unit 330 positioned downstream of the specimen unit 10, these protrusions 312 are coupled to drain lines entering from the downstream side of the specimen unit 10. The second side 313 of the first coupler 310 includes a corresponding number of recesses 314 which engage corresponding protrusions 322 formed on a first side 321 of the second coupler 320. The protrusions 322 are fit into the recesses 314, and an o-ring 319 may be used to improve a sealing characteristic therebetween. The second side 323 of the second coupler 320, which preferably faces the specimen unit 10, includes a number of corresponding protrusions 324 which extend toward the specimen unit 10 and specimen(s) 12 positioned therein so as to supply fluid/media thereto or drain fluid/media therefrom.

Thus, fluid/media from the flow loop passes through the first and then the second coupler 310, 320 of the upstream coupling unit 330, and then passes through the specimen unit 10, where the specimen(s) 12 are exposed to the fluid/media. The fluid/media is drained out of the specimen unit 10 and passes into the second coupler 320 and then first coupler 310 of the coupling unit 330 positioned on the downstream end of the specimen unit 10, where it is introduced back into the flow loop. In alternative embodiments, the second side 323 of the second coupler 320 may be used when individual chambers 11 and/or specimen(s) 12 are to be disengaged from the flow loop while others are to remain connected, such as, for example, during time series analysis, where different chamber(s) 11 and/or specimen(s) 12 must be disengaged at different points in time during a trial to provide sample data for progression type analysis.

Although the coupling units 330 are shown at upstream and downstream ends of the specimen unit 10, the quick disconnect/reconnect qualities and commensurate preservation of sterility afforded by these types of coupling units 330 may also be useful at numerous other locations throughout the flow loop. For example, a set of coupling units 330 may be positioned on opposite ends of the first pressure/flow control 40 or the second pressure/flow control 50 so as to make these systems modular and easily removable/replaceable as well.

The various components of the systems 1, 1101 described above may be joined to form the flow loop using, for example, tubing. This tubing generally comprises any suitable type of laboratory tubing which is capable of being sterilized, including silicone tubing, or other comparable laboratory or medical-surgical tubing. The distances between the various components and the corresponding length of the tubing may be chosen so as to minimize the total volume of fluid used. Preferably, these lengths are calculated to provide a maximum flow rate, and to avoid turbulence in the system, based upon boundary layer theory, as known to diose skilled in the art. Generally, it is preferable to minimize the amount of fluid used in order to reduce the costs of media utilization, drug treatment, and cell by-product (such as, but not limited to, proteins, metabolites and like) detection and the like.

Systems for reproducing a hemodynamic environment in accordance with other embodiments of the invention as broadly described herein will now be discussed with respect to FIGS. 3A-3D. The systems and combinations of components discussed above with respect to the embodiments of the system shown in FIGS. 2A-2E are readily adapted to the embodiments shown in FIGS. 3A-3D. Thus, for example, the coupling system 300, mounting system 80, and control system 70 as described above may each be applied to the systems as shown in FIGS. 3A-3D. Thus, there are any number of possible combinations of these components, as well as their placement within embodiments of the system, and, simply for ease of discussion, any duplicative description is omitted.

Figure 3A:
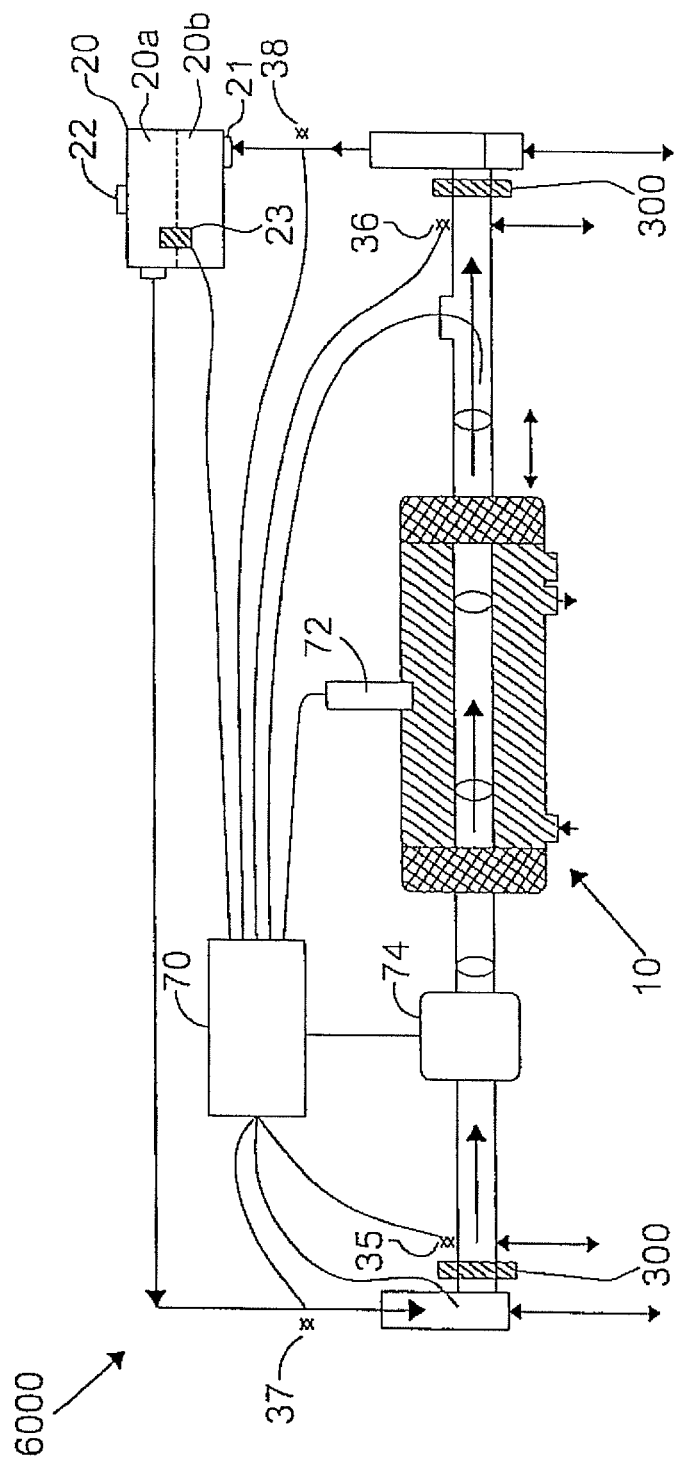
FIGS. 3A-3D are schematic views of systems for recreating a hemodynamic environment in accordance with embodiments of the invention.

The system 6000 shown in FIG. 3A includes a specimen unit 10 with a specimen 12 mounted therein by a mounting system 80 and coupled to a flow loop by coupling units 330. A reservoir 20, first pressure/flow control 40 and second pressure/flow control 50 cause fluid/media to flow from the reservoir 20 through the flow loop as described above. However, steady flow from the reservoir 20 through the first and second pressure/flow controls 40, 50 is now provided by a steady flow system 30 comprising a pair of upstream and downstream pressure/flow control occluders 35-38 provided upstream and downstream of the specimen unit 10 which provide for steady flow of fluid/media into the flow loop and appropriate flow into and out of the first and second pressure/flow controls 40, 50

These pressure/flow control occluders 35-38, which may be, for example, pinch valves, or flow occluders and the like, positioned upstream and downstream of the specimen unit 10 occlude flow and pressure in a controlled oscillatory manner, thus allowing for steady or mean flow without a steady flow pump.

In operation, when one occluder per pressure/flow control 40 or 50 is open, the other is preferably closed. Thus, for example, when the first upstream occluder 35 is open, the second upstream occluder 37 is closed and pump 40 can eject or push fluid toward the open occluder 35 which is connected to the specimen 12 at an appropriate pulsatile or other such rate as dictated by a required condition. Likewise, to fill or supply the pump 40 occluder 37 is open while occluder 35 is closed, allowing pump 40 to draw fluid from the reservoir 20 through the open occluder 37, where it may be held by the pump 40 and closed occluder 37 until, for example, sufficient fluid has been collected therein to operate the pump 40 to create the particular flow dictated by the desired condition. The downstream occluders 36, 38 operate in a similar manner. This allows for control of various hemodynamic parameters such as flow, pressure, and diameter and consequent hemodynamic forces in the specimen unit 10.

Alternatively, a variety of conditions may be achieved while maintaining a mean pressure by controlling the first pressure/flow control 40 and upstream occluders 35, 37 along with the second pressure/flow control 50 and downstream occluders 36, 38 to essentially maintain a mean pressure while still permitting control of flow and pressure. One exemplary manner in which this may be achieved is by closing upstream occluder 37 and opening upstream occluder 35. This will allow fluid to move toward the specimen unit 10 and pressure and flow will continue to increase in the specimen unit 10 until downstream occluder 36 is opened and 38 is closed (or open), thus allowing fluid to exit the specimen unit 10 and reducing pressure accordingly. As pressure and flow reach the desired value, upstream occluder 35 may be closed, and upstream occluder 37 may be opened. This allows a mean pressure and flow to be maintained in the specimen unit 10 through appropriate, coordinated timing of the opening and closing of the occluders 35-38.

Figure 3B:
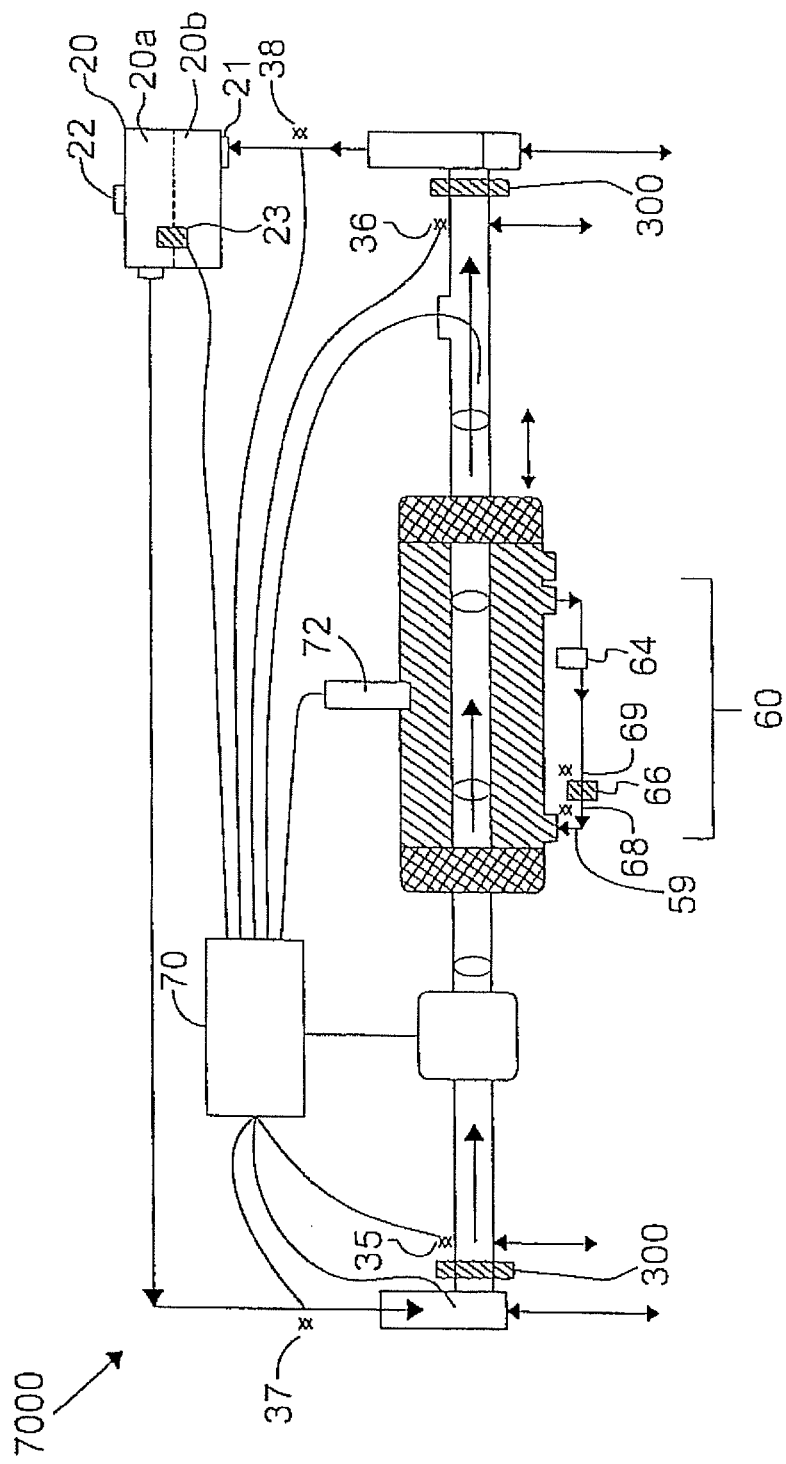
Figure 3C:
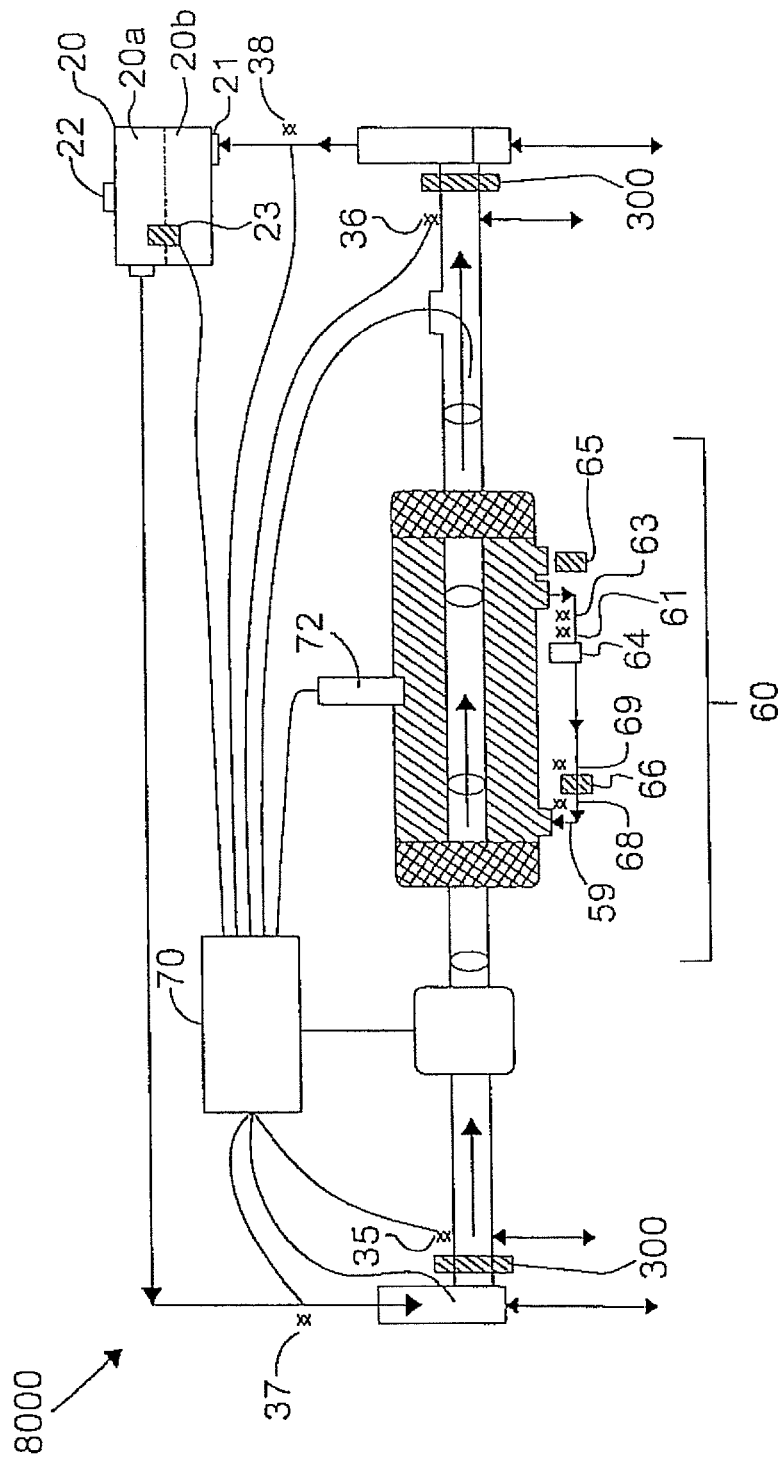
Figure 3D:
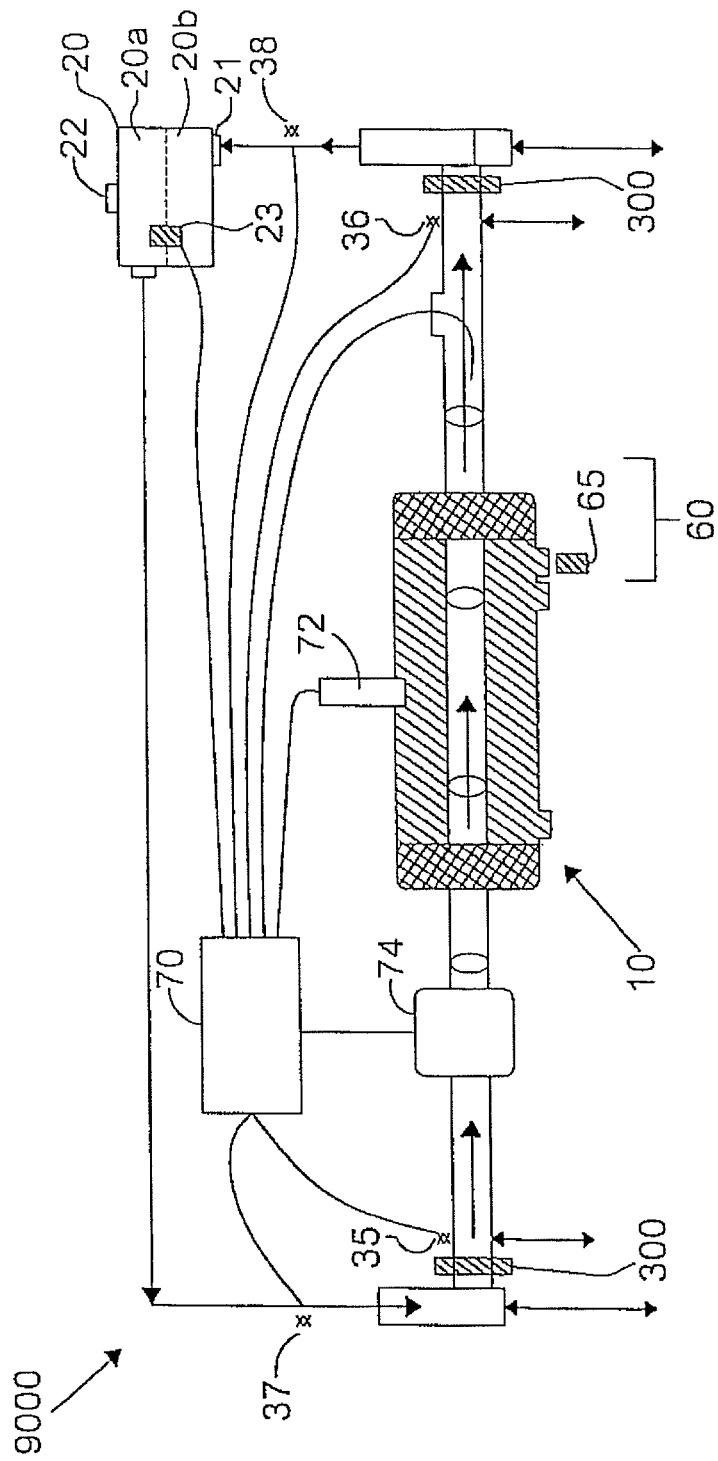

A system for reproducing a hemodynamic environment in accordance with another embodiment of the invention as broadly described herein is shown in FIG. 3B. The system 7000 shown in FIG. 3B is similar to the system 6000 shown in FIG. 3A. However, the system 7000 includes a third pressure/flow control 60 which includes an external flow loop 59 separately coupled to the specimen unit 10 as described above. However, the external flow loop 59 shown in FIG. 3B obtains steady flow in the external flow loop 59 from a pair of external pressure/flow control occluders 68, 69 (rather than an external steady flow pump). Likewise, the systems 8000 and 9000 shown in FIGS. 3C and 3D are similar to the system 7000 shown in FIG. 3B. However, the system 8000 includes an external pressure control 65 as discussed above, in combination with an external flow loop 59 which now includes another pair of external pressure/flow control occluders 61 and 63. This additional pair of external pressure/flow control occluders 61, 63 may be employed to further maintain constant pressure or flow in the chamber 11 if so desired. In the system 9000 shown in FIG. 3D, the third pressure/flow control 60 is simply an external pump 65 externally coupled to the chamber 11.

As can be well understood, the various means set forth herein may be combined as necessary and expedient to achieve a desired result. Thus, for example, steady flow may be provided both in the flow loop and in the external flow loop by a number of different component(s) and/or combination(s) of components, such as, for example, a steady flow pump, or a pairing of pressure/flow occluders and their operation with a corresponding pressure/flow control or pump. Likewise, a third, external pressure control may or may not be included in the pressure/flow control system, and may include, for example, simply an externally applied pressure/flow control in he form or a pump, or a partial or full external flow loop, or a combination thereof. The coupling system and mounting system discussed above may be applied to any of the combinations of components as appropriate/required to provide enhanced utility and/or ease of use.

Likewise, any of these systems may include a variety of other components not shown in detail in these particular figures, such as, for example, a flow damper, or noise filter, that reduces vibrations or noise in the fluid flow. Resistors, such as flow restrictors or clamps that restrict or reduce flow, may be used to increase pressure in the specimen unit 10 or other location within the flow loop if the resistor is appropriately positioned, such as downstream of the downstream pump if this condition is desired in the specimen unit 10. Capacitors, such a chamber that has air and fluid in it and acts as a compliance chamber, can be placed upstream or downstream of the specimen unit 10, preferably downstream, to help adjust various hemodynamic parameters such as the impedance between flow and pressure.

The various system components, such as, for example, tubing, reservoir(s), and pumps, may be made of a variety of materials. In certain embodiments, these components may be made from disposable materials such as, for example, plastic, polypropylene, PETG, and the like to facilitate providing and maintaining a sterile environment, as well as ease of set up and change out of test trials. In other embodiments, these components may be made of non-disposable materials, such as, for example, metals, to provided enhanced durability, structural integrity, and the like. In still other embodiments, these components may be made of a combination of disposable and non-disposable materials, that can be sterilized by, for example, ETO, autoclave, gamma irradiation, and the like, such materials preferably being non-toxic materials.

Figure 9A:
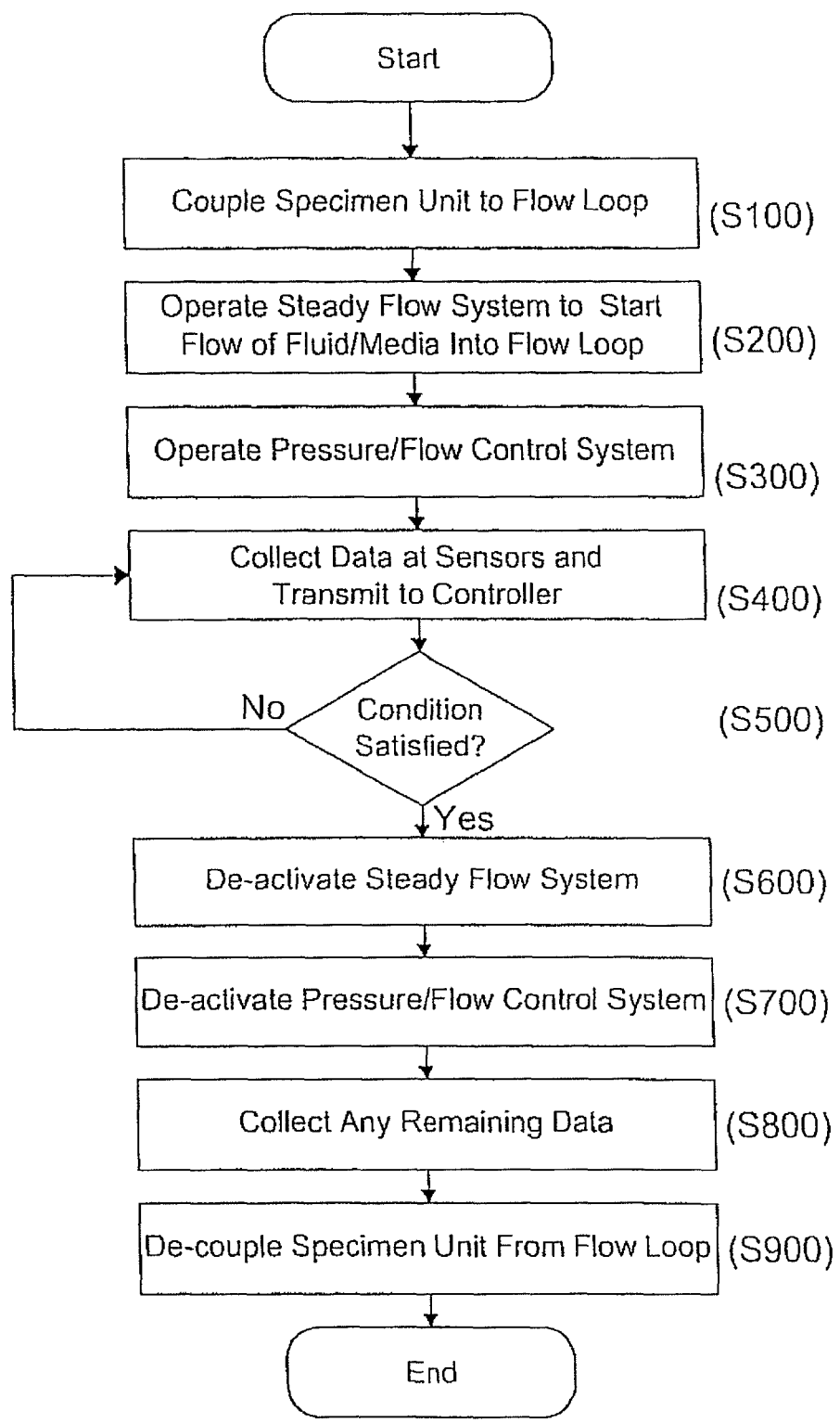

An exemplary operation of the systems shown in FIGS. 2A-2E and 3A-3D will now be discussed with reference to FIGS. 9A-9C. As shown in FIG. 9A, first, the specimen unit 10 is coupled to the flow loop (S100), preferably using the coupling units 330 as described above. The steady flow system 30 is activated to draw fluid/media from the reservoir 20, which is holding fluid and/or media therein, into the flow loop (S200), and the pressure/flow control system 200 is also activated (S300) so that as the fluid/media is drawn through the upstream coupling unit 330 and into the specimen unit 10, the appropriate dynamic conditions are present in the specimen unit 10. Alternatively, the pressure/flow control system 200 may be activated first, followed by the steady flow system 30, or the two systems may be activated simultaneously, depending on the requirements of a particular trial. The introduction of the fluid/media into the specimen unit 10, and particularly the characteristics of the fluid/media associated with pressure and/or flow, as well as the conditions within the specimen unit 10, and particularly those associated with pressure and/or flow of the fluid/media in the specimen unit 10, are established by the pressure/flow control system 200 based on parameters preset in the control unit 70. As the specimen 12 experiences the dynamic conditions reproduced in the specimen unit 10, the sensors collect data and transmit the data to the control system 70 for monitoring and analysis (S400). The control unit 70 may dynamically monitor, control, and adjust the operation of the steady flow system 30 and the pressure/flow control system 200 as necessary based on its substantially continuous analysis of the data collected.

The fluid/media then passes out of the specimen unit 10, again, at a pressure and/or flow condition established by the pressure/flow control system 200 based on control parameters in the control system 70. The outgoing fluid/media passes through the downstream coupling unit 330 and back towards the sampling port 21 of the reservoir 20. At the sampling port 21, the fluid/media is directed to either the reservoir 20, an outflow portion 20b of the reservoir 20, or a holding tank outside the flow loop, again based on preset parameters stored in the control system 70 and characteristics measured by the sensor 23.

The system 1000 continues to operate in accordance with the control parameters set by in the control system 70 until a preset condition or parameter is reached (S500). The governing parameter or condition, which may be preset in the control system 70, may be, for example, time/elapsed time, cycles, a remaining level of fluid and/or media in the reservoir 20, a concentration or other characteristic of the fluid/media as it is returned to the sampling port 21 of the reservoir 20, and other such parameters and/or conditions. When the preset condition has been satisfied, the steady flow system 30 and the pressure/flow control system 200 are deactivated (S600, S700), the control system 70 collects and analyzes any remaining data as required (S800), the specimen unit 10 is decoupled from the flow loop (S900) and post-processing analysis is performed. When other conditions are included, such as, for example, axial stretch and/or torsion components provided by the mounting system 80, these auxiliary systems may be activated as necessary after the flow conditions are set. The sensors can initiate sensing as required to either provide feedback or no feedback to the control system 70 throughout operation of embodiments of the system as required.

As discussed above, the processor 70 may be used to control the various components of embodiments of the system to produce a desired condition or set of conditions in the specimen unit 10 and/or at various locations throughout the flow loop. The control system 70 may control embodiments of the system to operate in numerous modes, including, for example, a first mode in which the control system 70 controls embodiments of the system based on manually entered or preset parameters/algorithms, with little to no feedback from various sensors which may be positioned throughout the flow loop, and no commensurate dynamic adjustment (an open loop control mode). The control system 70 may also control embodiments of the system in a second mode in which the manually entered or preset parameters/algorithms may be dynamically adjusted based on feedback received from the numerous sensors positioned throughout the flow loop (a closed loop control mode). Feedback may include, for example, pressure, flow, diameter, strain, metabolite production, and other such measurements related to a particular condition/set of conditions. Numerous other parameters may also be monitored and fed back to the control system 70 to provide for the dynamic adjustment of the control parameters and algorithms applied by the controller based on the parameters dictated by a particular condition/set of conditions. Other control modes, including a combination of the open and closed loop control modes, may also be appropriate. These control modes are discussed in more detail below.

Figure 9B:
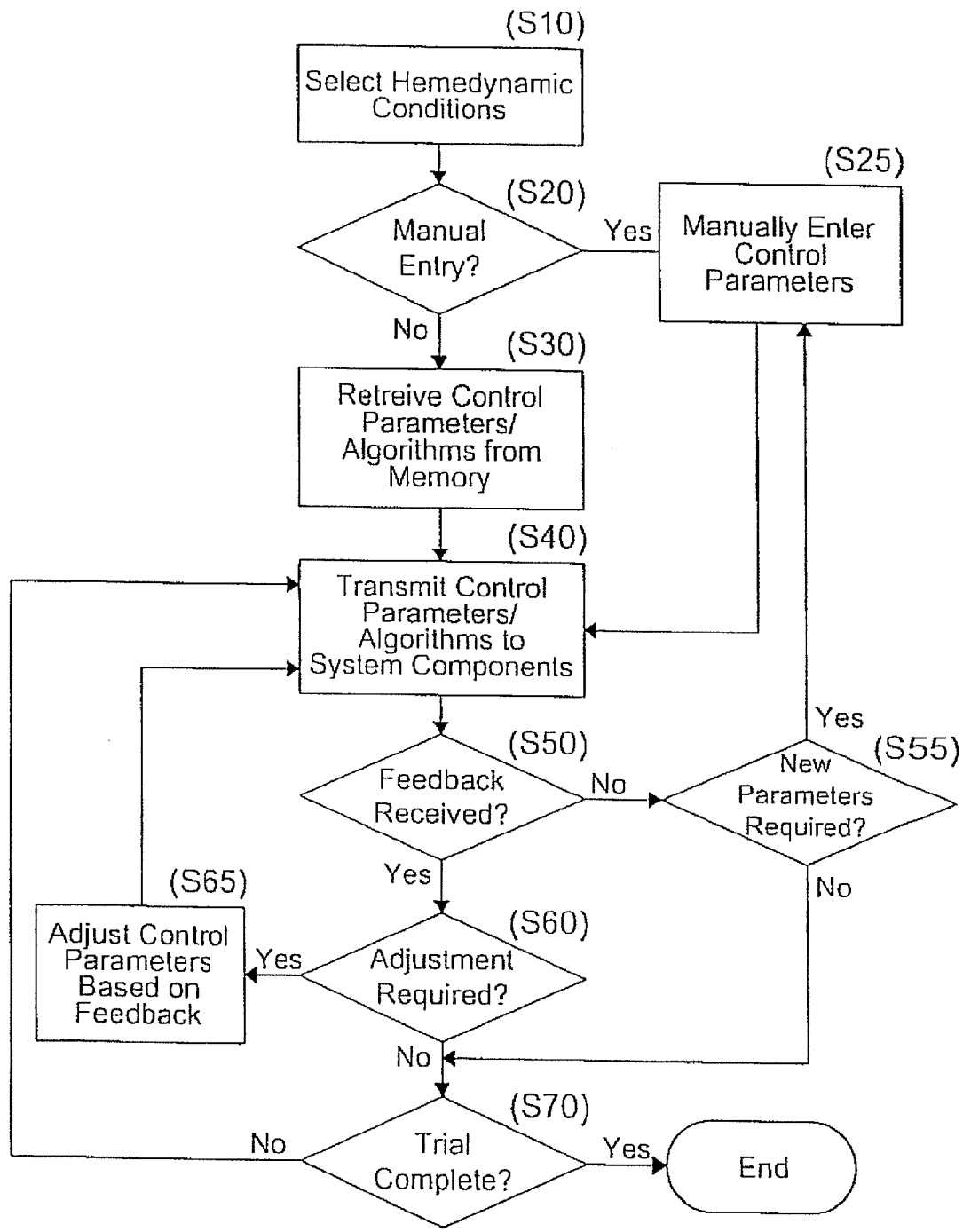

FIG. 9B is a flow chart of the operation of the controller throughout the process shown in FIG. 9A, in accordance with an embodiment of the invention. It is assumed that at least one, and preferably a plurality of dynamic conditions and associated control parameters/algorithms producing the consequent hemodynamic forces are previously stored in a memory portion (not shown) of the control system 70 for selection by an operator at the initiation of a particular trial. In alternative embodiments, conditions and/or control parameters may be selected or entered manually. Such manually entered conditions/parameters may include, for example, flow magnitude, pressure, magnitude, phase relation, and other such parameters which may produce a desired hemodynamic condition.

As shown in FIG. 9B, first a hemodynamic condition/set of conditions is selected (S10). The control parameters/algorithms associated with a selected condition/set of conditions may be retrieved from a previously stored set of control parameters/algorithms (S30), or may be manually entered (S25), based on requirements dictated by a particular trial and other such considerations (S20). For example, a specific hemodynamic region in which certain flow and pressure conditions will have certain associated wall shear stresses and circumferential strain levels may be chosen to produce a patient specific condition, such as, for example, a distressed coronary artery with a typical large phase difference between pressure and flow, or a healthy condition in which a phase difference between flow and pressure is relatively small. As discussed above, these conditions and associated control parameters may be previously stored in the control system 70. Likewise, parameters such as flow magnitude, pressure magnitude, phase relation, and the like may be manually entered, and then resulting conditions calculated by the control system 70, if desired.

Once the control parameters/algorithms have either been retrieved from memory (S30) or manually entered (S25), the control system 70 sends the corresponding control parameters/algorithms to the various affected components (S40) such as, for example, the steady flow system 30, the first second and third pressure/flow controls 40, 50, 60 and their corresponding components which are included in the pressure/flow control system 200, the mounting system 80 to provide for appropriate axial strain and/or torsion, and any other components linked to the flow loop which should be controlled in a given manner to produce the selected hemodynamic condition/set of conditions. These control parameters may include, for example, output voltages or currents with appropriate oscillatory patterns (such as, for example, sinusoids or blood pressure waveforms) to produce the desired conditions.

As the control system 70 operates embodiments of the system, it determines whether or not feedback has been received (S50). If no feedback has been received from the sensors, the control system 70 checks to see if any new/additional control parameters have been manually entered (S55). If new control parameters have been entered (S25), the new control parameters are received by the control system 70 and transmitted to the components (S40). If new control parameters have not been entered, the control system 70 can determine if the trial is complete (S70), and, if not, continues to transmit the valid control parameters to system components (S40). This process continues until the control system 70 determines that the trial is complete (S70).

If feedback is received from the sensors (S50), the control system 70 determines if adjustment to the control parameters is required based on the feedback (S60). To accomplish this, the control system 70 may, for example, conduct a comparison of the control parameters as originally established to a set of measured parameters. Alternatively, the control system 70 may receive the various feedback parameters, and perform a calculation to determine actual dynamic conditions at a particular location compared to conditions which were initially established for that location. If, based on these comparisons/calculations, the control system 70 determines that no adjustment is required, the control system 70 then determines whether the trial is complete (S70), and, if not, continues to transmit the valid control parameters to the system components (S40). If feedback is received from the sensors (S50) and adjustment of the control parameters is required based on the comparisons/calculations, then the control parameters are adjusted (S65) and the adjusted control parameters are transmitted to the system components (S40). This process continues until the control system 70 determines that the trial is complete (S70).

As set forth above, the various embodiments of the system described herein may be adapted to receive numerous different types of specimen and be operated and configured in a variety of different manners based on the requirements dictated by a particular trial. For illustrative purposes, operation of the system 2000 shown in FIG. 2B, in which a compliant specimen including, for example, a compliant silicone tube lined with endothelial cells so as to be representative of an actual vessel, in-vivo, with similar mechanical properties such as, for example, modulus of elasticity, compliance, and the like, has been mounted in the specimen unit 10 for drug screening and testing will now be discussed in more detail. It is well understood that this is just one example of the many applications of each of the various systems set forth herein, and is not meant to in any way be construed as so limiting the application or operation of embodiments of the system as embodied and broadly described herein.

If, for example, the silicone tube lined with endothelial cells discussed above is to be subjected to a particular hemodynamic condition for testing, appropriate parameters are set to produce such a condition. In this example, a healthy hemodynamic condition may be represented by a WSS of 10±10 dynes/cm$^2$ at a pressure of 70±20 mmHg and a circumferential strain represented by a change in diameter of ±4%, yielding an SPA of 0 degrees at a frequency of 1 Hz. As discussed above, these control parameters may be manually entered, or they may be stored in a memory portion of the control system 70 in association with a given hemodynamic condition, and accessed as necessary prior to the initiation of a trial.

Once the appropriate hemodynamic condition is selected and the corresponding control parameters are made available, the control system 70 controls to the steady flow pump 30a to operate to initiate a circulation of fluid through the flow loop. The first and second pressure/flow controls 40, 50, which, in this example, are likely to be bellows pumps, oscillate to produce oscillatory waveforms corresponding to the required dynamic conditions. This may be accomplished by, for example, the first pressure/flow control 40, considered in this example to be the upstream pump, creating an increase in flow and pressure directed toward the specimen unit 10, while the second pressure/flow control 50, considered in this example to be the downstream pump, simultaneously creating an increase in flow and pressure directed toward the specimen unit 10. The coordinated action of the upstream and downstream pumps and the resultant pressure and flow conditions produced in the specimen unit 10 result in an oscillatory component at or above the 0 degree SPA associated with a healthy hemodynamic condition for the such a specimen.

The oscillatory waveforms generated by the coordinated action of the upstream and downstream pumps in this example may be varied by varying the action of the upstream and downstream pumps accordingly. Thus, for example, rather than directing an increase in pressure and/or flow toward the specimen unit 10, one of both of the upstream and downstream pumps may instead operate to draw fluid collected in the specimen unit 10 out of/away from the specimen unit, thereby producing a differentiated effect on the specimen mounted therein. In this particular example, if bellows pumps are employed at the upstream and downstream positions, this may be accomplished by allowing the bellows portion of the pumps to fill with fluid from the flow loop through the action of the steady flow pump 30a which maintains a mean flow through the flow loop concurrent with the action of the upstream and downstream pumps, and then controlling a release of fluid from the bellows toward the specimen unit as required to produce the desired effect. Or, alternatively, the bellows may be filled from the specimen unit 10 side of the respective pump and the release of the collected fluid into the flow loop controlled to produce an alternately directed effect.

As described above, in this particular example, the steady flow pump 30a maintains a mean flow throughout the flow loop, concurrent with the action of the upstream and downstream pumps. Thus, as the upstream and downstream pumps collect and discharge fluid toward/away from the specimen unit 10, at least some, if not all of the fluid running through the pumps as they operate is replenished with circulating fluid. As fluid leaves the downstream pump, it travels toward the reservoir 20, where, in this particular example, a portion thereof is periodically siphoned off at the sampling port 21 for sampling. The remainder of the fluid is then returned to the reservoir 20 for recirculation in this particular example, although, as discussed above, in other applications, this return fluid may be fully or partially diverted to an outflow portion 20b or holding tank rather than recirculated. This recirculation of fluid and operation of the various pumps as described above is continued in accordance with the established algorithms until a preset stop condition is achieved. In an example such as this, in which a specimen is undergoing drug testing, this stop parameter is often time based, i.e., exposure of the specimen 12 to a particular set of conditions for a given amount of time, based on actual interaction of such drugs in-vivo. However, as discussed above, this stop condition may vary based on requirements dictated by a particular trial.

This is just one example of how one of the embodiments of the invention may be employed for a drug screening and testing trial on a compliant silicone tube lined with endothelial cells. It is well understood that the various other components described herein may also be applied to embodiments of the system to augment the capability of that system and provide further variation in the dynamic conditions to which a specimen may be exposed. For example, addition of a third pressure/flow control 60, which may include a pressure/flow control pump, a full external flow loop, or a combination thereof, may provide for further variation of the flow environment created within the specimen unit 10 and commensurate additional combinations of hemodynamic force. The addition of torsion and/or axial strain through implementation of the capabilities of the mounting system 80 may further expand the sets of condition(s) which may be created in the specimen unit 10 and experienced by a particular specimen. Numerous different environments and parameters may be monitored and/or control algorithms adjusted based on a number, type and placement of a variety of sensors throughout the selected system and the capabilities of the control system 70.

FIGS. 10A-10H provide graphical representations of the various stress (WSS) and strain (CS) conditions which may be achieved by the various systems FIGS. 2A-2E and 3A-3C, graphically depicted in terms of pressure (P), diameter (D) and flow rate (O). More specifically, FIGS. 10A-10H demonstrate control of magnitude, phase, and frequency of flow, pressure, and diameter waveforms in a specimen 12 such as, for example an artificial or silicone artery, and the unique conditions that may be achieved by the system 100 in the chamber 11. The various conditions and combinations of conditions graphically depicted in FIGS. 10A-10H are tabulated in Table 1 below.

TABLE 1

Various conditions shown in FIGS. 10A-10H, where an oscillatory condition is shown as T, and a constant condition is shown as F.

|  | Q | P | D |
|---|---|---|---|
| A and B | T | T | T |
| C | T | F | F |
| D | T | F | T |
| E | T | T | F |
| F | F | T | T |
| G | F | T | F |
| H | F | F | T |
| (not shown) | F | F | F |

In Table 1, an oscillatory condition for one of the parameters Q, P or D is shown as True or "T" state, while a constant or non-rime varying condition is shown as a False or "F" state. For example, a condition in which there is oscillatory flow Q (True state) with no change in pressure P or diameter D (False state) as shown in line C of Table 1 and graphically depicted in corresponding FIG. 10C may now be achieved due to the capabilities provided by the combination of components provided in the systems shown in FIGS. 2A-2E and 3A-3C. Further, a condition in which there is oscillatory flow Q (True state), oscillatory diameter D (True state), and no change in pressure P (False state) as shown in line D of Table 1 and graphically depicted in corresponding FIG. 10D may now be achieved due to the capabilities provided by the combination of components provided by the systems shown in FIGS. 2A-2E and 3A-3C.

Figure 11:
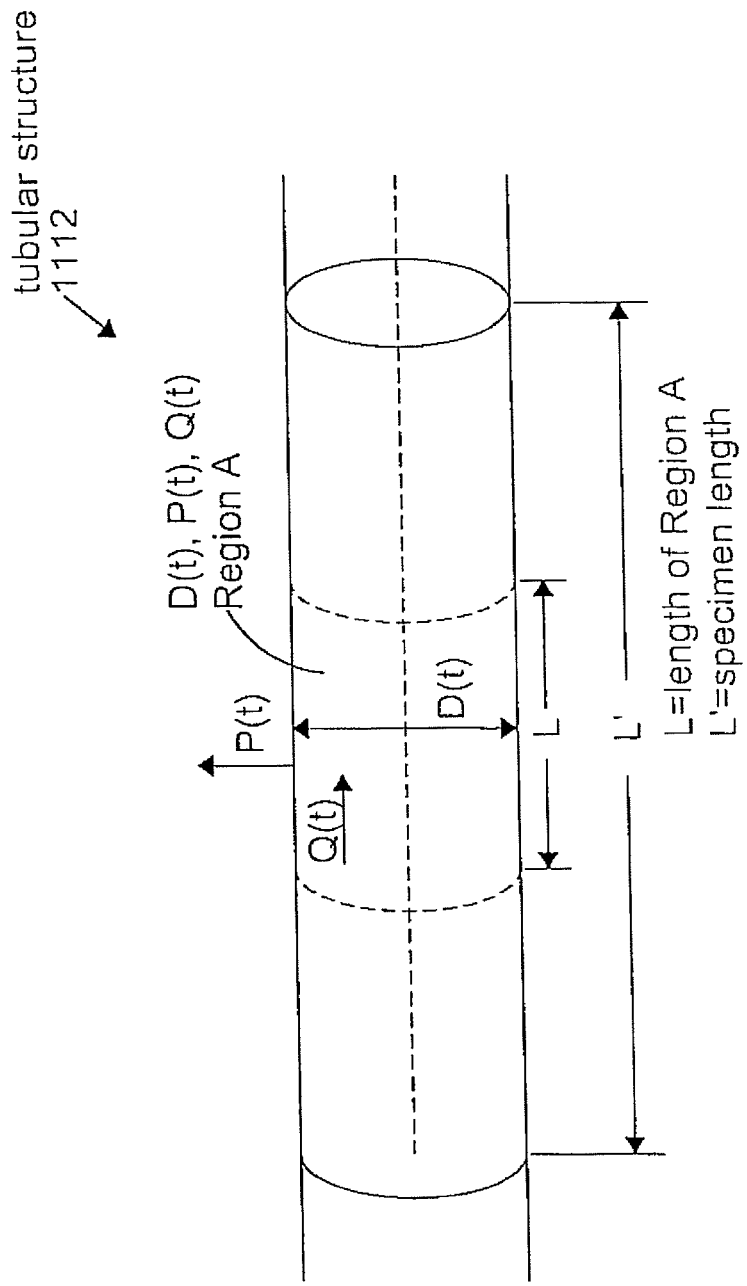
FIG. 11 shows a side view of a specimen in accordance with an embodiment of the invention.

FIG. 11 shows a side view of a specimen, shown as a tubular structure 1112, in a specimen unit (not shown) in accordance with an embodiment of the invention. Specimen 1112 is represented as a tubular structure having a length L1. Specimen 12, described above, includes, but is not limited to, a tubular structure 1112. As used herein, tubular structure 1112 includes any three dimensional structure capable of passing fluid from one location to another. This includes shapes of any section found in the cardiovascular system in humans or animals or any shapes of sections, including but not limited to C, I, T, Y of FIGS. 5A-5D and 11. Tubular structures 1112 further include any shapes of sections found in humans or animals that serve to transfer or pass fluid from one location to another. For example, tubular structures can include, but are not limited to, aortas, arteries, arterioles, capillaries, venules, veins, vena cavas, pulmonary arteries and pulmonary veins. Tubular structures can further be synthetic, partially porous, permeable, grooved, microgrooved, hybrid biological/synthetic and/or electrospun.

Region A as shown in FIG. 11 represents a portion or subsection of specimen or tubular structure 1112. Specimen 1112 has a diameter of approximately D(t) over a length L which is ≦L'. In accordance with one embodiment of the invention, a sample has pressure P and flow Q, if the measured pressure P and flow Q are substantially within ΔP and ΔQ of the values of P and Q over the Region A. Hence, region A represents a portion of tubular structure 1112 in which pressure is substantially between P±ΔP/2, flow is Q±ΔQ/2, and diameter is D±ΔD/2, and a specimen is said to have dynamic conditions P, Q and D, if the measured values of P, Q and D over a region A are substantially within the ratios $\Delta P/P_{Range}$, $\Delta Q/Q_{Range}$ and $\Delta D/D_{Range}$, respectively, where $P_{Range}$, $Q_{Range}$ and $D_{Range}$ can be, for example, mean values of the potential ranges of pressure, flow and diameter for specimen 1112. In preferred embodiments, $\Delta P/P_{Range} \leq 0.35$, and preferably $\Delta P/P_{Range} \leq 0.25$, and more preferably $\Delta P/P_{Range} \leq 0.15$ and even more preferably $\Delta P/P_{Range} \leq 0.05$, similarly $\Delta Q/Q_{Range} \leq 35$, and preferably $\Delta Q/Q_{Range} \leq 0.25$, and more preferably $\Delta Q/Q_{Range} \leq 0.15$ and even more preferably $\Delta Q/Q_{Range} \leq 0.05$, and similarly $\Delta D/D_{Range} \leq 0.35$, and preferably $\Delta D/D_{Range} \leq 0.25$, and more preferably $\Delta D/D_{Range} \leq 0.15$ and even more preferably $\Delta D/D_{Range} \leq 0.05$.

Figure 12:
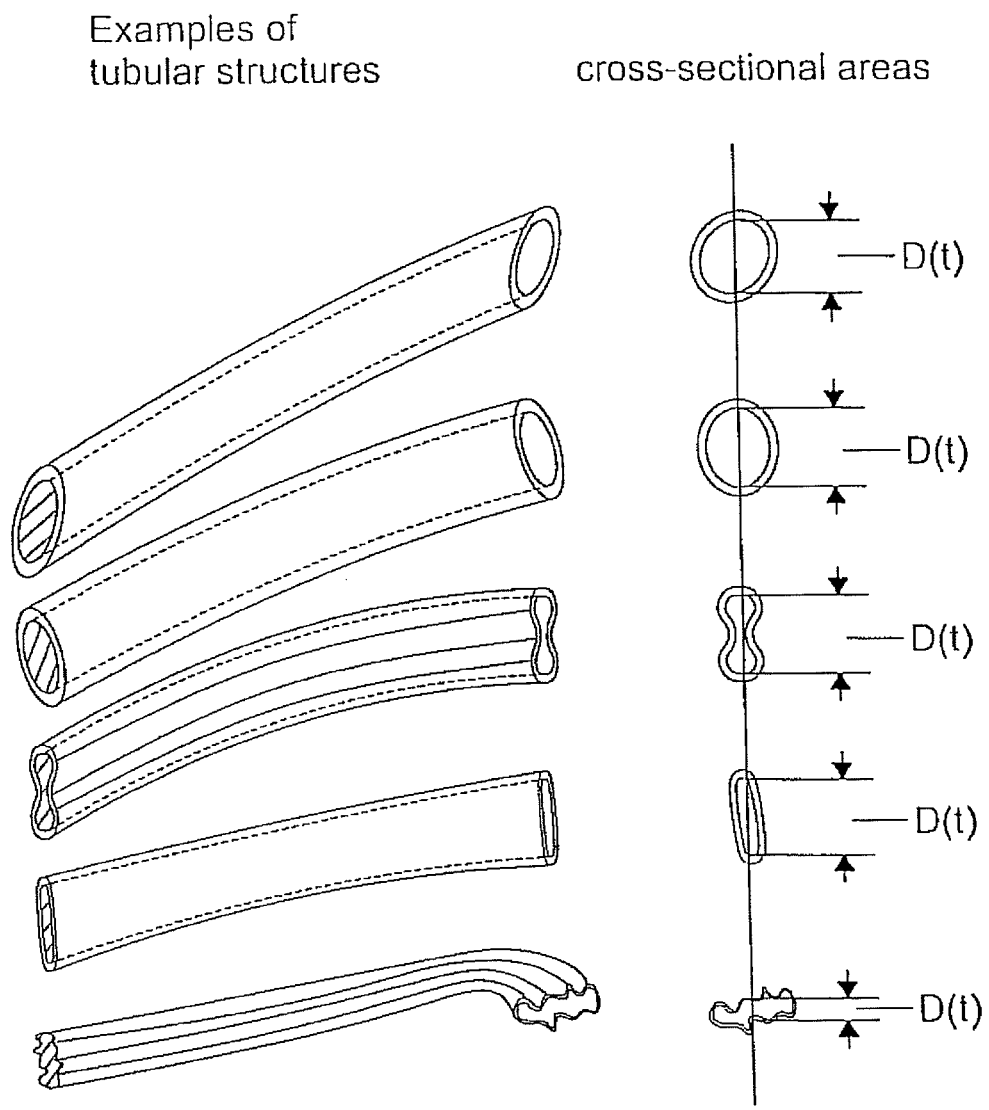
FIG. 12 shows examples of cross-sections of tubular structures according to various embodiments of the invention.

FIG. 12 shows examples of cross-sections of tubular structures 1112 according to various embodiments of the invention. The cross-sections of tubular structures can be circular, ovular or elliptical, even lobe shaped (such as a figure eight). Other embodiments of the invention may include, tubular structures having a nearly two dimensional flattened ribbon shape with an ovular and/or rippled shaped cross-section as shown in FIG. 12.

In a preferred embodiment of the invention, specimen 1112 is not completely rigid in that the shape of its cross-section may vary in response to sufficiently large variations in dynamic conditions such as pressure P(t), flow Q(t) will structures WSS, circumferential strain (CS), stretch or Length (L), twist/torque (T) and so forth. Hence, tubular structures preferably have at least some flexibility in the sense that the diameter D(t) (as generally defined herein) can vary in response to sufficiently large variations in pressure P(t), flow Q(t), stretch or Length (L), and/or twist/torque (T) along a selected direction of measurement.

Figure 13A:
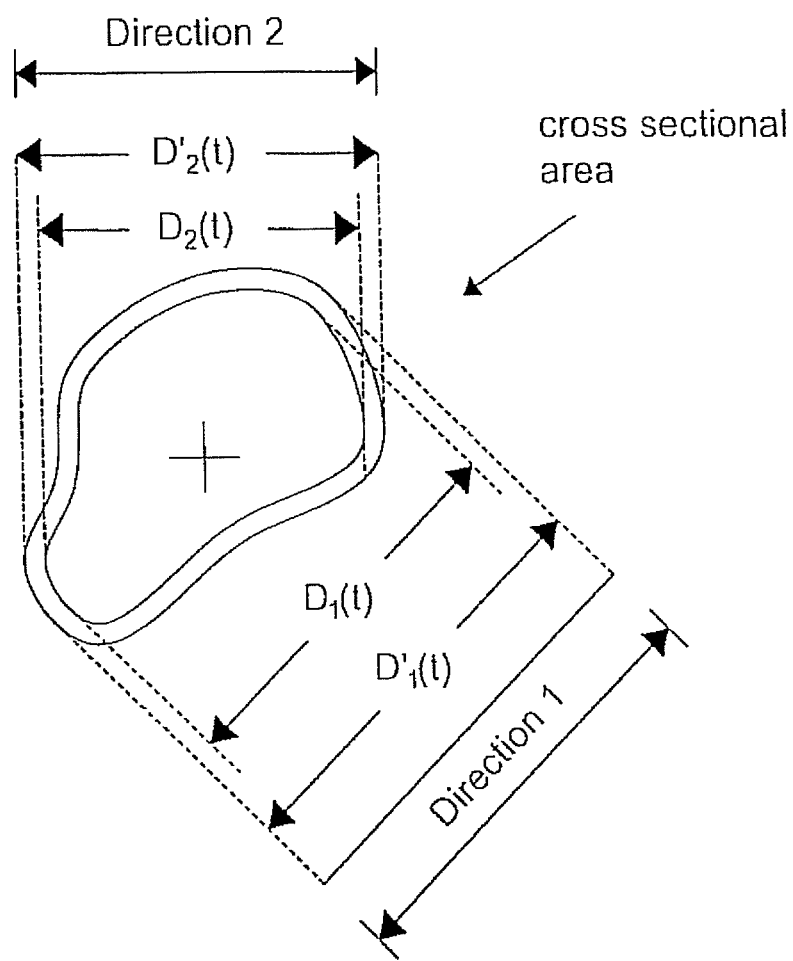
FIG. 13A shows several examples for the measurement of the parameter D(t)

FIGS. 12 and 13A demonstrate how diameter D(t) as used herein can be a parameter generally indicative of the shape of a cross-section of tubular structures. The shape of the tubular cross-section may be non-circular, such as elliptical or ovular, in which case the diameter D(t) represents a parameter indicative of variations in that cross-sectional shape. For example, parameter D(t) can represent the inner diameter, the outer diameter, the tubular structure's wall thickness along one or more directions of the cross-sectional area along a selected direction as shown in FIG. 12. The selected direction of measurement can be in any direction with respect to the cross-sectional area.

FIG. 13A shows several examples of how a direction of measurement can be selected for the measurement of the parameter D(t) as well as how the measurement of the inner and/or outer diameter of a cross-section of tubular structures can be accomplished according to alternative embodiments of the invention. For example, FIG. 13A shows parameters $D_1$ and $D'_1$ representing the inner and outer diameter, respectively, of a cross-sectional area of a tubular structure as measured along the direction 1. Similarly, parameters Dt and DS represent the inner and outer diameter, respectively, of the tubular structure as measured along the direction 2. The parameter D(t) can be combinations of $D_1$, $D'_1$, $D_2$, and/or $D'_1$. For example, parameter D(t) might be the thickness of the walls of the tubular structure along direction 1, namely, $D_1(t)-D'_1(t)$. Also, diameters can be measured along additional directions and those values combined by controller 70 and/or independently monitored by controller 70 as independent feedback signals.

The tubular structure may also be a multi-layer structure, in which case parameter $D_{xy}$ can represent the inner diameter of layer x along direction y and $D'_{xy}$ can represent the outer diameter of layer x along direction y.

Figure 13B:
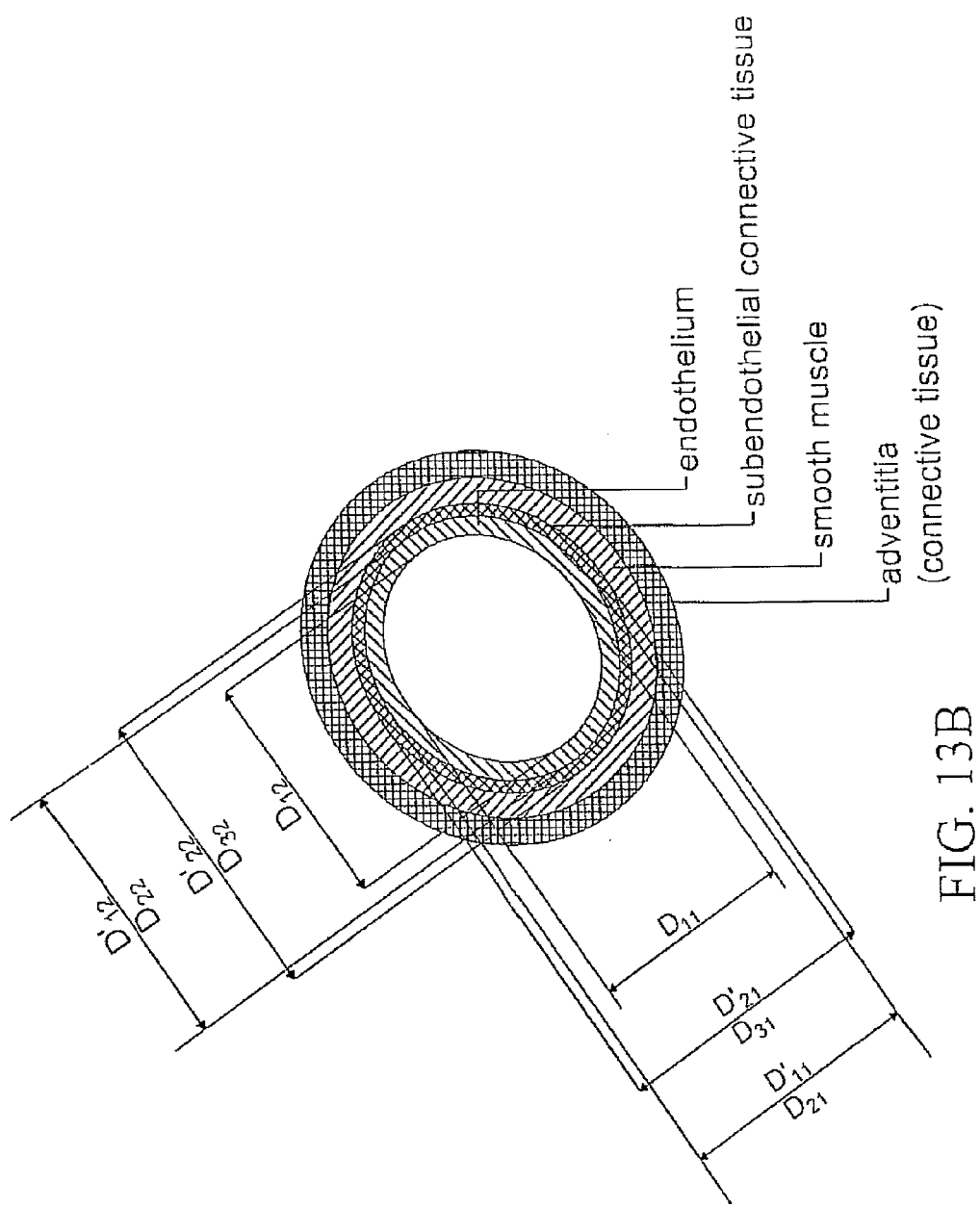
FIG. 13B is a schematic cross sectional view of an example of a multi-layer tubular structure.

FIG. 13B is a schematic cross sectional view of a human blood vessel (e.g., artery or vein), which is an example of a multi-layer tubular structure as broadly defined herein, which shows how the parameter D(t) inner and/or outer diameters of a cross-section of multi-layer tubular structures can be accomplished according to alternative embodiments of the invention. Arteries and veins follow substantially the same histological makeup. The inner most layer is an inner lining called the endothelium, followed by a second layer of subendothelial connective tissue. This is followed by a third layer of vascular smooth muscle, which is highly developed in arteries. Finally, there is a fourth layer of connective tissue called the adventitia, which contains nerves that supply the muscular layer, as well as nutrient capillaries in the larger blood vessels.

Parameters $D_{11}$ and $D'_{11}$ represent the inner and outer diameters, respectively, of a cross-sectional area of a first layer of a multi-layer tubular structure as measured along the direction 1. Similarly, parameters $D_{21}$ and $D'_{21}$ represent the inner and outer diameters, respectively, of a second layer of the multi-layer tubular structure as measured along the direction 1.

Parameters $D_{12}$ and $D'_{12}$ represent the inner and outer diameters, respectively, of a cross-sectional area of the first layer of the multi-layer tubular structure as measured along the direction 2. Similarly, parameters $D_{22}$ and $D'_{22}$ represent the inner and outer diameters, respectively, of the second layer of the multi-layer tubular structure as measured along the direction 2.

Tubular structures are further categorized into diose which respond to dynamic conditions in a substantially consistent manner and diose that do not.

Figure 14:
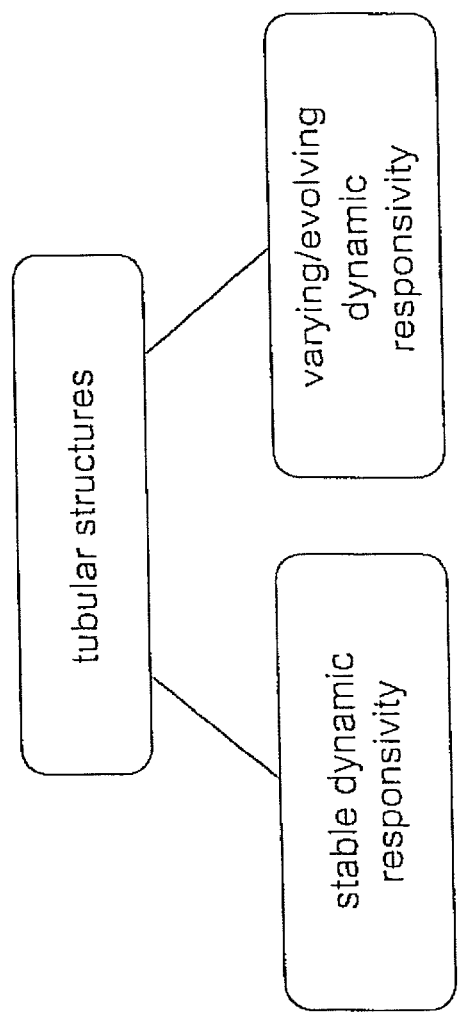
FIG. 14 shows examples of tubular structures.

Referring to FIG. 14, dynamic conditions $g_i(t)$ can be measured at various locations on systems, in accordance with embodiments of the invention. Feedback $FB_j(t)$ can include signals indicative of dynamic conditions at locations other than regions A of specimen 1112. Such dynamic conditions $g_i(t)$ might, from time to time, be referred to as system or global dynamic conditions.

As used herein, stable dynamically responsive tubular structures are tubular structures whose dynamic conditions at region A are substantially repeatable for a given set of global dynamic conditions and/or local dynamic conditions for a system 1101 according to embodiments of the invention.

A system can be trained using a first tubular structure with a stable and dynamic responsivity. If the relationship between the physical structure of the first and any subsequent tubular structures is known and these subsequent tubular structures have a stable dynamic responsivity, then global dynamic conditions can be translated by controller 1103 to yield dynamic conditions at the subsequent tubular structures a priori. For example, if a system 1101 is trained using a first tubular structure, and global dynamic conditions (e.g., $FB_j(t)$) and input information has been linked (in accordance with, for example, FIG. 29), then a second stable tubular structure with an outer wall thickness twice that of the first tubular structure, but the same inner diameter of the first tubular structure could be inserted in specimen unit 10 of pressure/flow loop subsystem 1105. Controller 1170 can then perform the appropriate translations to yield local dynamic conditions at a corresponding region A of the second tubular structure, provided the responsivity of a second tubular structure with twice the wall thickness is known a priori. Translation of properties between stable tubular structures can be ascertained as known to diose skilled in the art, for example, fluid dynamics and fluid mechanics.

As discussed above, sensors, detectors, transmitters, receivers and/or transceivers (referred to herein from time to time as "sensors") can be arranged within, on and/or around pressure/flow loop subsystem 1105 to sense, detect and/or measure various dynamic conditions at various locations in pressure/flow loop subsystem 1105 and/or to transmit information. The locations of such sensors will yield feedback signals $FB_j(t)$ corresponding to types of dynamic conditions (examples of which are shown in FIGS. 17A and 17B) that could be considered global dynamic conditions of system 1101. As with a single region A, known variations of stable tubular structures can be linked to global dynamic conditions by in controller 1103 in accordance with embodiments of the invention.

Figure 15:
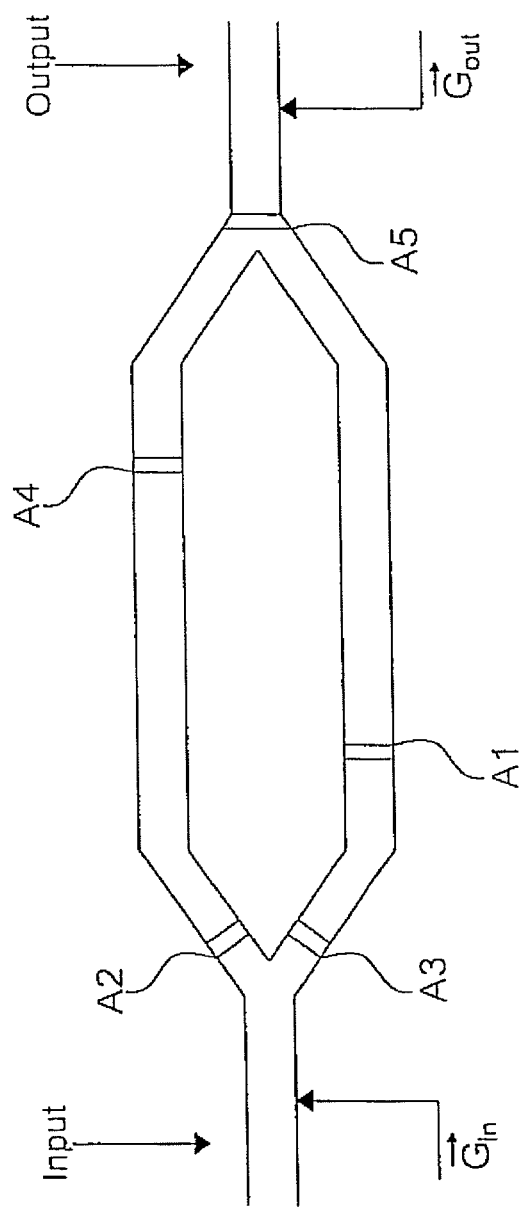
FIG. 15 shows multiple regions in an exemplary tubular structure where dynamic conditions can be linked to global dynamic conditions measured at the input and the output, respectively.

If a given controller 1103 is trained using a stable tubular structure having an architecture, for example, C, I, T, Y or some other architecture, then controller 1103 may include processing which maps those global dynamic conditions to multiple or alternative regions A for a given tubular structure in accordance with embodiments of the invention. For example, using a stable tubular structure, multiple regions A1-A5 can be selected can be selected during a training process and dynamic conditions at their respective locations can be linked to global dynamic conditions measured at the input ($\overline{G}_{in}$) and the output ($\overline{G}_{out}$) located at the input and output of specimen holder 10, respectively, as shown in FIG. 15.

These system sensors include sensors, transmitters, receivers, detectors, transceivers, etc., and can sense, detect, measure, transmit and/or receive information which can be directly or indirectly associated with dynamic conditions at any location. System sensors can be as small or smaller than nanosensors or be large or more sophisticated systems, such as an MM, PET or other systems, as will be discussed herein.

Figure 16:
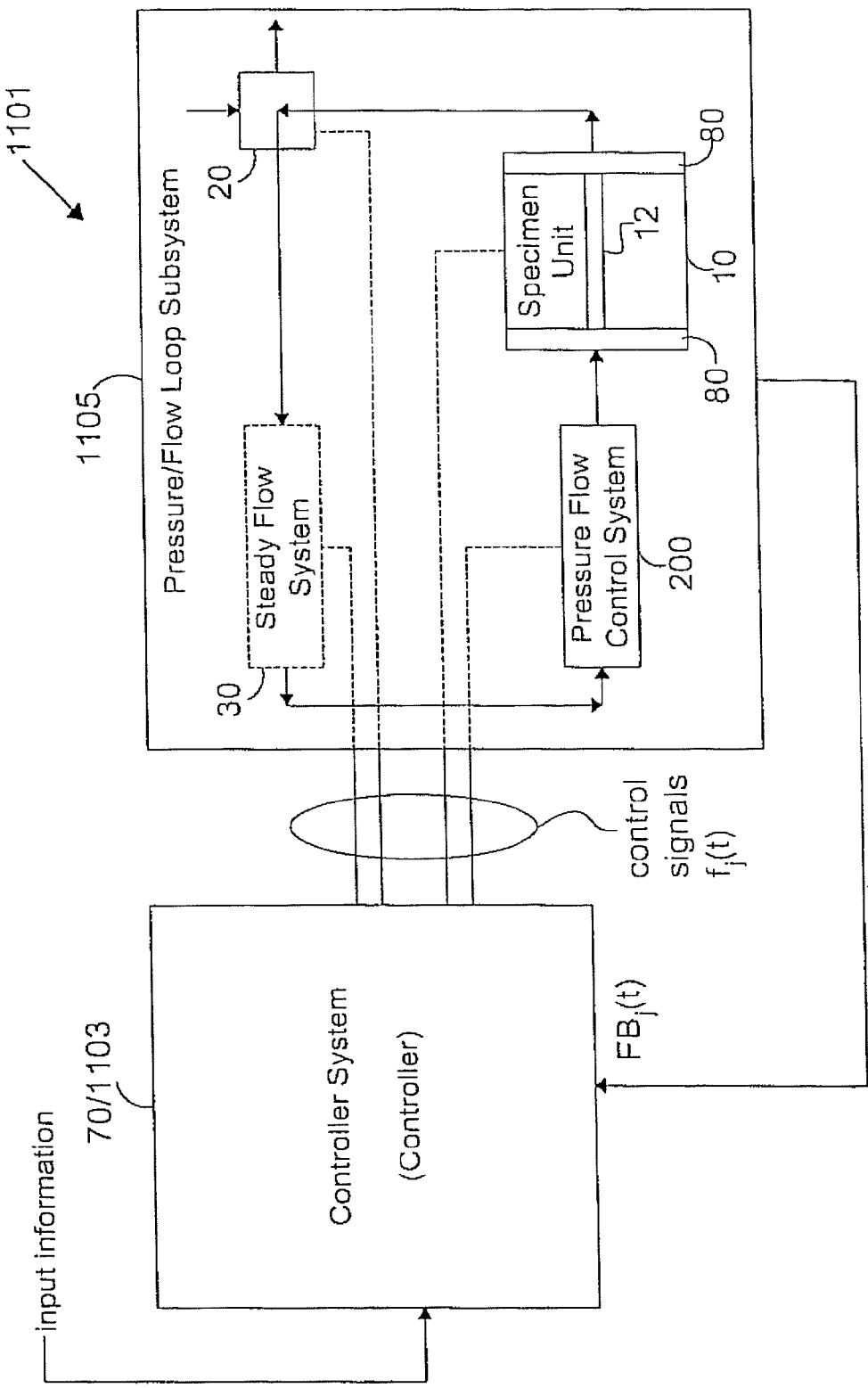
FIG. 16 shows an alternative block diagram of a system according to another embodiment of the invention.

FIG. 16 shows an alternative block diagram of a system 1101 with a specimen or tubular structure 12, such as system 1 of FIG. 1A according to another embodiment of the invention. System 1101 includes a controller 1103 and a pressure/flow loop subsystem 1105. Controller 1103 receives input data or information corresponding to desired dynamic conditions and translates that information to a set of N control signals $f_j(t)$, j=1, 2, 3, ..., N. The set of N control signals $f_j(t)$ can be a single control signal or multiple control signals. Pressure/flow loop subsystem 1105 includes pressure/flow loop components such as the various elements, devices or subsystems in the embodiments discussed herein. Pressure/flow loop components can include, for example, pressure/flow control system 200 (FIG. 1A) and any elements, devices or subsystems contained therein as well as other elements, devices or subsystems contained in the embodiments of the systems discussed herein, such as steady flow systems, specimen units, sensors, reservoirs, pumps, upstream or downstream pumps, steady flow pumps, occluders, external pressure controllers, axial strain system, slider carriage, torsion systems and any other elements in the pressure/flow control systems. Control signals $f_j(t)$ in turn are input to pressure/flow loop subsystem 1105 where each control signal $f_j(t)$ controls and/or adjusts one or more of the pressure/flow loop components.

As discussed above, the set of control signals $f_j(t)$ can be a single control signal or multiple control signals for driving the various components of the pressure/flow loop subsystem 1105. The various pressure/flow loop components of the pressure/flow loop subsystem 1105 can be controlled with respective control signals $f_j(t)$. In one embodiment, controller 1103 outputs a separate control signal $f_j(t)$ for each component to be controlled in the pressure/flow loop subsystem 1105.

Alternatively, some or all of the components that make up the pressure/flow loop subsystem 1105 could be mechanically coupled, such that an adjustment to one component using a control signal $f_j(t)$ will cause a predetermined adjustment in another component via such a mechanical coupling. This allows for the adjustment of multiple components using fewer control signals $f_j(t)$ than the number of components in the pressure/flow loop subsystem 1105. Such mechanical couplers are described in related U.S. Pat. No. 7,063,942 filed on Oct. 9, 2001, and incorporated by reference in its entirety.

Figure 27:
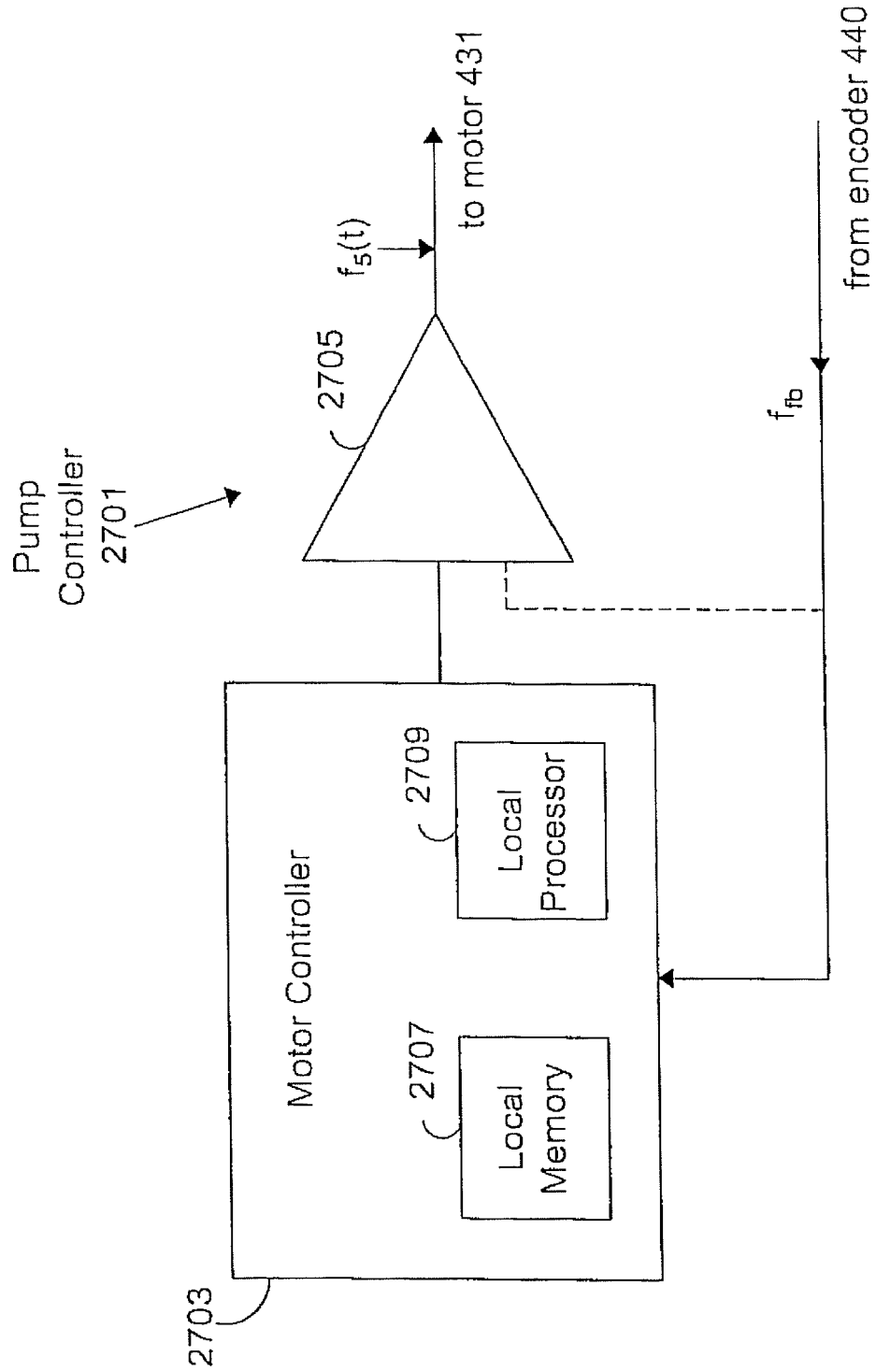
FIG. 27 shows a motor controller in accordance with an embodiment of the invention.

In addition, the individual components in the pressure/flow loop subsystem 1105 can also be non-mechanically coupled and adapted to communicate with each other independently of controller 1103, including, for example, feedback and status information of one or more of the individual components or feedback information. Such coupling of information or data among individual elements or components of the pressure/flow loop subsystem 1105 can include pressure/flow loop component feedback information, such as the status of respective pressure/flow loop components (see, for example, $F_{fb}$ in FIG. 27) and/or feedback data or information, such as $FB_j$ or other information. Such non-mechanical coupling provides a non-mechanical implementation of mechanical coupling, including but not limited to the mechanical coupling described in U.S. Pat. No. 7,063,942. Local processing can also be used, as discussed, for example, with respect to FIGS. 28 and 27.

Controller 1103 includes, for example, any control systems discussed herein including, for example, control systems 70 in FIGS. 1A-3D and 6A-6D. Controller 1103 can receive input information or input data corresponding to desired dynamic conditions such as desired pressure, flow and diameter, desired SPA's, sample dimensions and structural information related to a sample or samples. Controller 1103 can also receive feedback information such as feedback signals $FB_j(t)$ corresponding to one or more measured dynamic conditions such as pressure, flow, diameter, velocity, presence, amounts and concentrations of particles, nano-particles, organic and inorganic molecules and/or any biological substances, drugs or materials introduced into the fluid in pressure/flow loop subsystem 1105 or grown or emerging from the specimen 12 and/or the growth of biological materials in specimen unit 10 or as otherwise discussed herein.

Input information can also include information regarding the pathology and degree of pathology to be simulated, the structure and properties of the sample or samples, the length of time a sample should be subjected to a particular set of dynamic conditions, the rate and manner in which the dynamic conditions change or progress over time, the composition of the fluid and the rate and manner in which the composition of the fluid changes over time. Controller 1103 can also serve to couple various types of dynamic conditions such as pressure (P), flow (O), diameter (D), length or stretch (L) and twist/torque (T) to shear stress (WSS), circulation strain (CS), and in turn the SPA, and vice versa as discussed herein in accordance with preferred embodiments of the invention.

Input information can also include information corresponding to characteristics of signals representing the dynamic conditions including, for example, the frequency, phase, amplitude, slew rates and/or duty cycle of the dynamic conditions, which controller 1103 translates into control signals $f_j(t)$ which in turn drive the various components of the pressure/flow loop subsystem 1105 in accordance with embodiments of the invention. The dynamic conditions may be characterized by discrete or continuous random variables or stochastic variables.

Feedback signals $FB_j(t)$ are received by controller 1103, which correspond to one or more measured dynamic conditions in pressure/flow loop subsystem 1105, as discussed herein with respect to various embodiments of the invention. Feedback signals $FB_j(t)$ can be dynamic conditions actually measured at region A of specimen 1112 (as shown in FIG. 11, in accordance with an embodiment of the invention. Feedback signal $FB_j(t)$ can be measured dynamic conditions at other locations in pressure/flow loop system 1105, either upstream or downstream from specimen 12 in pressure/flow loop system 1105. Controller 1103 receives feedback signals $FB_j(t)$ and in turn can produces control signals $f_j(t)$ for pressure/flow loop subsystem 1105.

FIGS. 17A and 17B show examples of various forms or types of dynamic conditions g(t). Forms or types of dynamic conditions refers to a directly or indirectly measurable time varying physical condition of or related to tubular structures and/or fluids passed therethrough broadly defined herein. Examples of various forms of types of dynamic conditions g(t) which can be produced by system 1101 include pressure P(t), flow Q(t) wall shear stress WSS(t), circumferential strain CS(t,) diameter D(t), length or stretch (L) and twist/torque (T) as broadly defined herein in accordance with the embodiments of the invention. System 1101 can simulate one, two, three or more forms or types of dynamic conditions in states that may occur in biological as well as non-biological systems.

FIG. 17B lists types that are linked to dynamics of fluid materials. These include, but are not limited to, for example, concentration of fluid material ($C_{fm}$), expression of fluid material ($E_{fm}$), amounts of fluid material ($A_{fm}$), velocity of fluid material ($V_{fm}$) and flow of fluid material ($Q_{fm}$).

As above, region A represents a portion of the specimen 12 or tubular structure 1112 is said to have dynamic conditions $g_1, g_2, \ldots g_n$ if the measured values of $g_1, g_2, \ldots g_n$ over a region A are substantially within the ratios of $$\frac{\Delta g_1}{g_1 Range}, \frac{\Delta g_2}{g_2 Range} \ldots \frac{\Delta g_n}{g_n Range},$$

respectively, where $g_1$Range, $g_2$Range $\ldots g_n$Range can be, for example, mean values of the potential ranges of $g_1, g_2, \ldots g_n$, respectively. In preferred embodiments, over a region A, $$\frac{\Delta g_j}{\Delta g_j Range} \leq .35,$$

and preferably $$\frac{\Delta g_j}{\Delta g_j Range} \leq .25,$$

and more preferably $$\frac{\Delta g_j}{\Delta g_j Range} \leq .15$$

and even more preferably $$\frac{\Delta g_j}{\Delta g_j Range} \leq .05.$$

Figure 18:
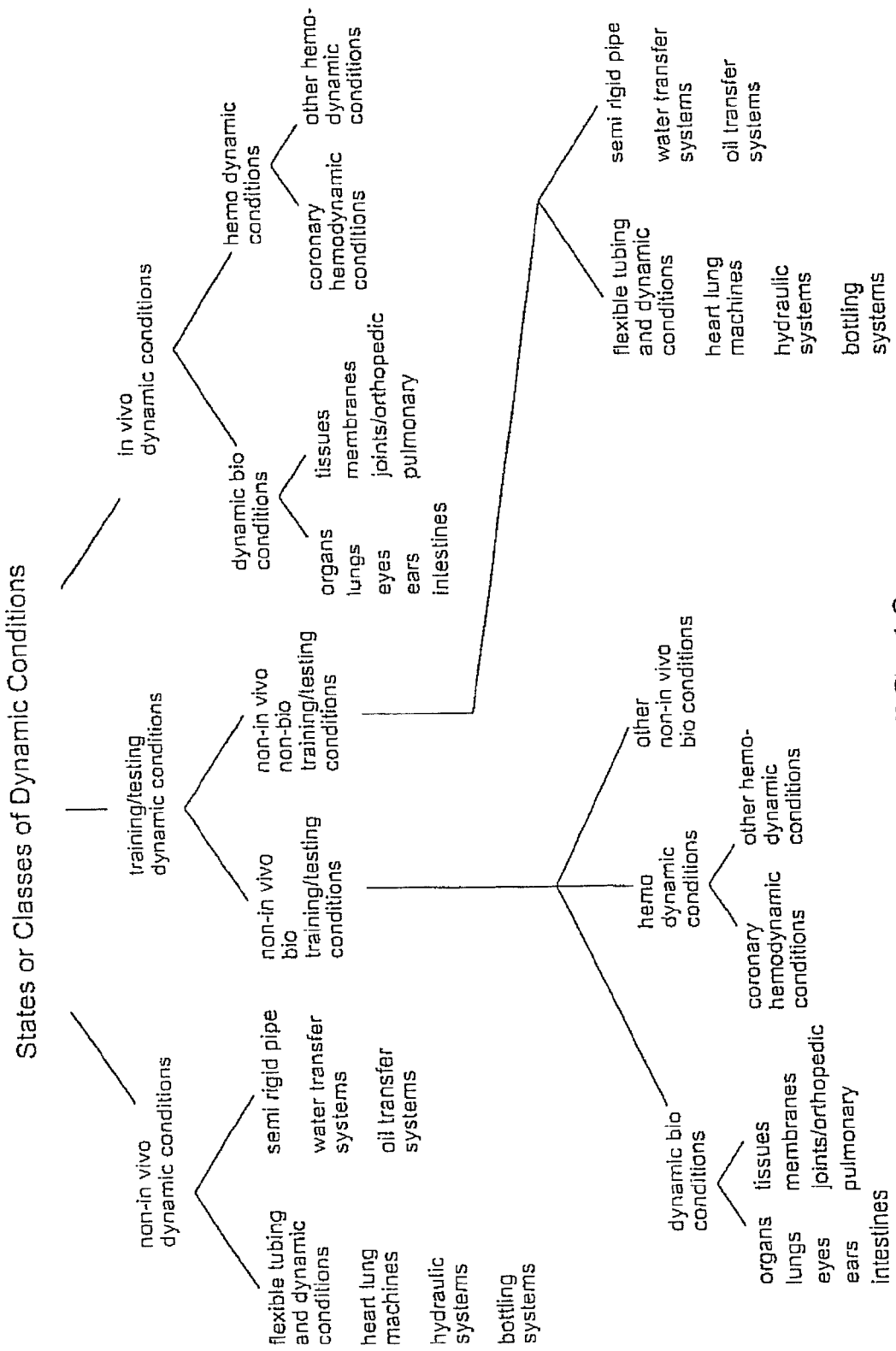
FIG. 18 shows examples of classes of dynamic conditions that can be simulated according to various embodiments of the invention.

FIG. 18 shows examples of classes of dynamic conditions that can be simulated by systems according to various embodiments of the invention. Classes of dynamic conditions refer to the location of the tubular structure at which a set of dynamic conditions to be simulated might occur. Dynamic conditions that occur in vivo are referred to herein from time to time as in vivo dynamic conditions. In vivo dynamic conditions include dynamic in vivo bio conditions and hemodynamic conditions. Dynamic in vivo bio conditions may include, for example, dynamic conditions that cells, tissues, or organs, experience in vivo other than hemodynamic conditions. Dynamic conditions can also include non-biological dynamic conditions found in tubular structures as broadly defined herein in accordance with alternative embodiments of the invention.

FIG. 19 shows a block diagram of controller 1103 which includes a translator 1113 and a dynamic parameter or dynamic condition generator 1117. Input information can include dynamic conditions represented by $g_i(t)$ according to an embodiment of the invention. For example, dynamic conditions $g_1(t)$, $g_2(t)$ and $g_3(t)$ could be pressure P(t), flow Q(t), and diameter D(t), at a region A, respectively. Input information can be information which is used to characterize the dynamic conditions $g_j(t)$. Input information can be used to retrieve certain preselected dynamic conditions $g_j(t)$ stored in controller 70 and/or generate dynamic conditions and/or associate or link dynamic conditions or states of physiology as required to produce control signals for pressure/flow loop subsystem 1105 in accordance with embodiments of the invention.

FIG. 20 shows a translator 1113 which receives dynamic conditions $g_j(t)$ and translates those dynamic conditions to N control signals $f_1(t) \ldots f_N(t)$. The number and characteristics of the control signals $f_j(t)$ depend on the architecture implemented for pressure/flow loop subsystem 1105 as will be discussed in accordance with various embodiments of the invention.

Figure 21:
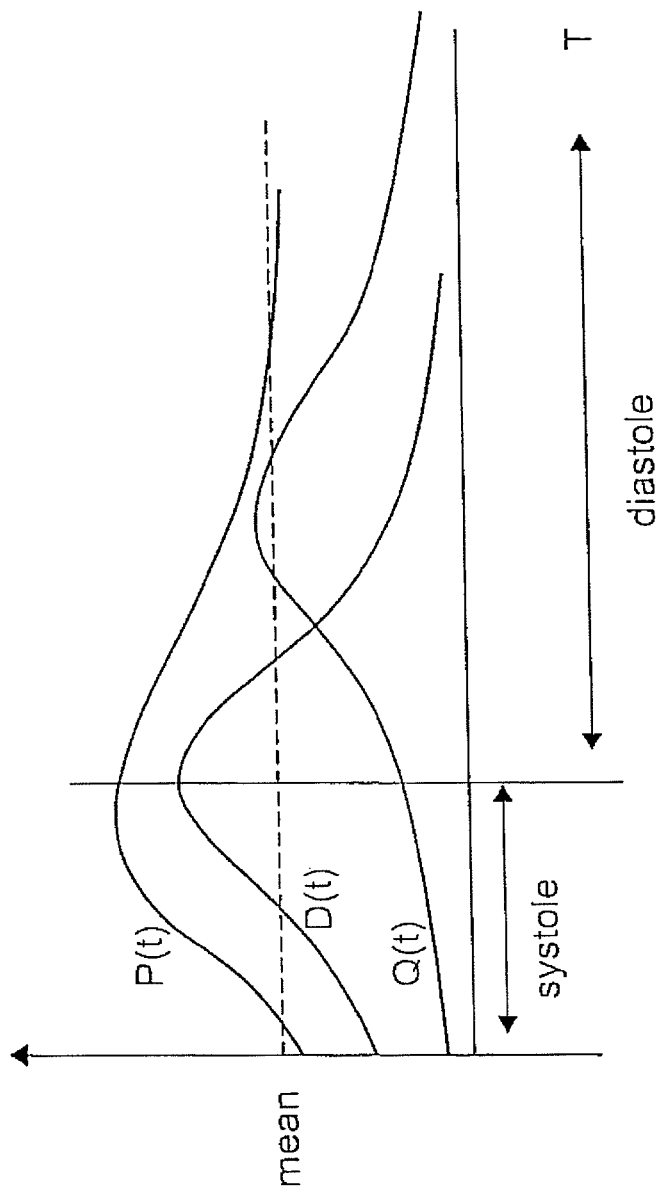
FIG. 21 shows an exemplary physiological coronary flow.

FIG. 21 shows physiological coronary flow Q(t) and pressure P(t) to be produced by system 1101 at, for example, specimen 12 of FIG. 18. In this example, the state includes types of dynamic conditions, pressure P(t), flow Q(t) and diameter D(t) where diameter represents the outer diameter of a tubular structure. The class of dynamic conditions is in vivo hemodynamic coronary conditions. A representative signal corresponding to pressure P(t) can be generated digitally with signal processing techniques or actually measured by sampling over a period T or other methods as known to one of ordinary skill in the art. Controller 1103 can perform a Fast Fourier Transform (FFT) on P(t) to yield the amplitude and phase of P(t) for the first and higher order harmonics. In embodiments of the invention, amplitude and phase of at least the first harmonic is determined and/or utilized, and preferably the first two harmonics, and more preferably the first three harmonics, and more preferably at least the first 4-10 or more harmonics are determined and utilized.

Controller 1103's capability to vary one dynamic variable while keeping others constant, for example, to vary pressure P(t) while maintaining flow Q(t) and/or diameter D(t) constant, enables controller 70 to "dial up" a preselected set of dynamic variables.

Figure 22:
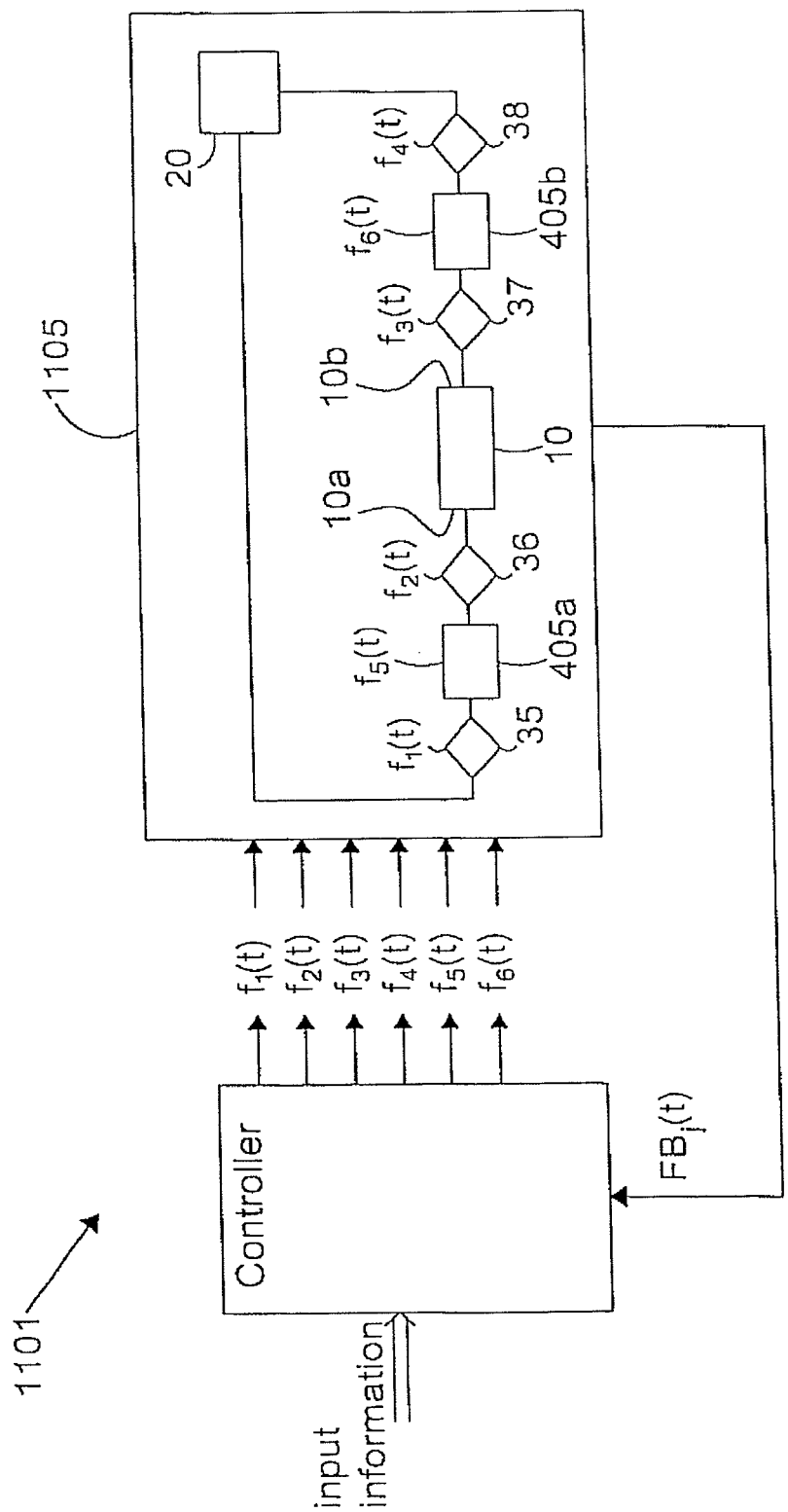
FIG. 22 shows an exemplary pressure/flow loop subsystem in accordance with an embodiment of the invention.

FIG. 22 shows an exemplary pressure/flow loop subsystem 1105 for system 1101 of FIG. 18 in accordance with an embodiment of the invention. Pressure flow loop subsystem 1105 includes bellows pumps 405a and 405b positioned at the upstream and downstream ends 10a and 10b, respectively, of the specimen unit 10 in concert with occluder valves 35-38 respectively positioned upstream and downstream of each of the bellows pumps 405a, 405b to generate an exemplary dynamic condition. A set of control signals $f_1$-$f_4$ which correspond to the desired condition are generated by the control system 70 to control the occluder valves 35-38, and dynamic control signals $f_5$ and $f_6$, control operation of each of the bellows pumps 405a, 405b to generate the desired condition in the specimen unit 10. For ease of discussion, the valves 35-38 are either fully open or fully closed. However, it is well understood that the valves 35-38 may at any given time be partially open/closed, and that appropriate slew rates may be applied to the opening/closing of any of the valves 35-38 to generate different conditions in the specimen unit 10 as required.

Figure 23A:
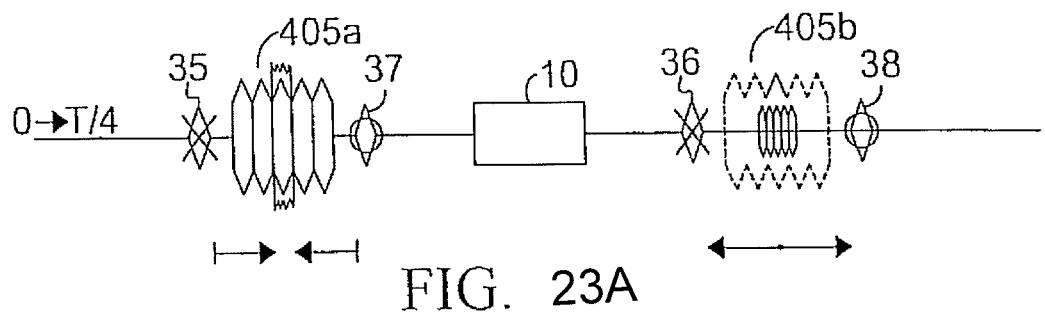
FIGS. 23a-23d are diagrams that show various stages of a plurality of pumps.
Figure 23B:
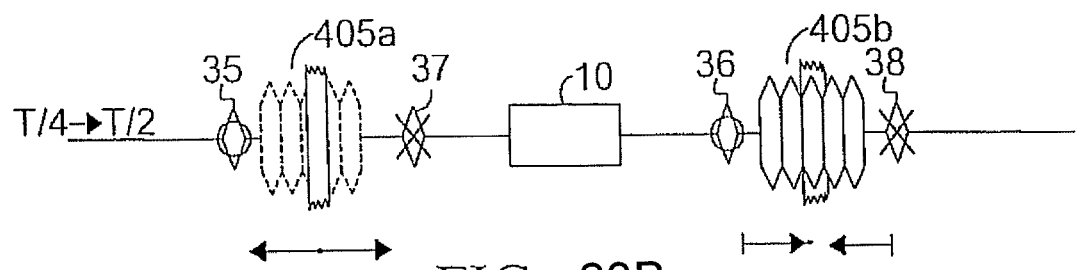
Figure 23C:
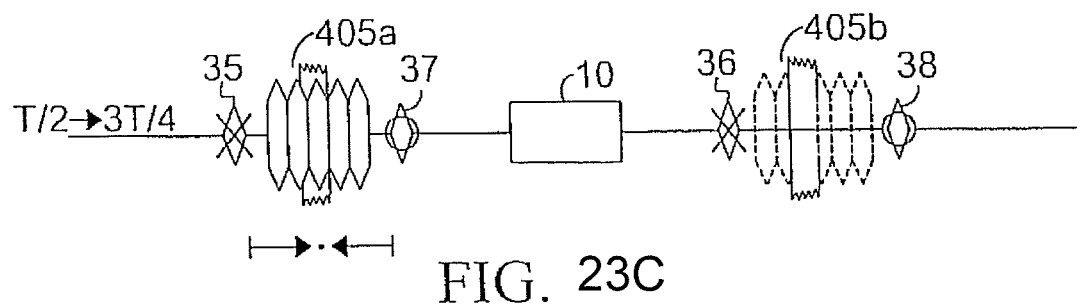
Figure 23D:
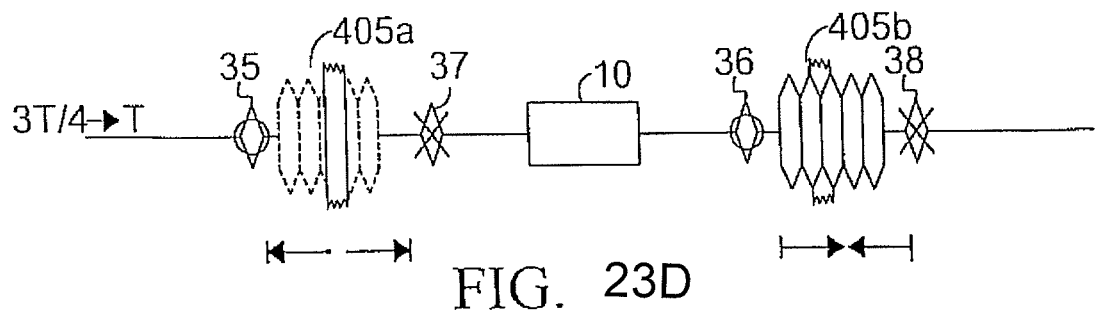
Figure 24:
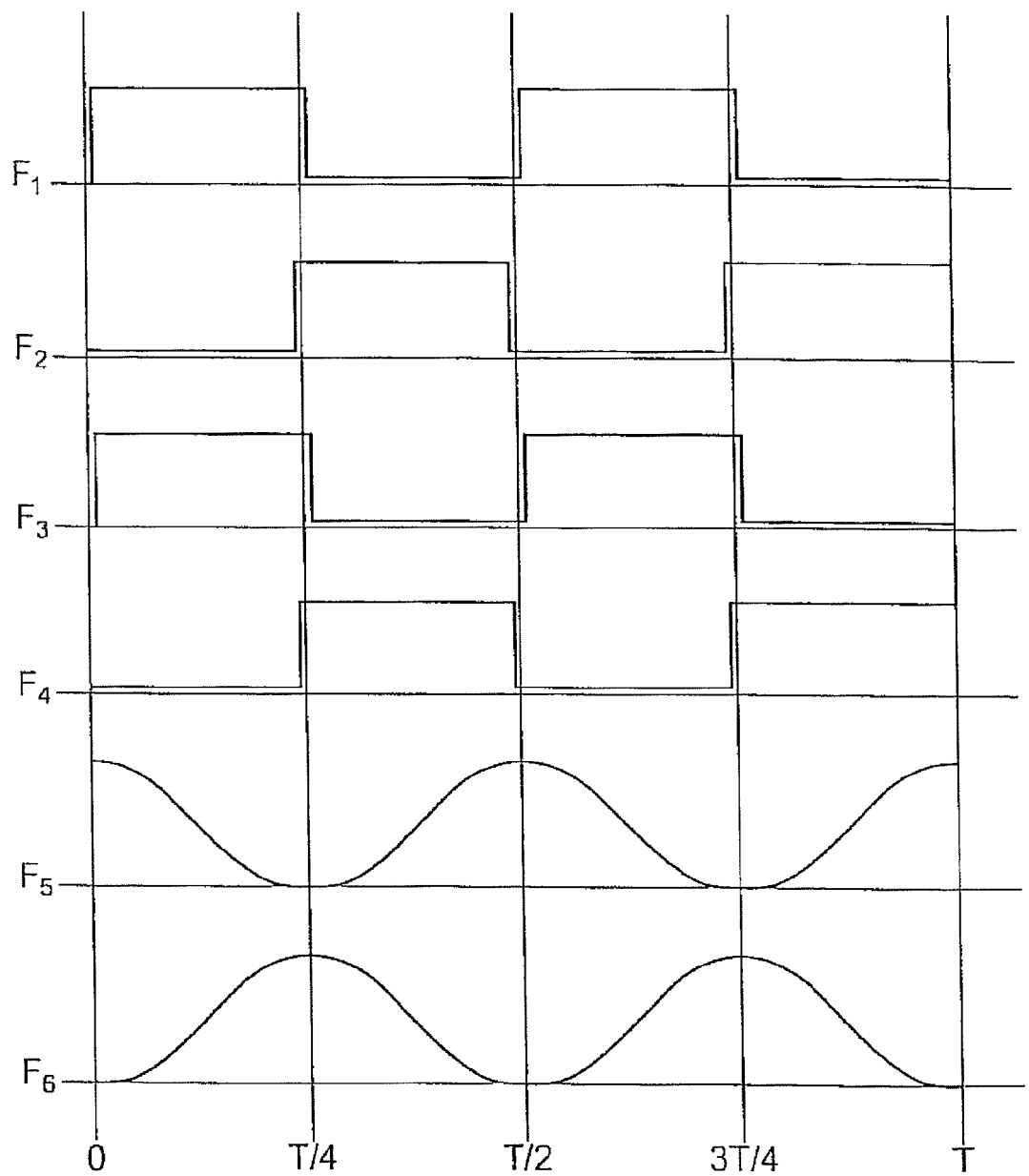
FIG. 24 shows a plurality of states during one cycle of operation.

FIGS. 23a-23d show various stages of bellows pumps 405a and 405b and FIG. 24 shows states during one cycle, or period T of operation has been divided into four segments 0-T/4, T/4-T/2, T/2-3T/4, and 3T/4-T. One period of operation can correspond to cycle of or heart beat or as described herein in accordance with embodiments of the invention. At time T=0, as shown in FIG. 23a, the upstream pump 405a is fully expanded and full of fluid, and the downstream pump 405b is fully contracted, thus having little to no fluid capacity. Both of the upstream valves 35 and 36 are closed, while the downstream valves 37 and 38 are open, thus containing the fluid between the valve 35, through the first pump 405a and the specimen unit, and to the valve 36. As the system moves to the condition T/4, with the valves 37 and 38 open, the upstream pump 405a contracts to push the fluid into the specimen unit 10, and the downstream pump 405b expands to prepare to draw fluid away from the specimen unit 10 and into the pump 405b once the valve 36 is opened. Thus, at time T/4, the valves 35 and 36 are open, the valves 37 and 38 are closed, the upstream pump 405a is contracted, and the downstream pump 405b is expanded.

As the system moves from this arrangement/condition at T/4, as shown in FIG. 23b, towards T/2, the valves 35 and 36 open, the valves 37 and 38 close, the upstream pump 405a expands once again fill with fluid, and the downstream pump 405b contracts to expel fluid from the pump 405b and out into the downstream end of the flow loop towards the reservoir 20. As the system moves from this arrangement/condition at T/2, as shown in FIG. 23c, towards 3T/4, the valves 35 and 36 once again close, the valves 37 and 38 once again open, the upstream pump 405a contracts to push fluid into the specimen unit 10, and the downstream pump 405b expands to draw fluid from the specimen unit 10 and into the pump 405b.

From this point, one cycle, or "pulse," is completed as the system moves to from 3T/4, as shown in FIG. 23d, to time T, where the valves 35 and 36 open, the valves 37 and 38 close, the upstream pump 405a expands once again fill with fluid, and the downstream pump 405b contracts to expel fluid from the pump 405b and out into the downstream end of the flow loop towards the reservoir 20.

It is noted that, in this particular example, the flow of fluid through the specimen unit 10 is a substantially regular pulsatile flow in which fluid is drawn into the specimen unit 10, held there for a given (small) amount to time, and then drawn out into the flow loop. In this particular example, simply for ease of discussion, the expansion and contraction of the bellows pumps 405a, 405b is shown to occur substantially about the centers of the bellows. However, by expanding and/or contracting the pumps 405a, 405b in different directions from those shown in FIGS. 23a-23d, such as by forcing all of the fluid held in the bellows to flow in a single direction which may be opposite that of the fluid held in the other bellows, and/or by varying the rate/timing of the opening and closing of the valves 35-38, numerous different conditions may be generated. More specifically, as the fluid flows into and out of the specimen unit 10 through the interaction of the fluid pushed into and drawn out of the specimen unit 10 by the upstream and downstream pumps 405a, 405b, numerous different combinations of pressure and/or flow rate may be generated as the fluid is forced to occupy the same space and/or change direction as it "collides" in the specimen unit 10, or is simultaneously drawn out of the specimen unit 10a from both the upstream and downstream ends 10a, 10b.

Figure 25A:
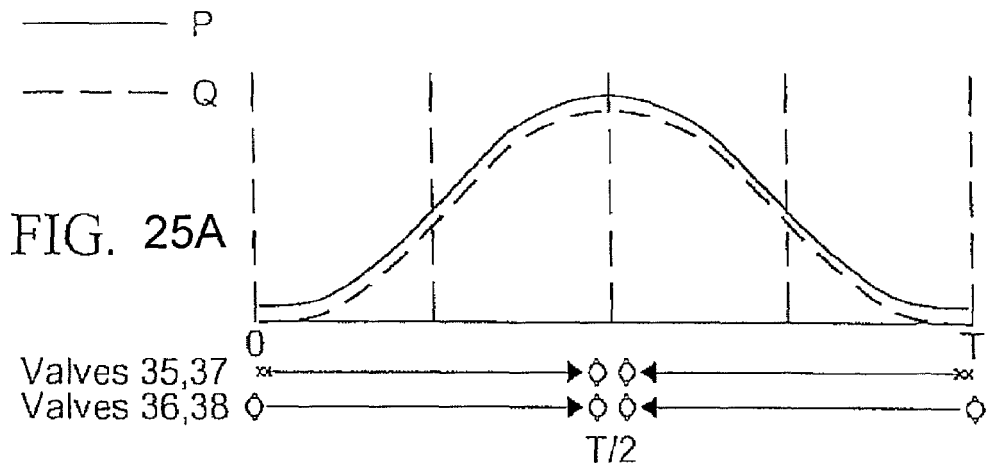
FIGS. 25A-25C exemplary dynamic conditions relating relative phases of pressure and flow.

An exemplary dynamic condition in which pressure and flow are substantially in phase, in which SPA is essentially 0°, is shown in FIG. 25A. In this essentially healthy condition, the valve 35 would initially be closed and the pump 405a full of fluid which is pumped through open valve 37 into the specimen unit 10, out of the specimen unit 10 through open valve 36, where it is stopped by closed valve 38, pushed back into the specimen unit 10 through the action of the pump 405b, and then drawn out again through open valves 37 and 38 into the flow loop and towards the reservoir 20.

Figure 25B:
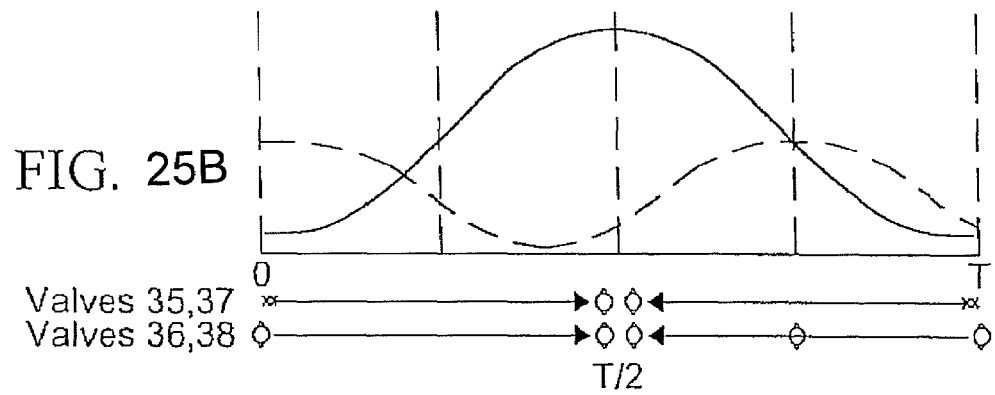
Figure 25C:
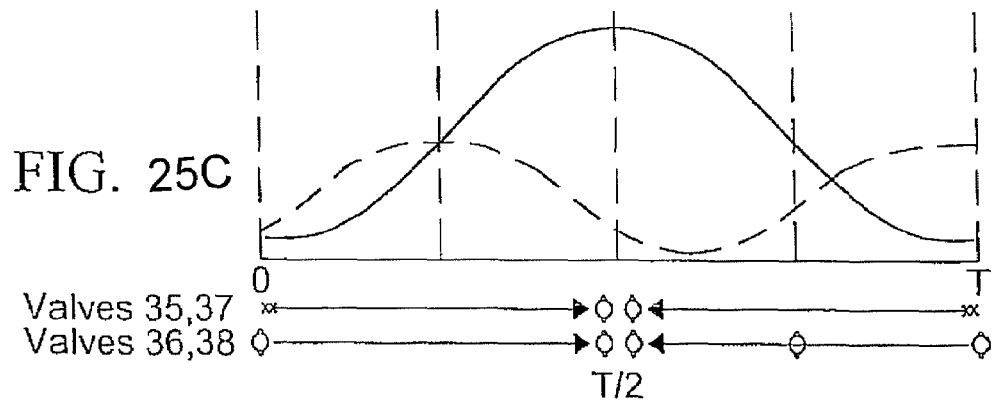

Another exemplary dynamic condition in which pressure and flow are 90° out of phase, or an SPA of essentially 90° representative of a somewhat diseased condition, is shown in FIG. 25B. Still another exemplary condition in which pressure and flow are 180° out of phase, or an SPA of essentially 180° representative of a more severely diseased condition, is shown in FIG. 25C. These conditions may be generated by varying the direction(s) in which the fluid is moved by the pumps 405a, 405b into and out of the specimen unit 10, and the varying degrees of pressure and/or flow disturbance or acceleration experienced as a result.

Figure 26:
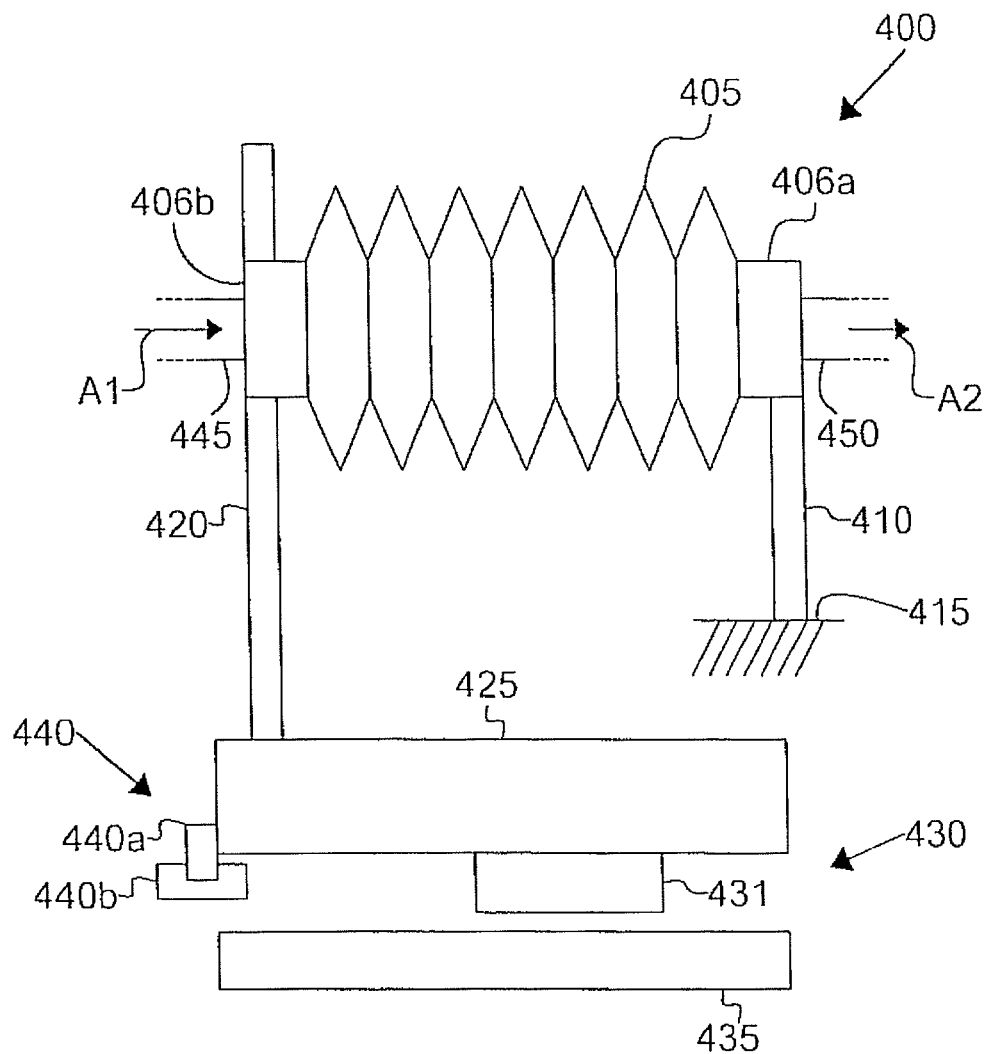
FIG. 26 shows a schematic diagram of an exemplary pump.

FIG. 26 shows a schematic diagram of features of a bellows pump 400 such as bellows pumps 405a and 405b of FIG. 22. Pump 400 is one example of a pump that can be implemented in systems. In accordance with alternative embodiments of the invention. A first end 406a of bellow 405 is fixed, for example, to a first support 410. The first support 410 is shown in FIG. 26 as attached to a structure 415 that renders it substantially unmovable. The second end 406b of the bellow 405 is attached to a movable support 420.

The movable support 420 is attached to a movable plate 425, which is in turn movable by means of a drive system 430 comprising a linear motor 431 and magnetic plate 435 in accordance with an embodiment of the invention. The linear motor 431 interacts with the magnetic plate 435 to move the movable plate 425 and therewith the movable support 420 and the second end 406b of the bellow 405. Other types of drive systems may also be appropriate.

The bellow 405 may be made, for example, of plastic, such as polypropylene, or silicon.

The drive system 430, and in particular, the linear motor 431 can be driven by one or more control signals. An encoder unit 440 may be arranged to include an encoder 440a attached to the movable plate 425, and a reader 440b, which senses a position of the movable plate 425 and provides the feedback signal $f_{fb}$ to the pump controller 2701. The encoder unit 440 may be, for example, a mechanical encoder, an optical encoder, a capacitive encoder, a magnetic encoder or a laser encoder, which would include a laser and corresponding reader.

In this exemplary pump, blood flows into the bellows pump 400 in a direction of arrow 36 in FIG. 26 via orifice 445 and exits the pump 400 in a direction of arrow A2 via orifice 450. The pump 400 is provided with the control signal, such as control signal $f_5(t)$ discussed above, received from controller 70, which controls the pumping of the pump 400 to provide the desired flow characteristics. That is, the drive system 430, including linear motor 431 and magnetic plate 435, move the movable support 420 and the second end 405b of the bellows pump 405 to create the desired pumping effect in response to the control signal $f_5$. The feedback signal $f_{fb}$ indicative of the position of the movable plate 425 is provided by the encoder unit 440 to pump controller 2701 to ensure the desired pumping effect is being created.

The drive system 430 is driven by a control signal, such as control signal $f_5(t)$ discussed above, received from controller 70. The control signal $f_5(t)$ controls the current to the linear motor 431 via pump controller 2701 shown in FIG. 27, according to an embodiment of the invention. Pump controller 2701 includes motor controller 2703 and amplifier 2705. Motor controller 2703 may reside in controller 70. In alternative embodiments of the invention, motor controller 2703 may reside in dynamic condition generator 1117 and/or translator 1113. Motor controller 2703 may independently control one or multiple motors 431. Feedback signal $f_{fb}$ can be received from encoder 440 by pump controller 2701 at motor controller 2703 and/or amplifier 2705. An example motor controller 2703 is SPii Plus HP Series motion controller by ACS Motion Control. Examples of motors 430 includes AC servo D/C brushless motors, DC brush motors nanomotion piezo-ceramic motors, step motors and servo motors. Motor 430 preferably has sub-nanometer resolution such as diose used in semiconductor manufacturing, water inspection, or flat panel display assembly and testing.

Figure 28:
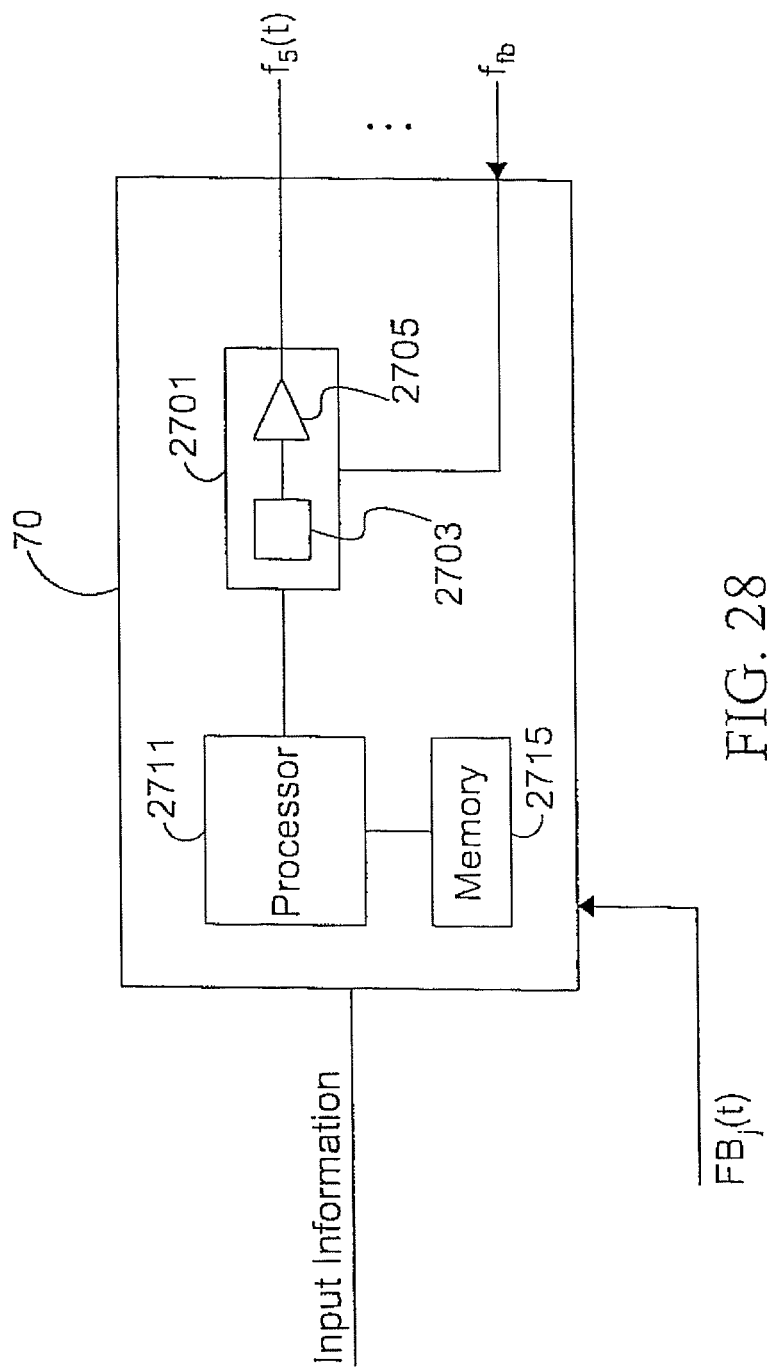
FIG. 28 shows a controller having a processor coupled to a pump controller in accordance with an embodiment of the invention.

FIG. 28 shows controller 70 with processor 2711 coupled to pump controller 2701 and memory 2715 in accordance with an embodiment of the invention. Motor controller 2703 in pump controller 2701 can be used to process input information received by controller 70. See also FIGS. 18, 28, 19 and 22. Motor controller 2703 may include a local processor 2709 and memory 2707 such as cache memory or older types of memory. Referring to FIGS. 19 and 28, the roles of dynamic condition generator 1117 and translator 1113 can be shared to varying degrees by processor 2711 and local processor 2709 in motor controller 2703. Pump controller 2701 may take on the built of the processing in controller 70 so that processor 2711 functions merely to synchronize generation of dynamic conditions $g_j(t)$ and translate the dynamic conditions to control signals $f_j(t)$ based on input information to controller 70 according to one embodiment of the invention. In alternative embodiments, processor 2711 may perform a greater portion of the processing in controller 70. For example, processor 2711 can generate process input information to link to pump controller 2701 to yield control signals $f_j(t)$. The dynamic conditions $g_j(t)$ can be linked to input information in controller 70 at, for example, local memory 2707 and/or in memory 2715.

Referring again to FIGS. 18, 19 and 20 in accordance with embodiments of the invention, control signals $f_j(t)$ for pressure flow loop subsystem 1105 are determined by operating with a first set of controls signals $f_j(t)$ input to pressure flow loop subsystem 1105 and measuring a resulting first set of dynamic conditions and linking that first set of control signals with the resulting first set of dynamic conditions. One or more of the control signals are then slightly varied to yield a second set of control signals, measuring a resulting second set of dynamic conditions and linking the second set of control signals to the resulting second set of dynamic conditions. This process is repeated to form a discrete set of dynamic conditions linked to a corresponding set of control signals which can be stored, for example, as a lookup table in controller 70. The number of sets of dynamic conditions can vary depending on the desired flexibility of system 1101. A variety of interpolation techniques can also be used to interpolate between sets of dynamic conditions to provide corresponding sets of control signals thereby yielding a fully flexible "dial-up" system 1101 capable of producing sets or states of dynamic conditions between those determined using the above approach in accordance with yet another embodiment of the invention.

Figure 29:
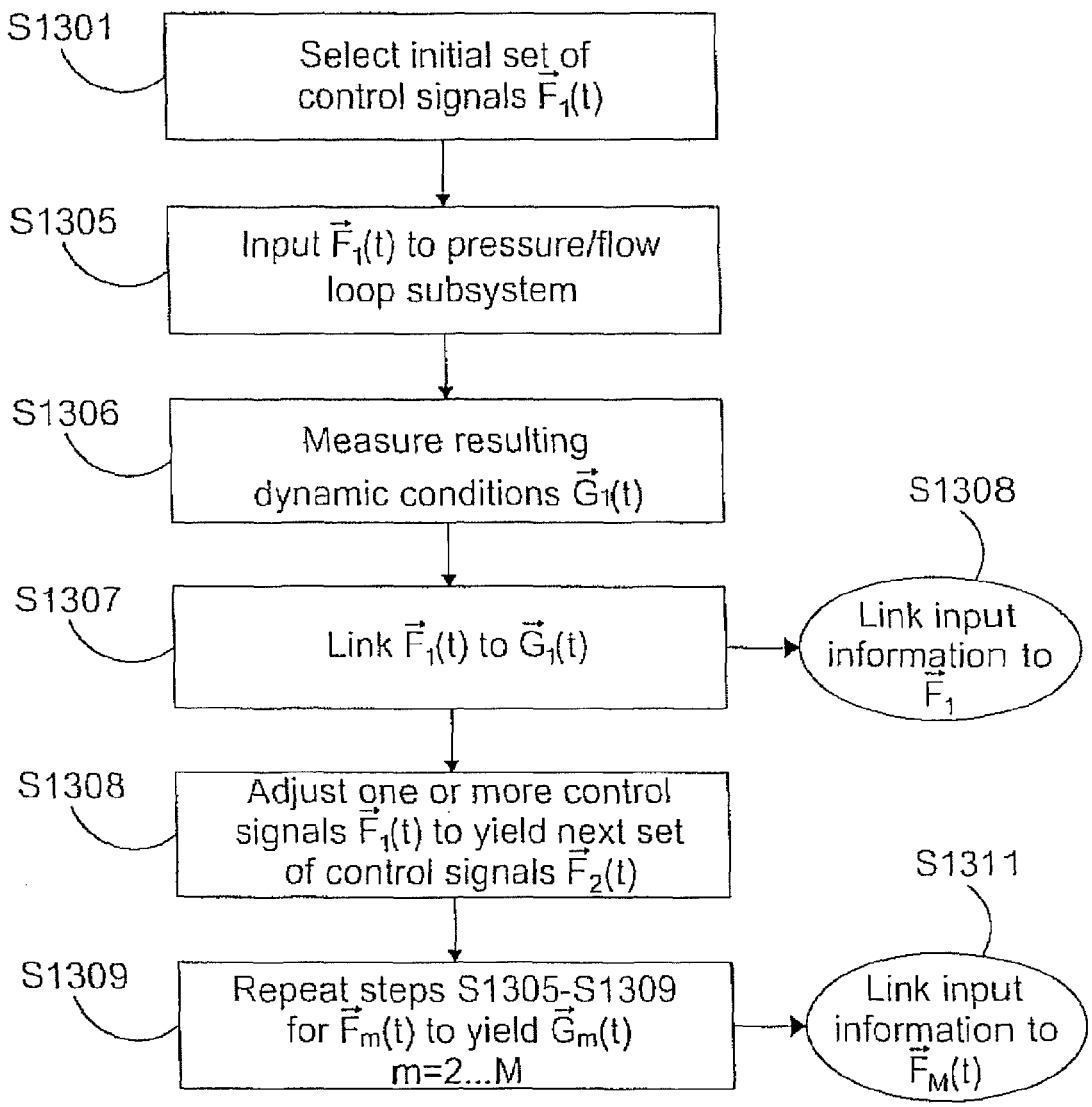
FIG. 29 shows an exemplary flowchart to determine control signals corresponding to dynamic conditions and/or input information according to an embodiment of the invention.

FIG. 29 shows steps that may be implemented to develop sets of control signals corresponding to dynamic conditions and/or input information according to an embodiment of the invention. Step S1301 involves selection of an initial set of control signals, which can be written as a vector $\overline{F}_1(t)$ of k control signals, namely, $\overline{F}_1(t)=(f_{11}(t),f_{12}(t) \ldots f_{1k}(t))$. As an example, an initial set of control signals can be a sinusoidal signal for pumps, as described in reference to various embodiments of the invention. Occluders in dynamic pressure/flow subsystem could be arranged to receive control signals as shown, for example, in FIGS. 22 and 24. At step S1305, the initial set of control signals $\overline{F}_1(t)$ are input to the pressure/flow loop subsystem 1105.

Step S1306 involves measuring an associated or corresponding set or state of dynamic conditions, which can be written as a vector $\overline{G}_1(t)$ of M dynamic conditions, namely, $\overline{G}_1(t)=(g_{11}(t),g_{12}(t) \ldots g_{1M}(t))$. Step S1307 involves linking or associating the resulting dynamic conditions $g_{1i}(t)$ to the initial stage or set of control signals $f_{1i}(t)$. Linking can include storing a lookup table in memories 2701 and/or 2705 (see FIGS. 28 and 27) of controller 70 or 1103 according to an embodiment of the invention. Step S1307 may also include storing characteristics of the measured dynamic conditions $g_{1j}(t)$ associating pathological as well as the shape or characterization of the signals representing the dynamic conditions to the control signals. Step S1309 involves adjusting or perturbing one or more control signals $f_{1j}(t)$ to yield a second set or state of control signals $\overline{F}_2$, which include element control signals $f_{2j}(t)$, then measuring the resulting second set or state of dynamic conditions $\overline{G}_2$, which include element dynamic conditions $g_{2j}(t)$.

This process can be repeated to produce a desired number of links between input information and/or dynamic conditions $\overline{G}_m$ and control signals $\overline{F}_m$ in accordance with embodiments of the invention. For example, implementation of steps S1301-S1309 involves assigning pumps in pressure/flow loop subsystem 1105, a sinusoidally varying control signal corresponding to position of the bellows versus time (as discussed with respect to bellows pumps 400 in FIG. 26) with a frequency approximately equal to a base heart rate. Step 1309 may then involve varying the phase of one of the bellows pumps with respect to the other bellows pump to establish a next set of control signals $\overline{F}_m$ and measuring the resulting set of dynamic conditions $\overline{G}_m$.

Alternatively, step 1309 might involve varying the amplitude or stroke length of one of the bellows pumps with respect to the other to establish a next set of control signals $\overline{F}_m$. Also, in accordance with linear and non-linear interpolation techniques, sets or states of dynamic conditions can be linked to associated sets of control signals to enable "dial-up" dynamic conditions.

Controller 70, 1103 can further be trained to produce dynamic conditions that evolve over time. This includes adjusting the frequency, phase or amplitude of the first and/or higher order harmonics of one or more dynamic conditions over multiple periods T of pulses.

For example, the first order frequency $\omega_1$ of one or more types of dynamic conditions can vary over time $TT^i$ in a predetermined manner. For example, the resting heart rate might be at 70 beats per minute. The dynamic conditions such as pressure P(t), flow Q(t) and/or diameter D(t) could gradually change from a first order frequency of 70 Hz to 130 Hz over a time span of minutes, hours, etc. The rate and progression of change for different order harmonics may differ for any one dynamic condition as well as for different types of dynamic conditions P(t) versus Q(t), D(t), etc. This holds for the phase $\theta j$ of the first or higher order harmonics of one or more dynamic conditions.

Figure 30:
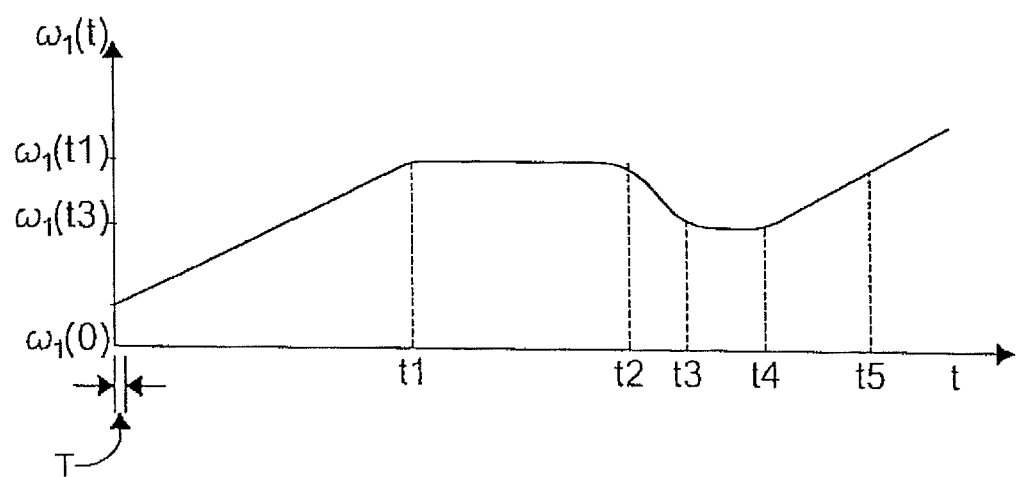
FIG. 30 shows variations of a first order harmonic $\omega_1(t)$ of a dynamic variable g(t) in accordance with an embodiment of the invention.

FIG. 30 shows variations over time in the first order harmonic $\omega_1(t)$ of a dynamic variable g(t) which can be produced in accordance with an embodiment of the invention. At t=0, might correspond to a resting heart rate $\omega_1(0)=1/T$ (say 70 cycles per second), where T is the period of the heartbeat. The first order frequency $\omega_1(t)$ then increases to $\psi_1(t1)$ (say 120 cycles per second) over multiple periods T (e.g. 5T, 10T, 100T, 1000T . . . ) at time $t_1$ ($t_1$=5T, 10T, 100T, 1000T . . . ). Between time $t_1$ and $t_2$, the first order harmonic $\omega_1(t)$ remains relatively constant at $\omega_1(t2)$ then decreases to $\omega_1(t)=\omega_1(t3)$ (say 100 cycles per second) at time $t_3$. Between time $t_3$ and $t_4$, $\omega_1(t)$ again remains relatively constant at $\omega_1(t3)$ and then increases back to $\omega_1(t)$ at $t_5$ and continues to increase for $t>t_5$. The above holds for higher order frequencies $\omega_{1j}(t)$ as well in accordance with embodiments of the invention.

Figure 31A:
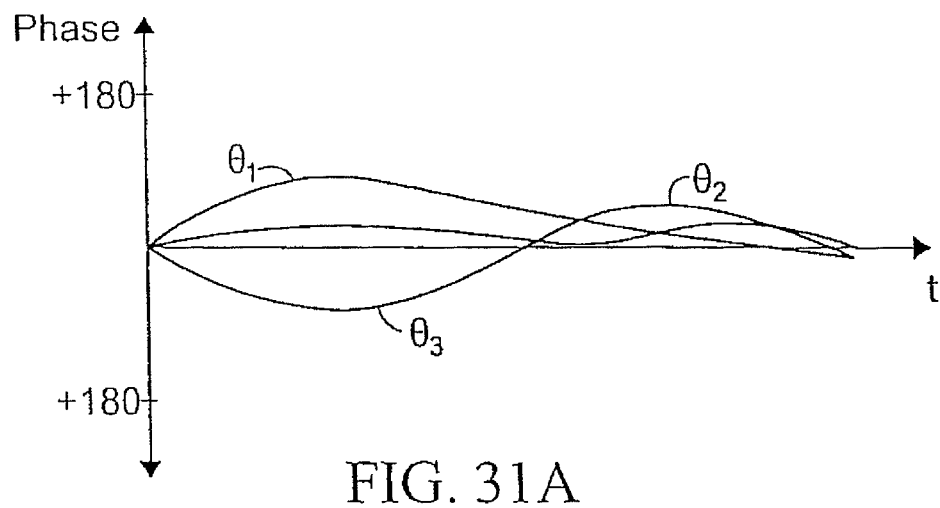
FIGS. 31A-31B shows an example of the variations in time of characteristics of three harmonics of a dynamic condition.

FIG. 31A shows an example of the variations in time of the phases $\theta_j$ of the first three harmonics for j=1, 2 and 3 of a dynamic condition g(t). The corresponding first three harmonics $\omega_1(t)$, $\omega_2(t)$ and $\omega_3(t)$ could remain constant or themselves varied over time in accordance with alternative embodiments of the invention. The number of harmonics whose phase and amplitude are utilized can be preferably 1, and more preferably at least 2 and more preferably at least 3 and more preferably at least 4-10. The same holds for multiple forms or types of dynamic conditions it being understood that the frequency $\omega_1(t)$ and phase $\omega_j(t)$ of one dynamic condition $g_1(t)$ may differ from the frequency $\omega_1(t)$ and phase $\theta_j(t)$ of a second or additional dynamic variables $g_1(t)$ in accordance with embodiments of the invention. In these embodiments of the invention, system 110 can be used to simulate a person or mammal exercising or exerting effort in any physical activity, experiencing shock, disease or any other situations which could naturally occur.

Figure 32:
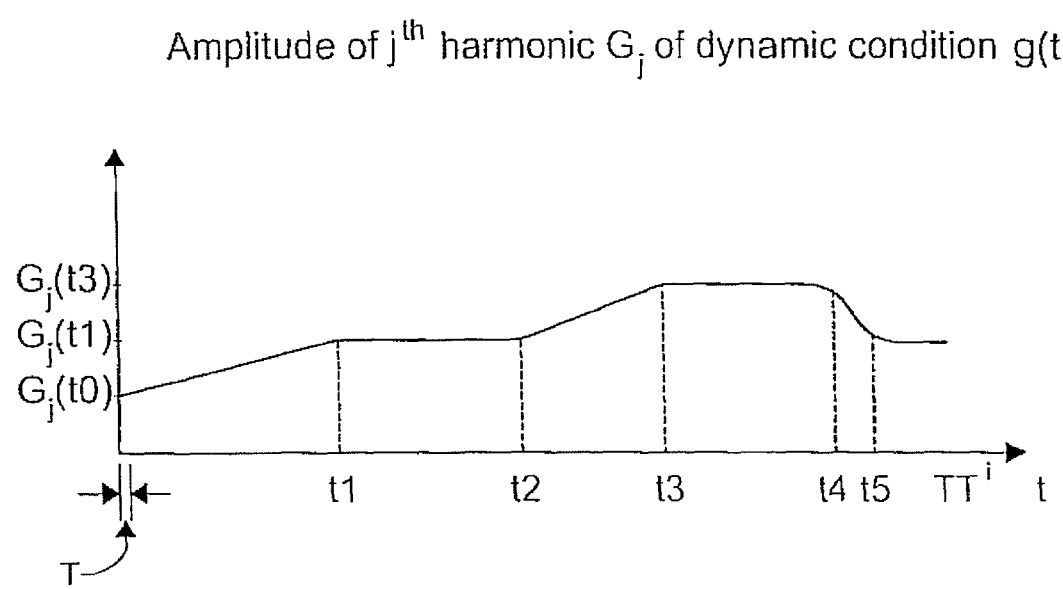
FIG. 32 shows variations of the jth harmonic amplitude of a dynamic condition in accordance with embodiments of the invention.

FIG. 32 shows variations of the jth harmonic amplitude $G_j$ of a dynamic condition g(t) where $$g(t) = \sum_{j=1}^{N} G_j \mu_j(\omega_j t + \theta_j) \tag{1}$$

where $\mu_j(\omega_j t+\theta_j)$ are normalized basis functions of dynamic condition g(t), such as sinusoids. Just as $(\omega_j(t)$ and $\theta_j(t))$ may vary over time T, the amplitude $G_j$ can vary over time in accordance with embodiments of the invention.

FIG. 32 presents one example of how the amplitude of the jth harmonic of dynamic condition g(t) (initially $G_j(0)$ at t=0), increases to $G_j(t_1)$ at t=$t_1$. The amplitude $G_j(t)$ remains at $G_j(t_1)$ until t=$t_2$, then increases to $G_j(t_3)$ at t=$t_3$, where it remains until t=$t_4$ at which point it decreases to $G_j(t_1)$ at t=$t_5$. Dynamic condition g(t) may be one of the types (FIGS. 17A and 17B) of dynamic conditions from one or more states or classes (FIG. 18) of dynamic conditions.

Figure 31B:
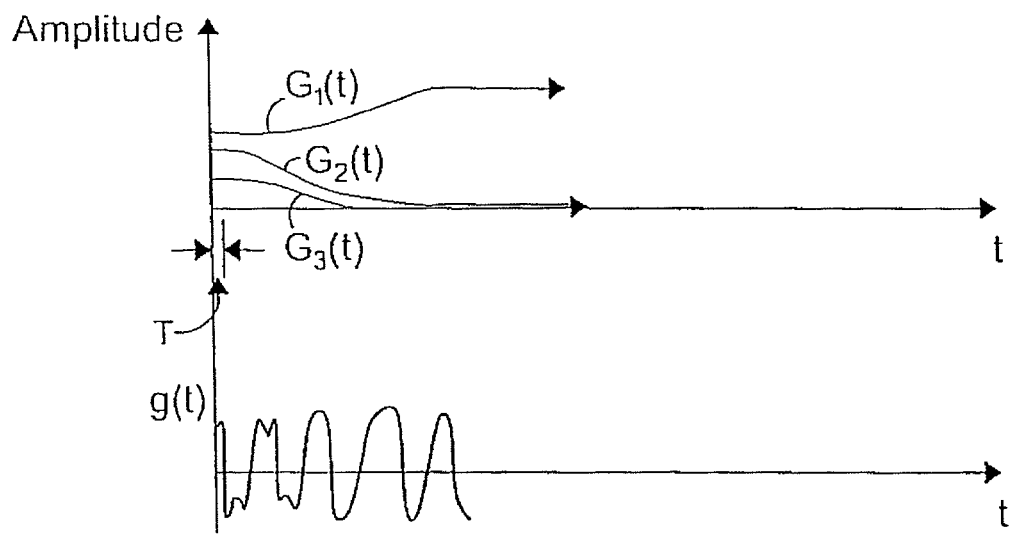

FIG. 31B shows an example of how amplitudes of the first three harmonics of a dynamic condition may vary with time as well as the corresponding dynamic condition in real time. At t=0, the first order amplitude $G_1(0)>G_2(0)$, the second order amplitude $G_2(0)$ is about 0.8 $G_1(0)$, and the third order $G_3(0)$ is about half of $G_1(0)$. The presence of the higher order terms for dynamic variable G(t) are apparent as variations in the plot of G(t) versus time. As t approaches $t_1$, the second and third order amplitudes $G_2(t)$ and $G_3(t)$ approach zero, which results in the dynamic condition $G(t)$ varying more sinusoidally.

Referring to Equation (1) above, $\overline{G}(t)$ represents a vector of N types of dynamic variables or conditions (FIGS. 17A and 17B) $g_i(t)$, that is i=1 . . . N where N≧2. Hence, $$\overline{G}=(g_1(t),g_2(t) \ldots g_N(t))$$

System 1101 produces an experience $\overline{G}$ at region A in a tubular structure in accordance with embodiments of the invention. An experience can correspond to actual dynamic conditions experienced at region A of tubular structures in vivo or actual dynamic conditions experienced at region A of tubular structures (including non-biological dynamic conditions) that are not in vivo. In addition, an experience can correspond to dynamic conditions which are used to train or condition a tubular structure.

For example, three experiences $\overline{G}^A(t), \overline{G}^B(t)$ and $\overline{G}^C(t)$ can be represented as:

$$\overline{G}^A=(g_1^A(t),g_2^A(t) \ldots g_N^A(t))$$

$$\overline{G}^B(t)=(g_1^B(t),g_2^B(t) \ldots g_N^B(t) \ldots g_{N'}^B(t))$$

$$\overline{G}^C(t)=(g_1^C(t),g_2^C(t) \ldots g_N^C(t) \ldots g_{N'}^C(t) \ldots g_{N''}^C(t))$$

where the experiences may be actual in vivo, actual non-biological, training or conditioning and/or combinations thereof in accordance with embodiments of the invention. The types of dynamic conditions (FIGS. 17A and 17B) for experiences $\overline{G}^A$, $\overline{G}^B$ or $\overline{G}^C$ are not necessarily the same. For example, $g_1^A$ is not necessarily the same as $g_1^B(t)$ or $g_1^C(t)$. Also, the number of dynamic conditions N, N' or N" can be different in accordance with embodiments of the invention.

Figure 33A:
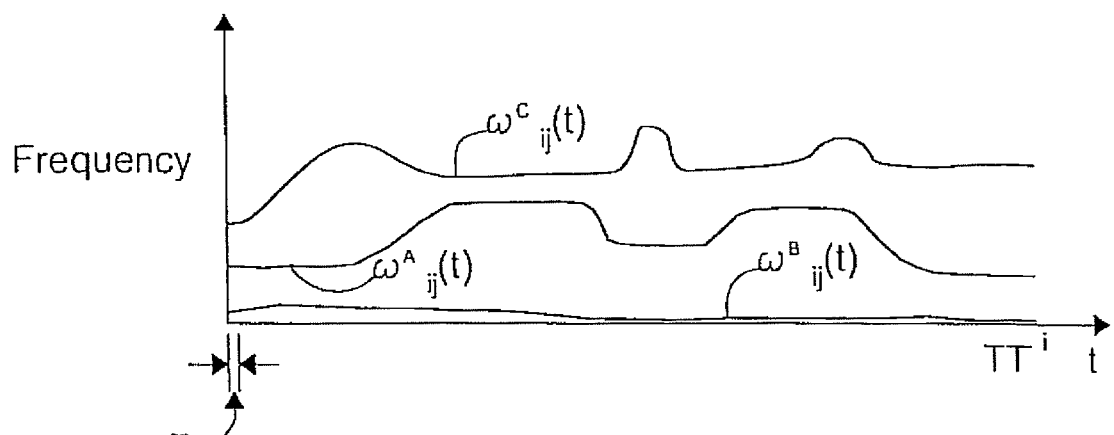
FIGS. 33A and 33B show representative frequencies and amplitudes for different physiological experiences, respectively.
Figure 33B:
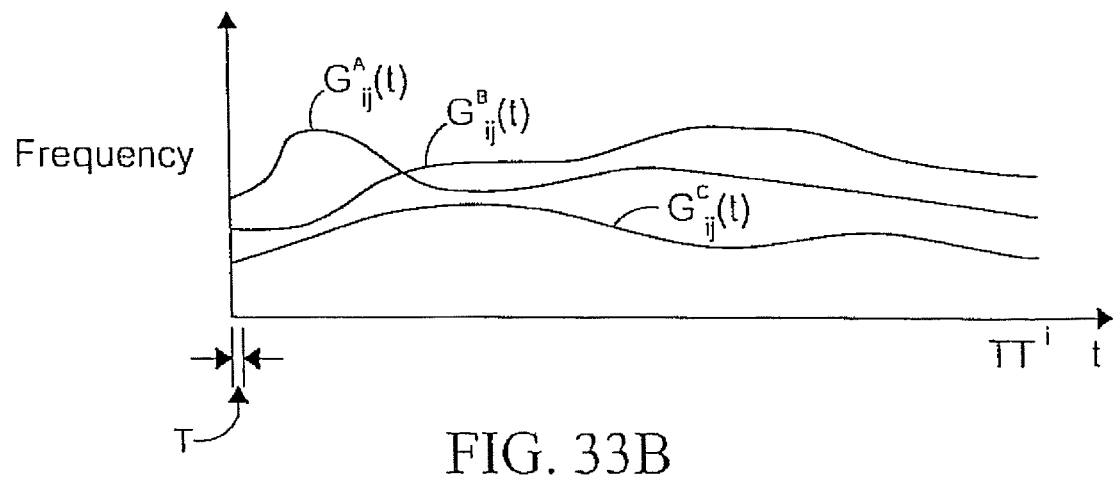

FIGS. 33A and 33B show representative frequencies $\omega_{ij}(t)$ and amplitudes $G_{ij}(t)$ for three different physiological experiences i=A, B, and C, respectively. Training time corresponds to the length of time that a set of dynamic conditions are to be produced at a tubular structure before they are repeated. Total training time $TTT^i$ corresponds to the total time a tubular structure is subjected to a set of dynamic conditions for the $i^{th}$ physiological experience.

Figure 34:
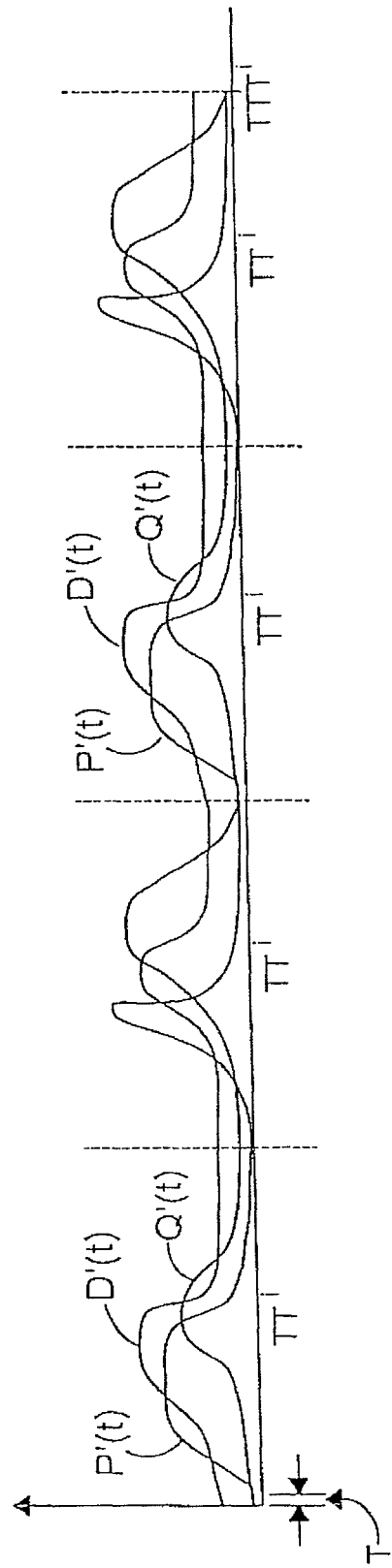
FIG. 34 shows evolution of a plurality of types of dynamic conditions for a physiological experience.

FIG. 34 shows an example of how systems such as systems 1 and 1101 produce a single experience using three dynamic variables P'(t)> Q'(t) and D'(t) and which exhibit a pattern of variations over a training time $TT^i$ which is repeated for a total training time $TTT^i=4 TT^i$. Hence, P', D' and Q' can represent, for example, the amplitude, phase or frequency of the pressure, flow and diameter at a specimen or tubular structure 12, 1112. In accordance with embodiments of the invention, total framing time $TTT^i$ can be multiple training times $TT^i$ and can include fractions of training time $TT^i$. For example, $TTT^i=xTT^i$, where x is a real number, for example x=0.3, 1 5/3, 20, 100, 1000 . . . and so forth.

Figure 35A:
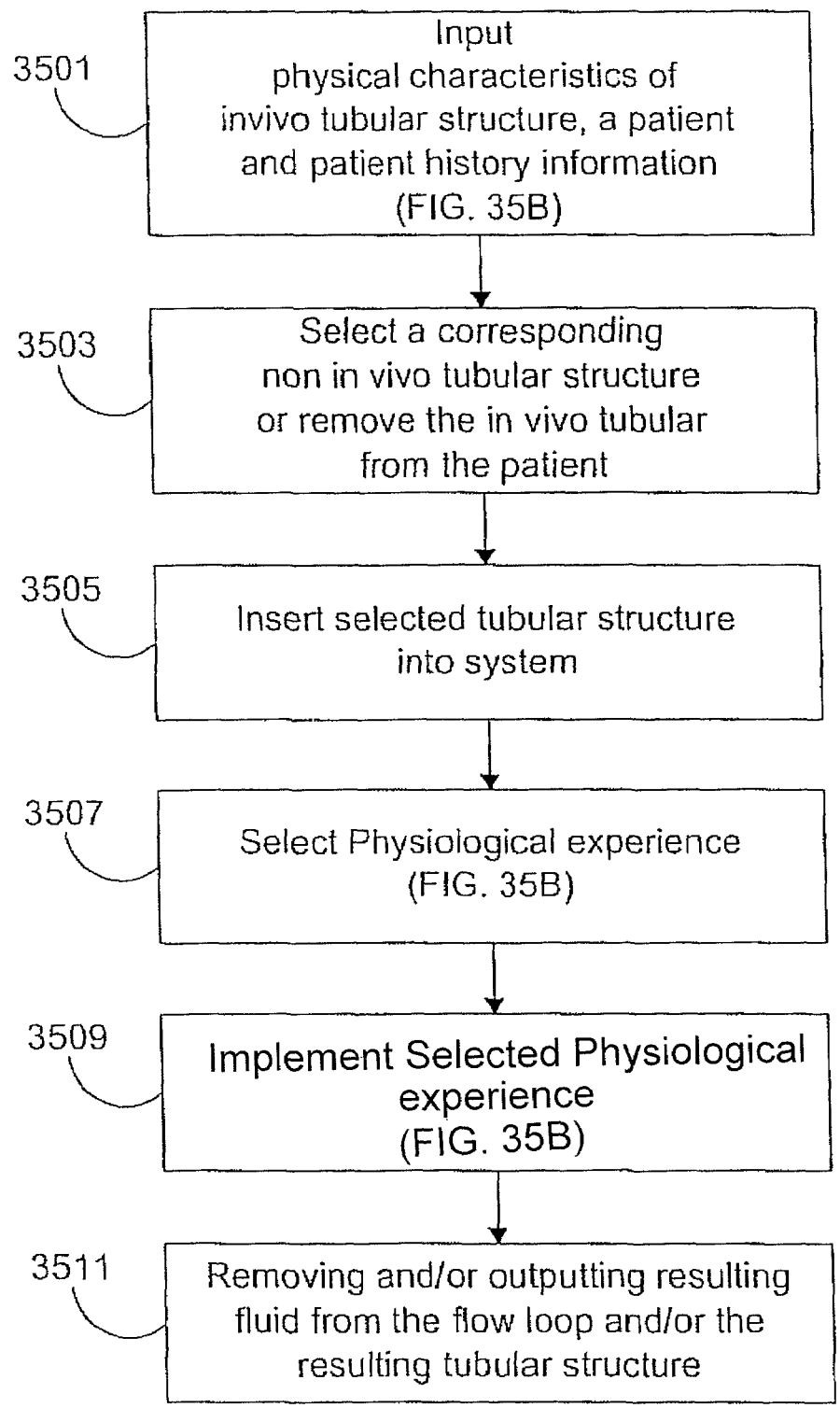
FIG. 35A shows a flowchart of a method for creating physiological experiences for a patient with a particular patient history.

FIG. 35A shows how systems 1, 1101 can be used to produce dynamic conditions which would be experienced by in vivo tubular structures in a patient with a particular patient history while undergoing a physiological experience. In particular, the dynamic conditions are reproduced at a specimen or tubular structure 12 or 1112 inserted into systems such as systems 1, 1101 in accordance with embodiments of the invention.

Figure 35B:
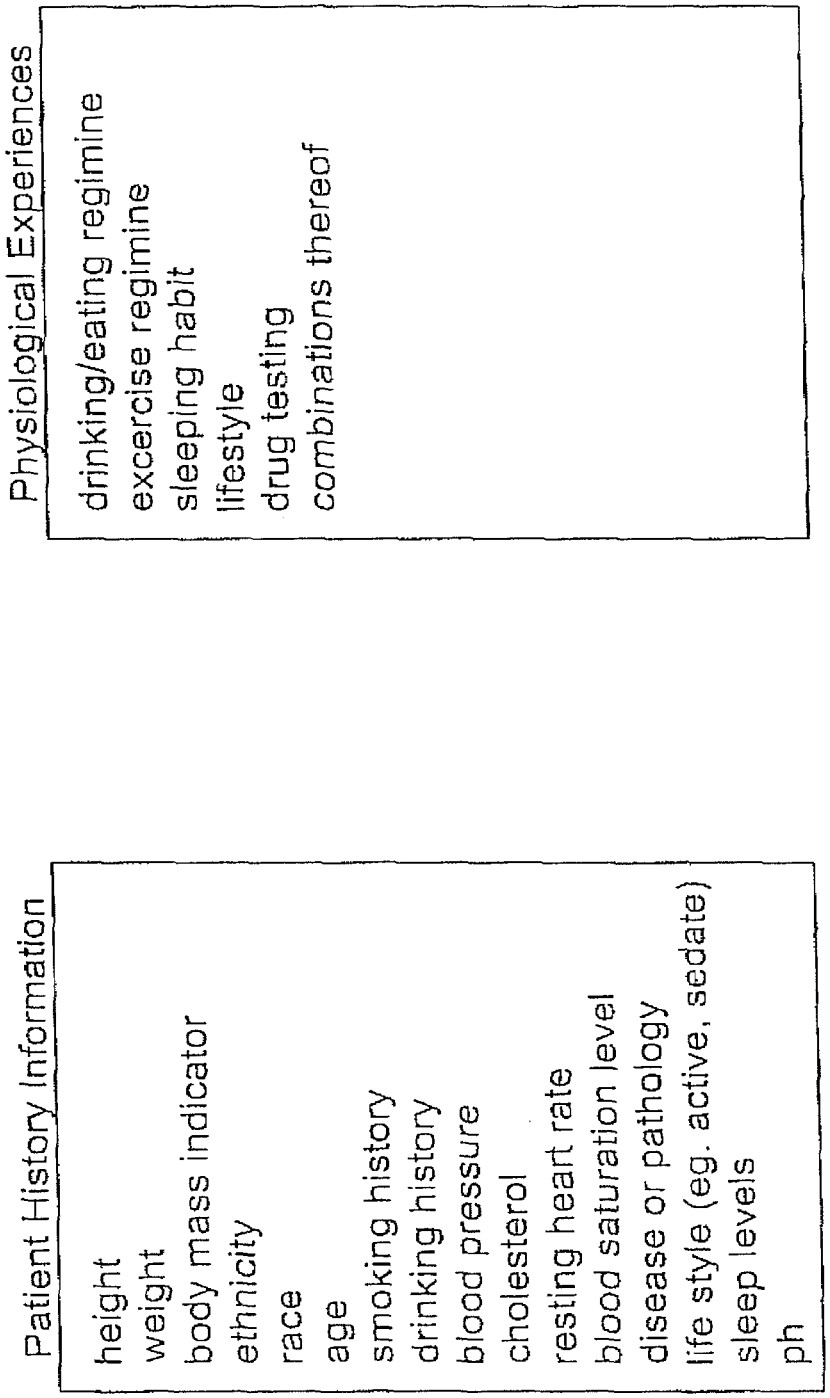
FIG. 35B lists examples of physiological experiences.

Step 3501 involves inputting physical characteristics of an in vivo tubular structure located in a patient and inputting patient history information. FIG. 35B shows exemplary patient history information.

Step 3503 involves either selecting a non in vivo tubular corresponding to the in vivo structure, or removing the in vivo tubular structure from the patient. Step 3505 involves inserting the selected tubular structure into system 1, 1101. Step 3507 involves selecting a physiological experience, examples of which are shown in FIG. 35B.

Step 3509 involves implementing the selected physiological experience using system 1, 1101 with the selected tubular structure and optionally adding, subtracting and/or altering the fluid and/or fluid material in the system 1, 1101 for a time $TTT^i$. Step 3511 involves testing, removing and/or outputting resulting fluid from the flow loop of system 1, 1101 and/or testing removing and/or outputting the resulting tubular structure from the system 1, 1101.

In accordance with additional embodiments of the invention, it should be understood that the number and types of dynamic variables used during training time $TT^i$ for a particular physiological experience can vary during a training time $TT^i$. For example, system 1101 could produce 2 dynamic variables $g_1(t)$ and $g_2(t)$ while measuring or monitoring the resulting third dynamic variable $g_3(t)$, then produce dynamic variables $g_2(t)$ and $g_3(t)$ while measuring or monitoring the resulting first dynamic variable $g_1(t)$. The measured/monitored dynamic variable can serve as feedback signals $FB_j$ (see, for example, FIG. 18) for controller 1103 in accordance with various embodiments of the invention.

The physiological experiences can be selected to train a tubular structure (biological or non biological as discussed above) and are represented by two or more types of dynamic conditions (or variables) for any state or class of dynamic conditions. For example, physiological experience A might have a training time $TT_A=24$ hours with dynamic conditions $\overline{G}^A(t)$ made up of a set of the three dynamic conditions pressure P'(t), diameter D'(t) as broadly defined herein, and flow Q'(t) experienced by a tubular structure located in the pulmonary artery of a 60-year old athletic male Caucasian (patient history) reported over multiple training times $TT^A$. Physiological experience B might, for example, correspond to a training time of $TT^B=1$ week with dynamic conditions $\overline{G}^B(t)$ made up of a set of two dynamic conditions experienced by a tubular structure located in the large intestine of a 25-year old athletic paraplegic (patient history). Again, other examples of physiological experiences are listed in FIG. 35B, it being understood that system 1101 is not necessarily limited physiological experiences listed therein.

Controller 1101 can be characterized by its flexibility, the classes (FIG. 18) of dynamic conditions and/or types (FIGS. 17A and 17B) of dynamic conditions that can be produced at a given region of a tubular structure.

Controller-Flexibility

For a given pressure/flow loop subsystem 1105, controller 1103 may be trained to provide a single state of dynamic conditions, (a single state controller) in accordance with embodiments of the invention. Similarly, for a given same pressure/flow loop subsystem 1105, controller 1103 may be trained to provide discrete states or sets of dynamic conditions, (a discrete controller) in accordance with other embodiments of the invention. Also, for a given same pressure/flow loop subsystem 1105, controller 1103 may be trained to provide multiple discrete and continuous states of dynamic conditions (a hybrid controller) in accordance with embodiments of the invention. Similarly, for a given pressure/flow loop subsystem 1105, controller 1103 may be trained to provide a single physiological experience (FIG. 34) (a single experience controller), multiple physiological experiences (a multi-experience controller), and a hybrid of discrete physiological experiences and also the flexibility to dialup various states of dynamic conditions, (a hybrid experience controller).

Controller—Type or Form (FIGS. 17A and 17B) of Dynamic Conditions

For a given pressure/flow loop subsystem 1105, controller 1103 can be trained to output control signals $f_j(t)$ which yield certain types of forms (FIGS. 17A and 17B) of dynamic conditions. For example, controller 1103, can be trained to output control signals that produce $g_1(t)$, $g_2(t)$, $g_3(t)$ and $g_4t(t)$ at a region A of a tubular structure, where $g_1(t)$ is pressure P(t), $g_1(t)$ is flow Q(t), $g_3(t)$ is the wall thickness along a first direction and $g_4(t)$ is the circumferential strain at region A.

Controller—Class of (FIG. 18) of Dynamic Conditions

For a given pressure/flow loop subsystem 1105, controller 1103 can be trained to output control signals $f_j(t)$ which yield states of a particular class (FIG. 18) of dynamic conditions. For example, if controller 1103 is trained to output control signals $f_j(t)$ to a given pressure/flow loop subsystem 1105 which yield one or more states in the dynamic bio class of conditions for example, controller 1103 is a non-invivo condition controller, and system 1101 is a dynamic bio condition system.

For a given pressure/flow loop subsystem 1105, system 1101 may be referred to as a single state system if controller 1103 is a single state controller, a discrete state system if controller is a discrete state controller, a hybrid system if controller is a hybrid controller, and a dial-up system if controller is a dial-up controller in accordance with embodiments of the invention.

Similarly, for a given pressure/flow subsystem 1105, system 1101 may be a single experience system if controller 1103 is a single experience controller, a multi-experience system if controller 1103 is a multi-experience controller, and a hybrid experience system, if controller 1103 is a hybrid experience controller.

Figure 36:
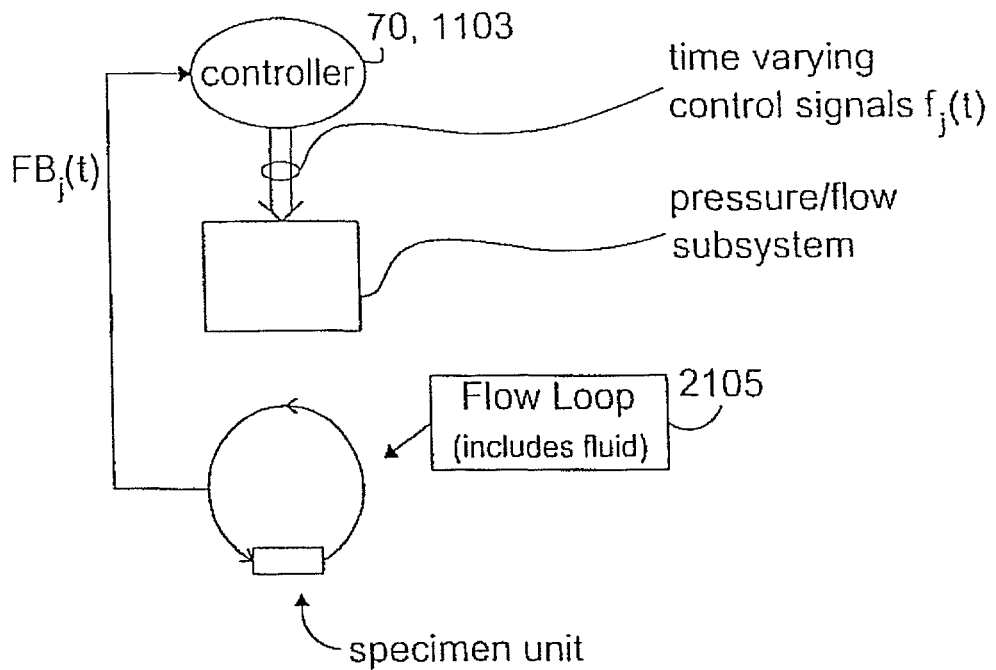
FIGS. 36 and 37 show block diagrams of systems with controller and a pressure/flow subsystem that generate a flow loop of fluid according to embodiments of the invention.
Figure 37:
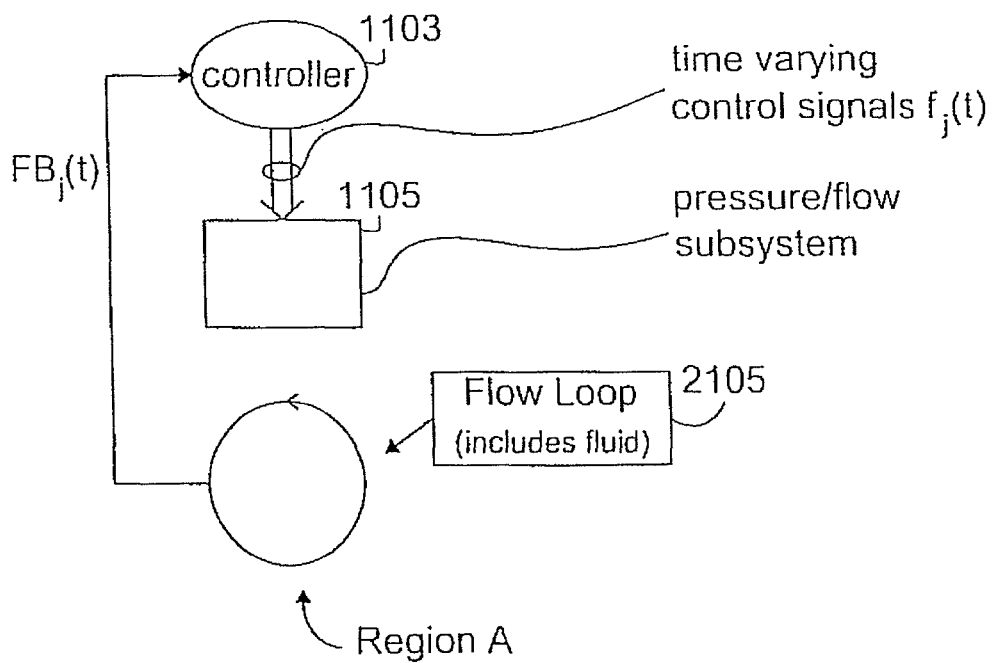

The method and systems described herein can be characterized by additional/alternative means in accordance with embodiments of the invention as shown in FIGS. 36, 37, 39 and 38. FIGS. 36 and 37 show block diagrams of system 1101 with controller 1103 and a pressure/flow subsystem 1105 which together generate a flow loop 2105 of fluid as broadly defined herein. System 1101 of FIG. 36 includes a specimen unit 10 in accordance with embodiments of the invention, whereas system 1101 in FIG. 37 shows a block diagram with controller 1103 and a pressure/flow subsystem 1105 with a flow loop 2105 of fluid, but without a specific specimen unit 10. Instead, a region of the flow loop 2105 itself serves as the region A of a tubular structure (e.g., FIG. 11) in accordance with embodiments of the invention. Controller 1103 is trained to generate control signals $f_j(t)$ which when input to pressure flow subsystem 1105 produce various dynamic conditions and/or physiological experiences at a tubular structure in accordance with embodiments of the invention.

Figure 39:
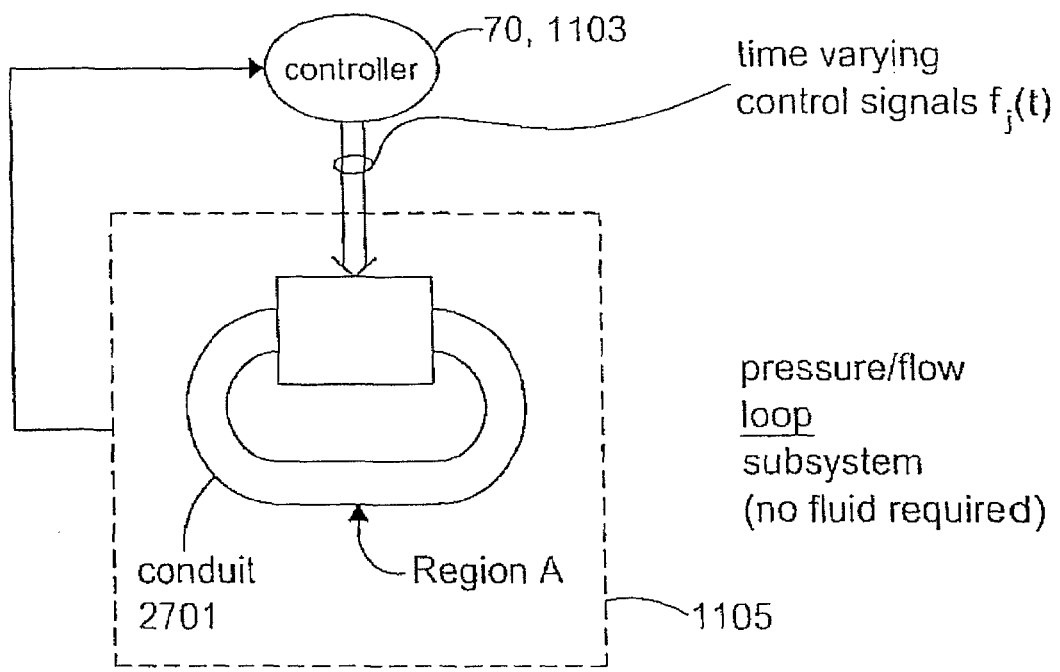
FIGS. 38 and 39 show block diagrams of systems with pressure/flow loop subsystems according to embodiments of the invention.
Figure 38:
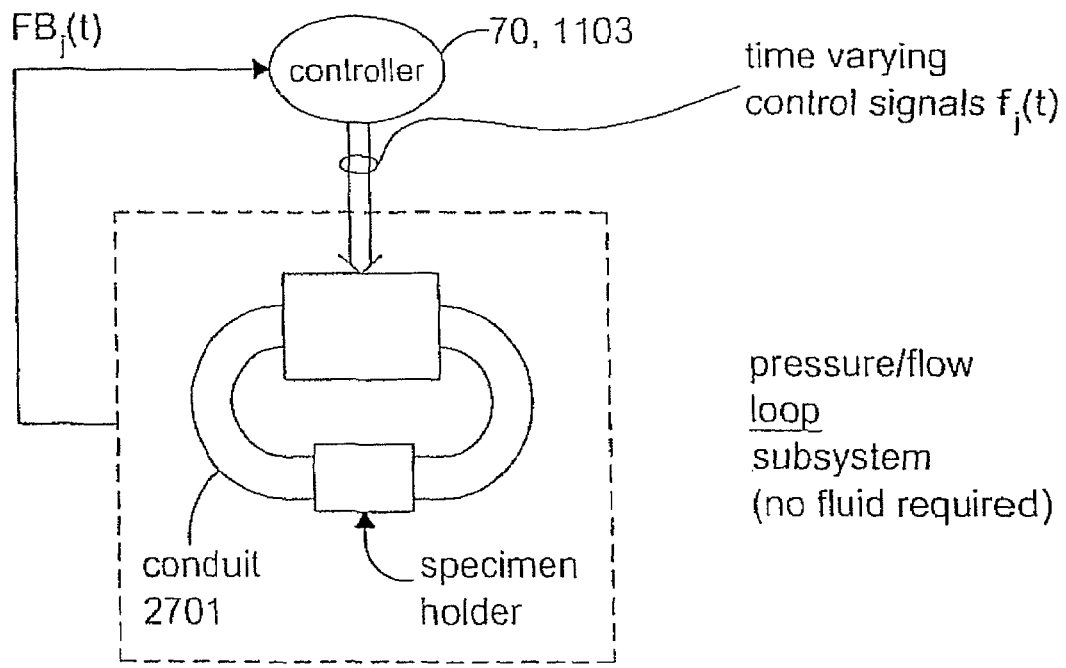

FIGS. 38 and 39 show system 1101 with pressure/flow loop subsystems 1105 in accordance with embodiments of the invention. Here pressure/flow loop subsystem 1105 does not include flow loop fluid but does include a conduit 3701, which operatively couples pressure/flow loop subsystem components, in accordance with various embodiments of the invention. Conduit 3701 can include any tubes, pipes, cylinders, tubular structures and any other coupling components described herein with respect to systems such as systems 1 and 1101 and others known to those of ordinary skill in the art. As with system 1101 of FIG. 36, system 1101 of FIG. 39 includes a specimen unit 10 in accordance with an embodiment of the invention. Similarly, as with system 1101 of FIG. 37, system 1101 of FIG. 38 does not include a specimen unit 10. Instead, a region of the pressure/flow loop subsystem 1105 itself serves as the region A of the tubular structure (FIG. 11) in accordance with embodiments of the invention. Again, controller 1103 is trained to generate control signals $f_j(t)$ which when input to pressure/flow loop subsystems 1105 produce various dynamic conditions at a region A in pressure/flow loop subsystem 1105.

Figure 40:
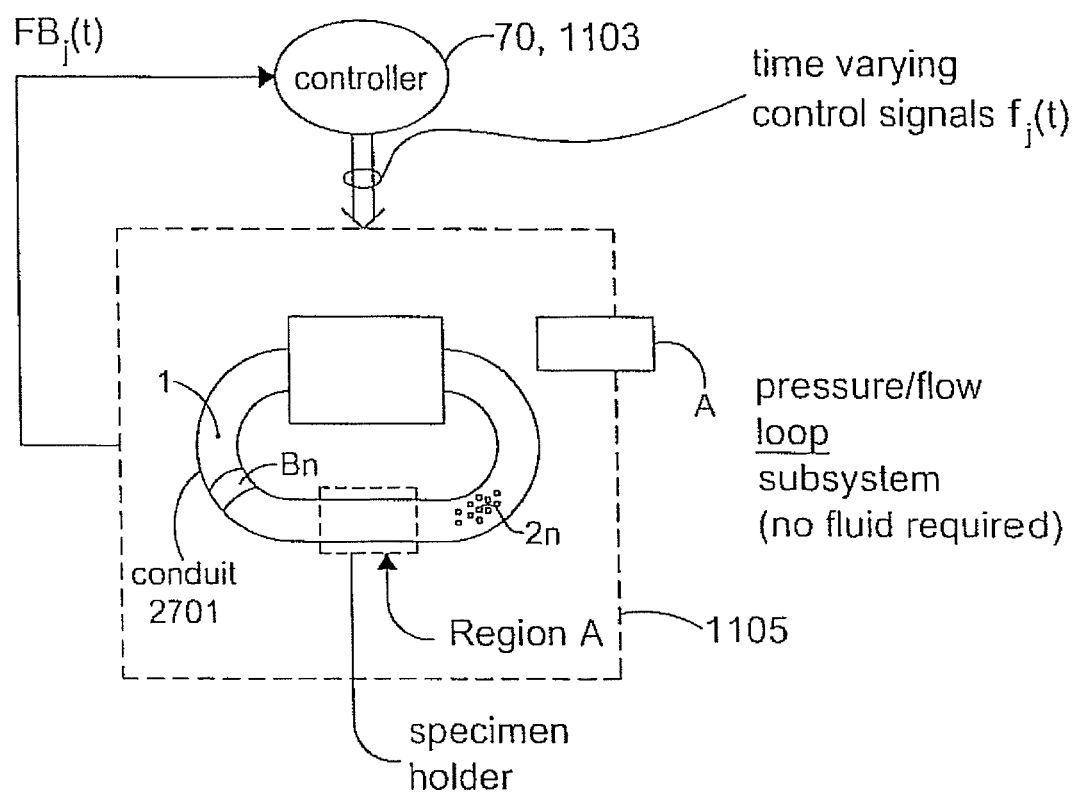
FIG. 40 shows system with sensors according to embodiments of the invention.
Figure 41A:
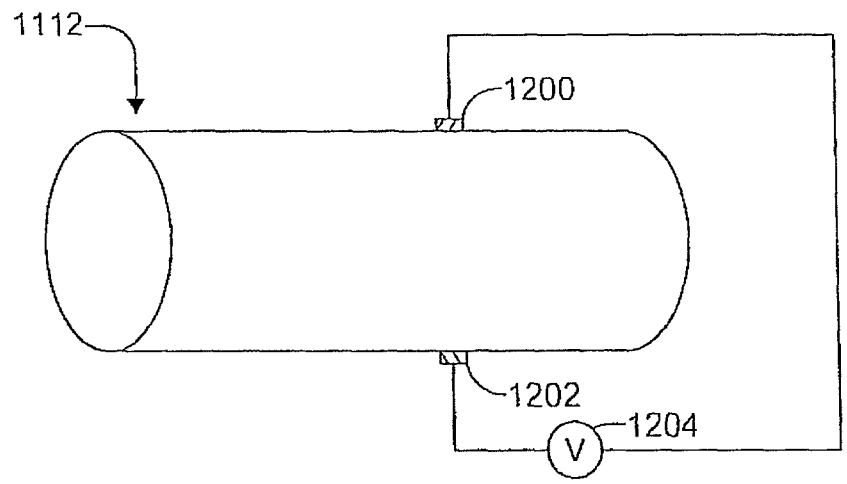
FIGS. 41A-41C show exemplary electrode configurations for measuring dynamic conditions.
Figure 41B:
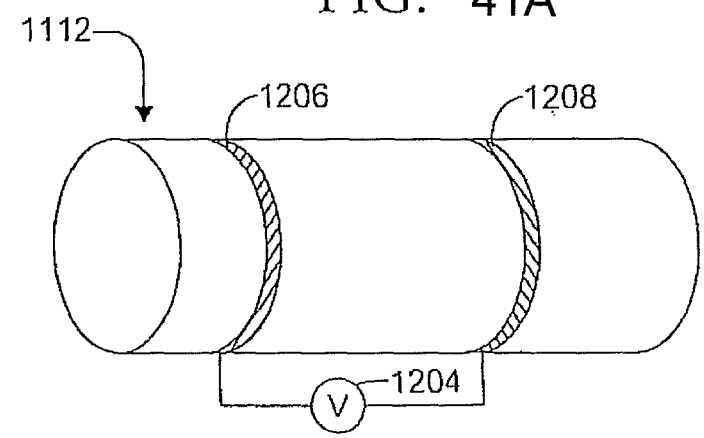
Figure 41C:
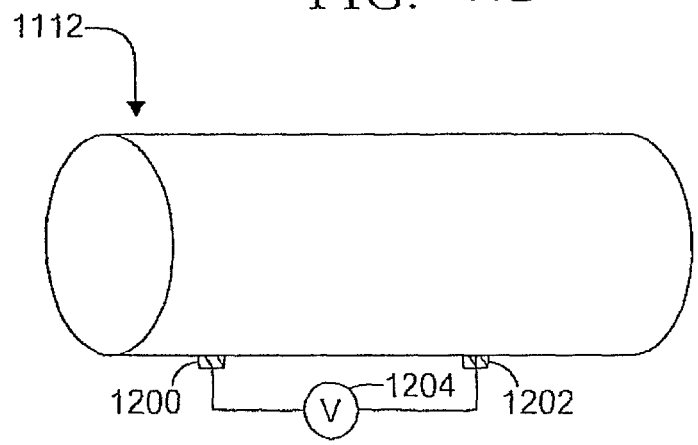

FIG. 40 shows system 1101 with sensors 1, 2n, A and Bn. Although four sensors are shown as an example, purposes, number and types can be greater or smaller than four. Sensors 1, 2n, A and/or Bn include, for example transmitters, receivers, transmitter/receivers, transducers, detectors and other sensors. Fluid sensors as used herein are sensors in the fluid which are added to the pressure/flow loop subsystem of FIGS. 38 and 39 or which comprise the flow loop shown in FIGS. 36 and 37.

System sensors (A) include any transmitters, receivers, transmitters/receivers, transceivers, transducers, detectors, as well as any devices which can be used to detect images or measure any one or more parameters related directly or indirectly to one or more dynamic conditions, such as those listed in FIGS. 17A and 17B and discussed herein.

FIGS. 41A-44C show three electrode configurations for measuring the conductivity of a fluid and/or a monolayer in a tubular structure 1112, in accordance with embodiments of the invention. In the embodiment of FIG. 17C, electrodes 1200 and 1202 are placed on opposite sides of the tubular structure 1112 and are connected to a voltage source 1204. In the embodiment of FIG. 17D, ring electrodes 1206 and 1208 are spaced apart and extend around at least a portion of the circumference of the tubular structure 1112, and preferably around the entire circumference of the tubular structure 1112. In the embodiment of FIG. 17E, electrodes 1200 and 1202 are placed on one side of the tubular structure 1112.

The three electrode configurations of FIGS. 41A-44C measure the conductivity of the fluid inside the tubular structure 1112 and/or a monolayer inside the tubular structure 1112 along different directions. For example, the configuration shown in FIG. 17E is particularly useful for measuring the conductivity of a monolayer (not shown) grown on the inside surface of the tubular structure 1112. Such a conductivity reading could be used, for example, to measure the functionality and/or the integrity of the monolayer in the tubular structure 1112.

The voltage source 1204 can be a direct current source or an alternating current source. Thus, the term "conductivity", as used herein, includes the measurement of resistivity, impedance and reactance.

System sensors A can include more complex detecting, measuring and/or imaging systems, including, but not limited to, digital cameras, MRI, NMR, and PET systems, microscopes, ultrasound systems, including 3D or 4D ultrasound imaging systems, chemical sensor systems, gas analyzers, electromagnetic detecting/measuring and/or imaging systems and any other fluid material (e.g., FIG. 17B, detecting/measuring and/or imaging systems.

System nanosensors (Bn) represent nanosensors, nanotransmitters, nanoreceivers, nanotransceivers, nanotransducers, nanodetectors, as well as any devices which can be used to detect, image or measure one or more parameters related directly or indirectly to one or more dynamic conditions, including, but not limited to, those listed in FIGS. 17A and 17B.

Referring back to FIG. 40, fluid sensors 1 include any transmitters, receivers, transmitters/receivers, transceivers, transducers, detectors, as well as any devices which can be used to detect images or measure any one or more parameters related directly or indirectly to one or more of the dynamic conditions, including those listed in FIGS. 17A and 17B.

Fluid sensors 2n represent nanosensors, nanotransmitters, nanoreceivers, nanotransceivers, nanotransducers, nanodetectors, as well as any devices which can be used to detect, image or measure one or more parameters related directly or indirectly to one or more dynamic conditions, including, but not limited to, diose listed in FIGS. 17A and 17B.

Figure 42A:
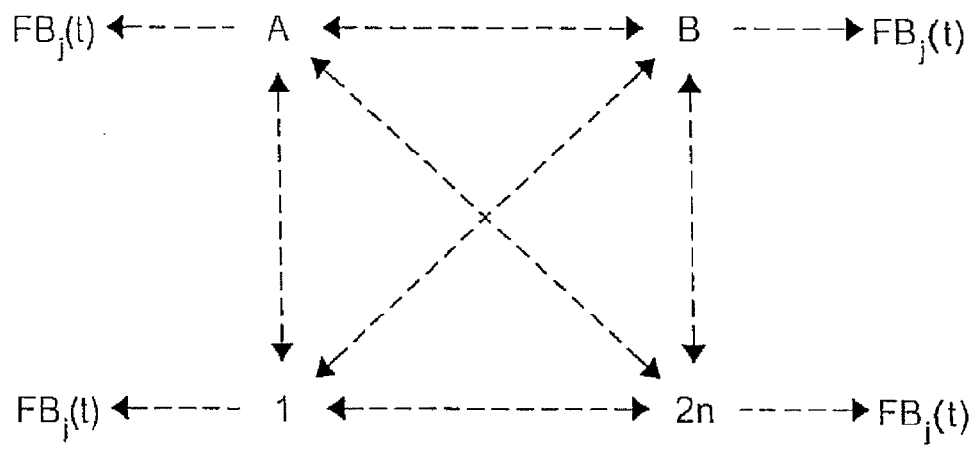
FIGS. 42A-42B and 43A-43B shows examples of exemplary sensors communicatively coupled to transmit, receive, transmit and receive, detect and forward data used as feedback.
Figure 42B:
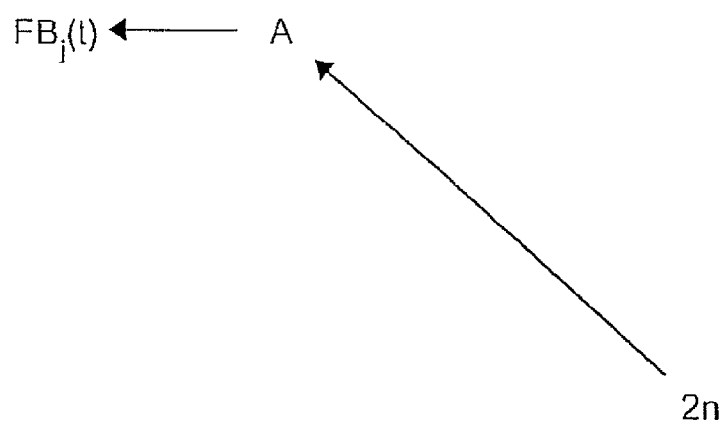

FIG. 42A shows examples of how exemplary sensors A, Bn, 1 and 2n can be communicatively coupled or can transmit, receive, transmit and receive, detect and forward data related to, for example, dynamic conditions and/or other data used as feedback $FB_j(t)$. Arrows indicate direction of flow of data or information. Dashed lines are used to indicate all possible data flow it being understood that actual information flow depends on the type of sensors. In some embodiments of the invention, sensors may not directly measure, but may instead serve as boosters or repeaters. For example, in one embodiment of the invention the fluid contains thousands of nanodetectors and receivers which detect one or more dynamic conditions and transmit photons of a certain frequency depending on the presence of certain gases, liquids, solids and/or biological materials, which in turn can be detected by system sensor A (e.g., photon detector), which in turn puts out a feedback signal $FB_j(t)$ to controller 70. Referring to FIG. 42A, this would be represented by the configuration shown in FIG. 42B.

Figure 43A:
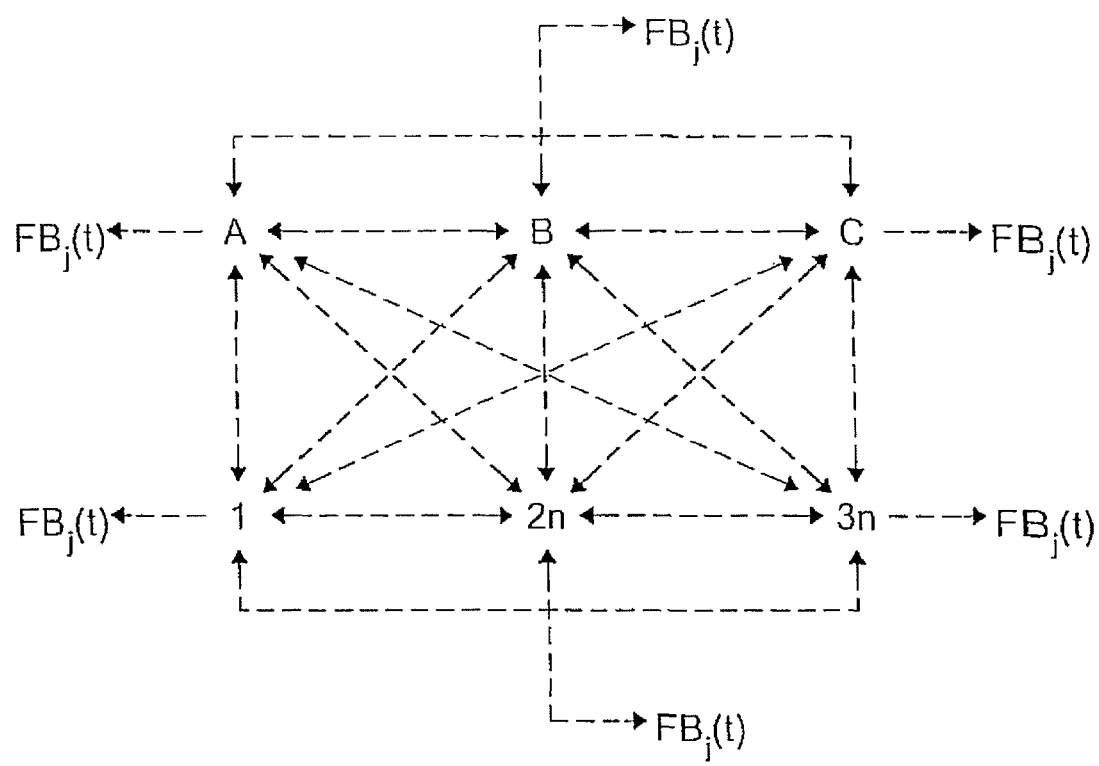
Figure 43B:
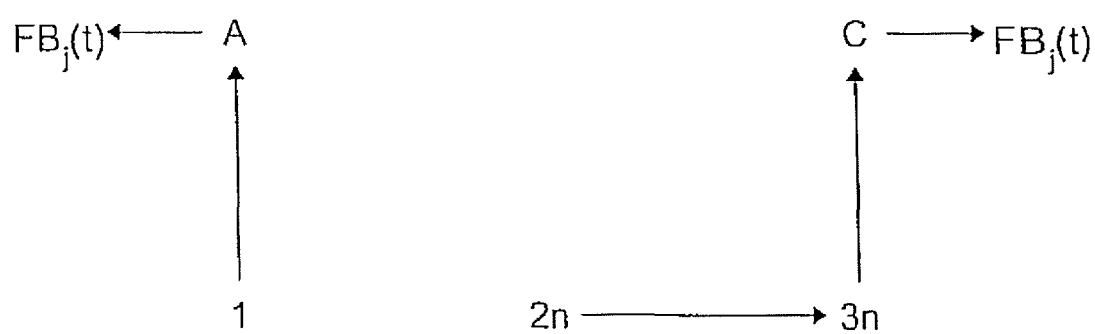

FIG. 43A shows various possibilities of how six sensors A, Bn, C, 1, 2n and 3n can be communicatively coupled or transmit, receive, transmit and receive, detect and forward data related to, for example, dynamic conditions or other data used as feedback $FB_j(t)$. Again, in some embodiments of the invention, sensors may not directly measure, but may instead serve as boosters or repeaters. Referring to FIG. 43A, this would be represented by the configuration shown in FIG. 43B.

According to embodiments of the invention, a receiver (e.g., system or fluid) can have exemplary volumes of less than 1 cm$^2$, less than 500 mm$^2$, less than 1 mm$^2$, less than 500 µm$^2$, less than 100 µm$^2$, less than 1 µm$^2$, less than 500 nm$^2$, less than 100 nm$^2$, less than 1 nm$^2$ or the like. According to other embodiments of the invention, at least one receiver (e.g., system or fluid) can have exemplary dimensions of less than or at least 500 mm along a first direction, 1 mm along a first direction, 500 µm along a first direction, 100 µm along a first direction, 1 µm along a first direction, 500 nm along a first direction, 100 nm along a first direction, 50 nm along a first direction, 1 nm along a first direction, 0.1 nm along a first direction or the like. In other embodiments, a receiver can have a similar size to a fluid receiver. In other embodiments, a transmitter, fluid transmitter, a transmitter/receiver, fluid transmitter/receiver can have a similar size to a fluid receiver or receiver. In other embodiments, a sensor (e.g., in a system, fluid, specimen or the like) can have similar sizes to a receiver, transmitter, or transmitter/receiver.

Fluid sensors, system sensors and/or specimen sensors (A, B, . . . A$_n$, B$_n$, . . . 1, 2, . . . 1$_n$, 2$_n$ . . . ) discussed herein (e.g., receivers, transmitters, transceivers) may further include probes in accordance with embodiments of the invention. Probes can be used as fluid, system and/or specimen sensors. Probes can characterize biological activity such as cell activity. For example, biological activity can be observed or detected using activity based probes. An activity based probe can form a bond (e.g., irreversible covalent bond) with a desired active biological target (e.g., protein target). Once the target is coupled to the probe, the target can be more easily detected, monitored or utilized.

Figure 44A:
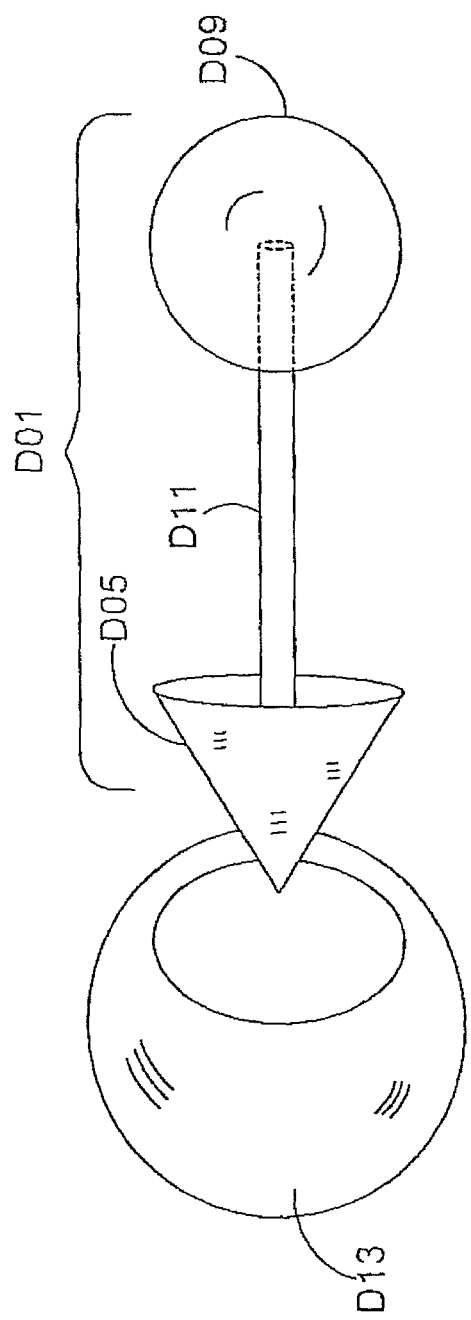
FIGS. 44A-44B show exemplary embodiments of a prove sensor according to an embodiment of the invention.

FIG. 44A shows an activity based probe D01 can include an engaging end D05 or warhead, a tag D09 and a connector portion D11 in accordance with one embodiment of the invention. Engaging end D05 can be designed to engage amino acid residue at an active enzyme site D13. Accordingly, the reactivity, polarity, charge, size and structure can set the effectiveness and selectivity of the probe. Tag D09 is used to detect and/or enrich the active target. Tag D09 can include a radioactive molecule, fluorescent or the like. Tag D09 can be, for example, a biotin, a radioactive molecule, or a fluorescent molecule such as fluorophore or 125I. Connector portion D11 is a molecular chain which can reduce interference between tag D09 and engaging end DOS as well as to assist in selecting the probes target D13 can be, for example, a peptide, alkyl polyether or the like. Engaging end DOS can be a phosphonate, fluorophosphonate, epoxyketone or the like.

Figure 44B:
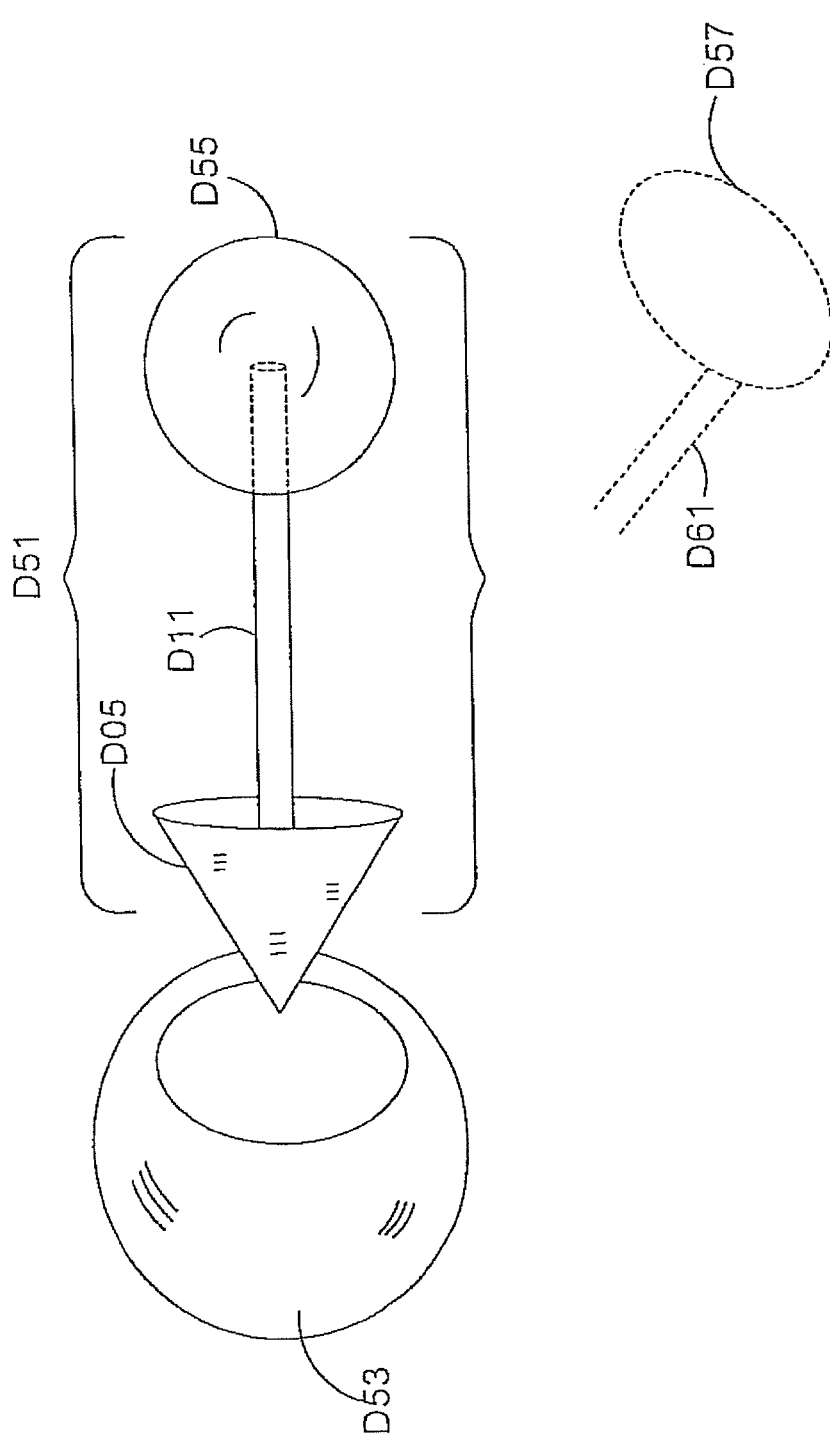

FIG. 44B shows a probe D51 which is smaller and preferably significant smaller than target D53. Here, probe D51 also has an engaging end D05 and a connector portion D11 but with tag D09 replaced with tag D55 which includes a drug or pharmacological agent or any small or large molecules (for example, see FIG. 17B). Hence probe D51 can provide a delivery mechanism such as a drug delivery mechanism to tubular structures in accordance with embodiments of the invention. In an alternative embodiment of the invention, tag D55 can be a combination of tag D09 of FIG. DA and a drug, pharmacological agent or any other small or large molecules, in which case probe D51 can serve both as a delivery mechanism and a sensor for the tubular structure or specimen and/or to fluid materials in fluids described herein and/or to flow loop fluids in systems such as systems 1, 1101 in accordance with other embodiments of the invention.

FIG. 44B shows yet another embodiment of probe D51 (dashed lines) in which a second tag D57 is attached with a second connector portion D61 in accordance with another embodiment of the invention. Hence, probe 51 with tag D55 functions in a similar manner to that described above with respect to FIG. DA, and probe 51 with tag D57 functions as a delivery mechanism as described herein.

Figure 45A:
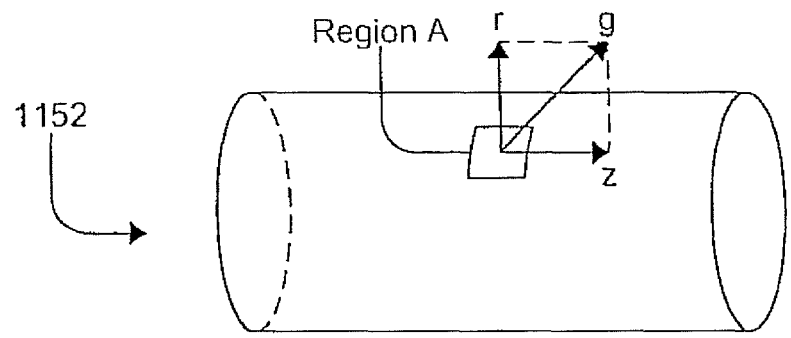
FIGS. 45A-45C and 46 show exemplary tubular structures in accordance with embodiments of the invention.

FIG. 45A shows tubular structures 1112 which are permeable or semipermeable to fluid materials of any kind, and shown as permeable tubular structures 1152, in accordance with embodiments of the invention. Permeable tubular structures 1152 allow for the migration, flow and/or diffusion of fluid and/or any fluid materials, such as particles, sensors, or molecules as described herein, examples of which are listed in FIGS. 17A and 17B. Hence, measurement of the amount, flow, velocity of fluid or fluid material corresponds to measurement of types of dynamic conditions, examples of which are shown in FIGS. 17A and 17B.

The direction of velocity and flow can include measurement of a directional dynamic condition $\overline{g}(t)$ having a component in the vertical direction, as well as measurement of nondirectional dynamic conditions g(t), such as amounts of fluid or fluid material. System and/or fluid sensors can be used to measure these types of dynamic conditions, in accordance with embodiments of the invention.

Figure 45B:
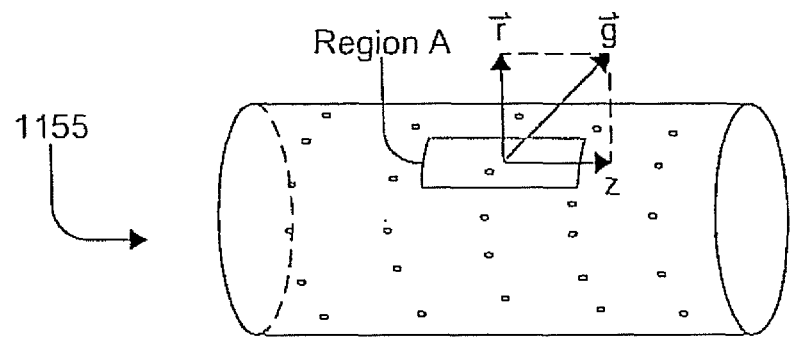

FIG. 45B shows other types of tubular structures 1112, which are porous or semi porous tubular structures 1155, in accordance with embodiments of the invention. Again, tubular structures 1155 allow for the migration, flow and/or outfusion of fluid and/or fluid material as described herein, examples of which are shown in FIGS. 17A and 17B. Hence, measurement of the amount, flow, velocity or other dynamic condition of fluid or fluid material constitutes measurement of types of directional dynamic conditions $\overline{g}(t)$ and/or measurement of types non-directional dynamic conditions g(t), as shown in FIGS. 17A and 17B. Again, directional dynamic variables may include a nonzero component in the radial direction.

Figure 45C:
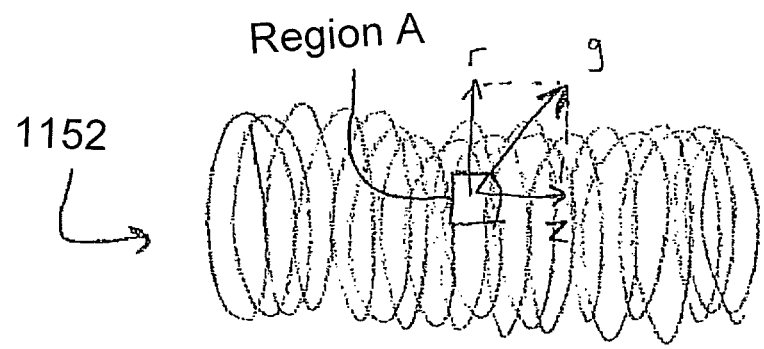

FIG. 45C shows other types of tubular structures 1112 which are electrospun tubular structures 1157, preferably made of fibrin in a manner such as that described, for example, in U.S. Pat. Nos. 6,592,623 and 6,787,357, the contents of which are incorporated herein by reference. Electrospun tubular structures 1157 can be permeable and/or porous.

Figure 46:
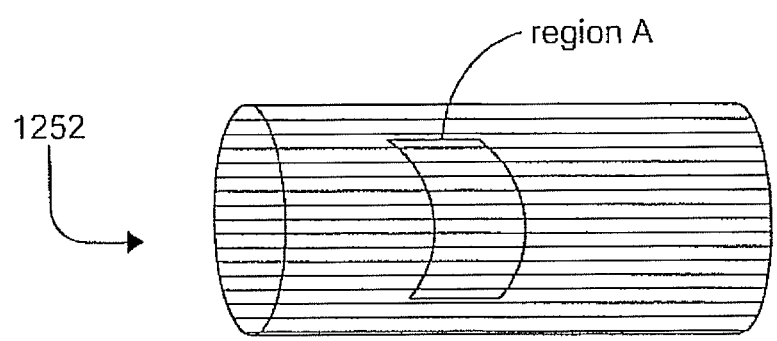

FIG. 46 shows other types of tubular structures 1112, which are microgrooved tubular structures 1252. Microgrooved tubular structures 1252 have depths of 50 nm and 700 nm, can have grooves with widths of between 40 nm and 2000 nm and preferably 70 nm and 1400 nm, and pitch between approximately 200 to approximately 5000, and preferably approximately 400 to approximately 4000 depending on the class of dynamic condition (FIG. 18) which it will be subjected to, as well as the type of cells and/or coatings which might be applied to it.

Tubular structures 1112 can be combinations of two or more of the above tubular structures, such as two or more tubular structures 1112 in FIGS. 11, 12, 13A, 13B, 14, 14, 16, tubular structures 1152, 1155, 1157 and 1252 and specimens 12 in FIGS. 1A, 2A-2E, 3A-3D, 5A-5D and 6A-6E. Hence, a tubular structure could be a combination of a porous tubular structure 1155 (FIG. 45B) and a microgrooved tubular structure 1252 (FIG. 46).

Second order dynamic conditions can include any type of dynamic conditions such as diose listed in FIGS. 17A and 17B and any others known in the art. Second order dynamic conditions are localized dynamic conditions produced by systems discussed herein, such as systems 1 and 1101, in conjunction with tubular structures having perturbed physical characteristics and/or properties when those systems operate to provide a given set of global dynamic conditions and/or dynamic conditions at one or multiple regions A in accordance with embodiments of the invention. When these systems operate to provide a given set of global dynamic conditions and/or known types of dynamic conditions at one or multiple regions A in accordance with embodiments of the invention.

Such perturbed tubular structure characteristics include, for example, shape, structure, porosity, permeability, dimensions, thickness, stiffness, elasticity, ridges, localized stiffness and elasticity, protrusions, bumps, rigid full rings or rigid partial rings, expandable full rings or partial rings with known elasticities, as well as rigid full sleeves or rigid partial sleeves, or full or partially expandable sleeves with known elasticity. Other perturbed tubular structure characteristics can include coatings with altered coefficients of friction, smoothness and/or roughness of the inner surface of the tubular structure, and the spatial frequencies of any repeating structure perturbation, such as small bumps, rings, grooves, sleeves, shapes and so forth, examples of which will be discussed with respect to FIGS. 47A-47H.

These dynamic conditions are referred to herein as second order dynamic conditions because they result the use of the perturbed tubular structures in systems which operate to provide predetermined or known global dynamic conditions of one or multiple regions A. Second order dynamic conditions can be used, for example, to effect additional sets of dynamic conditions which might be present in vivo for healthy, diseased, or other in vivo tubular structures. Second order dynamic conditions can also be used, for example, to create additional sets of dynamic conditions or other non-biological situations, as well as dynamic conditions useful for training and testing, or growing tubular structures, samples of which are shown in FIG. 18.

All tubular structures discussed throughout can include biological material, such as cells, etc., can include a hybrid of biological material and non-biological material, synthetic or non-synthetic non-biological material, or completely biological material, such as veins or arteries or tissues, or organs and so forth as described herein.

Variations in cross-sectional area along the z direction correspond to variations in D as broadly defined herein. Hence, tubular structure along Z can be represented by D(z). The z axis can represent an approximately straight line along the direction of the mean pulsatory flow in tubular structures, in accordance with embodiments of the invention. Alternatively, the Z direction can represent a line that follows approximately along the center of each cross-sectional area of a tubular structure, according to other embodiments of the invention.

Tubular structures also include, for example, biological or non-biological or hybrid biological and non-biological tubular structures which have been in any way slightly, moderately or substantially modified as a result of being subjected to one or more sets of dynamic conditions and second order dynamic conditions for an amount of time sufficient to yield any such slight, moderate or substantial modifications of the tubular structure itself. Again, tubular structures can have perturbed physical characteristics and/or properties which immediately yield desired dynamic conditions, including second order dynamic conditions, once placed in systems described herein with the appropriate global dynamic conditions, including systems 1 and 1101, according to embodiments of the invention.

FIGS. 47A-47H show examples of tubular structures or specimens 12, 1112 which can be used to effect second order dynamic conditions. Again, as discussed herein, these tubular structures and specimens, as well as all other specimens and tubular structures including, for example, anyone or more combinations of diose shown in FIGS. 1A, 11, 12, 13A, 13B, 14, 15, 16, 36, 38, 42, as well as any portion or section of systems, such as systems 1, 1101 which can pass fluid from one location to another as defined herein (see FIGS. 11 and 12), can be porous, non-porous, permeable or non-permeable or any hybrid thereof biological, non-biological or any hybrid thereof, multilayered, multi-channeled or multiple branched and any combination of these and one or multiple tubular structures shown in FIGS. XA-XH. Again, tubular structures can have perturbed physical characteristics and/or properties which nearly immediately yield the desired dynamic conditions including second order dynamic conditions once placed in systems 1, 101 and/or 1101 with the appropriate global dynamic conditions.

Figure 47A:
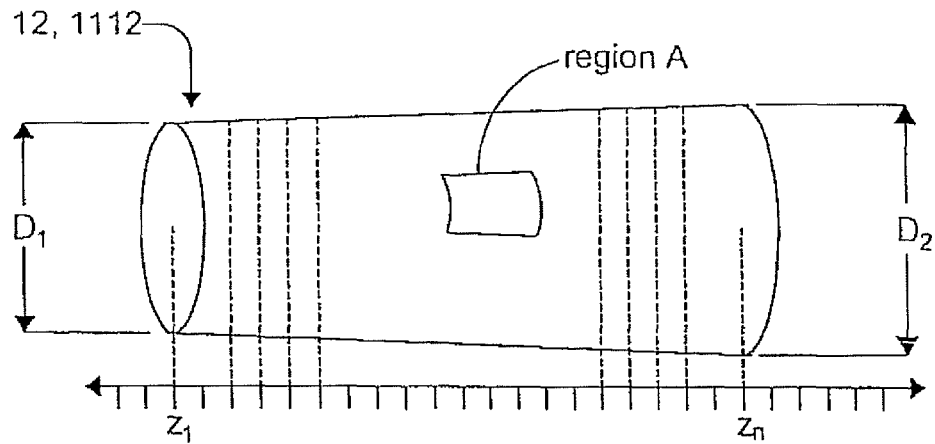
FIGS. 47A-47G show exemplary tubular structures illustrating exemplary second order dynamic conditions in accordance with embodiments of the invention.
Figure 47B:
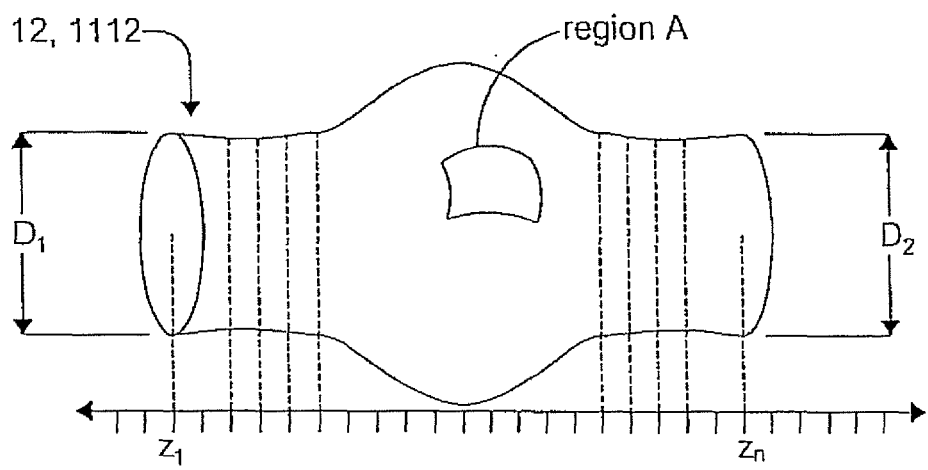
Figure 47C:
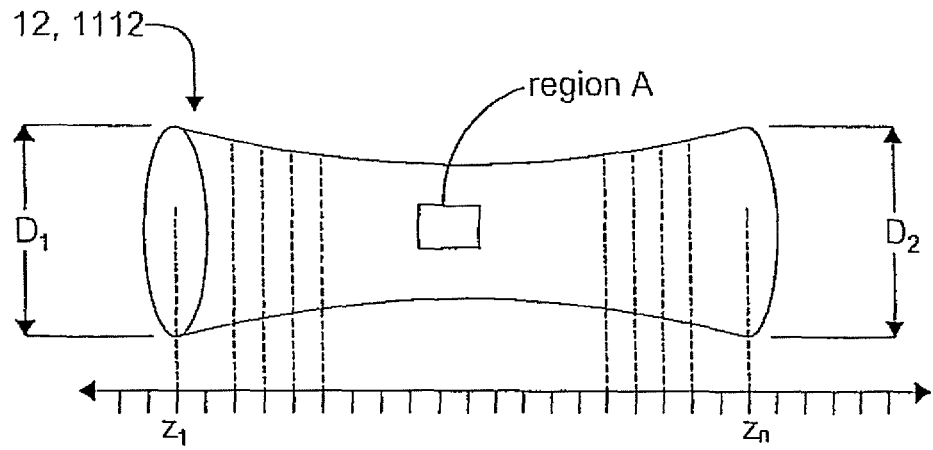
Figure 47D:
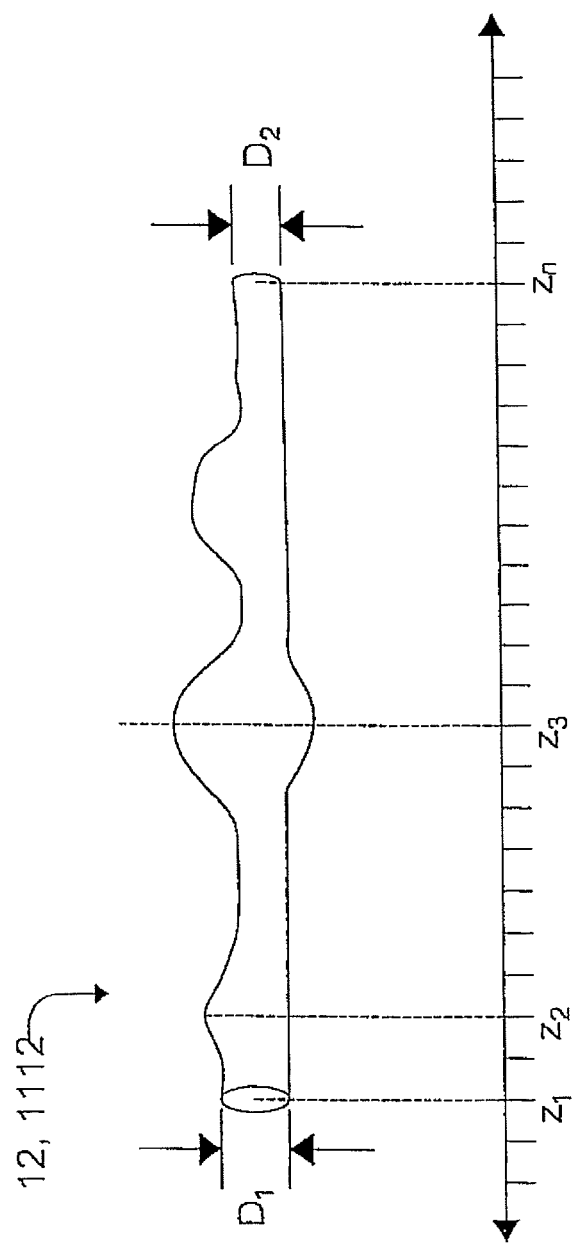

FIG. 47A shows a tubular structure 12, 1112 with varying diameter D along a z direction which, in accordance with embodiments of the invention, corresponds to variation of the cross-sectional areas of tubular structures along the z direction. Again, diameter D, and hence at cross-sectional areas at $Z_1 \ldots Z_n$ of tubular structures as defined herein can include FIGS. 12, 13A, 13B and 17. Hence, $D_1$ may correspond to a circular cross-sectional area and $D_2$ may correspond to an ovular cross-sectional area. Generally, $D_1$ and $D_2$ can be, for example, any cross-sectional area including those, for example, in FIG. 12, and the transition from $D_1$ to $D_2$ along the z direction can be any series of cross-sectional areas. FIGS. 47B, 47C, 47D show more examples of tubular structures in which $D_1$ and $D_2$ might be approximately the same, but the transition of cross-sectional areas varies along the z direction by becoming larger then smaller (FIG. 47B) or becoming smaller then larger (FIG. 47C).

FIG. 47D shows another example of tubular structures with cross-sectional variations along the z direction. If z represents the approximate center of cross-sectional areas D(z), $z=z_1-z_n$, then the first cross-sectional area $D(z_1)$ might represent a circle having a radius of $r_1$. $D(z_2)$ might represent a cross-sectional area which is ovular on the top half with a major axis radius $r_2$, and circular on the bottom half still with the radius $r_1$, where $r_2 > r_1$. Cross-sectional area $D(z_3)$ might be ovular with a major axis of $r_3$ and a minor axis $r_4$, where $r_3 > r_4$ and, for example, $r_4 > r_1$.

Figure 47E:
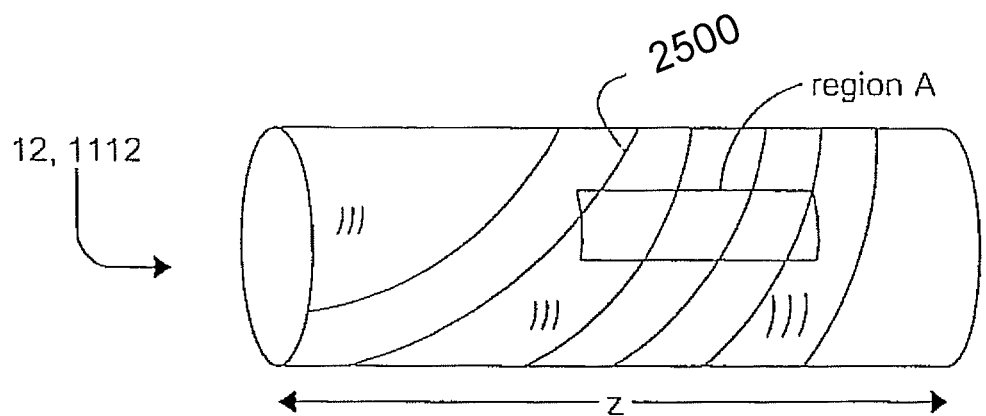

FIG. 47E shows a tubular structure with grooves 2500 according to additional embodiments of the invention. FIG. 47E has grooves angled with respect to the Z direction. Here, the grooves are considered completely aligned with the z direction if they run approximately parallel to the z direction. It should be understood that grooves can be any grooves, microgrooves, ridges, indentations and can be on the inner diameter, the outer diameter (to effect, for example, a particular flexibility of elasticity) of the tubular structure and/or within the wall of one or more layers of the tubular structure, according to embodiments of the invention. Grooves, as used herein, include the presence and/or absence of any biological and/or non-biological materials including, but not limited to, materials used or present in any tubular structures as defined herein. Accordingly, grooves can be troughs having a desired cross-sectional shape such as a "V" shape, semi or partially circular or ovular shape, rectangular shape and so forth. Variations in the depth, width, length, direction, shape and/or periodicity (for example, distance between grooves) can produce or alter the resulting second order dynamic conditions for a given set of global dynamic conditions and/or dynamic conditions at region (s) A.

Figure 47F:
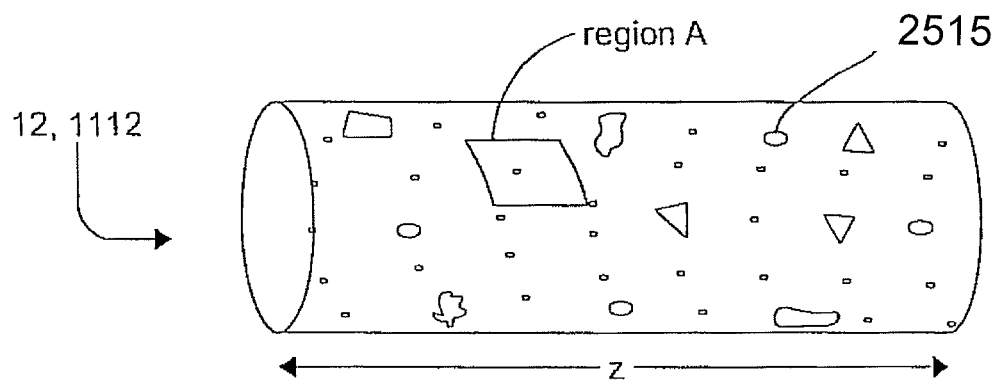

FIG. 47F shows a tubular structure with projections on an interior surface according to additional embodiments of the invention. Bumps 2515 can provide fluid perturbations as desired or that provide selected empirical results. Bumps 2515, as used herein, include the presence and/or absence of any biological and/or non-biological materials including, but not limited to, materials used or present in any tubular structures as defined herein. Bumps can have a desired cross-sectional shape such as a circular shape, semi or partially circular or ovular shape, rectangular shape and so forth. Variations in the depth, width, length, direction, shape and/or periodicity (for example, distance between bumps) can produce or alter the resulting second order dynamic conditions for a given set of global dynamic conditions and/or dynamic conditions at region(s) A.

Figure 47G:
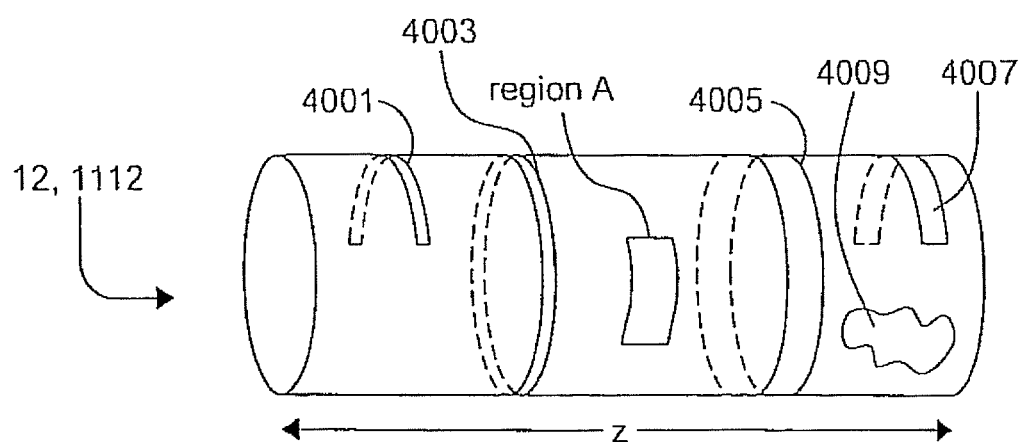

FIG. 47G shows a tubular structure 12, 1112 in accordance with another embodiment of the invention. Tubular structure 12, 1112 has a partial ring 4001, a full ring 4003, a full sleeve 4005, a partial sleeve 4007 and a patch 4009 attached and/or coupled to tubular structure 12, 1112 and/or fabricated into tubular structure 12, 1112. Rings 4001 and 4003, sleeves 4005 and 4007 and patch 4009 can be ridged or flexible to provide known variations in flexibility and elasticity of the walls of tubular structure 12, 1112 along the z axis. Such known variations in flexibility and elasticity yield sets of dynamic conditions including second order dynamic conditions at tubular structure 12, 1112 which correspond to certain desired dynamic conditions when used in systems herein in accordance with embodiments of the invention such as systems 1, 1101.

As discussed above, FIGS. 47A-47G are tubular structures which can be formed outside systems 1, 1101 or tubular structures that are formed, trained and/or grown after being subjected to predetermined dynamic conditions, including global and/or dynamic conditions at regions A for a predetermined amount of time. Hence, an initial tubular structure with initial perturbations and predetermined variations in shape D(z), can develop a desired shape and desired perturbations to effect the desired second order dynamic conditions as a result of the growth and/or further development of grooves, varying elasticity and/or any other perturbations of the tubular structure due to the growth and/or training of biological material on and/or the tubular structure.

Also, tubular structures can be a combination of one or more tubular structures with biological or non-biological materials which can be applied to the inner surface and/or the outer surface of the tubular structures. In addition, tubular structures include all of the above combinations which have been placed in the systems described herein and allowed to develop, grow under desired dynamic conditions for a desired length of time. Such tubular structures are said to have been tubular structures as shown in FIG. 18 under training/testing dynamic conditions and, in particular, non-in vivo bio training/testing conditions. In vivo dynamic conditions might also serve as training/testing conditions as well as combinations of in vivo dynamic conditions and training/testing dynamic conditions.

Tubular structures can be slightly, partially, substantially or completely trained in the absence of any biological materials as well. This might include subjecting tubular structures to training by the systems, in accordance with other embodiments of the invention in order to prepare them or alter them or test diem for a particular use.

Referring back to FIG. 18, classes of dynamic conditions can be subdivided into areas or locations at which the dynamic condition might occur. Hemodynamic conditions can, for example, be divided into hemodynamic conditions experienced by arteries in the upper leg or arteries in the lower leg, veins in the upper legs or veins in the lower legs, arteries in the arms, veins in the arms, pulmonary arteries, arteries in the neck and so forth. Hybrid tubular structures 1112 can include endothelial cells grown under dynamic conditions which include combinations of types of dynamic conditions (FIGS. 17A and 1713) for a particular class of dynamic conditions, e.g., a particular artery in the upper leg. Resulting morphology and functionality of the endothelial cells grown (from stem cells) and/or trained under upper leg artery hemodynamic conditions of a particular mammal will be different than the morphology and functionality of a particular vein grown and/or trained under hemodynamic conditions experienced by the particular vein in the particular mammal (see, for example, David G Harrison "The shear stress of keeping arteries clear" Nature Medicine, Vol. 11, No. 4, April 2005, pp. 375-376; James N. Topper et al., "Blood flow and vascular gene expression: fluid shear stress as a modulator of endothelial phenotype" Molecular Medicine Today, January 1999, pp. 40-46; Ulf Landmesser, Md. et al. "Endothelial Function, A Critical Determinant in Atherosclerosis" American Heart Association, Jun. 1, 2004, pp. 11-27-11-33; Edward M. Boyle, Jr., MD et al. "Atherosclerosis" 1997 by The Society of Thoracic Surgeons, pp. S47-S56; Peter F. Davis, et al. "Spatial Microstimuli in Endothelial Mechanosignaling" Circulation Research Mar. 7, 2003, pp. 359-370; Shu Chien "Molecular and mechanical bases of focal lipid accumulation in arterial wall" Progress in Biophysics & Molecular Biology 83 (2003), pp. 131-151; Michael B. Dancu et al. "Asynchronous Shear Stress and Circumferential Strain Reduces Endothelial NO Synthase and Cyclooxygenase-2 but Induces Endothelin-1 Gene Expression in Endothelial Cells" Arterioscler Thromb Vasc Biol., November 2004, pp. 2088-2094;

Ruey-Bing Yang et al. "Identification of a Novel Family of Cell-surface Proteins Expressed in Human Vascular Endothelium" The Journal of Biological Chemistry, Vol. 277, No. 48, Issue of Nov. 29, 2002, pp. 46364-46373; Filomena de Nigris et al. "Beneficial effects of pomegranate juice on oxidation-sensitive genes and endothelial nitric oxide synthase activity at sites of perturbed shear stress" PNAS, Mar. 29, 2005, vol. 102, no. 13, pp. 4896-4901; and Ralph L. Nachman et al. "Endothelial cell culture: beginnings of modern vascular biology" The Journal of Clinical Investigation, vol. 114, no, 8, October 2004, pp. 1037-1040, which are all hereby incorporated by reference in their entirety).

As used herein, fluids passing through pressure flow system, tubular structures specimen holders and/or grafts or the like have been variously described. However, fluids are not intended to be so limited. For example, fluids used in embodiments or as embodiments can include fluid materials such as liquids, solids, gases and/or miscellaneous items, individually or in various combinations, concentrations or mixtures. Exemplary fluids can include fluid materials such as cells, bacteria, minimum essential Eagles medium, growth factor, cell differentiating small molecule, cell differentiating biologics, cell culture medium or the like. Exemplary liquids can include plasma, saline, blood, water, cell culture medium, fetal bovine serum (FBS), bovine serum albumin (BSA), cerebral spinal fluid or the like. Fluid materials can include solids such as hormones, proteins, viruses, lipids, peptides, nucleotides, glycols, antibiotics, pharmacological agents, transmitters, receivers, transmitter/receivers, fluid nanoparticles, free electrons, minerals, iron, zinc, copper, magnesium, calcium or the like. Exemplary gases can include oxygen, nitric oxide, carbon dioxide, carbon monoxide or the like, Systems herein including systems 1 and 1101 can be used to model or simulate. According to one embodiment, systems 1 and 1101 together with perturbed tubular structures can model pathology or the departure or deviation from a normal condition at the tubular structure. This can include anatomic or functional manifestations of a disease (or structural and functional changes in cells, tissues and organs that underlie disease). Systems 1 and 1101 can model pathologies within various classes of dynamic conditions (e.g., see FIG. 18) using at least one and typically multiple types of dynamic conditions (e.g., see FIGS. 17A and 17B) according to embodiments of the invention. Accordingly, embodiments of systems 1 and 1101 can be used to determine or evaluate dynamic, static, time dependent, non-linear or changing behaviors.

The functional phenotype of vascular endothelium can be responsive (e.g., dynamically) to an array of physiological and pathophysiological stimuli all of which represent types of dynamic conditions as per FIGS. 17A and 17B. Such stimuli can include biochemical substances such as inflammatory cytokines, growth factors, circulating hormones and bacterial products. In addition, endothelium is exposed to a number of biomechanical stimuli resulting from the pulsatile flow of blood within the branched vascular tree including frictional forces, fluid shear stresses, cyclic strains (stretch) and hydrostatic pressures or the like (yet additional types of dynamic conditions as per FIGS. 17A and 17B).

Shear stress stimulates a myriad of intracellular events (e.g., intracellular signaling events) in endothelial cells which also represent types of dynamic conditions of FIGS. 17A and 17B. Some of these events, such as changes in intracellular calcium, protein phosphorylation and acute stimulation of nitric oxide production, occur within seconds after the onset of shear and other changes such as cell shape and gene expression, occur over hours to days.

Embodiments of the system can model vascular diseases using various types of dynamic conditions. For example, the interplay between hemodynamic stimuli and the functional phenotype of endothelium can affect a variety of vascular diseases.

One exemplary set of biomechanical and intracellular signaling dynamic conditions in endothelial cells can be for atherosclerosis. Atherosclerosis is a progressive disease, and changes within the arterial endothelium, such as an increased permeability to lipoproteins, endothelial cell damage and/or repair, and the expression of leukocyte adhesion molecules can be demonstrated in the atherosclerotic process. Interactions between apoptosis signaling kinase 1 (ASK1), Txnip, which is a molecule whose levels correlate with the degree of shear stress, and thioredoxin in endothelial cells can be related to shear stress. Txnip binds to catalytic cysteines of thioredoxin to reduce thioredoxin activity and its ability to bind to ASK1. See, for example, Blood Flow and Vascular Gene Expression: fluid shear stress as a modulator of endothelial pehenotype, Topper, J. N., and Gimbrone Jr., M. A., Molecular Medicine Today, January 1999, pp. 40-46; the contents of which are incorporated herein by reference.

Additional events that can be modeled include interactions of endothelial cells and the types of dynamic conditions measured and/or controlled by systems 1 and 1101 can include nitric oxide production, enhanced expression of antioxidant enzymes like superoxide dismutase and glutathione peroxidase or glutathione.

In one embodiment of the invention, a specimen 12 such as tubular structure 1112 with endothelial cells is placed in a specimen holder 10 in pressure flow loop subsystem 1105, while the dynamic condition of shear stress is controllable varied and detection of ASK1, thoioredoxin and Txnip are monitored by systems, specimens or fluid sensors. In the endothelial cells, shear stress associated to thoioredoxin can affect activation of ASK1. In the absence of shear stress, thioredoxin is bound by Txnip and maintained in an inactive state, which leads to increased activation of ASK1. This leads to increased expression of the vascular cell adhesion molecule 1 (VCAM1), which promotes leukocyte adhesion, inflammation and atherosclerosis. For example, cytokine TNF-α can lead to phosphorylation and activation of ASK1, and the activated ASK1 activates downstream MAP kinases and ultimately p38 and Jun-terminal kinase (JNK), which increases VCAM1.

However, in the presence of shear stress, Txnip can be reduced, liberating thioredoxin and leading to increased binding of thioredoxin to ASK1 and inhibition of ASK1 (e.g., less ASK1 activation by TNF-α). Thus, shear stress can be controllably set between 0 and a maximum value in a series of steps while data is collected according one embodiment. Then, results can be related to corresponding levels of the intercellular activity by, for example, controller 70 or 1103.

As described above, such interrelationships between dynamic conditions illustrate exemplary modeling targets for disclosed embodiments. Exemplary modeling that can be performed by system embodiments or modeling embodiments are shown in FIG. 40.

Similarly, embodiments of systems and methods described herein with respect to FIGS. 1-47 and be used for testing/training activities. Embodiments can be used for exemplary dynamic conditions related to testing and training as described herein.

Figure 48:
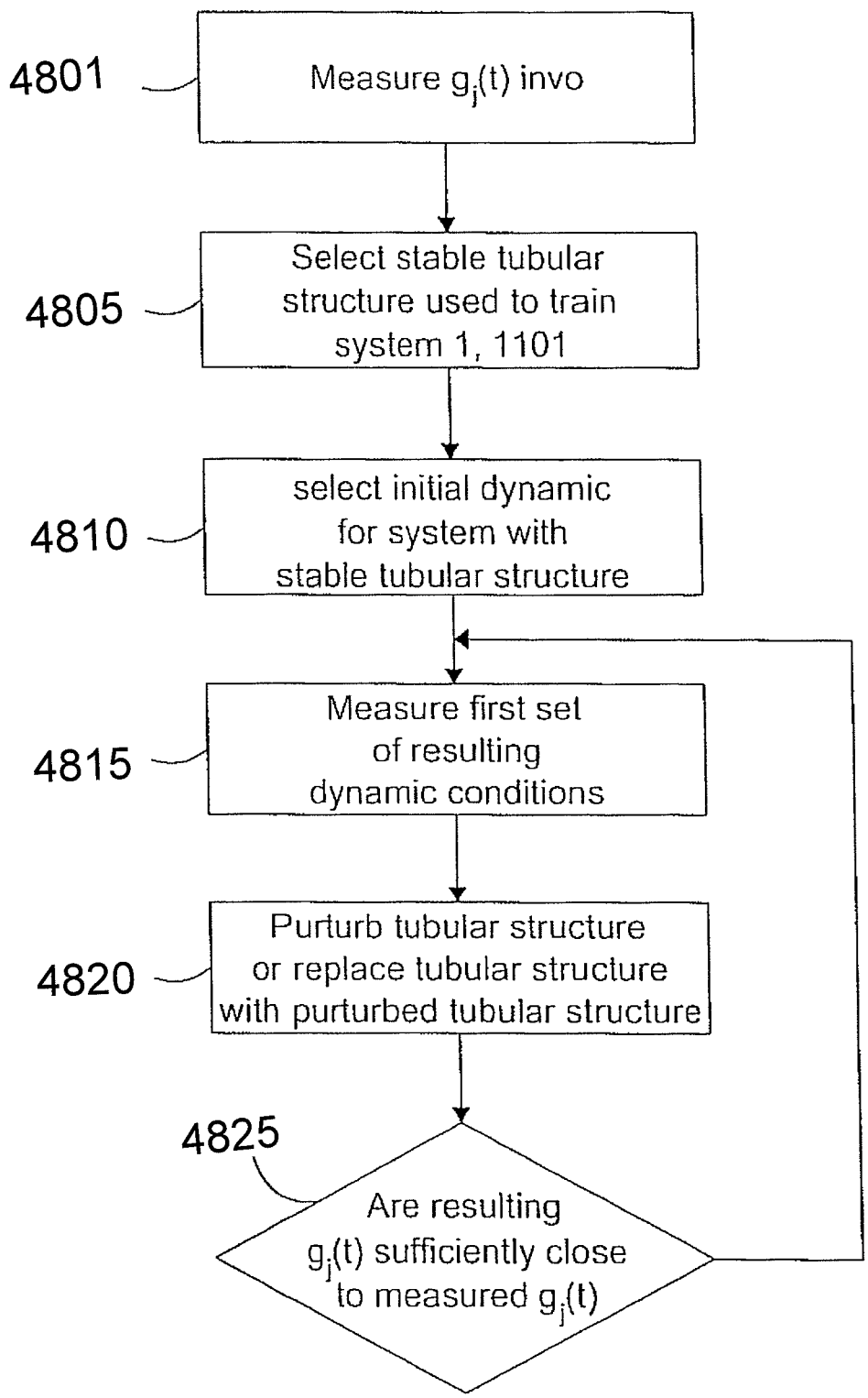
FIG. 48 show a flowchart of a process of matching second order dynamic conditions to a selected target according to an embodiment of the invention.

FIG. 48 shows steps of a preferred method for producing dynamic conditions at regions A, as well as second order dynamic conditions at a specimen or tubular structure 12 or 1112. The method starts at step 4801, at which dynamic conditions $g_i(t)$ (see FIG. 17), including second order dynamic conditions and mean dynamic conditions, are measured in vivo.

Step 4805 involves selecting a tubular structure used to train system 1, 1101 that yields a set of dynamic conditions closest to the dynamic conditions $g_i(t)$s measured in step 4801. Step 4810 involves selecting initial global dynamic conditions and/or conditions at one or more regions A for system 1, 1110 based on the mean of the measured dynamic conditions $g_i(t)$.

Step 4815 involves measuring a first set of resulting dynamic conditions g(t) at the known stable tubular structure. Any of the methods and systems described herein (for example, sensors A, B, Cn, Dn . . . and/or 1, 2, 3n, 4n . . . ), as well as any other methods and systems known in the art, can be used to directly and/or indirectly measure the resulting dynamic conditions.

Step 4820 involves perturbing the stable tubular structure in a manner, for example, as discussed above in connection with FIGS. 45A-45C, 46, and 47A-47H, or as otherwise discussed herein. This may involve replacing the stable tubular structure with a second perturbed tubular structure. The stable tubular structure is preferably perturbed in a manner which will change the set of resulting dynamic conditions, including resulting second order dynamic conditions, to values that are closer to the measured set of dynamic conditions. For example, a rigid full ring (FIG. 47H) can be used to alter the resulting dynamic conditions and second order dynamic conditions.

At step 4825, it is determined whether the resulting set of dynamic conditions measured at step 4801 is sufficiently close to the measured set of dynamic conditions or a desired set of dynamic conditions. If it is, the method ends. If not, then the method jumps back to step 4715.

In the method embodiment above, it is assumed that a selected class of dynamic conditions (e.g., FIG. 18) was determined prior to step 1. Further, steps 2 and 3 above presumes that a plurality of systems having different components have been trained using a plurality of initial tubular structures. The initial systems could include systems such as systems 1, 1000, 2000, 3000, 4000, 5000, 6000, 7000, 8000, 1101. Further, the known stable initial tubular structures could be any tubular structures such as shown in FIGS. 5A-5D, 45A-45C, 46 and 47A-47H. In addition, perturbing the known stable tubular structure can be considered to include another embodiment modifying the global dynamic conditions in the pressure flow loop subsystem (e.g., pressure flow loop subsystem 1105) to generate dynamic conditions at a tubular structure mounted therein or one or more regions A on such a tubular structure.

As discussed above, communications between the controller 1105 and sensors (e.g., A, B, . . . ; 1, 2, . . . ) can include communications between sensors in the fluid (represented herein by numbers such as 1, 2, . . . ) in the system (represented herein by letters A, B, . . . ) and/or in the specimen or tubular structure represented either by numbers 1, 2, or letters A, B, depending on whether they were part of the system or part of the fluid that can individually transmit (t), receive (r) or transmit and receive (tr). System sensor in system 1101 can be in the pressure flow loop subsystem 1105 including components thereof and/or the specimen 10 and directly or indirectly coupled to each other and to system 1101 including controller 70 to detect dynamic conditions (e.g., FIGS. 17A and 17B). Sensors in the fluid or fluid sensors are referred to herein from time to time as fluid transmitters, fluid receivers, fluid transmitter/receivers and/or fluid detectors. For example, such fluid sensors can include nanoparticles such as nanosensors and/or mems sensors which are indicated as 1n, 2n . . . rather than 1, 2, . . . . Exemplary transmitter, receiver or transmitter/receiver nanoparticles (system, fluid and/or specimen) can include a nanotransmitter, nanoreceiver or a nanosensor or a nanotransmitter/receiver.

A transmitter/receiver (system, fluid and/or specimen) is capable of receiving information from another transmitter/receiver (system, fluid and/or specimen) a transmitter (system, fluid and/or specimen), a transmitting nanoparticle (system, fluid and/or specimen) a transmitting sensor (system, fluid and/or specimen) or the like, and/or combinations thereof. The transmitter/receiver (system, fluid and/or specimen) is capable of sending information to another transmitter/receiver (system, fluid and/or specimen), a receiver (system, fluid and/or specimen), a receiving nanoparticle (system, fluid and/or specimen), a receiving sensor (system, fluid and/or specimen), or the like and/or combinations thereof. Further, a first transmitting or receiving sensor and/or mems or nanosensors (system, fluid and/or specimen) or a plurality of first transmitting or receiving sensors and/or mems or nanosensors each can be capable of sending or receiving information to/from at least one second transmitting or receiving sensors and/or mems or nanosensors (system, fluid and/or specimen) or vice versa.

Such transmitting or receiving relationships can exist for a transmitter or a receiver. A transmitter (system, fluid and/or specimen) is capable of sending information to a transmitter/receiver (system, fluid and/or specimen), a receiver (system, fluid and/or specimen), a receiving nanoparticle, a sensor or the like, a plurality of the same, individual items above or combinations thereof. Further, the transmitter is capable of sending information to one or more second receivers (e.g., system or fluid) and/or one or more third receivers (e.g., system or fluid). Similarly, a plurality of first transmitters (e.g., system or fluid) can each be capable of sending information to a single or designated receiver or sensor.

A receiver (e.g., system or fluid) is capable of receiving information from a fluid transmitter/receiver, a transmitter/receiver, a fluid transmitter, a transmitter, a transmitting nanoparticle, a sensor, a fluid sensor or the like, a plurality of the same, individual items above or combinations thereof. Further, the receiver is capable of receiving information from one or more second transmitters (e.g., system or fluid) and/or one or more third transmitters (e.g., system or fluid). A plurality of first receivers (e.g., system or fluid) can each be capable of receiving information from a single or designated transmitter or sensor.

A transmitter/receiver nanoparticle (e.g., system or fluid) is capable of sending and/or receiving information to/from a transmitter/receiver, a fluid transmitter/receiver, a transmitter/receiver nanoparticle, a transmitter, a fluid transmitter, a receiver, a fluid receiver, a nanoreceiver, nanotransmitter, a fluid sensor, a sensor or a nanosensor or the like, a plurality of the same, individual items above or combinations thereof. A first transmitting and/or receiving nanoparticle (e.g., system or fluid) is capable of sending or receiving information to/from one or more second transmitting and/or receiving nanoparticles and/or one or more third transmitting and/or receiving nanoparticles or more. A plurality of first transmitter/receiver nanoparticles is capable of sending or receiving information to/from a single or designated transmitter/receiver nanoparticle.

Such transmitting or receiving relationships can exist for a nanotransmitter or a nanoreceiver. A nanotransmitter (e.g., system or fluid) is capable of sending information to a nanotransmitter/receiver, a fluid nanoreceiver, a receiver, a fluid receiver, a fluid sensor, a sensor, a nanosensor, a nanoreceiver or the like, a plurality of the same, individual items above or combinations thereof. Further, a first nanotransmitter is capable of sending information to one or more second receiver nanoparticles (e.g., system or fluid) and/or one or more third receiver nanoparticles (e.g., system or fluid) or more. Similarly, a plurality of first nanotransmitters (e.g., system or fluid) can each be capable of sending information to a single or designated nanoreceiver or sensor (e.g., system or fluid).

A nanoreceiver (e.g., system or fluid) is capable of receiving information from a fluid nanotransmitter/receiver, a nanotransmitter/receiver, a transmitter/receiver, a fluid transmitter/receiver, a fluid transmitter, a transmitter, a nanotransmitter, a sensor or the like, a plurality of the same, individual items above or combinations thereof. A first receiver nanoparticle is capable of receiving information to/from one or more second transmitter nanoparticles (e.g., system or fluid) and/or one or more third transmitter nanoparticles (e.g., system or fluid) or more. A plurality of first nanoreceivers (e.g., system or fluid) can each be capable of receiving information from a single or designated nanotransmitter or a sensor (e.g., system or fluid).

Exemplary communications between sensors can be supported by described embodiments. For example, a transmitter/receiver (or a separate transmit sensor and receiver sensor) is capable of transmitting information to or transmitting/receiving information to/from a first transmitter/receiver (or a plurality of first transmitter/receivers) and a second transmitter/receiver (or a plurality of second transmitter/receivers) is capable of receiving information from the first transmitter/receiver (or the plurality of first transmitter/receivers) and transmitting information to the transmitter/receiver. In this case, the transmitter/receivers (e.g., system or fluid) can be transmitters or receivers and can be nanoparticles (e.g., system or fluid) or combinations thereof.

In another example supported by disclosed embodiments, a transmitter/receiver is capable of receiving information from or transmitting/receiving information to/from a first transmitter/receiver (or a plurality of first transmitter/receivers) and a second fluid transmitter/receiver (or a plurality of second transmitter/receivers) is capable of transmitting information to the first fluid transmitter/receiver (or the plurality of first transmitter/receivers) and receiving information from the transmitter/receiver. In this case, the transmitter/receivers (e.g., system or fluid) can be transmitters or receivers and can be nanoparticles (e.g., system or fluid) or combinations thereof.

A transmitter or receiver is capable of transmitting information to or transmitting/receiving information to/from a plurality of first transmitters or receivers and a plurality of second transmitters or receivers is capable of respective communications (e.g., 1-to-1, many-to-1, 1-to-many, many-to-many, 1-to-all, all to-1, all-to-all, or the like) with each of the first transmitters or receivers to then transmit information to the transmitter or receiver. A transmitter/receiver is capable of receiving information from or transmitting/receiving information to/from at least one first fluid transmitter/receiver, and a plurality of second fluid transmitter/receivers are capable of receiving information from the first fluid transmitter/receiver and transmitting information to at least one third fluid transmitter/receiver that can transmit information to the transmitter/receiver or vice versa. Further, a system 1, 1101 could include four or more plurality of sensors in respective communications (e.g., 1-to-1, many-to-1,1-to-many, many-to-many, 1-to-all, all to-1, all-to-all, or the like) with subsets or corresponding ones of each other pluralities to transmit respective information $f_i(t)$, $f_j(t)$ or $FB_j(t)$ therein. Again, sensors (e.g., system or fluid) can be nanoparticles (e.g., system or fluid) or combinations thereof.

Applications of Systems

Applications for embodiments of the system broadly described herein are numerous and varied. Although the exemplary discussion set forth herein has focused mainly on biological applications for embodiments of the system, and more particularly, on hemodynamic forces which act on blood flowing through blood carrying vessels, it is well understood that embodiments of the system may be used to reproduce any dynamic pressure and flow environment which would benefit from the ability to independently control pressure and flow, including both biological and non-biological applications. For example, embodiments of the system may be used to produce a biological environment which would simulate a number of other in vivo conditions. These conditions may include, for example, pressure and flow conditions within joints or on various bone/tendon/musculature structure. Embodiments of the system may also be used to reproduce conditions within, for example, the stomach, intestines, esophagus, lungs, or sinus cavities, or any other such dynamic in-vivo-environment in which such a reproduction of actual conditions would prove beneficial. Embodiments of the system may, with the proper cellular structure, seeding, and corresponding media, be used to initiate and grow replacement bone/cartilage/organ structure and the like.

Non-Biological Applications

In addition to these dynamic in-vivo conditions, certain systems as embodied and broadly described herein may also be used to reproduce dynamic pressure and flow environments to which non-biological elements are subjected during operations. Such non-biological applications may include, for example, dynamic pressure and flow through rigid/flexible pipes/tubes in a whole host of different systems. These systems may include, but are not limited to, for example, petroleum pipelines, fuel flow lines in a variety of different systems, hydraulic systems, lubrication systems, fluid lines in manufacturing facilities, and especially diose under pressure, drainage systems and related storm water and sewage treatment systems, and any other such practical/industrial application which would stand to benefit from such a modeling of actual conditions.

Biological Applications

Applications in the pharmaceutical, biotechnology, life science, academic, and research industries for a system as embodied and broadly described herein include, but are not limited to, therapeutic screening & testing and discovery & development of drugs, active biomolecules, regenerative medicines, medical devices, cell & tissue devices or therapies, drug delivery systems, personalized medicine, genomics/proteomics, small chemical, biologics, and the like. Embodiments of the system can be adapted to serve as a model for cardiovascular and related pathologies such as, for example, cancer or diabetes, via simulation of pathologic (or non-pathologic) hemodynamics that induce a consequent pathologic (or non-pathologic) response and phenotype on vascular cells as well as other cells. Therapies can then be designed, developed, and tested against the pathologic model. This dynamic cell and tissue culture environment captures in vivo phenotype, function, and physiology more closely than traditional static cultures.

Embodiments of the system can enhance and reduce therapeutic discovery times by providing a cost-effective platform to perform typical and novel cell, molecular biological, and pharmacological research and development. Embodiments of the system not only provides a means of studying hemodynamics in normal and diseased states, but can also be used for tissue engineering and regeneration, such as, for example, to test or train the function of bypass vessels prior to coronary bypass surgery or peripheral arteries or AV-shunts, or to investigate cryopreserved vessels or for research or medical use. Example applications include atherosclerosis, plaques (vulnerable plaque, protruding, calcified, soft, etc.), inflammation (i.e. leuokocyte adhesion), restenosis, cancer (metastasis-tumor spreading to other tissues, extravasation-tumor and leuokocyte adhesion, and the like), and diabetes (retinopathy, blindness, and the like).

Embodiments of the system can also provide essential capabilities and high-throughput abilities to the pharma/biotech industries, cell-based screening and testing, drug discovery and development, and the like. Cell-based assays inherently evaluate test compound activity in a biologically relevant context, with the added potential for extraction of high information content. Embodiments of the system can be used to systematically screen and test vast numbers of compound combinations, testing their effects using cell-lines or primary-cell or stem cell or patient specific stem cell cultures to allow interaction with complex biological pathways that cannot be replicated in a cell-free assay. Other multiple cell or tissue types can be added to certain systems such as hepatocytes, renal, cardiac, etc. for various purposes such as providing a test or growth environment that is representative of in-vivo environments.

Embodiments of the system may be used in identifying potential chemical inhibitors or activators of enzymes, receptors, or any proteins which have effects upon cell phenotype. One method generally employs two cell lines, preferably alike except for their expression (production) of the protein of interest at different levels (and any further differences necessitated by that difference in expression). Inhibitors or activators are identified by their greater effect on the phenotype of the higher producing cell line.

Any phenotypic characteristic of the cell which is affected by expression of the protein of interest, other, of course, than the level of the protein itself, may be assayed. The phenotypic characteristic is preferably a "cultural" or "morphological" characteristic of the cell. For purposes of this application, these terms may be defined as follows.

Cultural characteristics include, but are not limited to, the following: the nutrients required for growth; the nutrients which, though not required for growth, markedly promote growth; one or more physical conditions (temperature, pH, gaseous environment, osmotic state, and anchorage dependence or independence) of the culture which affect growth; and the substances which inhibit growth or even kill the cells.

Morphological characteristics include, but are not limited to, the following: the size and shape of cells; their arrangements; cell differentiation; and subcellular structures.

Where the protein of interest is implicated in tumorigenesis or related phenomena, the characteristic observed is preferably one related to cellular growth control, differentiation, de-differentiation, carcinogenic transformation, metastasis, tumorigenesis, or angiogenesis.

Phenotypic changes which are observable with the naked eye are of special interest. Changes in the ability of the cells to grow in an anchorage-independent manner, to grow in soft agar, to form foci in cell culture, and to take up selected stains, for example, are particularly appropriate phenomena for observation and comparison.

The higher producing cell line is preferably obtained by introducing a gene encoding the Protein of Interest (POI) into a host cell or, if a native protein of the cell, by introducing a promoter into the cellular genome upstream of and operatively linked to the POI. The gene may be a one isolated from the genome of an organism, a cDNA prepared from an mRNA transcript isolated from an organism, or a synthetic duplicate of a naturally occurring gene. It may also have a sequence which does not occur exactly in nature, but rather corresponds to a mutation (single or multiple) of a naturally occurring sequence (also referred to as a "wild-type sequence"). No limitation is intended on the manner in which this mutated sequence is obtained.

The gene is preferably operably linked to a promoter of gene expression which is functional in the host, such that the corresponding POI is stably "overproduced" in the recipient cells to differing degrees. The promoter may be constitutive or inducible. By "overproduced", it is meant that the POI is expressed at higher levels in the genetically manipulated cell line than in the original cell line. This allows one to generate cell lines which contain (or secrete) from as little as a few fold to more than 100-fold elevated levels of the POI relative to the control cells.

Any method may be used to introduce the gene into the host cell, including transfection with a retroviral vector, direct transfection (e.g., mediated by calcium phosphate or DEAE-dextran), and electroporation. Preferably, a retroviral vector is used The host cells should exhibit a readily observable phenotypic change as a result of enhanced production of the POI. Preferably, this response should be proportional to the level of production of the POI. Finally, the cells should not spontaneously manifest the desired phenotypic change. For example, 3T3 cells form foci spontaneously. Among the preferred cell lines for these methods are Rat-6 fibroblasts, C3H10T ½ fibroblasts, and HL60. (HL60 is a human cell line that differentiates in response to PKC activation.) 3T3 cells may be used, but with the reservation stated above.

Generally speaking, it is preferable to maximize the ratio of production by the "overproducing" cell line to production by the "native" line. This is facilitated by selecting a host cell line which produces little or no POI, and introducing multiple gene copies and/or using high signal strength promoters.

The Rat 6 embryo fibroblast cell line is a variant of the rat embryo fibroblast cell line established by Freeman et. al., (1972) and isolated by Hsiao et al., 1986. This cell line has an unusually flat morphology, even when maintained in culture at post-confluence for extended periods of time, displays anchorage dependent growth and, thus far, has not undergone spontaneous transformation. It was also ideal for these studies since it has a very low level of endogenous PKC activity and a low level of high affinity receptors for phorbol esters.

According to these methods, one looks for is a increase in the phenotypic change exhibited by the cell which becomes greater with increasing expression of the POI. This is a "graded cellular response," and it is by this specialized response that inhibitors or activators of the POI can be distinguished from agents that act upon other cell metabolites to effect a phenotypic change.

Thus, in a preferred embodiment, the cell lines are assayed for their relative levels of the POI, and their ability to grow in anchorage-independent systems (e.g., matrices such as soft agar or methocel), to form small "foci" (areas of dense groups of cells clustered together and growing on top of one another) in tissue culture dishes, to take up selected stains, or to bind an appropriately labeled antibody or other receptor for a cell surface epitope. In addition to exhibiting these growth control abnormalities, such cell lines will also be sensitive in their growth properties to chemical agents which are capable of binding to, or modifying the biological effects of, the POI.

In selected embodiments, the method is particularly unique in that it can be employed to search rapidly for EITHER activators OR inhibitors of a given POI, depending upon the need. The term "activators," as used herein, includes both substances necessary for the POI to become active in the first place, and substance which merely accentuate its activity. The term "inhibitors" includes both substance which reduce the activity of the POI and these which nullify it altogether. When a POI has more than one possible activity. The inhibitor or activator may modulate any or all of its activities.

The use of this screening method to identify inhibitors or activators of enzymes is of special interest. In certain preferred embodiments, the method is used to identify inhibitors or activators of enzymes involved in tumorigenesis and related phenomena, for example, protein kinase C, ornithine decarboxylase, cyclic AMP-dependent protein kinase, the protein kinase domains of the insulin and EGF receptors, and the enzyme products of various cellular one genes such as the c-src or c-ras genes.

Protein kinase C (PKC) is a Ca and phospholipid-dependent serine/threonine protein kinase of fundamental importance in cellular growth control. PKC is activated endogenously by a wide variety of growth factors, hormones, and neurotransmitters, and has been shown to be a high affinity receptor for the phorbol ester tumor promoters as well as other agents which possess tumor promoting activity (for reviews see Nishizuka 1986; 1984; Ashendel, 1984). PKC has been shown to phosphorylate several intracellular protein substrates, including the epidermal growth factor (EGF) receptor (Hunter et al., 1984), pp60src (Gould et al, 1985), the insulin receptor (Bollag et al., 1986), p21 ras Jeng et al., 1987), and many others (Nishizuka, 1986). Several laboratories have recently isolated cDNA clones encoding distinct forms of PKC, thus demonstrating that PKC is encoded by a multigene family (Ono et al., 1986, Knopf et al., 1986, Parker et al., 1986; Coussens et al., 1986; Makowske et al., 1986; Ohno et al., 1987; Housey et al., 1987). The multiple forms of PKC exhibit considerable tissue specificity (Knopf, et. al., 1986; Brandt et al., 1987; Ohno, et al, 1987; Housey, et al., 1987) which suggests that there may be subtle differences in the function(s) of each of the distinct forms. However, all of the cDNA clones which have been isolated thus far that encode distinct forms of PKC share at least 65% overall deduced homology at the amino acid level, and transient expression experiments with some of these cDNA clones have shown that they encode serine/threonine protein kinase activities which bind to, or are activated by, the phorbol ester tumor promoters (Knopf, et. al., 1986, Ono, et. al., 1987).

With the exception of the brain, where its expression is very high, PKCbeta-1 is expressed at very low levels in most tissues, and its expression is virtually undetectable in Rat 6 fibroblasts (see below). Thus, using this form will maximize the phenotypic differences observed between control cells and cells overexpressing the introduced form of PKC. The PKCbeta-form is also of particular interest because within the PKC gene family its deduced carboxy terminal domain displays the highest overall homology to the catalytic subunit of the cyclic AMP-dependent protein kinase (PKAc) and the cyclic GMP-dependent protein kinase (PKG) (Housey et al., 1987). The latter observation suggests that PKAc, PKG, and the beta-1 form of PKC may share a common ancestral serine/threonine protein kinase progenitor, and that the additional PKC genes may have been derived through evolutionary divergence from the beta-1 form.

Agents that interact with certain structural proteins, such as actin and myosin, are also of interest. Mutations in the genes expressing these proteins may be involved in tumorigenesis and metastasization. Such interactions can lead to changes in cell phenotype which can be assayed by this method.

In additional studies with other genes, most notably the c-H-ras oncogene, the catalytic subunit of the cyclic AMP-dependent protein kinase, the c-myc oncogene, and certain cDNA clones encoding phorbol-ester inducible proteins, similar results have been obtained. Thus it is also clear that the method can be generalized to a wide variety of genes encoding proteins which are involved in cellular growth control in numerous cell types.

One embodiment of a preferred protein inhibitor/activator drug screening method of the invention can include the following steps:

1. Construction of an expression vector which is capable of expressing the protein of interest in the selected host by inserting a gene encoding that protein into a transfer vector. The gene may be inserted 3' of a promoter already borne by the transfer vector, or a gene and a promoter may be inserted sequentially or simultaneously.

2. Introduction of the expression vector (a) into cells which produce recombinant retrovirus particles, or (b) directly into host cells which will be used for subsequent drug screening tests (the resulting cells are called herein "test" cells). In parallel, the transfer vector (i.e., the vector lacking the gene of interest and possibly a linked promoter but otherwise identical to the expression vector) is preferably also introduced into the host cells. Cell lines derived from this latter case will be used as negative controls in the subsequent drug screening tests. Alternatively, the unmodified host cells may be used as controls.

If (a) was employed above, after an appropriate time (e.g., 48 hours), media containing recombinant virus particles is transferred onto host cells so as to obtain test or control cells.

3. The test and control cells are transferred to selective growth medium containing the appropriate drug which will only allow those cells harboring the expression vector containing the selectable marker gene (as well as the gene or cDNA of experimental interest) to grow. After an appropriate selection time (usually 7-10 days), individual clones of cells (derivative cell lines) are isolated and propagated separately.

4. Each independent cell line is tested for the level of production of the POI. By this method, a range of cell lines is generated which overproduce from a few fold to more that 100-fold levels of the POI. In parallel, the control cell lines which contain only the transfer vector alone (with the selectable marker gene) are also assayed for their endogenous levels of the POI.

5. Each independent line is then tested for its growth capability in soft agar (or methocel, or any other similar matrix) of various percentages and containing different types of growth media until cell lines are identified which possess the desired growth characteristics as compared to the control cell lines.

6. Each cell line is also tested for its ability to form "foci", or areas of dense cellular growth, in tissue culture plates using media containing various percentages and types of serum (20%, 10%, 5% serum, fetal calf serum, calf serum, horse serum, etc.) and under various conditions of growth (e.g. addition of other hormones, growth factors, or other growth supplements to the medium, temperature and humidity variations, etc.). In these tests, the cells are maintained at post-confluence for extended periods of time (from two to eight weeks) with media changes every three days or as required. Such growth parameters are varied until cell lines are identified which possess the desired foci formation capacity relative to the control cell lines under the identical conditions.

7. After a cell line possessing the required growth characteristics is identified, the cells are grown under the conditions determined in (5) above with the growth medium supplemented with either crude or purified substances which may contain biologically active agents specific to the POI. Thus, crude or purified substances possessing the latter properties can be rapidly identified by their ability to differentially alter the growth properties of the experimental cells (which overproduce the POI) relative to the control cells (which do not). This can be done rapidly even by simple observation with the naked eye, since the colonies which grow in soft agar after 2 weeks are easily seen even without staining, although they may be stained for easier detection.

Similarly, if the post-confluence foci formation assay is chosen, the foci which result after approximately two weeks can be easily seen with the naked eye, or these foci can also be stained. Results of the assays can be rapidly determined by measuring the relative absorbance of the test cells as compared to the control cells (at 500 nm, or another appropriate wavelength). In this fashion, thousands of compounds could be screened per month for their biological activity with very low labor and materials costs.

Furthermore, if antigen expression varies on the test cells expressing high levels of the POI relative to the control cells, a simple Enzyme-Linked Immunoadsorption Assay (ELISA) could be performed and an antibody specific to the antigen.

While the assay may be performed with one control cell line and one test cell line, it is possible to use additional lines, tests lines with differing POI levels. Also additional sets of control/test lines, originating from other hosts, may be tested.

The system can also be used for identifying agents that bind to cellular targets, such as membrane proteins, but without necessarily affecting or altering the phenotype of the cell.

For example, the system may be used determine the ability of an agent to bind to a particular site on a membrane protein and thereby alter the level of surface expression thereof. Such an alteration in surface expression may result from the agent blocking a site on the mutant that corresponds to an active site on the wild-type membrane protein and/or by blocking intracellular trafficking and/or processing of the mutant membrane protein. Alternatively, an alteration in surface expression may result from the agent improving intracellular trafficking of the mutant membrane protein.

As described above, there are a wide variety of formats known and available to those skilled in the art for appropriate binding assays. According to certain embodiments of the invention, one or more cells expressing a membrane POI may be provided in a suitable liquid medium and exposed to one or more candidate compounds, while in other embodiments the cells may be immobilized on a surface and then exposed to the candidate compound(s). Similarly, according to still other embodiments of the invention, one or more candidate compounds may be immobilized on a surface and exposed to a liquid medium containing one or more cells that express a membrane protein of interest or the candidate compound(s) may be included in a suitable liquid medium to which one or more cells expressing a membrane protein of interest is added.

Binding is often easier to detect in systems in which at least one of the candidate compound and the membrane POI is labeled (e.g., with fluorescence, radioactivity, an enzyme, an antibody, etc., including combinations thereof, as known to those skilled in the art). After exposing the candidate compound to the cell expressing a membrane protein and washing off or otherwise removing unbound reagents, the presence of the labeled moiety (i.e., bound to the unlabelled component of the test system) is measured.

Methods for performing various binding assays are known in the art, including but not limited to the assay systems such as those described in PCT Application US98/18368. Various references provide general descriptions of various formats for protein binding assays, including competitive binding assays and direct binding assays, (see e.g., Stites and Terr, *Basic and Clinical Immunology*, 7th ed. (1991); Maggio, *Enzyme Immunoassay*, CRC Press, Boca Raton, Fla. (1980); and Tijssen, *Practice and Theory of Enzyme Immunoassays*, in *Laboratory Techniques in Biochemistry and Molecular Biology*, Elsevier Science Publishers, B.V. Amsterdam, (1985)).

Thus, according to certain embodiments, immunoassays are provided in which one or more cells expressing a membrane protein of interest are generally bound to a suitable solid support and combined with a candidate agent, and observing changes in the level of surface expression of the membrane POI. In these embodiments, one or more of the assay components is attached to a solid surface.

In some embodiments, an assay system may used (as known in the art) to detect the change in the surface expression of the membrane protein due to the binding of the candidate agent. For example, if the membrane protein of interest is a membrane ion channel, a patch clamp assay may be employed to detect a change in the flux of ions across the membrane, thus evidencing an increase in the level of surface expression of the ion channel.

In alternative embodiments, an indirect immunoassay system is used in which the membrane protein on the surface of the cell(s) is detected by the addition of one or more antibodies directed against an extracellular epitope of the membrane protein, as known in the art.

When using a solid support in embodiments of methods according to the invention, virtually any solid surface is suitable, as long as the surface material is compatible with the assay reagents and it is possible to attach the component to the surface without unduly altering the reactivity of the assay components. Those of skill in the art recognize that some components exhibit reduced activity in solid phase assays, but this is generally acceptable, as long as the activity is sufficient to be detected and/or quantified. Suitable solid supports include, but are not limited, to any solid surface such as glass beads, planar glasses, controlled pore glasses, plastic porous plastic metals, or resins to which a material or cell may be adhered, etc.). Those of skill in the art recognize that in some embodiments, the solid supports used in the methods of the invention may be derivatized with functional groups (e.g., hydroxyls, amines, carboxyls, esters, and sulfhydryls) to provide reactive sites for the attachment of linkers or the direct attachment of the candidate agent or other assay component.

Adhesion of an assay component to a solid support can be direct (i.e. the component directly contacts the solid surface) or indirect (i.e. an agent and/or component (e.g. an antibody) is/are bound to a support, and the other assay component(s) binds to this agent or component rather than to the solid support). In some embodiments, the agent or component is covalently immobilized (e.g., utilizing single reactive thiol groups of cysteine for anchoring proteinaceous components (see e.g., *Bioconjug. Chem.*, 4:528-536 (1993)), or non-covalently, but specifically (e.g., via immobilized antibodies or other specific binding proteins (see e.g., *Adv. Mater.*, 3:388-391 (1991); *Anal. Chem.*, 67:83-87 (1995))), the biotin/streptavidin system (see e.g., *Biophys. Biochem. Res. Commun.*, 230:76-80 (1997)), or metal-chelating Langmuir-Blodgett films (see e.g., *Langmuir* 11:4048-4055 (1995); *Angew. Chem. Int. Ed. Engl.*, 35:317-320 (1996); *Proc. Natl. Acad. Sci. USA* 93:4937-4941 (1996); and *J. Struct. Biol.*, 113:117-123 (1994)), and metal-chelating self-assembled monolayers (see e.g., *Anal. Chem.*, 68:490-497 (1996)), for binding of polyhistidine fusion proteins.

In some embodiments, standard direct or indirect ELISA, IFA, or RIA methods as generally known in the art are used to detect the binding of a candidate agent to a membrane POI. In some embodiments, an increase in the level of surface expression of the membrane protein is detected in a sample; while in other embodiments, a decrease in the level of surface expression is detected. Thus, it is clear that embodiments of methods according to the invention are adaptable to the detection, identification, and characterization of multiple elements.

Accordingly, in some particularly preferred embodiments of the methods of the invention, a sandwich ELISA (enzyme-linked immunosorbent assay) with a monoclonal or polyclonal antibody for capture ("a capture antibody") and a secondary antibody ("a reporter antibody") for detection of bound antibody-antigen complex may be used.

In some preferred ELISA embodiments, alkaline phosphatase conjugates are used, while in still other preferred embodiments, horseradish peroxidase conjugates are used. In addition, avidin/biotin systems may also be used, particularly for assay systems in which increased signal are desired. Suitable enzymes for use in preferred embodiments include, but are not limited to, peroxidases, luciferases, alkaline phosphatases, glucose oxidases, beta-galactosidases and mixtures of two or more thereof.

In addition to the assay systems in which a solid support is utilized, the invention provides embodiments of methods in which the assay components remain suspended in solution.

Any change, such as an increase or decrease, in the level of binding in the presence of the candidate agent relative to control indicates that the candidate agent alters the level of surface expression of the first mutant form of the membrane protein.

The determination of the level of surface expression of the integral membrane protein of interest may be performed using any of the methods and techniques known and available to diose skilled in the art. Preferably, the level of binding is determined by fluorescence, luminescence, radioactivity, absorbance or a combination of two or more of these.

According to certain embodiments of the invention, the extracellular epitope to which the antibody binds on the membrane protein is preferably the same as a wild-type epitope, i.e. an extracellular epitope found on the naturally-occurring form(s) of the membrane protein of interest. Without wishing to be bound to any theory of operability or the like, such an arrangement may have the potential to reduce errors arising from differences in protein structure, for example by a change in one or more of the functional properties of the protein.

According to certain embodiments of the invention, the extracellular epitope may also contain a tag. Suitable tags are known and available to those skilled in the art. A particularly preferred tag for use in selected methods of the invention is a hemagglutinin (HA) tag. The tag may be inserted in an extracellular domain of the POI or may replace a portion of an extracellular domain thereof.

A method of identifying an agent that alters the level of surface expression or binds to an extracellular epitope of a membrane protein in a mammalian cell according to disclosed embodiments can include preparing a first medium containing mammalian cells that express the membrane protein, adding to the first medium containing mammalian cells an effective amount of a candidate agent, incubating the cells in the presence of the candidate agent for a sufficient period of time in a system according to embodiments, adding to the first medium containing mammalian cells an effective amount of at least one antibody which binds to at least one extracellular epitope of the membrane protein and determining the level of binding of the at least one antibody to the extracellular epitope following incubation with the candidate agent, wherein a change in the level of binding relative to control indicates that the candidate agent alters the level of surface expression of the membrane protein or binds to the extracellular epitope of the membrane protein.

A method for detecting the presence of a protein or gene of interest in a sample, according to one embodiment can include (a) placing a sample in a system according embodiments, (b) contacting the sample with a compound which selectively hybridizes to the gene of interest or binds to the protein and (c) determining whether the compound hybridizes to the gene of interest or binds to the protein in the sample.

A method for identifying a compound which binds to or modulates the activity of a protein according to one embodiment can include (a) immobilizing a cell expressing the protein in a system according embodiments, (b) contacting the cell with a test compound and (c) determining whether the protein binds to the test compound or determining the effect of the test compound on the activity of the protein.

A method of identifying a nucleic acid molecule associated with a disorder or identifying a subject having a disorder or at risk for developing a disorder according to embodiments of the invention can include (a) placing a sample containing nucleic acid molecules from a subject with or at risk of developing a disorder in a system according embodiments, (b) contacting the sample with a hybridization probe that contains a nucleic acid sequence indicative of the disorder or risk for developing the disorder and (c) detecting the presence of a nucleic acid molecule in the sample that hybridizes to the probe, thereby identifying a nucleic acid molecule associated with a disorder or the subject having the disorder or at risk for developing the disorder.

In accordance with another embodiment, a pharmaceutical composition can include a therapeutically effective amount of an agent identified or described herein and a pharmaceutically effective carrier.

In accordance with another embodiment, a method can include adding an effective amount of at least one primary antibody and an effective amount of at least one secondary antibody, wherein the primary antibody binds to an extracellular epitope of a membrane protein and the secondary antibody binds to the first antibody. In accordance with another embodiment, a level of binding can be measured by fluorescence, luminescence, radioactivity, absorbance or a combination of two or more thereof.

In accordance with another embodiment, an integral membrane protein can be a membrane ion channel. In accordance with another embodiment, a membrane ion channel can be a sodium channel, a potassium channel, a calcium channel or a chloride channel.

In accordance with another embodiment, a primary or secondary antibody can be coupled to an enzyme. In accordance with another embodiment, an enzyme can be selected from the group including or consisting of peroxidases, luciferases, alkaline phosphatases, glucose oxidases, beta-galactosidases, or the like and mixtures of two or more thereof.

Other applications in the tissue regeneration and engineering, clinical, and research industries include, but are not limited to, tissue engineering arteries and veins for cardiovascular repair or replacement and training ex vivo veins or arteries prior to implantation or applying a treatment to the specimen prior to implantation. For example, embodiments of the system can simulate complex coronary hemodynamics for growing tissue engineered or regenerated arteries and for training saphenous veins or defrosting cryogenic arteries in preparation for the harsh and dynamic coronary environment or other peripheral arterial disease regions. Another example may include treating an artery or vein with gene, RNAi, or other biomolecular therapy in conjunction with hemodynamic simulation prior to therapeutic intervention. Embodiments of the system can provide accurate and precise control of physiologic parameters for applications in the tissue regeneration and engineering industries. For example, to grow vascular grafts seeded with stem cells, hemodynamic stimuli ranging from coronary to peripheral arteries, as well as biochemical stimuli, such as growth factors, can be applied to condition the stem cells to differentiate to vascular cells that are preferable functional.

The surfaces of synthetic vascular prostheses are capable of provoking platelet activation and blood coagulation, generating clots that can rapidly occlude the engrafted prosthetic. Thus, the field of synthetic vascular grafts has developed at a cautious pace, and efforts to ensure their safety have included the testing of different graft materials and the inclusion of anti-thrombogenic materials in the pre-treatment used to seal the interstices of the graft to prevent blood loss from the vessel. (Sauvage, L. R., in Haimovici et al, eds., Haimovici's Vascular Surgery, 4th ed., 1996). Today, only polyethylene terephthalate (DACRON) and polytetrafluoroethylene (TEFLON) are approved by the Federal Drug Administration for this use.

Even so, autologous grafts still are considered superior to synthetic ones because their endothelial linings, which secrete a number of natural anti-thrombotic substances, provide a far better flow surface than the material used for today's synthetic prostheses. Unfortunately, only a limited number of the body's blood vessels provide tissue suitable for use in autologous vascular transplants, and improvements in the field of synthetic prostheses would prove a boon to many patients, especially diose requiring multiple heart bypasses.

Another limitation of synthetic vascular prostheses currently approved for use is that the caliber, i.e., inner diameter, of grafts deemed as acceptable must be at least 6 mm. It is believed, in fact, that no satisfactory synthetic prosthesis having a caliber below 6 mm exists today (e.g., Sauvage, 1996). Thus, the need for smaller caliber grafts remains unfulfilled, even though numerous patients require repeat coronary bypass, or have peripheral arterial occlusions below the knee or in the cerebrovascular tree, which would use small caliber synthetic grafts if these were available.

In recent years, a number of investigators have reported the occasional appearance of patches of endothelial cells growing on the walls of synthetic vascular grafts (e.g., Wu et al., J Vasc. Surg. 21:862-867, 1995; Scott et al., J Vasc. Surg. 19:585-593, 1994; Shi et al., J Vasc. Surg. 25:736-742, 1997). Several studies have suggested that this graft surface endothelialization originates primarily from transmural microvessels, i.e., tiny blood vessels that infiltrate the graft wall, and that originate themselves from pre-existing blood vessels (e.g., Clowes et al., Am. J. Pathol. 123:220-230, 1986; Wu et al., Ann. Vase. Surg. 10:11-15, 1996). However, other studies have indicated that at least some of the endothelialization observed in internal segments of synthetic vascular grafts appears to originate from blood-borne cells that became attached to the vessel walls (Scott et al., J Vasc. Surg. 19:585-593, 1994; Shi et al., J Vasc. Surg. 20:546-555, 1994; Wu et al. J Vasc Surg. 21:862-867, 1995; Shi et al. J Vase. Surg. 25:736-42, 1997; Frazier et al. Tex. Heart Inst. J 20:78-82, 1993; Hammond et al., Blood 88 (suppl. 1):511a (abstract, 1996)). This phenomenon is called "fallout endothelialization." More specifically, it has been proposed that the circulating cells that give rise to endothelial coatings of vascular prostheses may arise from the bone marrow (Hammond et al. 1996).

Indeed, circulating endothelial cells have been observed by many investigators (Asahara et al., Science 275:965-967, 1997; Percivalle et al. J. Clin. Invest. 92:663-670, 1993; George et al. Thrombosis Haemostasis 67:147-153, 1992). The latter two of these provide evidence that circulating endothelial cells originate from the walls of blood vessels (George et al., 1992; Percivalle et al., 1993), and the study of Asahara et al. (1997) provides evidence for a circulating endothelial progenitor cell that expresses CD34, an antigen also associated hematopoietic progenitor cells, and that can participate in angiogenesis in ischemic tissues. Whatever their source, graft recipients clearly would benefit from the development of treatments promoting the deposition and outgrowth of circulating endothelial cells on the inner walls of synthetic vascular grafts.

In view of the superior anti-thrombotic properties of endothelial flow surfaces, various experimental approaches have been devised for increasing the rate of endothelialization of synthetic grafts. These include seeding prior to implant with autogenous endothelium, cultured endothelium or bone marrow cells (Herring et al. Surgery 84:498-504, 1978; Anderson et al., Surgery 101:577-586, 1987; Kadletz et al., J Thorac. Cardiovasc. Surg. 104:736-742, 1992; Mazzucotelli et al., Artif Organs 17:787-790, 1993; Noishiki et al., Artif. Organs 19:17-26, 1995; Noishiki et al., Nat. Med. 2:90-93, 1996; Onuki et al. Ann. Vase. Surg. 11:141-148, 1997). None of these, however, have been able to replicate the in vivo hemodynamic environment necessary for complete endothelialization with a confluent monolayer of cells that can be achieved with embodiments of the system according to the invention.

One application of exemplary embodiments of systems and methods described herein is combination (or hybrid) medical devices and cell therapy. A hybrid or combination vascular graft is one exemplary medical device. A hybrid vascular graft is made up of both synthetic material and living cells. Embodiments of a hybrid or combination vascular graft will now be described. Embodiments of a hybrid vascular graft can be developed using exemplary embodiments of systems and methods described herein (e.g., FIGS. 1-48), however, an embodiment of the hybrid vascular graft is not intended to be so limited thereby.

An embodiment of a hybrid vascular graft can be a synthetic vascular graft (e.g., silicon) combined with living cells (e.g., a biomaterial) that can reduce or eliminate the need for the costly dependence on drugs, reduce subsequent surgeries and more accurately reflect human biology. For example, the hybrid graft embodiment can recapitulate native function and/or the living cells can be functional endothelial cells (e.g., evidenced by cell characteristics, expression profiles or metabolism). The hybrid graft embodiment can replicate the original physiologic function of living arteries and veins with vascular cells. Further, the hybrid graft embodiment can be used for the difficult or previously impossible small diameter synthetic grafts (e.g., 6 mm or less, 4 mm or less). The hybrid graft embodiment can use endothelial cells or other cells (e.g., stem cells) that differentiate into in endothelial cells that are attached to a synthetic graft. Once cells (e.g., endothelial cells) are attached (e.g., as conventionally known) to the synthetic graft a functional coating (e.g., a confluent monolayer) of cells is grown on the hybrid grafts using disclosed systems and methods (e.g., FIGS. 36-39).

According to one embodiment of a hybrid vascular graft (combination synthetic vascular graft) or combination medical device, it can be used for synthetic vascular grafts for selected uses, including 1) hemodialysis access vascular graft, 2) femoral artery graft and/or 3) coronary bypass graft. Additional exemplary uses of embodiments of a hybrid graft can include coronary replacements, repair of obstructive disease, aneurysm repair, trauma repair, cardiovascular disease treatment or the Kite.

Arterial diseases include Peripheral Arterial Disease (PAD), which is the build up of fat on the artery wall and narrowing of the artery structure limiting blood supply and atherosclerosis. PAD can occur in locations, such as carotid artery, renal artery, iliac artery, femoral artery, popliteal artery, or tibial artery. Atherosclerosis is a chronic disease in which thickening, hardening, and loss of elasticity of the arterial walls result in impaired blood flow. In addition, vascular failures can cause diseases including angina, high blood pressure, high cholesterol, heart attack, stroke, and arrhythmia.

Treatment of such diseases can include bypass or graft surgery. An exemplary double bypass graft can use one bypass to connect the internal mammary artery to a branch of the left coronary artery and the other bypass to connect the aorta to the right coronary artery. A major mode of treatment for cardiovascular diseases using bypass or graft surgery is via synthetic vascular grafts.

However, disadvantages of prosthetics or synthetic vascular grafts include mechanical disadvantages, such as poor compliance (e.g., rigid), size mismatch and viscoelasticity, and biocompatibility disadvantages. Biocompatibility complications include intimal hyperplasia at anastamoses, thrombosis, restenosis (lipid uptake), infection, bacteria colonization, dilatation or rupture. Vascular grafts can also fail because of compliance mismatch, such as within the built material, within the sutured attachment to the existing vessel or at the anastamosis.

A hemodialysis access graft through an arterio-venous (AV) shunt is a looped graft between an artery and a vein (e.g., in the body). For example, the AV shunt can be located in the upper arm, middle arm, lower arm or combinations thereof. The blood can be transferred to a dialysis machine from the portion of the AV shunt connected to the artery and returned from the dialysis machine to the portion of the AV shunt connected to the vein.

Stents elicit negative reactions from the body since the material is non-living or non-biological, and thus subsequently fail because of re-closure of a treated blood vessel caused by growth of smooth muscle cells, stent thrombosis, and structural/mechanical failure of the graft or the like.

In contrast, embodiments of hybrid grafts can consider the biophysical environment the graft will be in, such as, for example, the cardiovascular system, including simulation of in vivo hemodynamics (e.g., concurrent wall shear stress, stretch, and pressure). Embodiments of the hybrid vascular graft can be processed in vitro to grow or train endothelial cells on the vascular graft surface (e.g., tubular structure) that can function as if it was in a desired in vivo environment. Related art technologies cannot grow cells on a vascular graft let alone functional endothelial cells because stretch devices produce only a biaxial or heterogeneous strain field without applied flow, and flow devices produce only a flow field without stretch.

Embodiments of hybrid vascular grafts can utilize/train with regard to a physical nature of a graft or disease, a dynamic environment of a graft and/or the dynamic nature of disease. Further, embodiments of hybrid vascular grafts can be developed at a size greater than 6 mm, but also at a size 6 mm or less, 5 mm or less, 4 mm or less or the like and have significantly reduced risks or clogging or thrombosis. Such risk reduction is achieved by training the endothelial cells or stem cells that ultimately differentiate into endothelial cells that yields functional endothelial cells that line the hybrid graft.

One embodiment of a hybrid graft can be developed using a synthetic vascular graft provided with stem cells (as is known in the art, e.g., vascular cell origin from hemangioblast) and exposed to controlled hemodynamics resulting in an exemplary graft with functional vascular endothelial cells. Such an exemplary embodiment of a hybrid vascular graft with functional vascular endothelial cells can be used as described above. According to another embodiment, stem cells can be extracted from the patient intended to receive the embodiment of a hybrid vascular graft (a combination synthetic graft).

In one embodiment for preparing a hybrid vascular graft, a plurality of cells is affixed to a surface of a synthetic graft. A binding material (e.g., adhesion proteins, fibronectin) can be used to coat a surface of the synthetic graft to affix the plurality of cells. In another embodiment for preparing a hybrid vascular graft, etching of the synthetic graft can improve surface adhesion of proteins and cells that can reduce or remove the necessity of a binding material. Etching with plasma treatments can include oxygen plasma, glow-discharge plasmas or amide and amine containing plasmas. Further, for polytetrafluoroethylene (PTFE) or ePTFE, ammonia and oxygen plasmas can be used and fluorine can be replaced with amines and nitrogen groups to help facilitate adhesion of proteins and cells (e.g., EC).

Additional exemplary embodiments of methods for processing biomaterials, non-biomaterials or combinations thereof (e.g., hybrid vascular grafts) will now be described.

An exemplary method embodiment of preparing a biomaterial intended for implantation into a mammal in need thereof can include placing the biomaterial in a system according embodiments of the invention for a sufficient time prior to implantation of the biomaterial into the mammal. An exemplary method embodiment of promoting engraftment of a biomaterial following implantation into a mammal's body can include placing the biomaterial in a system according to disclosed embodiments prior to implantation of the biomaterial into the mammal's body.

Figure 49:
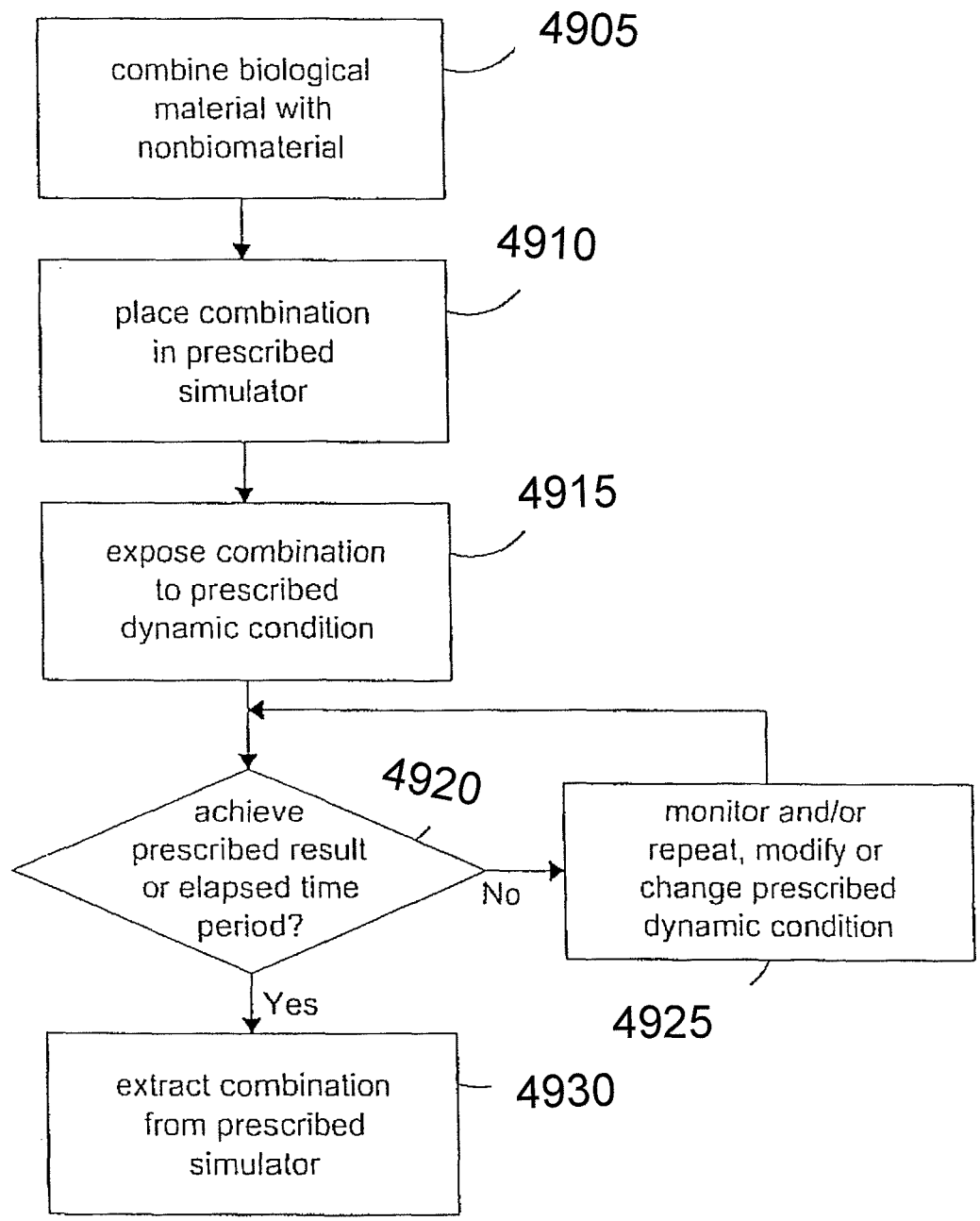
FIG. 49 shows a flowchart of a process for combining biologic and non-biological materials according to an embodiment of the invention.

As shown in FIG. 49, an exemplary method of using systems disclosed herein (e.g., systems 1, 1101) for treating or processing a biomaterial will now be described, As shown in FIG. 49, selected biomaterials such as cells (e.g., endothelial cells, stem cells) can be combined with a non-biomaterial (e.g., a synthetic graft) (block 4905). The combination can then be placed in a simulator of a selected class of dynamic conditions (e.g., selected system embodiment 1, 1101) (block 4910). The combination is then exposed to a selected or prescribed dynamic condition or series of conditions (e.g., hemodynamic conditions of an abdominal aorta) (block 4915). The combination (e.g., a hybrid synthetic graft) can then be continuously monitored or periodically monitored for desired results (e.g., generation of a confluent functional monolayer of endothelial cells) or for a selected period of time (block 4920). Optionally, the controlled dynamic conditions can be repeated or modified (e.g., "dial-up") according to feedback (e.g., $FB_f(t)$) from the monitored combination or its environment or desired results (block 4925). When the time periods have elapsed or results have been obtained, the combination can be extracted from the selected dynamic condition class simulator (block 4830). The modified combination can then be implanted in a mammal. The method embodiment of FIG. 49 can be performed on biomaterials alone.

An exemplary method embodiment of promoting endothelialization of a vascular graft can include (a) immobilizing a plurality of endothelial cells on at least one surface of a vascular graft and (b) placing the vascular graft in a system according to disclosed embodiments under conditions effective to promote the endothelial cells to form a confluent monolayer on the surface of the vascular graft.

An exemplary method embodiment of coating a vascular graft with a confluent monolayer of endothelial cells can include (a) immobilizing a plurality of endothelial cells on at least one surface of a vascular graft; and (b) placing the vascular graft in a system according disclosed embodiments under conditions effective to promote the endothelial cells to form a confluent monolayer on the surface of the vascular graft. An exemplary method embodiment of coating a vascular graft with a confluent monolayer of endothelial cells can include (a) immobilizing a plurality of multipotent stem cells on at least one surface of a vascular graft, (b) placing the vascular graft in a system according to disclosed embodiments under conditions effective to promote the stem cells to form confluent monolayer on the surface of the vascular graft and (c) placing the vascular graft in an environment that promotes the stem cells to differentiate into endothelial cells.

An exemplary method embodiment of promoting endothelialization of a vascular graft can include (a) immobilizing a plurality of multipotent stem cells on at least one surface of a vascular graft; and (b) placing the vascular graft in a system according to disclosed embodiments under conditions effective to promote the stem cells to form a confluent monolayer on the surface of the vascular graft or to differentiate into endothelial cells on the surface of the vascular graft.

An exemplary method embodiment for the generation of tissue can include (a) immobilizing a plurality of cells in at least one surface of a matrix, the matrix including a suitable biomedical material; and (b) placing the matrix in a system according to disclosed embodiments under conditions effective to promote the cells to grow on the surface of the matrix. An exemplary method embodiment of storing an organ prior to transplantation into a patient in need thereof, can include placing the organ in a system according to disclosed embodiments under conditions in which the organ remains substantially unchanged or viable for an extended period of time.

In accordance with another embodiment, a coating including at least one cell is applied to at least a portion of at least one surface of the biomaterial (e.g., vascular graft, matrix or the like) prior to placement in the system. In accordance with another embodiment, the cell is selected from embryonic stem cells, adult stem cells, mesenchymal stem cells, endothelial cells, smooth muscle cells, osteocytes, or osteoblasts. In accordance with another embodiment, the coating can include an affixing substance selected from fibronectin, fibrin glue, combinations of fibrinogen and thrombin, collagen, basement membrane, or alginate, and mixtures of two or more thereof.

In accordance with another embodiment, the coating further can include at least one supplement selected from an analgesic, an anesthetic, an antimicrobial compound, an antibody, an anticoagulant, an antifibrinolytic agent, an anti-inflammatory compound, an antiparasitic agent, an antiviral compound, a cytokine, a cytotoxin or cell proliferation inhibiting compound, a chemotherapeutic drug, a growth factor, an osteogenic or cartilage inducing compound, a hormone, an interferon, a lipid, an oligonucleotide, a polysaccharide, a protease inhibitor, a proteoglycan, a polypeptide, a steroid, a vasoconstrictor, a vasodilator, a vitamin, or a mineral, and mixtures of any two or more thereof.

In accordance with another embodiment, a supplemented coating is applied to the biomaterial in an amount effective to promote cell migration, cell proliferation and/or cell differentiation in a cell-containing environment. In accordance with another embodiment, a supplemented coating is applied to the biomaterial in an amount effective to promote endothelialization of the biomaterial in an endothelial cell-containing environment, where such endothelialization can cause a confluent layer of cells to form on the surface of the biomaterial when the biomaterial is placed into the endothelial cell-containing environment. In accordance with another embodiment, a supplemented coating is applied to the biomaterial in an amount effective for the prophylaxis or treatment of infection in a patient when the biomaterial is placed into a patient.

In accordance with another embodiment, a biomaterial can include or combine with an orthopedic device, a urinary catheter, an intravascular catheter, a suture, a vascular prosthesis, an intraocular lens, a contact lens, a heart valve, a shoulder replacement device, an elbow replacement device, a hip replacement device, a knee replacement device, an artificial heart, a fixation plate, a dental implant, a nasal implant, a breast implant, a testicular implant, a sponge, a film or a bag. In accordance with another embodiment, a biomaterial can be prepared according to such exemplary method embodiments.

In accordance with another embodiment, the biomaterial can be combined with a synthetic vascular graft or prosthesis. In accordance with another embodiment, the biomaterial intended for implantation into a mammal includes a synthetic vascular graft or hybrid vascular graft.

In accordance with another embodiment, the biomaterial intended for implantation into a mammal can be used for a hybrid hemodialysis access graft, a hybrid femoral artery graft or a hybrid coronary bypass vascular graft. In accordance with another embodiment, a hybrid vascular graft is one of at least 8 mm, less than 8 mm, in less than 6 mm, less than 5 mm, less than 4 mm less than 3 mm less than 2 mm less than 1 mm, or less than 0.5 mm in diameter.

Embodiments of the system may also be used to differentiate undifferentiated cells, such as, for example, adult stem cells or progenitor cells, toward a particular differentiated state such as, for example, an adult stem cell to an endothelial cell or a smooth muscle cell. The technology can also be used to train or condition cells or tissue such as saphenous vein or tissue engineered artery or vein. Organs or tissues can also be used in embodiments of the system to provide the correct physiologic simulation for various applications such as research, development, organ transport, or the construction of a more in vivo like system and the like. Embodiments of the system can also be used to maintain, grow, or enhance the growth of various organs, cells, and tissues such as liver, kidney, heart, bone, or synovial tissue.

The most promising source of organs and tissues for transplantation lies in the development of stem cell technology. Theoretically, stem cells can undergo self-renewing cell division to give rise to phenotypically and genotypically identical daughters for an indefinite time and ultimately can differentiate into at least one final cell type. By generating tissues or organs from a patient's own stem cells, or by genetically altering heterologous cells so that the recipient immune system does not recognize them as foreign, transplant tissues can be generated to provide the advantages associated with xenotransplantation without the associated risk of infection or tissue rejection.

Stem cells also provide promise for improving the results of gene therapy. A patient's own stem cells could be genetically altered in vitro, then reintroduced in vivo to produce a desired gene product. These genetically altered stem cells would have the potential to be induced to differentiate to form a multitude of cell types for implantation at specific sites in the body, or for systemic application. Alternately, heterologous stem cells could be genetically altered to express the recipient's major histocompatibility complex (MHC) antigen, or no MHC, to allow transplant of diose cells from donor to recipient without the associated risk of rejection.

Stem cells are defined as cells that have extensive, perhaps indefinite, proliferation potential that differentiate into several cell lineages, and that can repopulate tissues upon transplantation. The quintessential stem cell is the embryonal stem (ES) cell, as it has unlimited self-renewal and multipotent differentiation potential. These cells are derived from the inner cell mass of the blastocyst, or can be derived from the primordial germ cells from a post-implantation embryo (embryonal germ cells or EG cells). ES and EG cells have been derived from mouse, and more recently also from non-human primates and humans. When introduced into mouse blastocysts or blastocysts of other animals, ES cells can contribute to all tissues of the mouse (animal). When transplanted in post-natal animals, ES and EG cells generate teratomas, which again demonstrates their multipotency. ES (and EG) cells can be identified by positive staining with the antibodies SSEA1 and SSEA4.

At the molecular level, ES and EG cells express a number of transcription factors highly specific for these undifferentiated cells. These include oct-4 and Rox-1. Also found are the LIF-R and the transcription factors sox-2 and Rex-1, even though the latter two are also expressed in non-ES cells. Oct-4 is a transcription factor expressed in the pregastrulation embryo, early cleavage stage embryo, cells of the inner cell mass of the blastocyst, and in embryonic carcinoma (EC) cells. Oct-4 is down-regulated when cells are induced to differentiate in vitro and in the adult animal oct-4 is only found in germ cells. Several studies have shown that oct-4 is required for maintaining the undifferentiated phenotype of ES cells, and plays a major role in determining early steps in embryogenesis and differentiation, oct-4, in combination with Rox-1, causes transcriptional activation of the Zn-finger protein Rex-1, and is also required for maintaining ES in an undifferentiated state. Likewise, sox-2, is needed together with oct-4 to retain the undifferentiated state of ES/EC and to maintain murine (but not human) ES cells. Human or murine primordial germ cells require presence of LIF. Another hallmark of ES cells is presence of telomerase, which provides these cells with an unlimited self-renewal potential in vitro.

Stem cells have been identified in most organ tissues. The best characterized is the hematopoietic stem cell. This is a mesoderm-derived cell that has been purified based on cell surface markers and functional characteristics. The hematopoietic stem cell, isolated from bone marrow, blood, cord blood, fetal liver and yolk sac, is the progenitor cell that reinitiates hematopoiesis for the life of a recipient and generates multiple hematopoietic lineages (see Fei, R., et al., U.S. Pat. No. 5,635,387; McGlave, et al., U.S. Pat. No. 5,460,964; Simmons, P., et al., U.S. Pat. No. 5,677,136; Tsukamoto, et al., U.S. Pat. No. 5,750,397; Schwartz, et al., U.S. Pat. No. 5,759,793; DiGuisto, et al., U.S. Pat. No. 5,681,599; Tsukamoto, et al., U.S. Pat. No. 5,716,827; Hill, B., et al., Exp. Hematol. (1996) 24 (8): 936 943). When transplanted into lethally irradiated animals or humans, hematopoietic stem cells can repopulate the erythroid, neutrophil-macrophage, megakaryocyte and lymphoid hemopoietic cell pool. In vitro, hemopoietic stem cells can be induced to undergo at least some self-renewing cell divisions and can be induced to differentiate to the same lineages as is seen in vivo. Therefore, this cell fulfills the criteria of a stem cell. Stem cells which differentiate only to form cells of hematopoietic lineage, however, are unable to provide a source of cells for repair of other damaged tissues, for example, heart or lung tissue damaged by high-dose chemotherapeutic agents.

A second stem cell that has been studied extensively is the neural stem cell (Gage F H: Science 287:1433 1438, 2000; Svendsen C N et al, Brain Path 9:499 513, 1999; Okabe S et al, Mech Dev 59:89 102, 1996). Neural stem cells were initially identified in the subventricular zone and the olfactory bulb of fetal brain. Until recently, it was believed that the adult brain no longer contained cells with stem cell potential. However, several studies in rodents, and more recently also non-human primates and humans, have shown that stem cells continue to be present in adult brain. These stem cells can proliferate in vivo and continuously regenerate at least some neuronal cells in vivo. When cultured ex vivo, neural stem cells can be induced to proliferate, as well as to differentiate into different types of neurons and glial cells. When transplanted into the brain, neural stem cells can engraft and generate neural cells and glial cells. Therefore, this cell too fulfills the definition of a stem cell.

Mesenchymal stem cells (MSC), originally derived from the embryonal mesoderm and isolated from adult bone marrow, can differentiate to form muscle, bone, cartilage, fat, marrow stroma, and tendon. During embryogenesis, the mesoderm develops into limb-bud mesoderm, tissue that generates bone, cartilage, fat, skeletal muscle and possibly endothelium. Mesoderm also differentiates to visceral mesoderm, which can give rise to cardiac muscle, smooth muscle, or blood islands consisting of endothelium and hematopoietic progenitor cells. Primitive mesodermal or mesenchymal stem cells, therefore, could provide a source for a number of cell and tissue types. A third tissue specific cell that has been named a stem cell is the mesenchymal stem cell, initially described by Fridenshtein (Fridenshtein, Arkh. Patol., 44:3 11, 1982). A number of mesenchymal stem cells have been isolated (see, for example, Caplan, A., et al., U.S. Pat. No. 5,486,359; Young, H., et al., U.S. Pat. No. 5,827,735; Caplan, A., et al, U.S. Pat. No. 5,811,094; Bruder, S., et al, U.S. Pat. No. 5,736,396; Caplan, A., et al., U.S. Pat. No. 5,837,539; Masinovsky, B., U.S. Pat. No. 5,837,670; Pittenger, M., U.S. Pat. No. 5,827,740; Jaiswal, N., et al., J. Cell Biochem. (1997) 64(2): 295 312; Cassiede P., et al., J. Bone Miner. Res. (1996) 11(9): 1264 1273; Johnstone, B., et al., (1998) 238(1): 265 272; Yoo, et al., J. Bone Joint Sure. Am. (1998) 80(12): 1745 1757; Gronthos, S., Blood (1994) 84(12): 416-44173; Makino, S., et al., J. Clin. Invest. (1999) 103(5): 697 705).

Other stem cells have been identified, including gastrointestinal stem cells, epidermal stem cells, and hepatic stem cells, also termed oval cells (Potten C, Philos Trans R Soc Lond B Biol Sci 353:82130, 1998; Watt F, Philos. Trans R Soc Lond B Biol Sci 353:831, 1997; Alison M et al, Hepatol 29:678 83, 1998).

Compared with ES cells, tissue specific stem cells have less self-renewal ability and, although they differentiate into multiple lineages, they are not multipotent. No studies have addressed whether tissue specific cells express markers described above of ES cells. In addition, the degree of telomerase activity in tissue specific stem cells has not been fully explored, in part because large numbers of highly enriched populations of these cells are difficult to obtain.

Until recently, it was thought that organ specific stem cells could only differentiate into cells of the same tissue. A number of recent publications have suggested that adult organ specific stem cells may be capable of differentiating into cells of different tissues. A number of studies have shown that cells transplanted at the time of a bone marrow transplant can differentiate into skeletal muscle (Ferrari Science 279:528 30, 1998; Gussoni Nature 401:390 4, 1999). This could be considered within the realm of possible differentiation potential of mesenchymal cells that are present in marrow. Jackson published that muscle satellite cells can differentiate into hemopoietic cells, again a switch in phenotype within the splanchnic mesoderm (Jackson PNAS USA 96:14482 6, 1999). Other studies have shown that stem cells from one embryonal layer (for instance splanchnic mesoderm) can differentiate into tissues thought to be derived during embryogenesis from a different embryonal layer. For instance, endothelial cells or their precursors detected in humans or animals that underwent marrow transplantation are at least in part derived from the marrow donor (Takahashi, Nat Med 5:434 8, 1999; Lin, Clin Invest 105:71 7, 2000). Thus, visceral mesoderm and not splanchnic mesoderm, such as MSC, derived progeny are transferred with the infused marrow. Even more surprising are the reports demonstrating both in rodents and humans that hepatic epithelial cells and biliary duct epithelial cells are derived from the donor marrow (Petersen, Science 284:1168 1170, 1999; Theise, Hepatology 31:235 40, 2000; Theise, Hepatology 32:11 6, 2000). Likewise, three groups have shown that neural stem cells can differentiate into hemopoietic cells. Finally, Clarke et al. reported that neural stem cells injected into blastocysts can contribute to all tissues of the chimeric mouse (Clarke, Science 288:1660 3, 2000).

Transplantation of tissues and organs generated from heterologous embryonic stem cells requires either that the cells be further genetically modified to inhibit expression of certain cell surface markers, or that the use of chemotherapeutic immune suppressors continue in order to protect against transplant rejection. Thus, although embryonic stem cell research provides a promising alternative solution to the problem of a limited supply of organs for transplantation, the problems and risks associated with the need for immunosuppression to sustain transplantation of heterologous cells or tissue would remain. An estimated 20 immunologically different lines of embryonic stem cells would need to be established in order to provide immunocompatible cells for therapies directed to the majority of the population (Wadman, M., Nature (1999) 398: 551). Using cells from the developed individual, rather than an embryo, as a source of autologous or allogeneic stem cells would overcome the problem of tissue incompatibility associated with the use of transplanted embryonic stem cells, as well as solve the ethical dilemma associated with embryonic stem cell research.

A method for differentiating mammalian stem cells according to one embodiment can include (a) preparing a medium containing mammalian stem cells and placing the medium in a system according embodiments, (b) adding to the medium an effective amount of an agent which causes differentiation of the cells, producing differentiated cells, (c) contacting the cells from step (b) with an effective amount of an agent that causes stabilization of cells produced in step (b) and (d) recovering stabilized, differentiated cells.

A method for generating differentiated cells from mammalian mesenchymal stem cells according to one embodiment can include (a) placing the mesenchymal stem cells in a system according embodiments, (b) incubating the mesenchymal stem cells under conditions that induce the mesenchymal stem cells to differentiate and (c) recovering the differentiated cells.

A method of producing a genetically engineered cell such as stem cells according to one embodiment can include (a) placing cells such as stem cells in a system according embodiments under conditions that do not cause the cells to differentiate, (b) transfecting the cells such as stem cells with a DNA construct including at least one gene of interest, (c) selecting for expression of the gene of interest in the cells such as stem cells and (d) culturing the cells such as stem cells selected in step (c).

A method of in vivo administration of a protein or gene of interest according to one embodiment can include (a) placing cells such as stem cells in a system according embodiments, (b) transfecting the cells such as stem cells with a vector including DNA or RNA that expresses a protein or gene of interest, (c) selecting for expression of the protein or gene of interest in the cells such as stem cells and (d) delivering the cells such as stem cells selected in step (c) to a mammal in need thereof.

A method of testing the ability of a candidate agent to modulate the proliferation of a lineage uncommitted cell according to one embodiment can include (a) placing stem cells in a system according embodiments, (b) culturing the stem cells in a growth medium that maintains the stem cells as lineage uncommitted cells, (c) adding the candidate agent to the medium and (d) determining the proliferation and lineage of the cells by mRNA expression, antigen expression or other means.

A method of preparing a stem cell matrix for use in tissue or organ repair according to one embodiment can include (a) admixing a preparation including stem cells with a physiologically acceptable matrix material to form a stem cell matrix and (b) incubating the stem cell matrix in a system according embodiments prior to use in tissue or organ repair or treatment.

A method of tissue or organ repair or treatment, according to one embodiment can include (a) preparing a stem cell matrix by admixing a preparation including stem cells with a physiologically acceptable matrix, (b) incubating the stem cell matrix in a system according to embodiments prior to use and (c) introducing the stem cell matrix into a patient in need thereof.

In accordance with another embodiment, mammalian stem cells can be pluripotent or multipotent stem cells or totipotent stem cells. In accordance with another embodiment, stem cells can be homogeneous stem cells or heterogeneous stem cells. In accordance with another embodiment, stem cells can be autologous or allogeneic to a recipient or a mammal.

In accordance with another embodiment, a physiologically acceptable matrix material can be selected from the group including or consisting of small intestine submucosa (SIS), crosslinked alginate, hydrocolloid, collagen, polyglycolic acid (PGA, polyglactin (PGL), fleeces, silk, keratin, dead de-epidermized skin equivalents, polyesters, polyalkylenes, polyfluoroethylenes, polyvinyl chloride (PVC), polystyrene, polysulfones, cellulose acetate, glass fibers, and inert metal fibers.

In accordance with another embodiment, stem cells can be obtained from a tissue selected from the group consisting of adult, embryonic, and fetal tissue. In accordance with another embodiment, such tissue can include bone marrow, muscle, adipose, liver, heart, lung, or nervous system tissue.

In accordance with another embodiment, a stem cell matrix can be used for wound healing, surgical incision repair, tissue augmentation, organ augmentation, smooth muscle repair, non-smooth muscle repair, or blood vessel repair or the like.

In accordance with another embodiment, stem cells are affixed to a physiologically acceptable matrix material using a biological adhesive such as fibrin glue. In accordance with another embodiment, the fibrin glue can be supplemented with at least one agent. In accordance with another embodiment, a physiologically acceptable matrix material can be absorbable or non-absorbable.

A method for producing a protein of interest according to one embodiment can include (a) culturing a host cell in a system according to disclosed embodiments under conditions in which the protein is expressed; and (b) recovering the protein. A method for maintaining a culture of cells according to one embodiment can include placing the cells in a system according to disclosed embodiments under conditions in which the cells remain substantially unchanged for an extended period of time. In accordance with another embodiment, an isolated culture of cells can be prepared according to disclosed embodiments of methods.

In accordance with another embodiment, immune cells (e.g., killer cells, T-cells or the like) can be used in various fluids as described herein or used in systems 1, 1101. Further, immune cells can be used in various fluids during preparation or differentiation of stem cells according to methods otherwise known in the art. Such immune cells can be used to clean or decontaminate contaminated cells. Further, such cells can be used to detect otherwise undetectable contaminants such as fungi or mold. In addition, according to embodiments, the immune cells can immunize or destroy contaminants such as mycoplasma, fungi, bacteria or the like. Accordingly, the effectiveness of biological embodiments disclosed herein can be increased.

Embodiments of the system may be applied at any or all the stages of cardiovascular disease, such as the early to late stages and spanning through drug treatment to tissue and cell regeneration. The early stages are often treated medically with drugs and biomolecules that can be screened and tested, discovered and developed using the technology. The next stages are often treated with drug-eluting stents where in this example, the 'drug-elutant' can be discovered, screened, and tested, discovered and developed using embodiments of the system. The late stages often require arterial bypass where embodiments of the system can be used to produce tissue regenerated or engineered products, for example arteries, from patient cells such as, for example, stem cells or progenitor cells with various possible scaffolds such as a ePTFE or collagen composites.

Embodiments of the system may also be used as a vascular trainer, to recondition a vein or artery under various dynamic conditions, with various growth factors or genetic or chemical treatment and other additives enhancing the therapeutic outcome of such a conditioning environment. This may also be also useful in reviving cryogenically preserved specimens.

The invention also provides embodiments of a system and a method by which appropriate mechanical environments are applied ex vivo to direct the remodeling of small, excised blood vessels to create tissue-engineered vessels characterized by increased length, internal diameter, and wall thickness. Thus, the small excised vessels, arteries, or even veins, become tissue-engineered blood vessels for use in vascular surgery. Embodiments of the invention further provide an evaluation of the performance of these tissue-engineered blood vessels in vivo.

Embodiments of the system allow investigations of the hypothesis that longitudinal stress or strain induces artery elongation. In addition, while there are autologous donor arteries with proper diameter and wall thickness for vascular grafts, they often are of an insufficient length to meet the required need. For example, the internal thoracic artery has excellent long-term patency, but is of an adequate length for only a single bypass graft. However, recognizing that if the artery could be elongated, it could be used to bypass multiple occlusions, and the use of vessels demonstrating inferior performance could be avoided, embodiments of the invention advantageously provides reliable tissue-engineered blood vessels of sufficient length to meet this need.

In addition, embodiments of the system are further used to explore the molecular regulation of mechanically induced vascular remodeling by characterizing the expression and regulation of key regulator) factors, for which the spatial expression and distribution of mRNA and protein are monitored as a result of various mechanical loads.

Thus, embodiments of the invention also provide a protocol by which localized intravascular and extravascular pressures are measured in real time, and the measured pressures are compared with the calculated pressure estimates.

The graft tissue component of the vascular graft may be derived from essentially any biological tissue of interest provided the tissue has the proper geometrical dimensions and/or configurations for its intended application. Typically, the graft tissue will be comprised of vascular tissue removed from a human or from an animal species, e.g., bovine, porcine, ovine, equine, canine, goat, etc., and may be removed from various anatomical positions within the body. For example, the graft tissue may be derived from carotid arteries, thoracic arteries, mammary arteries, and the like. The graft tissue must have a structure, e.g., a tubular structure, which defines an interior lumen having dimensions sufficient for allowing blood to flow therethrough following implantation.

The primary component of the biological tissues used to fabricate bioprostheses is collagen, a generic term for a family of related extracellular proteins. Collagen molecules consists of three chains of poly (amino acids) arranged in a trihelical configuration ending in non-helical carboxyl and amino termini. These collagen molecules assemble to form microfibrils, which in turn assemble into fibrils, resulting in collagen fibers. The amino acids which make up the collagen molecules contain side groups, including amine, acid and hydroxyl groups, in addition to the amide bonds of the polymer backbone, all of which are sites for potential chemical reaction on these molecules.

Because collagenous tissues degrade very rapidly upon implantation, it is preferable to stabilize the tissue if it is to be implanted into a living system. The tissue can be stabilized using embodiments of the system of the invention in combination with any of a variety of conventional approaches. For example, chemical stabilization by tissue cross-linking, also referred to as tissue fixation, can be achieved using bi-functional and multi-functional molecules having reactive groups capable of forming irreversible and stable intramolecular and intermolecular chemical bonds with the reactive amino acid side groups present on the collagen molecules. An additional method for the fixation/stabilization of the graft tissues involves a photooxidation process.

Such photooxidation may be carried out according to conventional methodologies. Suitable photooxidation process have been described, for example in U.S. Pat. No. 5,854,397, the disclosure of which is incorporated herein by reference, and in Moore et al. (1994). The photooxidation process provides an efficient and effective method for cross-linking and stabilizing various proteinaceous materials including, but not limited to, collagen, collagen fibrils and collagen matrices. The term proteinaceous material as used herein includes both proteins such as collagen and protein-containing materials such as tissues. The material to be cross-linked is generally provided as a vascular tissue sample. Such materials are harvested from the donor animal and immediately immersed in cold buffered saline for storage, with frequent rinses and/or changes with fresh saline, until a fixation process is performed.

The vascular tissue material to be photooxidized is then immersed, dispersed, or suspended (depending upon its previous processing) in an aqueous media for processing. Suitable media for immersion of the material (for purposes of convenience, the word "immersion" shall be considered to include suspension and/or solubilization of the proteinaceous material) include aqueous and organic buffer solutions having a neutral to alkaline pH, preferably a pH of about 6.5 and above because of the denaturation caused by acid pH. Particularly preferred are buffered aqueous solutions having a pH of from about 6.8 to about 8.6.

In a preferred photooxidation process, two media solutions are utilized for what is referred to herein as "preconditioning" the vascular tissue material before irradiation. The material is "preconditioned" in the sense that tissue soaked in the first media solution and irradiated in the second are apparently better cross-linked, e.g., they show improved mechanical properties and decreased susceptibility to proteolytic degradation. The efficacy of this preconditioning is affected by the osmolality of the first media solution, it being preferred that solutions of high osmolality be used as the first media solution. Particularly preferred are sodium potassium, or organic buffer solutions such as sodium, chloride, sodium phosphate, potassium chloride, potassium phosphate, and Good's buffers having a pH of from about 6.8 to about 8.6, the osmolality of which have been increased by addition of a solute such as 4M sucrose or other soluble, high molecular weight carbohydrate to between about 393 mosm and about 800 mosm.

The solute added to increase the osmolality of the first media may have an adverse effect on the degree of cross-linking of the product when present during irradiation. Consequently, after soaking in the first media, the tissue is preferably removed therefrom and immersed in a second media for irradiation. The second media is preferably an aqueous buffered solution having a pH of from about 6.8 to about 8.6 in which the photo-catalyst is dissolved. Preferred second media are sodium and potassium phosphate buffers having a pH of from about 7.4 to about 8.0 and an osmolality of from about 150 to about 400 mosm.

The tissue may be advantageously immersed sequentially in the first media and then in the catalyst-incorporated second media prior to photooxidation for a total period of time sufficient to allow tissue, dye, and medium to reach equilibrium. When the ratio of the concentration of the medium to that of the material to be cross-linked is in the range of from about 10:1 to 30:1, equilibrium can generally be readily achieved. The ratio of the concentrations is generally not critical, and may be adjusted up or down as desired. Once an equilibrium is reached, the sample is photooxidized in the catalyst-incorporated medium. The time required to reach equilibrium varies depending upon such factors as, for instance, the temperature of the media solutions, the osmolality of the first media, and the thickness of the tissue or other sample of proteinaceous material. A period of time as short as a few minutes or as long as several days may be sufficient, but it has been found that periods of from minutes to hours duration is generally sufficient to allow sufficient time for most collagenous materials and media to equilibrate.

The catalysts for use in the photofixation process include photooxidative catalysts (photo-catalysts) that when activated will cause transfer of electrons or hydrogen atoms and thereby oxidize a substrate in the presence of oxygen. Although varied results are possible depending upon the particular catalyst utilized, appropriate catalysts include, but are not limited to, those listed in Oster, et al., J. Am. Chem. Soc. 81: 5095, 5096 (1959). Particularly preferred catalysts include methylene blue, methylene green, rose bengal, riboflavin, proflavin, fluorescein, eosin, and pyridoxal-5-phosphate.

The concentration of catalyst in the media will vary based on several process parameters, but should be sufficient to insure adequate penetration into the material to be cross-linked and to catalyze the photooxidation of the protein. A typical catalyst concentration ranges from about 0.0001%-0.25% (wt/vol); the preferred concentration ranges from about 0.001 to about 0.01%.

To achieve maximum cross-linking and stabilization of the vascular tissue, the following steps may be taken: (1) the photooxidative catalyst should be completely solubilized in the reaction medium prior to use to ensure that the desired dye concentration is achieved; (2) the concentration of the catalyst in the tissue or suspension should be in equilibrium with that in the surrounding medium; and (3) the catalyst solution should be filtered to remove any sizable particulate matter, including chemical particulates, therefrom.

Because the photofixation process involves primarily an oxidative reaction, to assure completion of the reaction, an adequate supply of oxygen must be provided during photooxidation. While an oxygen concentration of about 20% by volume (referring to the concentration of oxygen in the atmosphere over the media) is preferred to assure sufficient dissolved oxygen in the media to prevent oxygen content from becoming rate limiting, all concentrations >0% can also be used. Depending upon the temperature at which the material is held during exposure to light, the oxygen requirement can be met, for instance, by agitating the solution or otherwise mixing the solution, suspension, or sample during the reaction process. Oxygen concentration in the atmosphere over the media during irradiation is preferably maintained in the range of from about 5% to about 40%. Such concentrations (again depending upon temperature) can also be achieved, for instance, by bubbling air into the media during irradiation of the tissue or, if concentrations higher than about 20% are desired, by bubbling oxygen mixtures or air having an increased oxygen content into the media.

As with other catalytic or kinetic-type reactions, the temperature at which the reaction is run directly affects the reaction rate and the oxygen available in the media. Tests conducted with various media ranging in pH from about 6.8 up to about 7.4 indicate that as the temperature of the media increases from about 4 C to about 50° C., oxygen concentration drops in roughly linear fashion from about 11-12 ppm to about 5 ppm. The dye-catalyzed photooxidation process is exothermic, and it is, therefore, preferred that a relatively constant temperature be maintained during irradiation of the proteinaceous material to prevent denaturation of the proteinaceous material and the driving of the oxygen out of the media by the increase in temperature. Usually, a recirculating bath is sufficient to maintain and control the temperature within the jacketed reaction vessel or chamber but placement of the reaction chamber within a controlled environment such as a refrigerator or freezer will work as well. As disclosed herein, photooxidation conducted at temperatures ranging from about −2 C to 40 C. has been shown to be effective; the preferred temperatures being about 0 C to about 25 C. To prevent or alleviate denaturation of the protein comprising the vascular tissue, temperatures below the denaturation temperature of that protein are preferred. Likewise, temperatures above the freezing point of the reaction medium are also preferred.

The process is conducted at temperatures low enough to avoid heat denaturation and pH high enough to avoid acid denaturation of the collagen or other proteinaceous material during cross-linking. Likewise, temperature is held at a level sufficient to maintain the oxygen concentration in the media in which the proteinaceous material is immersed during irradiation.

Once the tissue is prepared, it is photo-irradiated, preferably in a controlled system wherein temperature, distance to light source, irradiation energy and wavelength, oxygen concentration and period of irradiation can be monitored and/or maintained. The tissue is photo-irradiated under conditions sufficient to cause cross-linking. Photooxidation is generally achieved using incandescent, white light or fluorescent light, i.e., visible light, or that portion of light in the visible range that is absorbed by the catalyst.

The intensity of the light employed, and the length of time required to cross-link a given proteinaceous material will vary depending upon several factors. These include: (1) the type and amount of proteinaceous material; (2) the thickness of the tissue sample; (3) the distance between the proteinaceous material and the irradiation source; (4) the catalyst employed; (5) the concentration of catalyst; and (6) the type and intensity of the light source. For instance, exposure time may vary from as little as a few seconds up to as much as about 160 hours. With regard to the intensity of the light, one or more lights may be used of intensity preferably ranging up to about 150 watts, preferably held at a distance from about 2.5 cm to 12 cm from the sample surface. Greater exposure time is required when fluorescent or lower power lights are utilized. These ranges are quite variable; however, they may be easily determined for a given Material without resort to undue experimentation.

Evidence of the cross-linking of the vascular tissue by photooxidation may be provided by several approaches. For instance, polyacrylamide gel electrophoresis of the irradiated material in sodium dodecylsulfate (for example, 0.1%) evidences such cross-linking by a significant decrease in the amount of lower molecular weight material with the simultaneous appearance of high molecular weight material.

Further evidence of cross-linking may be provided by known solubility and digestibility tests. For instance, cross-linked collagen is generally insoluble such that solubility tests provide direct evidence of the degree of cross-linking. The digestibility tests involve incubation of the proteinaceous product with a proteolytic enzyme such as papain, trypsin, pepsin, or bacterial collagenase, and the subsequent testing of the media in which the product and enzyme are incubated for soluble degradation products of the cross-linked product. The test is generally accomplished by pelletizing the undigested, cross-linked tissue by centrifugation and testing the resulting supernatant for degradation products.

Following photo-irradiation, the cross-linked product may be advantageously subjected to additional treatments for the removal of the catalyst and other chemicals or impurities found therein before being used as a vascular graft. Multiple rinses in a fresh buffer solution, for example, may be used, followed by at least partial removal of water by treatment with, for instance, ethanol. The number of rinses and the volume of rinse solution required depend upon the mass of the tissue and the catalyst concentration utilized.

In addition to the use of photooxidation processes for the fixation of the graft tissue, numerous other fixation methods have been described and are readily available in the art and may be used in conjunction with embodiments of the invention. For example, glutaraldehyde, and other related aldehydes, have seen widespread use in preparing cross-linked biological tissues. Methods for glutaraldehyde fixation of biological tissues have been extensively described and are well known in the art. In general, a tissue sample to be cross-linked is simply contacted with a glutaraldeyde solution for a duration effective to cause the desired degree of cross-linking within the biological tissue being treated.

Many variations and conditions have been applied to optimize glutaraldehyde fixation procedures. For example, lower concentrations have been found to be better in bulk tissue cross-linking compared to higher concentrations. It has been proposed that higher concentrations of glutaraldehyde may promote rapid surface cross-linking of the tissue, generating a barrier that impedes or prevents the further diffusion of glutaraldehdye into the tissue bulk. For most bioprosthesis applications, the tissue is treated with a relatively low concentration glutaraldehyde solution, e.g., typically between 0.1%-5%, for 24 hours or more to ensure optimum fixation. Of course, various other combinations of glutaraldehyde concentrations and treatment times will also be suitable depending on the objectives for a given application.

In addition to bifunctional aldehydes, many other chemical fixation procedures have been described (for review, see Khor, Biomaterials 18: 95-105, 1997). For example, some such methods have employed polyethers, polyepoxy compounds, diisocyanates, azides, etc. These and other approaches available to the skilled individual in the art for treating biological tissues will be suitable for cross-linking vascular graft tissue in embodiments of systems according to this invention.

The hemodynamic forces recreated within and by embodiments of the system may also be used to improve organ transplant procedures and make these procedures more successful by providing an appropriate environments (e.g., hemodynamic) for an organ prior to transplant, both during the transport period and while awaiting actual transplant. More particularly, providing a simulated pulsatile or hemodynamic environment, which may represent in vivo conditions of the particular organ, to the organ during these periods protects the integrity of the organ by maintaining its proper functionality after it has been removed so as to provide the best possible transition and adaptation in a new host. Also, embodiments of the system may be used to re-vive an organ that was cryopreserved or treated with a type of preservation treatment as well.

The invention also provides an embodiment of a system for applying controlled shear flow stress to mammalian cell cultures used for artificial cartilage production.

Applying shear flow stress to a three-dimensional or monolayer chondrocyte culture advantageously increases the ratio of type II to type I collagen produced by the chondrocytes. The shear flow stress also advantageously enhances maintenance of the chondrocyte phenotype. Thus, application of shear flow stress according to embodiments of this invention improves the functional outcome of a three-dimensional or monolayer chondrocyte culture and increases the useful lifetime of the monolayer culture.

Applying shear flow stress to stem cells induces or promotes differentiation of the stem cells into chondrocytes. Inducing or promoting stem cells to differentiate into chondrocytes is accomplished by substituting stem cells for chondrocytes in the shear flow method described herein with regard to chondrocytes. The chondrocytes arising from the stem cell differentiation process are maintained in the culture, under shear flow stress, for a sufficient time to allow production of artificial cartilage.

Shear flow stress also can be used according to embodiments of this invention to induce transdifferentiation of differentiated cells into chondrocytes. Transdifferentiation is accomplished by substituting, differentiated cells other than chondrocytes, e.g., myoblasts or fibroblasts, in the shear flow method described herein with regard to chondrocytes. In response to the shear flow stress, the differentiated cells transdifferentiate into chondrocytes. The chondrocytes arising from the transdifferentiation process are maintained in the culture, under shear flow stress, for a sufficient time to allow production of artificial cartilage.

Artificial cartilage produced according to any embodiment of this invention can be used for surgical transplantation, according to established medical procedures, to replace damaged or missing cartilage. Typically, artificial cartilage is employed in the repair of human joints, e.g., knees and elbows.

Preferably, the cultured chondrocytes are anchored, i.e., attached, to a substrate, whether grown as a monolayer or grown in a 3-dimensional culture. A monolayer-supporting surface, or a 3-dimensional scaffold, in a bioreactor is inoculated with chondrocytes, stem cells, or differentiated cells suitable for transdifferentiation. Artificial cartilage can be produced by growing chondrocytes in a conventional mammalian tissue culture medium, e.g., RPMI 1640, Fisher's, Iscove's or McCoy's. Such media are well known in the art, and are commercially available. Typically, the cells are cultured at 37 C in air supplemented with 5% CO2. Under these conditions, a chondrocyte monolayer or a three dimensional cartilage matrix is produced in approximately 7 to 56 days, depending on the cell type used for inoculation and the culture conditions.

Isolated chondrocytes can be used to inoculate the surface of a support or a 3-dimensional matrix. Alternately, stem cells, or cells suitable for transdifferentiation can be used for inoculation.

Cells used for inoculation of cultures used in the invention can be isolated by any suitable method. Various starting materials and methods for chondrocyte isolation are known. See generally, Freshney, Culture of Animal Cells. A Manual of Basic Techniques, 2d ed., A. R. Liss Inc., New York, pp 137-168 (1987). Examples of starting materials for chondrocyte isolation include mammalian knee joints or rib cages.

If the starting material is a tissue in which chondrocytes are essentially the only cell type present, e.g., articular cartilage, the cells can be obtained directly by conventional collagenase digestion and tissue culture methods. Alternatively, the cells can be isolated from other cell types present in the starting material. One known method for chondrocyte isolation includes differential adhesion to plastic tissue culture vessels. In a second method, antibodies that bind to chondrocyte cell surface markers can be coated on tissue culture plates and then used to selectively bind chondrocytes from a heterogeneous cell population. In a third method, fluorescence activated cell sorting (FACS) using chondrocyte-specific antibodies is used to isolate chondrocytes. In a fourth method, chondrocytes are isolated on the basis of their buoyant density, by centrifugation through a density gradient such as Ficoll.

Examples of tissues from which stem cells for differentiation, or differentiated cells suitable for transdifferentiation, can be isolated include placenta, umbilical cord, bone marrow, skin, muscle, periosteum, or perichondrium. Cells can be isolated from these tissues by explant culture and/or enzymatic digestion of surrounding matrix using conventional methods.

When the artificial cartilage construct has grown to the desired size and composition, a cryopreservative fluid can be introduced into embodiments of the system. The cryopreservative fluid freezes the artificial cartilage construct for future use. Cryopreservation methods and materials for mammalian tissue culture material are known to those of ordinary skill in the art.

Methods and materials for 3-dimensional cultures of mammalian cells are known in the art. See, e.g., U.S. Pat. No. 5,266,480. Typically, a scaffold is used in a bioreactor growth chamber to support a 3-dimensional culture. The scaffold can be made of any porous, tissue culture-compatible material into which cultured mammalian cells can enter and attach or anchor. Such materials include nylon (polyamides), dacron (polyesters), polystyrene, polypropylene, polyacrylates, polyvinyl chloride, polytetrafluoroethylene (teflon), nitrocellulose, and cotton. Preferably, the scaffold is a bioabsorbable or biodegradable material such as polyglycolic acid, catgut suture material, or gelatin. In general, the shape of the scaffold is not critical.

Optionally, prior to inoculating chondrocytes into the scaffold, stromal cells are inoculated into the scaffold and allowed to form a stromal matrix. The chondrocytes are then inoculated into the stromal matrix. The stromal cells can include fibroblasts. The stromal cells can also include other cell types.

A 3-dimensional culture can be used in a system of the invention and shear flow stress applied to the chondrocytes by the movement of the liquid culture medium pumped through the growth chamber, which contains the 3-dimensional culture. Preferably, in such embodiments, the scaffold and attached cells are static.

Embodiments of the system for simulating hemodynamic forces as embodied and broadly described herein is capable of generating the complete range of hemodynamic force patterns in the interest and advancement of cardiovascular research, and will make new avenues of research and development available which were never before possible, at any cost. Embodiments of systems and methods will greatly advance our understanding of cardiovascular function and disease, and allow pharmacologic and genetic strategies to be tested at much lower costs than conventional methods of experimentation. Ultimately, patients will benefit the most, since embodiments of the invention will advance new concepts in cardiovascular disease progression, development, and treatment. Healthy patients can function as productive members of society, improve their quality of life, and reduce the cost of medical treatment.

Hemodynamic conditions are one class of dynamic conditions (FIG. 18) and affect cardiovascular physiology and pathology. Pulsatile flow (Q), pressure (P), and diameter (D) waveforms exert wall shear stress (WSS), normal stress, and circumferential strain (CS) (types of dynamic conditions as shown in FIG. 17) on blood vessels, hi vitro studies to date have focused on either WSS or CS but not their interaction. Studies caused at using embodiments of systems 1 and 1101 have demonstrated that concomitant WSS and CS affect endothelial cell (EC) biochemical response modulated by the temporal phase angle between WSS and CS (stress phase angle, SPA) (one type of dynamic condition as shown in FIG. 17). Systems 1, 1101 have shown that large negative SPA occurs in regions of the circulation where atherosclerosis and intimal hyperplasia are prevalent, and that nitric oxide (NO) biochemical secretion was significantly decreased in response to a large negative SPA of −180 deg with respect to an SPA of 0° in bovine aortic endothelial cells (BAEC) at 5 hr. Systems 1, 1101 use the discrete hemodynamic conditions of pro-atherogenic (SPA=−180 deg) and normopathic (SPA=0 deg) states as input information to study the physiologic SPA used to produce the corresponding hemodynamic conditions at the tubular structures. Accordingly, systems 1, 1101 demonstrate that one type of dynamic condition (SPA) plays an important role in hemodynamics with respect to vascular remodeling, homeostasis, and pathogenesis, and that a large negative SPA is pro-atherogenic.

Endothelial cells (EC) lining all blood vessel walls serve as sensors and transducers of two types of dynamic conditions, namely, wall shear stress (WSS) and circumferential strain (CS), in the class of hemodynamic conditions. WSS and CS (also referred to as stretch) independently influence EC morphology and biochemistry. See, for example, Davies, P. F. et al., 2001, "Hemodynamics and the Focal Origin of Atherosclerosis: A Spatial Approach to Endothelial Structure, Gene Expression, and Function," Ann. N.Y. Acad. Sri., 947, pp. 7-16; 947, pp. 16-17; Kito, H. et al., 1998, "Cyclooxygenase Expression in Bovine Aortic Endothelial Cells Exposed to Cyclic Strain," Endothelium, 6(2), pp. 107-112 and Frangos, S. G. et al, 2001, "The Integrin-Mediated Cyclic Strain-Induced Signaling Pathway in Vascular Endothelial Cells," Endothelium, 8(1), pp. 1-10, the contents of which are incorporated herein by reference.

WSS and CS also independently influence EC monolayer permeability to macromolecules and water. See, for example, Sill, H. W. et al., 1995, "Shear Stress Increases Hydraulic Conductivity of Cultured Endothelial Monolayers," Am. J. Physiol, 268 (2 Pt 2), pp. H535-H543 and Lever, M. J., Tarbell, J. M., and Caro, C. G., 1992, "The Effect of Juminal Flow in Rabbit Carotid Artery on Transmural Fluid Transport," Exp. Physiol., 77(4), pp. 553-563, the contents of which are incorporated herein by reference. WSS is an important fluid mechanical mediator of atherosclerosis and together with CS is important in vascular regulation and remodeling. See, for example, Gimbrone, Jr., M. A., 1999, "Vascular Endothelium, Hemodynamic Forces, and Atherogenesis," Am. J. Pathol., 155(1), pp. 1-5, the contents of which are incorporated herein by reference.

Changes in flow rate are sensed by the endothelium through the WSS by releasing vasoactive agents that modulate smooth muscle contraction or dilation as discussed for example in Furchgott, R. F., and Zawadzki, J. V., 1980, "The Obligatory Role of Endothelial Cells in the Relaxation of Arterial Smooth Muscle by Acetylcholine," Nature (London), 288(5789), pp. 373-376; Kohler, T. R., and Jawien, A., 1992, "Flow Affects Development of Intimal Hyperplasia After Arterial Injury in Rats," Arterioscler. Thromb., 12(8), pp. 963-971 and Cooke, J. P. et al., 1990, "Flow Stimulates Endothelial Cells to Release a Nitrovasodilator That is Potentiated by Reduced Thiol," Am. J. Physiol., 259(3 Pt 2), pp. H804-H812, the contents of which are incorporated herein by reference. Different mechanical environments give rise to different endothelial cell phenotypes throughout the circulation. See, for example, Chappell, D. C. et al., 1998, "Oscillatory Shear Stress Stimulates Adhesion Molecule Expression in Cultured Human Endothelium," Circ. Res., 82, pp. 532-539 and Nerem, R. M. et al., 1998, "The Study of the Influence of Flow on Vascular Endothlial Cell Biology," Am. J. Med. Sci., 316, pp. 169-175, the contents of which are incorporated herein by reference.

Vascular smooth muscle cells also experience hemodynamic forces that have been implicated in their proliferation and migration as observed in atherosclerosis. See, for example, Kohler, T. R., and Jawien, A., 1992, "Flow Affects Development of Intimal Hyperplasia After Arterial Injury in Rats," Arterioscler. Thromb., 12(8), pp. 963-971 and Kohler, T. R., and Jawien, A., 1992, "Flow Affects Development of Intimal Hyperplasia After Arterial Injury in Rats," Arterioscler. Thromb., 12(8), pp. 963-971, the contents of which are incorporated herein by reference. Most studies that examined simultaneous WSS and CS have not controlled or had limited control of the temporal phase angle between WSS and CS (stress phase angle, SPA). See, for example, Zhao, S. et al., 1995, "Synergistic Effects of Fluid Shear Stress and Cyclic Circumferential Stretch on Vascular Endothelial Cell Morphology and Cytoskeleton," Arterioscler., Thromb., Vase. Biol, 15(10), pp. 1781-1786; Benbrahim, A. et al., 1994, "A Compliant Tubular Device to Study the Influences of Wall Strain and Fluid Shear Stress on Cells of the Vascular-Wall," J. Vase. Surg., 20(2), pp. 184-194; Ziegler, T. et al., 1998, "Influence of Oscillatory and Unidirectional Flow Environments on the Expression of Endothelin and Nitric Oxide Synthase in Cultured Endothelial Cells," Arteriosler., Thromb., Vase. Biol., 18(5), pp. 686-692 and Qiu, Y., and Tarbell, J. M., 2000, "Interaction Between Wall Shear Stress and Circumferential Strain Affects Endothelial Cell Biochemical Production," J. Vase. Res., 37(3), pp. 147-157, the contents of which are incorporated herein by reference.

Nitric oxide (NO) is one of the smallest biomolecules produced in mammalian cells and plays a major role in vascular homeostasis, as discussed, for example, in Ignarro, L. J., 1990, "Nitric Oxide. A Novel Signal Transduction Mechanism for Transcellular Communication," Hypertension, 16(5), pp. 477-483, the contents of which are incorporated herein by reference. The content longitudinal and/or radial velocity/flow concentration of NO are types of dynamic conditions (FIG. 17). The small size of NO permits unhindered movement to neighboring cells, however, the short half-life (<5 seconds) limits its range. Red blood cells can aid in the transport of NO through binding with hemoglobin to form nitrosyl-heme adducts that are more stable than free NO. NO production occurs through a redox reaction involving three cosubstrates, five cofactors, and nitric oxide synthase (NOS) that leads to the conversion of L-arginine to L-citrulline and release of NO. See, for example, Nathan, C, and Xie, Q. W., 1994, "Nitric Oxide Synthases: Roles, Tolls, and Controls," Cell, 78(6), pp. 915-918 and Nathan, C, and Xie, Q. W., 1994, "Regulation of Biosynthesis of Nitric Oxide," J. Biol. Chem., 269(19), pp. 13725-13728, the contents of which are incorporated herein by reference.

Three iso-forms of NOS exist: nNOS—predominant in neuronal cells; iNOS—constitutive expression and mainly in found in macrophages; and eNOS—located in endothelial cells and the only isoform to form a membrane-bound linkage in the signal-transducing domains of the plasmalemma, the caveolae. See, for example, Bevan, J. A., and Siegel, G., 1991, "Blood Vessel Wall Matrix Flow Sensor: Evidence and Speculation," Blood Vessels, 28(6), pp. 552-556; Bevan, J. A., and Laher, I., 1991, "Pressure and Flow-Dependent Vascular Tone," FASEB J., 5(9), pp. 2267-2273; Bevan, J. A., 1991, "Pressure and Flow: Are These the True Vascular Neuroeffectors" Blood Vessels, 28(1-3), pp. 164-172; Davies, P. F., 1995, "Flow-Mediated Endothelial Mechanotransduction," Physiol. Rev., 75(3), pp. 519-560; Gimbrone, Jr., M. A. et al., 2000, "Endothelial Dysfunction, Hemodynamic Forces, and Atherogenesis," Ann. N.Y. Acad. Sci., 902, pp. 230-239; 902, pp. 239-240 and Cahill, P. A. et al., 1996, "Increased Endothelial Nitric Oxide Synthase Activity in the Hyperemic Vessels of Portal Hypertensive Rats," J. Hepatol, 25(3), pp. 370-378, the contents of which are incorporated herein by reference. WSS increases NO secretion. See for example, Cahill, P. A. et al., 1996, "Increased Endothelial Nitric Oxide Synthase Activity in the Hyperemic Vessels of Portal Hypertensive Rats," J. Hepatol, 25(3), pp. 370-378, the contents of which are incorporated herein by reference. CS alone and CS combined with WSS also augment NO release. See, for example, Awolesi, M. A., Sessa, W. C., and Sumpio, B. E., 1995, "Cyclic Strain Up-regulates Nitric Oxide Synthase in Cultured Bovine Aortic Endothelial Cells," J. Clin. Invest., 96(3), pp. 1449-1454, the contents of which are incorporated herein by reference.

Pulsatile blood flow in the arterial circulation produces oscillatory wall shear stress with mean values from 5 to 40 dyne/cm². See, for example, Lipowsky, H. H., 1995, "Shear Stress in the Circulation," in Flow-dependent Regulation of Vascular Function, edited by J. A. Bevan et al., the contents of which are incorporated herein by reference. Pulsatile blood pressure causes large arteries to expand predominantly in the circumferential direction, whereas longitudinal expansion is constrained by blood vessel branching and tethering. See, for example, Dobrin, P. B., 1978, "Mechanical Properties of Arteries," Physiol. Rev., 58, pp. 397-460, the contents of which are incorporated herein by reference. As the vessel expands, a uniform circumferential strain is produced. For this reason, a three-dimensional geometry tube or tubular structure, instead of a two-dimensional flat membrane, is used in systems 1, 1101, which produces heterogeneous strain fields. See, for example, Brown, T. D., 2000, "Techniques for Mechanical Stimulation of Cells in Vitro: A Review," J. Biomech., 33, pp. 3-14, the contents of which are incorporated herein by reference. In one embodiment of the invention, systems 1, 101, 1101 produce a maximum cyclic strain or diameter variation, $CS=(D_{max}-D_{min})/D_{mean}$, driven by pulsing transmural pressure in large arteries such as the thoracic aorta, carotid artery, femoral artery, and pulmonary artery ranges from 2% to 18% over the pressure pulse. The venous systemic circulation has almost no diameter variation due to the low pressure pulse. Atherosclerosis occurs in the large arteries where CS is significant. Accordingly in one embodiment of the invention, systems 1, 1101 produces both hemodynamic conditions CS and WSS.

Blood vessel endothelial cells in vivo are subjected to simultaneous pulsatile CS and WSS acting approximately in perpendicular directions. The temporal phase angle between pressure and flow (e.g., impedance phase angle, IPA also a type of dynamic condition as per FIG. 17) generated by global wave reflection in the circulation, as well as the inertial effects of blood flow, cause temporal phase shifts to occur between CS and WSS. The temporal phase angle between CS and WSS(SPA) in vivo generates complex, time-varying mechanical force patterns on the EC monolayer, as shown in FIGS. 10A-10H, 25A-25C and 30-34.

Physiologic factors contribute to variations in SPA throughout the circulation. SPA can be described as the phase angle between diameter (D) and WSS (τ), denoted as $\phi(D-\tau)$, that shows CS is generally synchronous with vessel diameter (D) variation. The SPA can be decomposed into two parts $$\phi(D-\tau)=\phi(D-Q)-\phi(\tau-Q)\approx 4 > \phi(P-Q)-\phi(\tau-Q)$$

where $\phi(D-Q)$ is approximately equal to the IPA, $\phi(P-Q)$, since diameter (D) and pressure (P) are nearly in phase for an elastic vessel or tubular structure, and $\phi(P-Q)$ is the phase angle between the WSS and flow rate. $\phi(P-Q)$ is determined from distal resistance, compliance, and wave reflections. $\phi(P-Q)$ of the first harmonic of a physiologic waveform approaches −45 deg (P lags Q by 45 deg) in the aorta and large arteries that feed high impedance flow circuits (except for coronary arteries due to their unique flow circuit), approaches 0 deg in small arteries due to reduced distal compliance, and also approaches 0 deg in veins that feed low impedance flow circuits. See, for example, Nichols, W. W., and O'Rourke, M. F., 1998, McDonald's Blood Flow in Arteries Theoretical, Experimental, and Clinical Principles, Arnold and Oxford University Press, New York, the contents of which are incorporated herein by reference.

$\phi(\tau-Q)$, the shear-flow phase angle, in straight vessels is determined by the relative importance of unsteady inertia and viscous forces and depends strongly on the unsteadiness parameter $|\alpha=\alpha\sqrt{(w/v)}$; α=vessel radius, w=fundamental frequency of the heart beat, and v=kinematic viscosity of blood. For large straight arteries and veins with high α,$\phi(\tau-Q)$ approaches +45 deg and for small, straight arteries and veins with low α,$\phi(\tau-Q)$ approaches 0 deg, which systems 1, 1101 can produce in specimen 12 or tubular structure 1112. See, for example, Womersley, J. R., 1955, "Method for Calculation of Velocity, Rate of Flow and Viscous Drag in Arteries When the Pressure Gradient is Known," J. Physiol. (London), 127, pp. 553-563, the contents of which are incorporated herein by reference.

Based on the above discussion, the following SPA approximations in straight vessels can be summarized and produced by systems 1, 1101:

Large artery (straight): $\phi(D-\tau)$=−45 deg–45 deg=−90 deg

Large vein (straight): $\phi(D-\tau)$=0 deg–45 deg=45 deg

Small artery (straight): $\phi(D-\tau)$=0 deg–0 deg=0 deg

Small vein (straight): $\phi(D-\tau)$=0 deg–0 deg=0 deg

The shear-flow phase angle is strongly dependent on local vessel geometric factors that can induce spatial skewing of velocity profiles and flow separation. This can lead to local spatial distribution of SPA (a type of dynamic condition as shown in FIG. 17) in certain vessels such as diose associated with intimal hyperplasia and atherosclerosis. Several high-risk arterial geometries include the aortic abdominal bifurcation (see, for example, Lee, C. S., and Tarbell, J. M., 1997, "Wall Shear Rate Distribution in an Abdominal Aortic Bifurcation Model: Effects of Vessel Compliance and Phase Angle Between Pressure and Flow Waveforms," J. Biomech. Eng., 119(3), pp. 333-342, the contents of which are incorporated herein by reference) curved coronary artery (see, for example, Qiu, Y., and Tarbell, J. M., 2000, "Numerical Simulation of Pulsatile Flow in a Compliant Curved Tube Model of a Coronary Artery," J. Biomech. Eng., 122(1), pp. 77-85, the contents of which are incorporated herein by reference), and end-to-end undersized graft anastomosis, all of which can be produced at a specimen 12 in systems 1, 101, 1101. For example, in the aortic abdominal bifurcation, the SPA drops along the outer wall, especially near the disease-prone region opposite the flow divider to −80 deg (e.g., normal) and −100 deg (e.g., hypertensive case). This region of complex hemodynamic conditions in the aortic abdominal bifurcation is also characterized by low shear stress as opposed to the high shear region of flow divider. The inner wall (flow divider) has a higher SPA (e.g., −20 deg normal and −55 deg hypertensive) and higher shear stress. Systems 1, 1101 can produce all of these hemodynamic conditions at specimen 12 or tubular structure 1112. Not only is the SPA large and negative in the region of atherosclerotic plaque development, but also hypertension will further decrease the SPA, resulting in a more atherogenic condition. Such pathology (e.g., dynamic conditions as shown in FIG. 17) can be reproduced by systems 1, 1101.

A curved coronary artery experiences complex hemodynamics primarily caused by the unique coronary flow circuit that allows for the most extreme SPA in the cardiovascular circulation. The entire coronary artery experiences a large negative SPA (e.g., SPA<−180 deg: −250 deg on the inner wall, −220 deg on the outer wall) which can be produced at specimen 12 or tubular structure 1112 by systems 1, 1101.

Coronary arteries arc the most disease-prone arteries in the cardiovascular circulation. In all instances, the SPA is more negative in low shear pathologic regions than in high shear healthy regions.

Thus, regions of the circulation prone to pathologic development such as atherosclerosis and intimal hyperplasia are characterized by large negative SPA values relative to regions typically without pathologic development (e.g., veins, small arteries, high shear regions in large arteries). Accordingly, pathologic development or conditions can be modeled using systems 1, 1101. Endothelial biomolecule production is affected by a negative SPA (−100 deg). See, for example, Qiu, Y., and Tarbell, J. M., 2000, "Interaction Between Wall Shear Stress and Circumferential Strain Affects Endothelial Cell Biochemical Production," J. Vase. Res., 37(3), pp. 147-157, the contents of which are incorporated herein by reference.

Detection of fluid molecules (e.g., endothelial cell NO production) can demonstrate affects of dynamic conditions of FIG. 17 (e.g., highly negative SPA) for a class of dynamic conditions, as shown in FIG. 18 (e.g., hemodynamic conditions) on EC and the cardiovascular system (e.g., coronary arteries).

The present example (e.g., FIG. 46) is provided to demonstrate the capability and utility of the embodiments of the invention for reproducing in vivo mammalian hemodynamic conditions in vitro. In particular aspects, the present example will also demonstrate the exemplary utility of the equipment for obtaining a in vitro and in vivo information relating to classes and types of dynamic conditions (e.g., FIGS. 17A, 17B and 18). Types of dynamic conditions g(t) that were measured in the present study include changes in production of NO from ECs exposed to pathologic (e.g., BAECs−180 SPA, FIG. 10B) hemodynamic conditions versus production of NO from ECs exposed to normal (e.g., BAES, 0 deg SPA, FIG. 10A). Additional types of dynamic conditions which systems 1, 1001 measured and/or controlled include changes in specimens 12 or tubular structure 1112 hemodynamic conditions monitored for Q(t), D(t), P(t), pH, temperature viability, (directly) and NO, WSS, CS, SPA (indirectly).

The cell culture consisted of primary bovine aortic endothelial cells (BAECs) obtained from fresh aortas. Briefly, fresh bovine aortas were obtained and rinsed with cold HBSS and 1% penicillin-streptomycin. The aorta was cut longitudinally along the intercostal arteries and formed into a trough. Ten ml of collagenase (e.g., Blendzyme from Roche Diagnostics Corp.) was placed in the trough for 40 min, removed, and centrifuged (e.g., repeated five times). The cell population purity was 97%-99% as determined via labeled Dil-acetylated LDL, a common marker for endothelial cells, and flow cytometry.

The BAECs were grown with 10% FBS (e.g., F-2442 from Sigma Chemical Co.), MEM w/ phenol red (e.g., M-0769 from Sigma Chemical Co.), 1% bovine serum albumin (e.g., BSA 30%, A-7284 from Sigma Chemical Co.), 1% penicillin-streptomycin (e.g., 50 U/mL and 50 µg/mL, P0906 from Sigma Chemical Co.), and L-glutamine (2 mM) until passage (4-8) (population doubling 15-18). Experimental medium was phenol red free MEM+9.5% dextran (e.g., 148 kD, D4876 from Sigma Chemical Co.) to increase viscosity (6.38 cP) to achieve desired shear stress. BAECs were plated on fibronectin (e.g., bovine plasma F-1141 from Sigma Chemical Co., 30 µg/ml in MEM) treated silicone tubes (e.g., pretreated with 70% sulfuric acid for 10 min). The plating density was $4-6 \times 10^4$ cells/ml. The cultured tubes were grown in the incubator for 3-4 days until confluence prior to experiment. The tube surface area was 38 cm². Each experiment consisted of pulsatile conditions (SPA=0 deg or −180 deg) with companion controls: steady shear stress (SS), static control (SC), and pressurized control (PC). The conditions were 10±10 dynes/cm², 70±20 mmHg, and 4±4% diameter variation at 1 Hz and 37° C. Direct microscope visualization verified cell attachment before and after experiments.

Nitric oxide (NO) measurement was performed via a fluorometric method. Indirect determination was performed via examination of NO breakdown products $NO_3^-$ and $NO_2^-$. The fluorometric quantification is based on the reaction of nitrite with 2,3-diaminonapthalene (DAN) that produces the fluorescent compound 1-(H)-napthotriazole and can detect concentrations as low as 10 nM. See, for example, Stamler, J. S., 1995, "S-Nitrosothiols and the Bioregulatory Actions of Nitrogen Oxides Through Reactions With Thiol Groups," Curr. Top. Microbiol. Immunol., 196, pp. 19-36, the contents of which are incorporated herein by reference. Next, 10 µl of DAN solution (0.05 mg/ml in 0.62 M HCl) was added to each well and refrigerated at 4° C. for 10 min and the reaction was terminated with 10 µl of 2.8 M NaOH. The fluorometer utilized filters for excitation at 360 ran and emission at 425 nm (e.g., Packard Fluorocount fluorometer and PLATE READER Version 3.0 software). Nitrite standards were made with the same experimental media, phenol red free MEM with 1% BSA+9.5% dextran, in the range 60 nM-8 µM. The NO concentration range was ~0.5-3 µM.

A two-factor analysis of variance model was used with the Tukey method on a 95% confidence interval. The standardized residuals and normal probability plot of residuals satisfied model requirements for linearity (e.g., statistics software from MINITAB™).

Figure 10A:
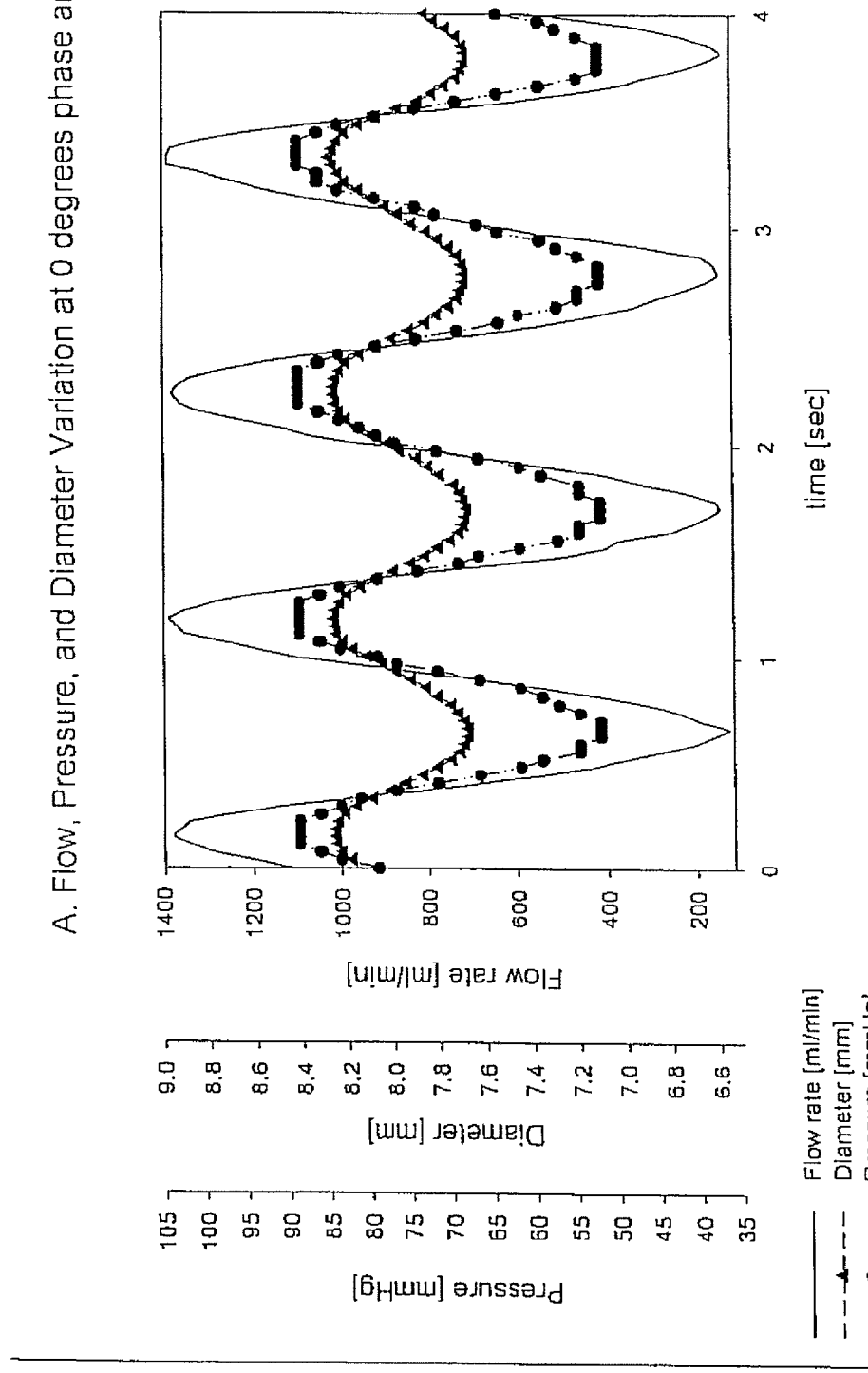
FIGS. 10A-10H are graphs of pressure, diameter and flow rate conditions generated by the systems shown in FIGS. 2A-2E and 3A-3D.
Figure 10B:
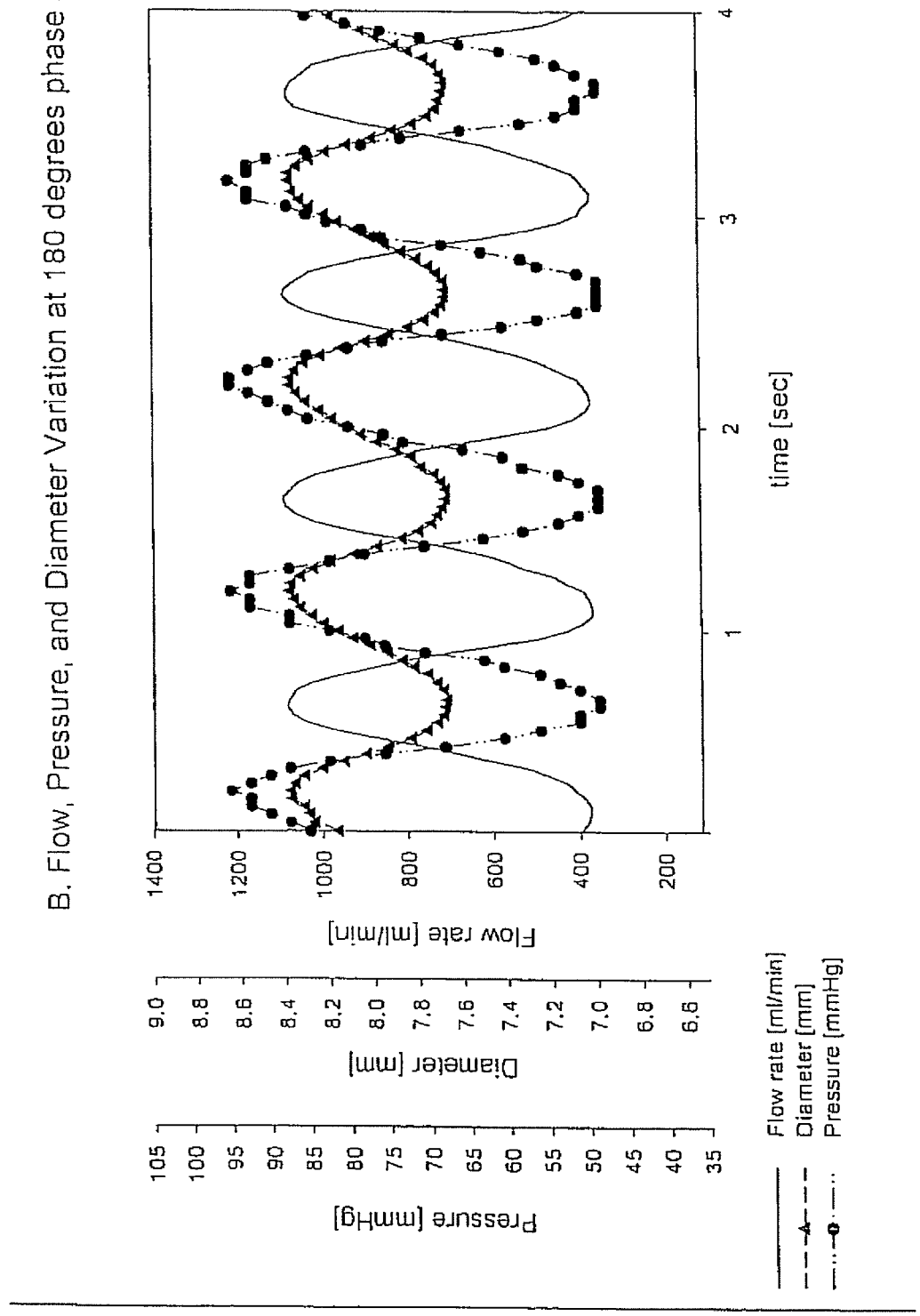
Figure 10C:
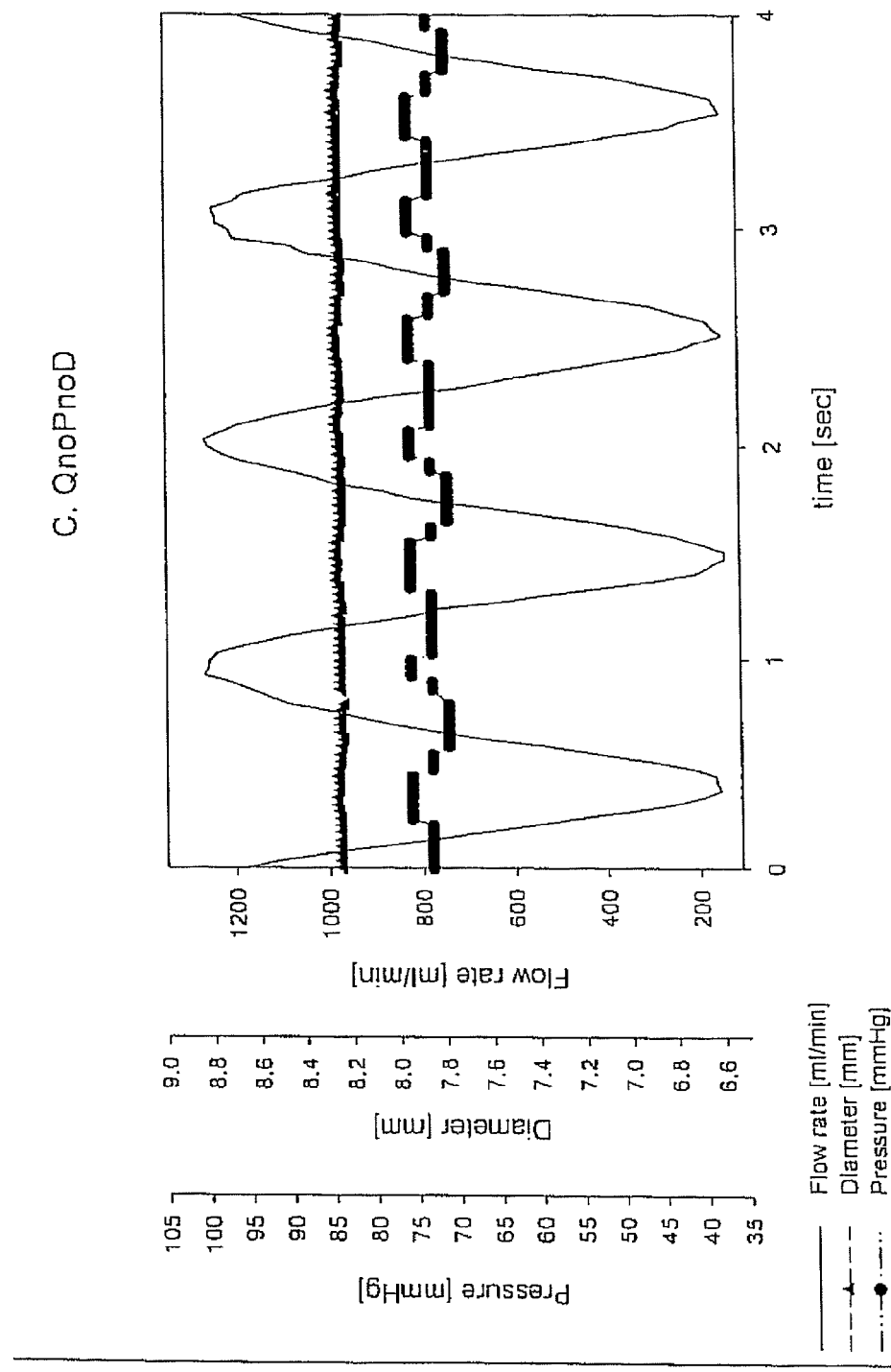
Figure 10D:
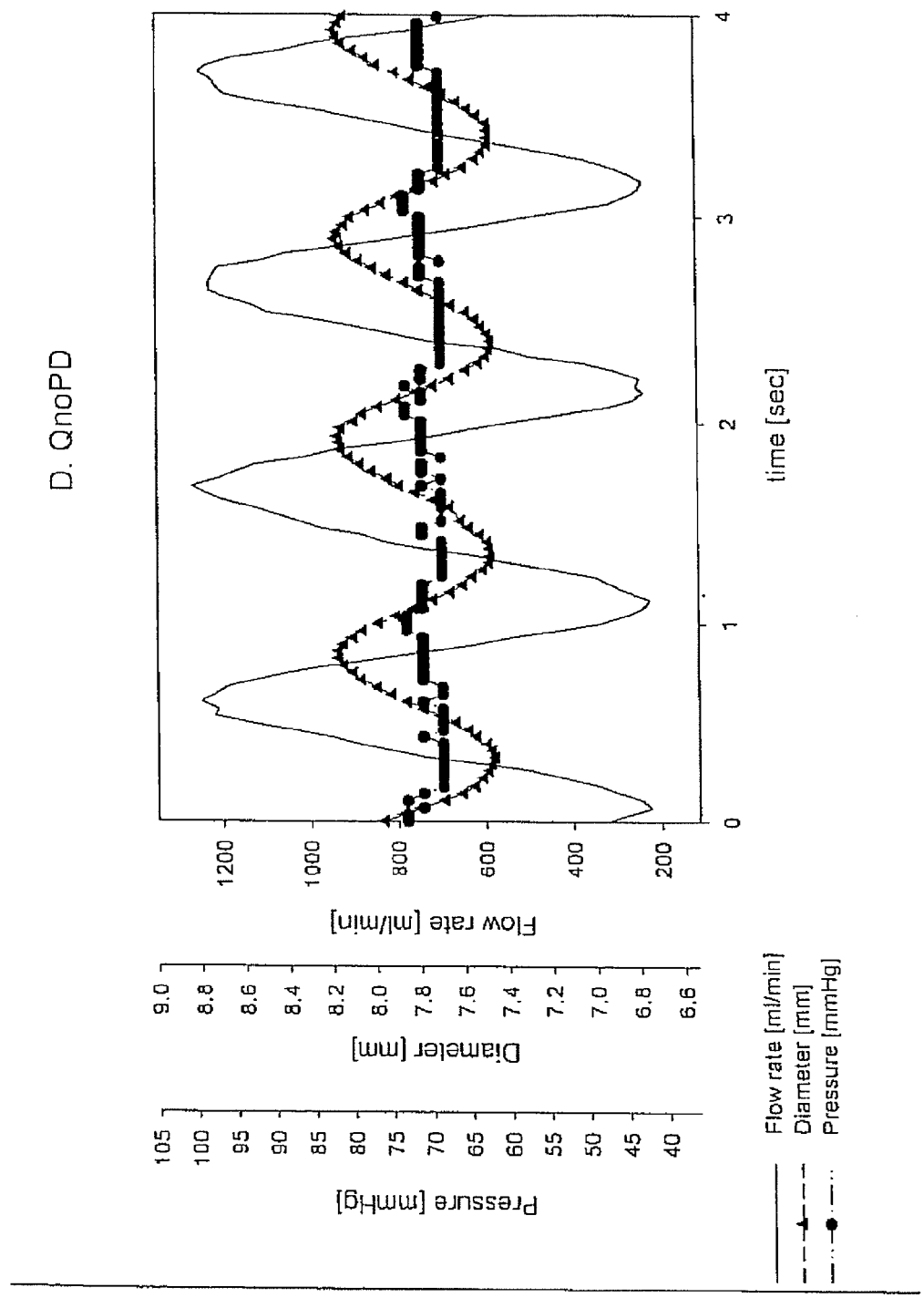
Figure 10E:
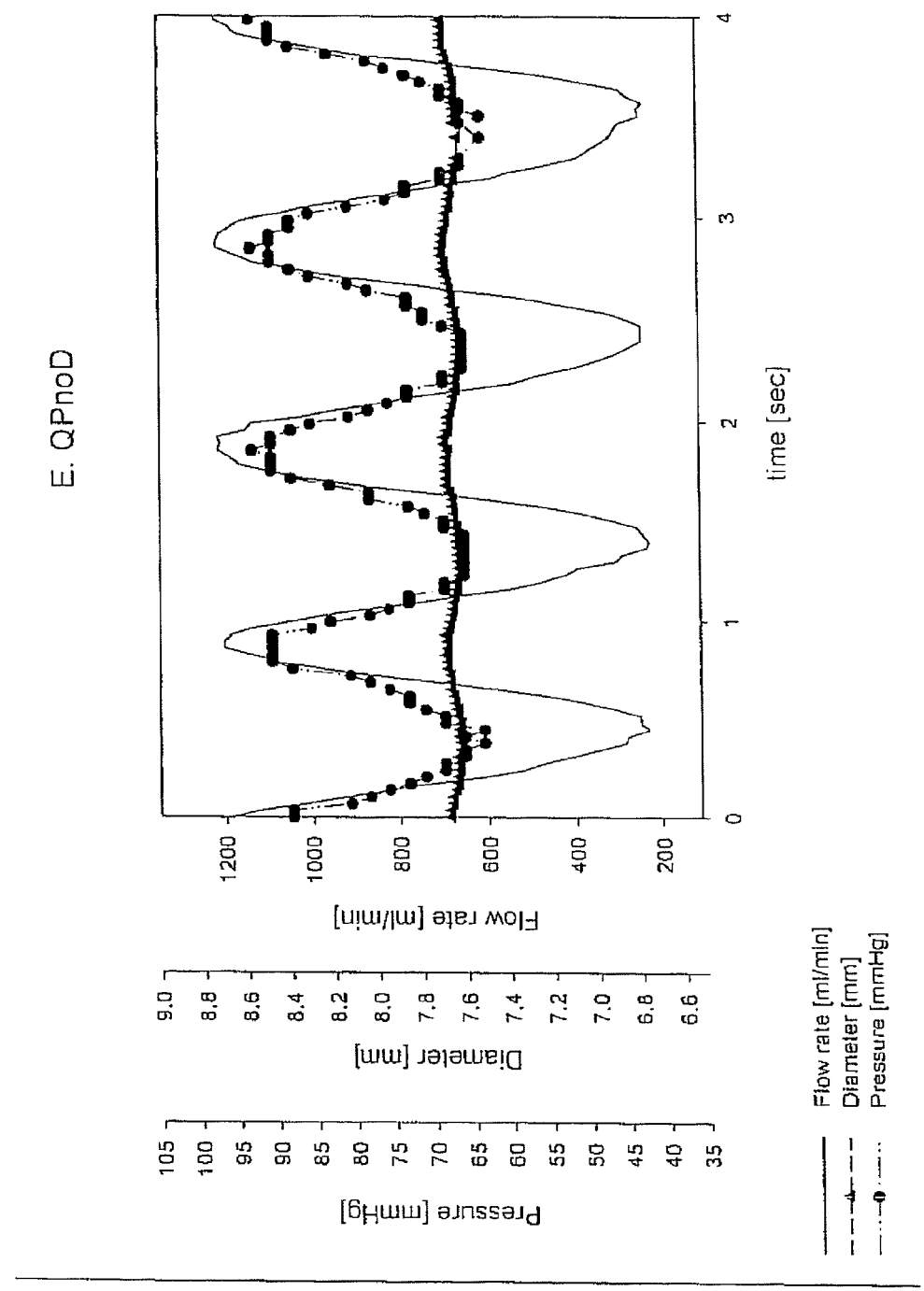
Figure 10F:
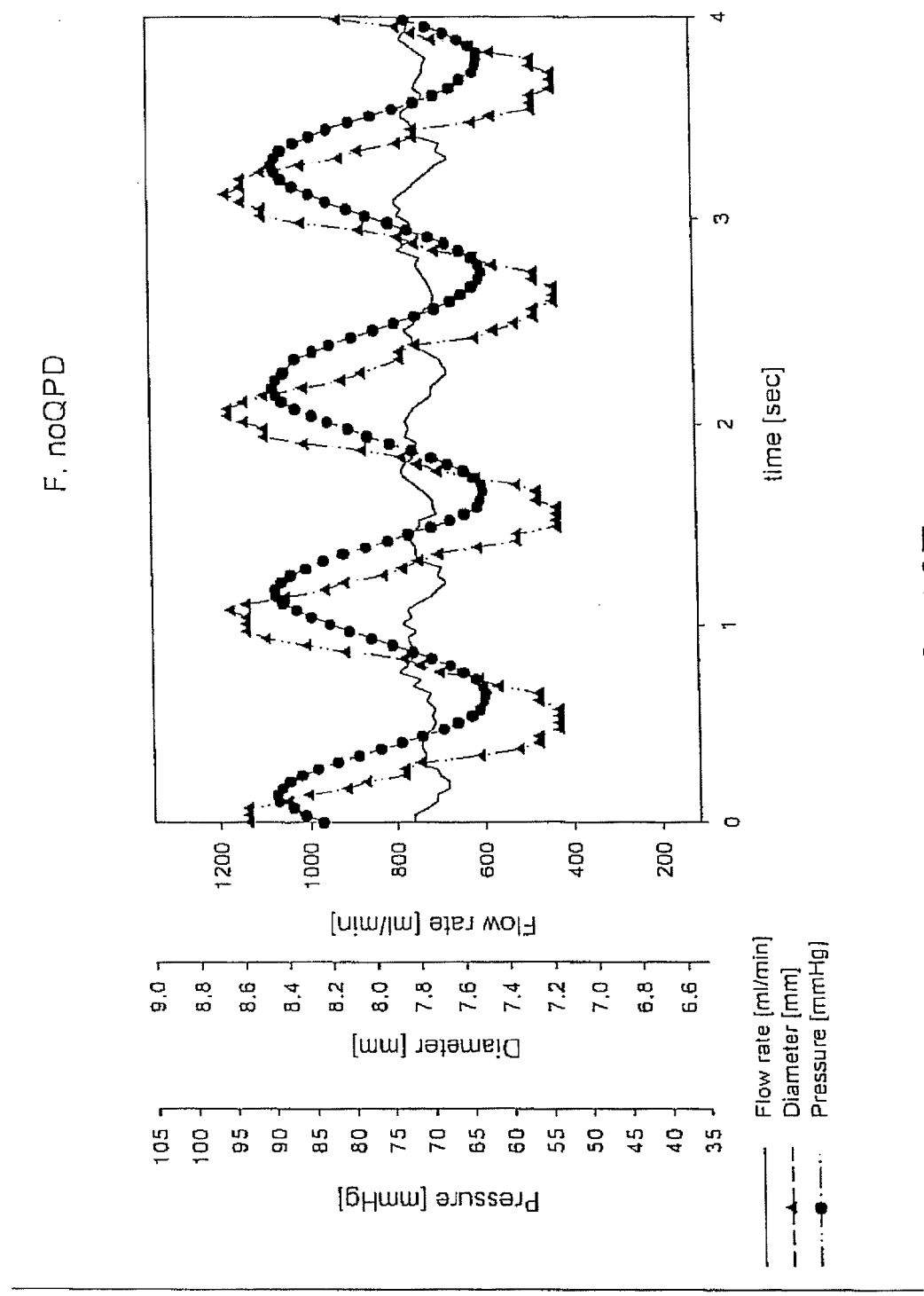
Figure 10G:
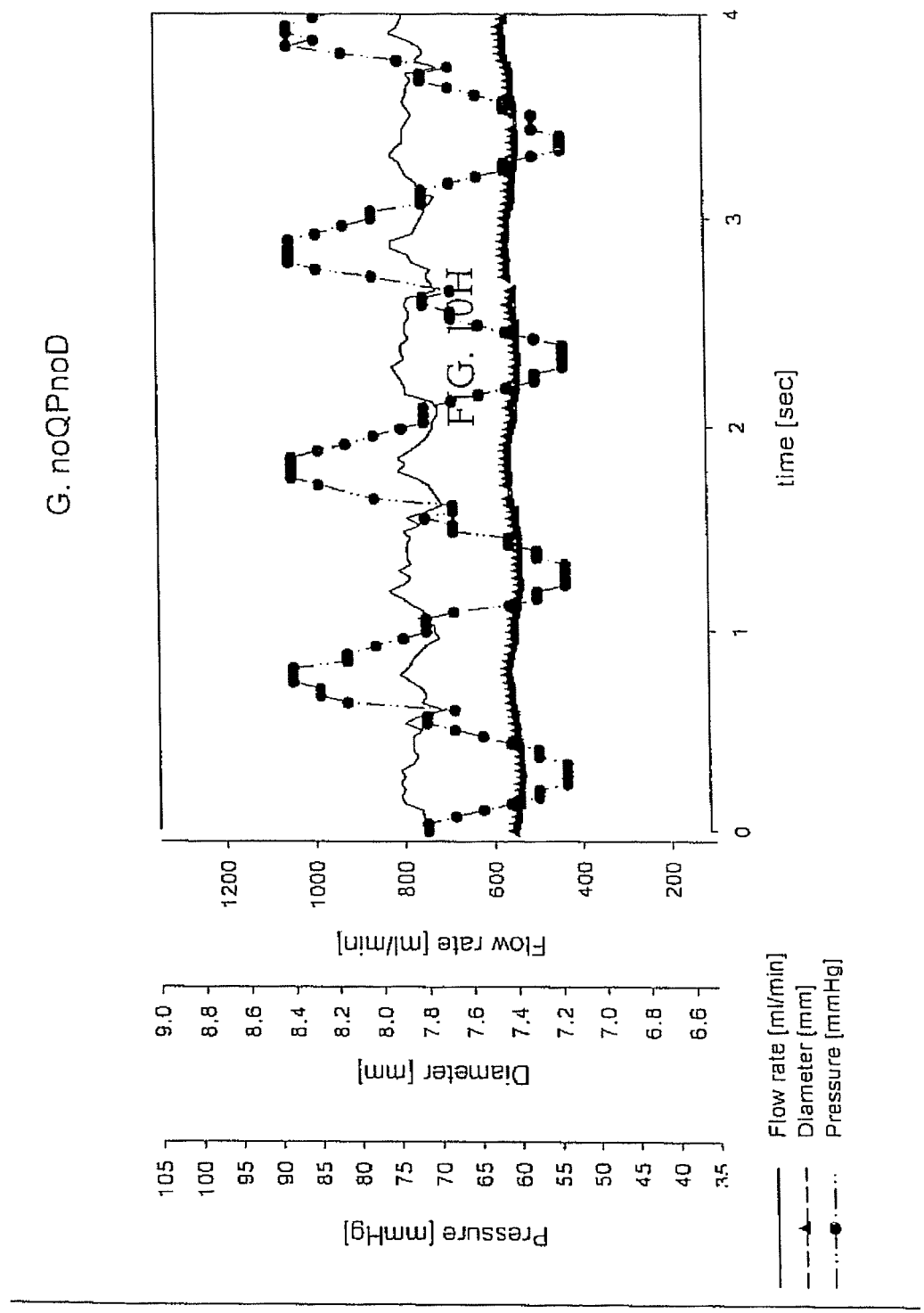
Figure 10H:
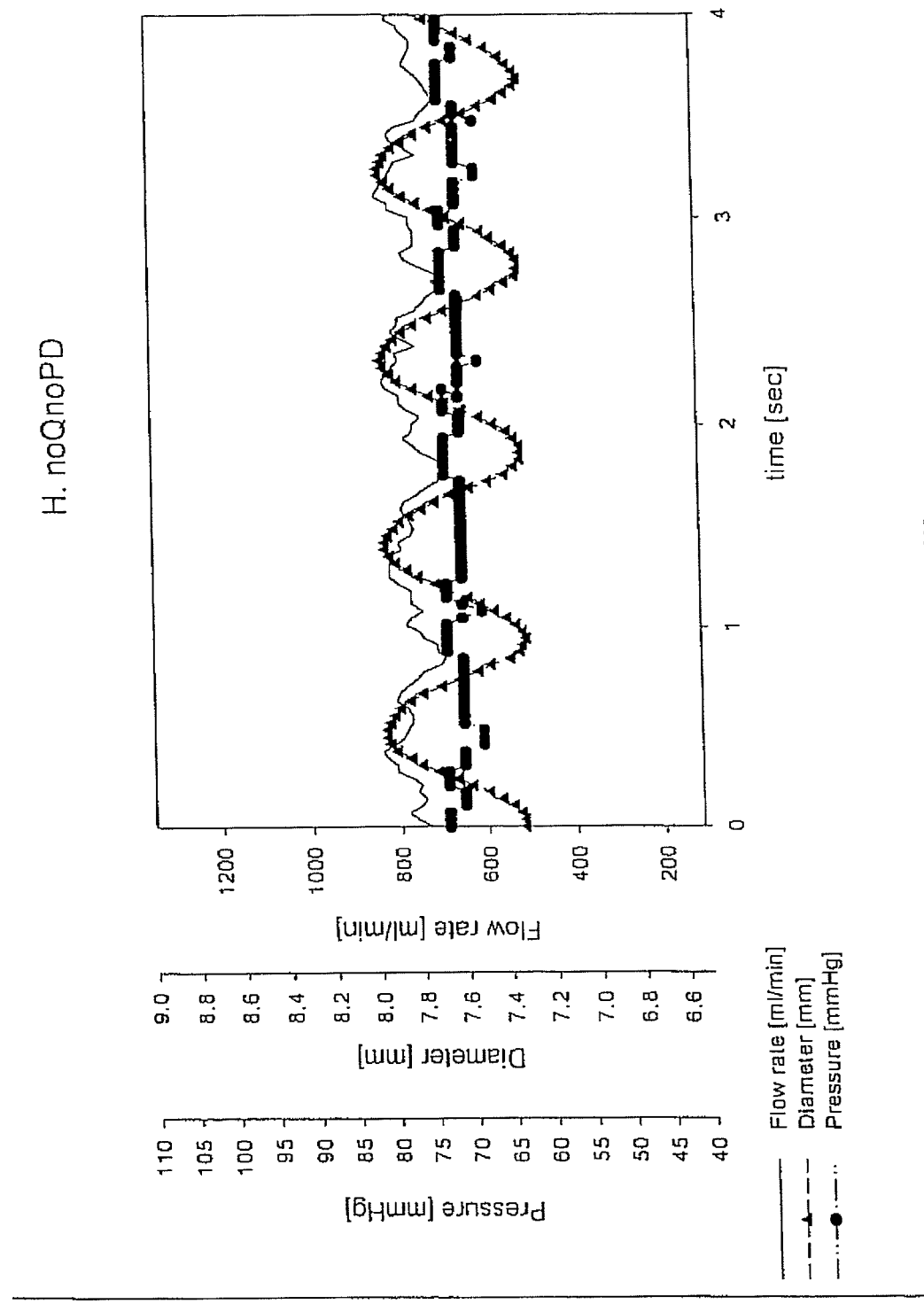

Embodiments of the systems 1, 1101 can include the steady flow component entering (upstream) the test section where the upstream, downstream, and external pressures are modulated to impose an oscillatory component on the steady flow component that resulted in controlled pulsatile conditions, as shown in FIGS. 10A and 10B. As discussed above, by appropriate control of these three pressures (types of dynamic condition shown in FIG. 17), a wide variety of classes of dynamic conditions (here hemodynamic conditions) can be simulated. FIGS. 10A and 10B show flow, pressure and diameter variation, and 0 deg and −180 deg SPA, which may be referred to as normal and pathologic hemodynamics from time to time. In this study, specimen holder 10 was multiplexed to accommodate six tubes with individual media lines each including real-time monitoring and visualization of flow, pressure, and diameter waveforms therein via a data acquisition system and software. Flow measurement utilized a noninvasive Doppler ultrasound probe and flow meter (flow meter model T110 from Transonics™). Pressure measurement was via an invasive catheter pressure sensor (MPC-500 from Millar). Noninvasive inner diameter monitoring required an ultrasound system that utilized a 10 MHz transducer, pulser/receiver, and 50 MHz high-frequency data acquisition card (compulite 1250 from GAGE™ Applied Technologies). Sensor signals were acquired in real time with custom data acquisition software written in LAB VIEW and utilized a DAQ card (400 kHz, PCI-6024E from National Instruments™). Waveform data was analyzed for desired time periods (e.g., 1 min) and an FFT analysis was performed to determine functions such as waveform phase angle differences, magnitude and frequency, calibration scaling, peak max/min, autoscale, sample acquisition rate. Time lags between DAQ cards, sensors, CPU/BUS, and software were assessed via an external function generator. The flow, pressure, and diameter measurements were calibrated from the mass flow rate, a pneumatic transducer tester (DPM-1B, BIO-TEK Instruments), and a precision fabricated tube. All sensors were robust except for the pressure sensor that would require calibration prior to each experiment.

$PO_2/PCO_2$ control was necessary to ensure proper pH and gas concentrations for biological experiments. A pH system accommodated six pH probes (e.g., one per tube) that are multiplexed with a pH meter. $PO_2/PCO_2$ was measured with a blood gas analyzer (CDI300 blood/gas analyzer from Terumo). Temperature was controlled at 37° C. via a hot plate and large water bath that was enclosed in a thermal hood. Cell viability was assessed from direct microscope visualization through an intact tube as well as en face staining (slicing the tube open).

The tubular structures 1112 required characteristics of noncytotoxicity, optical transparency for microscope visualization, and mechanical properties (e.g., verified using longitudinal stiffness, $K_L$, where $K_L/A=\Delta F/\Delta L/L/A$:F is force, A is cross-sectional area, and L is length) allowing physiologic diameter variation (±4%) under pressures of 70±20 mmHg. The silicone elastomer (Sylgard® 184, Dow Corning) was used to fabricate the tubes or tubular structures 1112, which in this case were six tubes of 8 mm inner diameter×15 cm length and wall thicknesses of 500 μm.

Results

One embodiment of the controller 1103 can produce time varying control signals $f_j(t)$ (e.g., 0 deg SPA and −180 deg SPA) based on input information $f_i(t)$ including specimen size, fluid moving capacity (e.g., pump size) and location, and desired dynamic conditions at or along region A or specimen 12 for pressure flow loop subsystem 1105 components. One exemplary method (e.g., controller 1103) will now be described.

In this experiment, theoretical approaches for WSS characterization in straight elastic tubes used sinusoids to approximate prominent characteristics of physiologic waveforms and to allow emphasis on the SPA. Alternatively, in vivo measurements of WSS distribution can be used. See, for example, Shung, K. K., Smith, M. B., and Tsui, B. M. W., 1992, Principles of Medical Imaging, Academic, San Diego, the contents of which are incorporated herein by reference. Note that physiologic waveforms with multiple harmonics cannot be characterized by sa single value of SPA. The calculation of WSS for pulsatile flow in a rigid tube is known as Womersley's solution. The wall motion in an elastic tube imposes a radial convective component that affects the WSS. The nonlinear, elastic tube problem was solved by a perturbation technique that produced correction factors for Womersley's solution. The corrected pulsatile WSS component is then added to the steady flow WSS component that can be determined from a correction factor applied to Poiseuille flow. See, for example, Womersley, J. R., 1955, "Method for Calculation of Velocity, Rate of Flow and Viscous Drag in Arteries When the Pressure Gradient is Known," j. Physiol. (London), 127, pp. 553-563; Wang, D. M., and Tarbell, J. M., 1992, "Nonlinear Analysis of Flow in an Elastic Tube (Artery): Steady Streaming Effects," J. Fluid Mech., 239, pp. 341-358; Wang, D. M., and Tarbell J. M., 1995, "Nonlinear Analysis of Oscillatory Flow, With a Nonzero Mean, in an Elastic Tube (Artery)," J. Biomech. Eng., 117(1), pp. 127-135, the contents of which are incorporated herein by reference.

Thus, the WSS solution depends on the phase angle (SPA), α, and the Q, P, and D (e.g., CS) waveforms, which can be provided as input information $f_i(t)$ to controller 1103, which then can determine time varying control signals $f_j(t)$ for a selected embodiment of pressure flow loop subsystem 1105 components as described below. The waveforms are decomposed into mean and oscillatory components, where mean components are defined with a single overbar and oscillatory (sinusoidal) components are defined with a double overba $$WSS = \overline{WSS} \pm \overline{\overline{WSS}} \qquad (1)$$

$$Q = \overline{Q} \pm \overline{\overline{Q}} \qquad (2)$$

$$D = \overline{D} \pm \overline{\overline{D}} = \overline{D} \pm \varepsilon \qquad (3)$$

$$WSS = \overline{WSS}_{pois}(\overline{Q}, \overline{D}) \cdot \overline{C}(\overline{Q}, \varepsilon, \varphi \pm \overline{\overline{WSS}}_{worm}(\overline{\overline{Q}}, \overline{D}) \cdot \overline{\overline{C}}(\overline{Q}, \overline{\overline{Q}}, \varepsilon, \varphi) \qquad (4)$$

where $\overline{WSS}_{pais}$ is the mean WSS determined from Poiseuille flow; $\overline{\overline{WSS}}_{worm}$ is the oscillatory WSS determined from Womersley' solution; $\overline{C}$ is the correction factor for the mean component [37]; $\overline{\overline{C}}$ is the correction factor for the oscillatory component [38]; ε is the amplitude of diameter variation; φ is the SPA. The terms in Eq. (4) are functions of the parameters in parentheses [i.e., for $\overline{WSS}_{pais}(\overline{Q},\overline{D})$, $\overline{WSS}_{pais}$ is a function $\overline{Q}$ and $\overline{D}$]. The correction factors for the experimental conditions shown in FIG. 3(A) (0 deg) and FIG. 3(B) (−180 deg) are $\overline{C}(500,0.04,0 \text{ deg})=0.993$, $\overline{C}(500,0.04,-180 \text{ deg})=1.007$, $\overline{C}(500,700.0.04,0 \text{ deg})=0.83$, $\overline{C}(500,700.0.04,-180 \text{ deg})=1.23$ The resulting WSS waveforms are WSS=10±10 dyne/cm² for both cases. Note that the correction factors for these experimental conditions indicate that for SPA=−180 deg, the flow amplitude, $\overline{\overline{Q}}$, should be 23% lower than the Womersley flow amplitude, and at SPA=0 deg, $\overline{\overline{Q}}$ should be 17% larger than the Womersley flow amplitude. The correction factors for the mean components were negligible for these conditions.

Feedback information $FB_j(t)$ can be determined in the selected embodiments of pressure flow loop subsystem 1105 components and output to controller 1103 to assess conditions in system 1101 (e.g., at region A or along conduit 3701) In this study, $FB_j(t)$ included at least Q(t), D(t), P(t), pH, temperature, viability and NO, WSS, CS, SPA.

In this study, long-term stability of the system under pulsatile conditions was assessed via continuous monitoring of the Q, P, and D waveforms over a 36 hr period at 37 deg, which showed controlled maintenance of the dynamic conditions or waveforms. $PO_2PCO_2$ concentrations were measured after pulsatile conditions with a blood gas analyzer and were shown to have similar values to incubator controls of the same time duration of 17 h, $PO_2$-141 mmHg and $PCO_2$=40 mmHg. The temperature was very stable (±0.5° C.) and was not affected by opening/closing the thermal hood door. In this study, there were minor variations in the operating conditions over the 15 cm tube length in the test section. The variations across the tube length (L) during pulsatile flow at SPA=0 deg and −180 deg were: ΔP=1.5-2 mmHg, ΔQ=10 ml/min, Δτ=0.2 dyne/cm² (calculated), and ΔSPA=2-6 deg.

Figure 50:
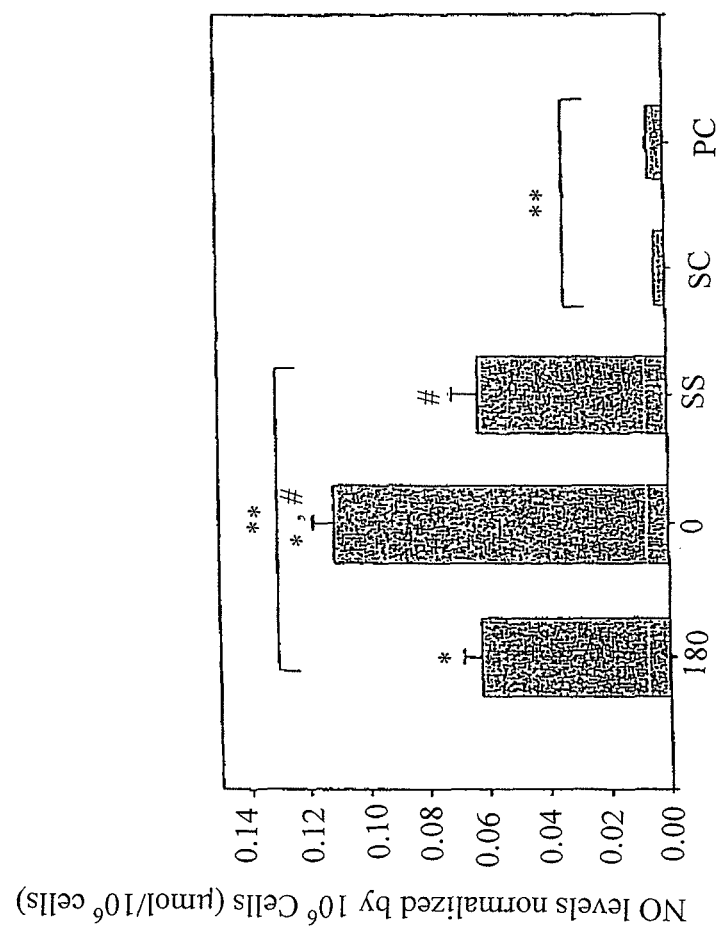
FIG. 50 shows NO levels for cells experiencing different dynamic conditions produced by an embodiment of a system according to the invention.

FIG. 50 shows production of NO from BAECs exposed to hemodynamic conditions in media at 5 hr. In FIG. 50, pairwise significant differences indicated by * for 0 deg SPA and −180 deg SPA, # for 0 deg SPA and steady state (SS), and ** for dynamic and static controls with p values <0.05 (n=5). The biological results in this study depicted in FIG. 46 show a significant decrease in NO quantity for the pathologic −180 deg SPA versus the normal 0 deg SPA case (p<0.05). The 0 deg SPA case was significantly higher than the steady shear (SS) case (p<0.05). All the dynamic conditions were significantly higher than the static cases, static control (SC), and pressurized control (PC) (p<0.05). The SS case verified that the endothelial cells exhibited the anticipated increased NO shear response compared to the SC case. The PC case was not significantly greater than the SC case.

Systems 1, 1101 simulate normal and pathologic hemodynamics (e.g., FIG. 46). Complex physiologic hemodynamic features associated with different vascular beds can be simulated in vitro. In this embodiment the system utilized three-dimensional geometries (i.e., silicone tubes) to provide a physiologic environment to control or systematically evaluate or model concomitant influences of Q, P, and D waveforms on vascular physiology and/or pathology (e.g., fluid molecules such as gene and protein expression profiles).

As shown in FIG. 50, the pressurized control (PC) case was not significantly increased compared to the static control (SC) case, implying that the mean pressure and circumferential strain (CS) do not have a significant influence on NO production compared to steady shear stress. However, concomitant SS and CS affected the NO response of endothelial cells, modulated by the SPA. The significantly lower NO response of the −180 deg versus the 0 deg SPA case along with companion controls indicated that the large negative SPA had a negative or pathologic effect on the NO response. Regions of the circulation prone to pathologic development (i.e., atherosclerosis and intimal hyperplasia), such as the aortic abdominal bifurcation and curved coronary artery, experience a highly negative SPA. See, for example, Lee, C. S., and Tarbell, J. M., 1997, "Wall Shear Rate Distribution in an Abdominal Aortic Bifurcation Model: Effects of Vessel Compliance and Phase Angle Between Pressure and Flow Waveforms," J. Biomech. Eng., 119(3), pp. 333-342; and Qiu, Y., and Tarbell, J. M., 2000, "Numerical Simulation of Pulsatile Flow in a Compliant Curved Tube Model of a Coronary Artery," J. Biomech. Eng., 122(1), pp. 77-85; the contents of which are incorporated herein by reference.

Although embodiments of the invention have been described with reference to a number of illustrative embodiments thereof, it should be understood that numerous other modifications and embodiments can be devised by those skilled in the art that will fall within the spirit and scope of the principles of this invention. More particularly, reasonable variations and modifications are possible in the component parts and/or arrangements of the subject combination arrangement within the scope of the foregoing disclosure, the drawings and the appended claims without departing from the spirit of the invention. In addition to variations and modifications in the component parts and/or arrangements, alternative uses will also be apparent to diose skilled in the art.

What is claimed is:

1. A method, comprising:
providing a tubular structure;
placing cells in contact with the tubular structure; and
placing the tubular structure and cells in a system that exposes the tubular structure and cells to dynamic conditions in an ex vivo fluid environment effective to promote the cells to exhibit in vivo physiologic function, wherein the system comprises:
a specimen holder for holding the tubular structure and cells,
a pressure/flow control system that is fluidly coupled to the specimen holder so as to form a flow loop through which fluid traverse, wherein the pressure/flow control system generates and maintains dynamic fluid pressure and flow conditions within the specimen holder and is capable of independently controlling fluid pressure and flow rate in the specimen holder, and
a control system for sending control signals to the pressure/flow system.

2. The method of claim 1, wherein the ex vivo fluid environment contains a chemical.

3. The method of claim 2, wherein the chemical comprises at least one of a drug, a reagent, or combinations thereof.

4. A device comprising a tubular structure at least partially coated with or at least partially impregnated with cells that exhibit an in vivo physiologic function, and prepared according to the method of claim 1.

5. The device of claim 4, wherein the tubular structure and cells have been exposed to dynamic conditions that were adjusted based on feedback from the cells.

6. The device of claim 5, wherein the feedback from the cells was based on metabolites secreted by the cells.

7. The device of claim 6, wherein the feedback from the cells was based on a concentration of metabolites secreted by the cells or on a time rate of secretion of metabolites by the cells.

8. The device of claim 4, wherein the cells comprise stem cells.

9. The device of claim 4, wherein the cells comprise endothelial cells.

10. The device of claim 4, wherein the cells comprise genetically modified cells.

11. The device of claim 4, wherein the cells comprise at least two types of cells taken from the group consisting of stem cells, endothelial cells and genetically modified cells.

12. The device of claim 4, wherein the cells comprise a confluent monolayer of cells affixed to the tubular structure.

13. The device of claim 4, wherein the cells are affixed to a surface of the tubular structure with a binding material.

14. The device of claim 4, wherein the cells are affixed to a surface of the tubular structure via surface adhesion between the cells and the inner surface of the tubular structure.

15. The device of claim 14, wherein the surface of the tubular structure is treated so as to improve the surface adhesion between the cells and the surface of the tubular structure.

16. The device of claim 15, wherein the surface of the tubular structure is treated by at least one of etching, plasma treatment, chemical vapor deposition, surface chemistry treatment or combinations thereof.

17. The device of claim 4, wherein the tubular structure comprises a non-synthetic material.

18. The device of claim 4, wherein the tubular structure comprises a synthetic material.

19. The device of claim 18, wherein the synthetic material comprises a polymer.

20. The device of claim 19, wherein the polymer comprises a degradable polymer.

21. The device of claim 19, wherein the polymer comprises a tissue engineered polymer.

22. The device of claim 18, wherein the device comprises a vascular conduit.

23. The device of claim 18, wherein the tubular structure comprises a stent.

24. The device of claim 23, wherein the device comprises a drug-eluting stent.

25. The device of claim 4, wherein the tubular structure comprises a heart valve.

26. The device of claim 4, wherein the in vivo physiologic function comprises a physiologic function exhibited in vivo by a biological system.

27. The device of claim 26, wherein the biological system comprises a cell.

28. The device of claim 26, wherein the biological system comprises tissue.

29. The device of claim 26, wherein the biological system comprises an organ.

30. The device of claim 26, wherein the biological system comprises a vessel in the peripheral vasculature.

31. The device of claim 26, wherein the biological system comprises a coronary vessel.

32. The device of claim 26, wherein the biological system comprises a neurovascular vessel.

33. The device of claim 26, wherein the biological system comprises a thoracic vessel.

34. The device of claim 26, wherein the biological system comprises an organ vessel.

35. The device of claim 26, wherein the physiologic function comprises at least one of an expression profile and metabolism.

36. The device of claim 26, wherein the physiologic function comprises a cell characteristic.

37. The device of claim 4, wherein the cells are affixed to an inner surface of the tubular structure.

38. The device of claim 4, wherein the dynamic conditions are adapted to promote adhesion of the cells to the surface of the tubular structure by triggering the cells to secrete attachment proteins.

39. The device of claim 4, wherein the ex vivo fluid environment contains a biochemical.

40. The device of claim 39, wherein the biochemical comprises at least one of growth factors, amino acids, hormones or combinations thereof.

41. The device of claim 4, wherein the cells were grown within a wall of the tubular structure.

* * * * *